United States Patent [19]

Nagase et al.

[11] Patent Number: 5,739,145

[45] Date of Patent: Apr. 14, 1998

[54] ANTITUSSIVE AGENTS

[75] Inventors: Hiroshi Nagase; Koji Kawai, both of Kamakura; Takashi Endoh, Chigasaki; Shinya Ueno, Kamakura; Yuji Negishi, Kagoshima, all of Japan

[73] Assignee: Toray Industries, Inc., Tokyo, Japan

[21] Appl. No.: 393,020

[22] PCT Filed: Jun. 28, 1995

[86] PCT No.: PCT/JP94/01047

§ 371 Date: Apr. 27, 1995

§ 102(e) Date: Apr. 27, 1995

[87] PCT Pub. No.: WO95/01178

PCT Pub. Date: Jan. 12, 1995

[30] Foreign Application Priority Data

Jun. 30, 1993 [JP] Japan .................... 5-161626

[51] Int. Cl.[6] .................. A61K 31/47; A61K 31/485; C07D 221/28; C07D 489/00
[52] U.S. Cl. .................. 514/282; 514/212; 514/289; 240/597; 546/44; 546/741
[58] Field of Search .................. 546/44, 74; 514/282, 514/289, 212; 540/897

[56] References Cited

U.S. PATENT DOCUMENTS

| | | | |
|---|---|---|---|
| 3,865,943 | 2/1975 | Merz et al. | 424/260 |
| 3,880,863 | 4/1975 | Meltzer | 546/46 |
| 3,917,606 | 11/1975 | Merz et al. | 260/285 |
| 4,401,672 | 8/1983 | Portoghese | 424/260 |
| 4,521,601 | 6/1985 | Rice | 546/45 |
| 4,613,668 | 9/1986 | Rice | 546/44 |
| 4,730,048 | 3/1988 | Portoghese | 546/45 |
| 4,912,114 | 3/1990 | Revesz | 514/282 |

FOREIGN PATENT DOCUMENTS

| | | |
|---|---|---|
| 0415693 | 3/1991 | European Pat. Off. . |
| 46-3375 | 1/1971 | Japan . |
| 46-28034 | 8/1971 | Japan . |
| 47-084705 | 9/1972 | Japan . |
| 0843908 | 8/1960 | United Kingdom . |
| 1064539 | 4/1967 | United Kingdom . |
| 93-15081 | 8/1993 | WIPO . |

OTHER PUBLICATIONS

Seki et al., Chemical & Pharmaceutical Bulletin (1971), vol. 19, No. 1, pp. 4–5.
Mohacsi et al., J. Med. Chem., (1982) 25:1264–1266.
J. Med. Chem., 25(10), 1264–1266 (1982).
Psychopharmacology, 76(4), 385–395 (1982).
Chem. Pharm. Bull., 19(1), 1–5 (1971).

*Primary Examiner*—C. Warren Ivy
*Assistant Examiner*—Evelyn Huang
*Attorney, Agent, or Firm*—Birch, Stewart, Kolasch & Birch, LLP

[57] ABSTRACT

There are provided novel antitussive agents different from existing antitussive agents or those under development. Antitussive agents containing morphinan derivatives represented by compound 6:

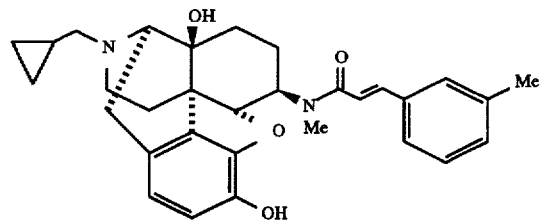

or pharmacologically acceptable acid-addition salts thereof and those derivatives or their salts as effective components.

The antitussive agents according to the present invention have strong antitussive effects as highly selective κ-opioid agonists, and may thus be applied as useful antitussive agents in the prophylaxis and treatment of coughing in a patient in need thereof.

5 Claims, No Drawings

ANTITUSSIVE AGENTS

This application is the National phase of PCT/JP94/10477 filed on Jun. 28, 1994.

1. Technical Field

The present invention relates to antitussive agents whose effective components are morphinan derivatives or pharmacologically acceptable acid-addition salts thereof. The compounds to be used according to the present invention have strong antitussive activity, and thus suppress coughing which accompanies bronchography, bronchoscopy, and a host of respiratory diseases including colds, acute bronchities, chronic bronchitis, bronchiectasis, pneumonia, lung tuberculosis, silicosis, silicotuberculosis, pulmonary cancer, upper respiratory inflammations (pharyngitis, laryngitis, nasal catarrh), asthmatic bronchitis, bronchial asthma, infantile asthma, (chronic) pulmonary emphysema, pneumoconiosis, pulmonary fibrosis, pulmonary silicosis, pulmonary suppuration, pleuritis, tonsillitis, coughing hives and whooping cough.

2. Related Art

Codeine, dextromethorphan and the like are known as high-strength antitussive agents acting on central nervous system. These drugs are used not only by doctors, but also as single components in combination cold medicines; however, they inherently have side effects serious enough to be clinically problematic, including drug dependence, respiratory depression, smooth muscle depressomotor effects (constipation) and psychotomimetic effects. Of particular seriousness is the overuse of antitussive agents containing codeine, and the psychotomimetic effects of dextromethorphan, for which reasons safer centrically acting high-strength antitussive agents have been desired.

The existence of opioid receptors as receptors which contribute to a variety of pharmacological effects, mainly analgesic, has been demonstrated, and they are known to be further classified into three types, μ, δ, and κ. σ-receptors are also known which exhibit a psychotomimetic effect. The antitussive effects of morphine and codeine which act on the μ-type receptors and dextromethorphan which acts on the σ-type have long been known, but it has not been possible to avoid the serious side effects such as drug dependence, respiratory depression, smooth muscle depressomotor effects (constipation) and psychotomimetic effects.

Incidentally, agonists with affinity to the κ-receptor, one of the four types mentioned above, are said not to exhibit the serious side effects which are clinically problematic, such as drug dependence, respiratory depression, smooth muscle depressomotor effects, etc. experienced with μ-receptor agonists such as morphine. Furthermore, the psychotomimetic effects experienced with existing κ-receptor agonists are said to be caused by their affinity to σ-receptors. Consequently, it is an object of the present invention to provide antitussive agents whose effective components are κ-receptor agonists which do not exhibit the serious side effects associated with μ-agonists and σ-agonists.

DISCLOSURE OF THE INVENTION

The present inventors, as a result of diligent research aimed at overcoming the aforementioned problems, have found that morphinan derivatives represented by general formula (I) are antitussive compounds with the above-mentioned excellent characteristics, and the present invention has been completed upon this finding.

Namely, the present invention relates to the use as antitussive agent of a morphinan derivative represented with general formula (I) below or pharmacologically acceptable acid salt thereof:

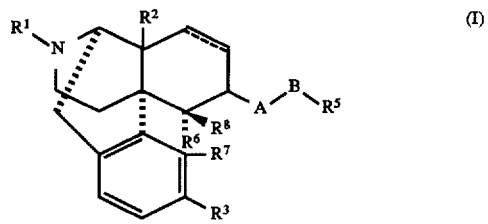

[wherein, ‒‒‒‒‒ represents a single or double bond; $R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms, or a thiophen-2-ylalkyl group having 1–5 carbon atoms; $R^2$ represents a hydrogen atoms, a hydroxy group, a nitro group, an alkanoyloxy group having 1–5 carbon atoms, an alkoxy group having 1–5 carbon atoms, an alkyl group having 1–5 carbon atoms, or —$NR^9R^{10}$ (wherein $R^9$ represents a hydrogen atom or an alkyl group having 1–5 carbon atoms, and $R^{10}$ represents a hydrogen atom, an alkyl group having 1–5 carbon atoms, or —$C(=O)R^{11}$ (wherein $R^{11}$ represents a hydrogen atom, a phenyl group or an alkyl group having 1–5 carbon atoms)); $R^3$ represents a hydrogen atom, a hydroxy group, an alkanoyloxy group having 1–5 carbon atoms, or an alkoxy group having 1–5 carbon atoms; A represents —XC(=Y)—, —XC(=Y)Z—, —X—, —XSO$_2$, or —OC(OR$^4$)R$^4$— (where, X, Y and Z each independently represent NR$^4$, S or O (wherein R$^4$ represents a hydrogen atom, a straight-chain or branched chain alkyl group having 1–5 carbon atoms or an aryl group having 6–12 carbon atoms, and wherein R$^4$ may be identical or different); B represents a valence bond, a straight-chain or branched chain alkylene group having 1–14 carbon atoms (which may be substituted with at least one type of substituent groups selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein 1 to 3 methylene groups may be replaced with carbonyl groups), an acyclic unsaturated hydrocarbon containing from 1 to 3 double bonds and/or triple bonds and having 2–14 carbon atoms (which may be substituted with at least one substituent group selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups may be replaced with carbonyl groups), or a straight-chain or branched chain saturated or unsaturated hydrocarbon group containing from 1 to 5 thioether, ether and/or amino bonds and having 1–14 carbon atoms (wherein hetero atoms are not bonded directly to A, and 1 to 3 methylene groups may be replaced with carbonyl groups); $R^5$ represents a hydrogen atom or an organic group having the following basic skeleton (which may be substituted with at least one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanato group, a trifluoromethyl group, a trifluoromethoxy group and a methylenedioxy group),

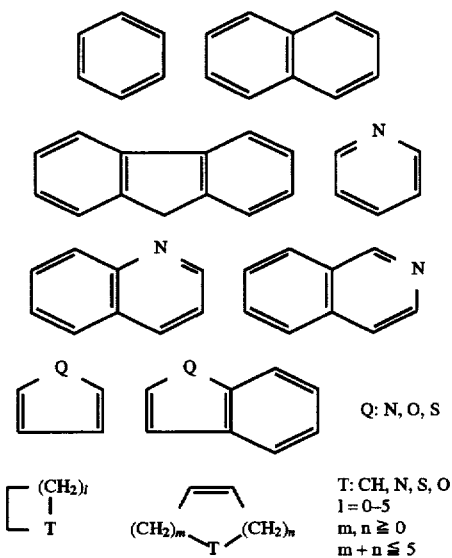

$R^6$ represents a hydrogen atom; $R^7$ represents a hydrogen atom, a hydroxy group, an alkoxy group having 1–5 carbon atoms, an alkanoyloxy group having 1–5 carbon atoms, or $R^6$ and $R^7$ together represent —O—, —CH$_2$— or —S—; $R^8$ represents a hydrogen atom, an alkyl group having 1–5 carbon atoms, or an alkanoyl group having 1–5 carbon atoms, and the general formula (I) includes the (+) form, (−) form and (±) form].

Here, preferable examples of $R^1$ include an alkyl group having 1–5 carbon atoms, a cycloalkylmethyl group having 4–7 carbon atoms, a cycloalkenylmethyl group having 5–7 carbon atoms, a phenylalkyl group having 7–13 carbon atoms, an alkenyl group having 4–7 carbon atoms, an allyl group, a furan-2-yl-alkyl group having 1–5 carbon atoms and a thiophen-2-yl-alkyl group having 1–5 carbon atoms, while particularly preferable examples of $R^1$ include methyl, ethyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl, allyl, furan-2-yl-methyl and thiophen-2-yl-methyl groups.

Preferable examples of $R^2$ include a hydrogen atom, and hydroxy, nitro, acetoxy, methoxy, methyl, ethyl, propyl, amino, dimethylamino, acetylamino and benzoylamino groups, while particularly preferable examples include a hydrogen atom, and hydroxy, nitro, acetoxy, methyl and dimethylamino groups.

Preferable examples of $R^3$ include a hydrogen atom, and hydroxy, acetoxy and methoxy groups.

Preferable examples of A include —NR$^4$C(=O)—, —NR$^4$C(=S)—, —NR$^4$C(=O)O—, —NR$^4$C(=O)NR$^4$—, —NR$^4$C(=S)NR$^4$—, —NR$^4$C(=O)S—, —OC(=O)—, —OC(=O)O—, —SC(=O)—, —NR$^4$—, —O—, —NR$^4$SO$_2$— and —OSO$_2$—, while particularly preferable examples include —NR$^4$C(=O)—, —NR$^4$C(=S)—, —NR$^4$C(=O)O—, —NR$^4$C(=O)NR$^4$—, —NR$^4$C(=S) NR$^4$—, —OC(=O)—, —NR$^4$—, —NR$^4$SO$_2$—, and more specifically —NR$^4$C(=O)—, —NR$^4$C(=O)O—, —OC(=O)— and —NR$^4$— are preferable.

Preferable examples of $R^4$ include a hydrogen atom, a straight-chain or branched alkyl group having 1–5 carbon atoms and phenyl group, while particularly preferable examples include a straight-chain or branched alkyl group having 1–5 carbon atoms, and particularly methyl, ethyl, propyl, isopropyl, butyl and isobutyl groups.

Preferable examples of B include —(CH$_2$)n— (n=0–6), —(CH$_2$)n—C(=O)— (n=1–4), —CH=CH—(CH$_2$)n— (n=0–4), —C≡C—(CH$_2$)n— (n=0–4), —CH$_2$—O—, —CH$_2$—S—, —CH$_2$—O—(CH$_2$)$_2$—O—(CH$_2$)$_2$—, —CH$_2$—O—CH$_2$—NH—CH$_2$—O—CH$_2$— and —CH$_2$—O—CH$_2$—S—CH$_2$—O—CH$_2$—, while particularly preferable examples include —(CH$_2$)n— (n=0–6), —CH=CH—(CH$_2$)n— (n=0–4), —C≡C—(CH$_2$)n— (n=0–4), —CH$_2$—O— and —CH$_2$—S—. Preferable examples of $R^5$ include a hydrogen atom or an organic group having the following basic skeleton indicated in (which may be substituted with at least one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, an amino group, a nitro group, a cyano group, an isothiocyanato group, trifluoromethyl group and a trifluoromethoxy group), (Formula 1-1)

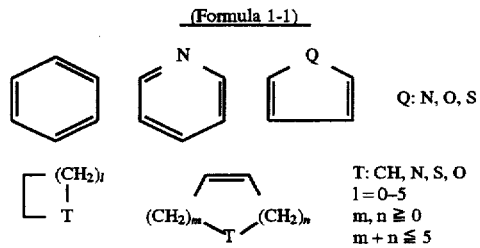

while particularly preferable examples include, a hydrogen atom and phenyl, 3,4-dichlorophenyl, 4-chlorophenyl, 3-chlorophenyl, 2-chlorophenyl, 3,4-difluorophenyl, 4-fluorophenyl, 3-fluorophenyl, 2-fluorophenyl, 4-bromophenyl, 3-bromophenyl, 2-bromophenyl, 4-nitrophenyl, 3-nitrophenyl, 2-nitrophenyl, 4-trifluoromethylphenyl, 3-trifluoromethylphenyl, 2-trifluoromethylphenyl, 4-methylphenyl, 3-methylphenyl, 2-methylphenyl, 4-methoxyphenyl, 3-methoxyphenyl, 2-methoxyphenyl, 4-trifluoromethoxyphenyl, 3-trifluoromethoxyphenyl, 2-trifluoromethoxyphenyl, 3-furanyl, 2-furanyl, 3-thienyl, 2-thienyl, cyclopentyl and cyclohexyl groups. But naturally the present invention is not limited to these examples.

Preferable examples of pharmacologically preferable acid addition salts include, but are naturally not limited to, inorganic acid salts such as hydrochloride, sulfate, nitrate, hydrobromide, hydroiodide and phosphate; organic carboxylates such as acetate, lactate, citrate, oxalate, glutarate, malate, tartrate, fumarate, mandelate, maleate, benzoate and phthalate; and, organic sulfonates such as methanesulfonate, ethanesulfonate, benzenesulfonate, p-toluenesulfonate and camphorsulfonate, while particularly preferable examples include hydrochloride, hydrobromide, phosphate, tartrate and methanesulfonate.

Among the compounds of the general formula (I) of the present invention, compound 1

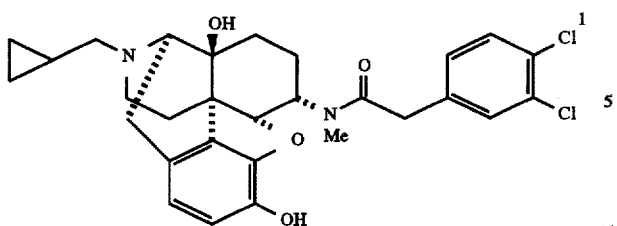

wherein ⁓ is a single bond, $R^1$ is a cyclopropylmethyl group, $R^2$ and $R^3$ are hydroxy groups, A is α—$NR^4C(=O)$—, $R^4$ is a methyl group, B is —$CH_2$—, $R^5$ is 3,4-dichlorophenyl, $R^6$ and $R^7$ are together —O— and $R^8$ is a hydrogen atom is named 17-cyclopropylmethyl-4,5α-epoxy-3,14β-dihydroxy-6α-(N-methyl-3,4-dichlorophenylacetamido)morphinan.

In accordance with the above nomenclature system, concrete examples of the compound of the present invention are as follows:

17-cyclopropylmethyl-4,5α-epoxy-3,14β-dihydroxy-6α-(N-methylcinnamamido)morphinan, 17-cyclopropylmethyl-4,5α-epoxy-3,14β-dihydroxy-6α-(N-methylbenzyloxycarbamido)morphinan, 17-cyclopropylmethyl-4,5α-epoxy-3,14β-dihydroxy-6α-(N-methylphenylmethanesulfonamido)morphinan, 17-allyl-4,5α-epoxy-3,14β-dihydroxy-6α-(N-methyl-3,4-dichlorophenylacetamido)morphinan, 17-allyl-4,5α-epoxy-3,14β-dihydroxy-6β-(N-methylcinnamamido)morphinan, 17-allyl-4,5α-epoxy-3,14β-dihydroxy-6α-(N-methylbenzyloxycarbamido) morphinan, 17-allyl-4,5α-epoxy-3,14β-dihydroxy-6α-(N-methylphenylmethanesulfonamido)morphinan, 17-methyl-4,5α-epoxy-3,14β-dihydroxy-6α-(N-methyl-3,4-dichlorophenylacetamido)morphinan, 17-methyl-4,5α-epoxy-3,14β-dihydroxy-6α-(N-methylcinnamamido)morphinan, 17-methyl-4,5α-epoxy-3,14β-dihydroxy-6α-(N-methylbenzyloxycarbamido)morphinan, 17-methyl-4,5α-epoxy-3,14β-dihydroxy-6α-(N-methylphenylmethanesulfonamido)morphinan, 17-phenethyl-4,5α-epoxy-3,14β-dihydroxy-6α-(N-methyl-3,4-dichlorophenylacetamido)morphinan, 17-phenethyl-4,5α-epoxy-3,14β-dihydroxy-6α-(N-methylcinnamamido)morphinan, 17-phenethyl-4,5α-epoxy-3,14β-dihydroxy-6α-(N-methylbenzyloxycarbamido)morphinan, 17-phenethyl-4,5α-epoxy-3,14β-dihydroxy-6α-(N-methylphenylmethanesulfonamido)morphinan, 17-cyclopropylmetyl-4,5α-epoxy-3-hydroxy-14β-acetoxy-6α-(N-methyl-3,4-dichlorophenylacetamido) morphinan, 17-cyclopropylmethyl-4,5α-epoxy-3-hydroxy-14β-acetoxy-6α-(N-methylcinnamamido) morphinan, 17-cyclopropylmethyl-4,5α-epoxy-3-hydroxy-14β-acetoxy-6α-(N-methylbenzyloxycarbamido)morphinan, 17-cyclopropylmethyl-4,5α-epoxy-3-hydroxy-14β-acetoxy-6α-(N-methylphenylmethanesulfonamido) morphinan, 17-allyl-4,5α-epoxy-3-hydroxy-14β-acetoxy-6α-(N-methyl-3,4-dichlorophenylacetamido) morphinan, 17-allyl-4,5α-epoxy-3-hydroxy-14β-acetoxy-6α-(N-methylcinnamamido)morphinan, 17-allyl-4,5α-epoxy-3-hydroxy-14β-acetoxy-6α-(N-methylbenzyloxycarbamido)morphinan, 17-allyl-4,5α-epoxy-3-hydroxy-14α-acetoxy-6α-(N-methylphenylmethanesulfonamido)morphinan, 17-methyl-4,5α-epoxy-3-hydroxy-14β-acetoxy-6α-(N-methyl-3,4-dichlorophenylacetamido)morphinan, 17-methyl-4,5α-epoxy-3-hydroxy-14β-acetoxy-6α-(N-methylcinnamamido)morphinan, 17-methyl-4,5α-epoxy-3-hydroxy-14β-acetoxy-6α-(N-methylbenzyloxycarbamido)morphinan, 17-methyl-4,5α-epoxy-3-hydroxy-14β-acetoxy-6α-(N-methylphenylmethanesulfonamido)morphinan, 17-phenethyl-4,5α-epoxy-3-hydroxy-14β-acetoxy-6α-(N-methyl-3,4-dichlorophenylacetamido)morphinan, 17-phenethyl-4,5α-epoxy-3-hydroxy-14β-acetoxy-6α-(N-methylcinnamamido)morphinan, 17-phenethyl-4,5α-epoxy-3-hydroxy-14β-acetoxy-6α-(N-methylbenzyloxycarbamido)morphinan, 17-phenethyl-4,5α-epoxy-3-hydroxy-14β-acetoxy-6α-(N-methylphenylmethanesulfonamido)morphinan, 17-cyclopropylmethyl-4,5α-epoxy-14β-hydroxy-6α-(N-methyl-3,4-dichlorophenylacetamido)morphinan, 17-cyclopropylmetyl-4,5α-epoxy-14β-hydroxy-6α-(N-methylcinnamamido)morphinan, 17-cyclopropylmethyl-4,5α-epoxy-14β-hydroxy-6α-(N-methylbenzyloxycarbamido)morphinan, 17-cyclopropylmethyl-4,5α-epoxy-14β-hydroxy-6α-(N-methylphenylmethanesulfonamido)morphinan, 17-allyl-4,5α-epoxy-14β-hydroxy-6α-(N-methyl-3,4-dichlorophenylacetamido)morphinan, 17-allyl-4,5α-epoxy-14β-hydroxy-6α-(N-methylcinnamamido) morphinan, 17-allyl-4,5α-epoxy-14β-hydroxy-6α-(N-methylbenzyloxycarbamido)morphinan, 17-allyl-4,5α-epoxy-14β-hydroxy-6α-(N-methylphenylmethanesulfonamido)morphinan, 17-methyl-4,5α-epoxy-14β-hydroxy-6α-(N-methyl-3,4-dichlorophenylacetoamido)morphinan, 17-methyl-4,5α-epoxy-14β-hydroxy-6α-(N-methylcinnamamido)morphinan, 17-methyl-4,5α-epoxy-14β-hydroxy-6α-(N-methylbenzyloxycarbamido)morphinan, 17-methyl-4,5α-epoxy-14β-hydroxy-6α-(N-methylphenylmethanesulfonamido)morphinan, 17-phenethyl-4,5α-epoxy-14β-hydroxy-6α-(N-methyl-3,4-dichlorophenylacetamido)morphinan, 17-phenethyl-4,5α-epoxy-14β-hydroxy-6α-(N-methylcinnamamido)morphinan, 17-phenethyl-4,5α-epoxy-14β-hydroxy-6α-(N-methylbenzyloxycarbamido)morphinan, 17-phenethyl-4,5α-epoxy-14β-hydroxy-6α-(N-methylphenylmethanesulfonamido)morphinan, 17-cyclopropylmethyl-4,5α-epoxy-14β-acetoxy-6α-(N-methyl-3,4-dichlorophenylacetamido)morphinan, 17-cyclopropylmethyl-4,5α-epoxy-14β-acetoxy-6α-(N-methylcinnamamido)morphinan, 17-cyclopropylmethyl-4,5α-epoxy-14β-acetoxy-6α-(N-methylbenzyloxycarbamido)morphinan, 17-cyclopropylmethyl-4,5α-epoxy-14β-acetoxy-6α-(N-methylphenylmethanesulfonamido)morphinan, 17-allyl-4,5α-epoxy-14β-actoxy-6α-(N-methyl-3,4-dichlorophenylacetamido)morphinan, 17-allyl-4,5α-epoxy-14β-acetoxy-6α-(N-methylcinnamamido) morphinan, 17-allyl-4,5α-epoxy-14β-acetoxy-6α-(N-methylbenzyloxycarbamido)morphinan, 17-allyl-4,5α-epoxy-14β-acetoxy-6α-(N-methylphenylmethanesulfonamido)morphinan, 17-methyl-4,5α-epoxy-14β-acetoxy-6α-(N-methyl-3,4-dichlorophenylacetamido)morphinan, 17-methyl-4,5α-epoxy-14β-acetoxy-6α-(N-methylcinnamamido)morphinan, 17-methyl-4,5α-epoxy-14β-acetoxy-6α-(N- methylbenzyloxycarbamido)morphinan, 17-methyl-4,5α-epoxy-14β-acetoxy-6α-(N-methylphenylmethanesulfonamido)morphinan, 17-phenethyl-4,5α-epoxy-14β-acetoxy-6α-(N-methyl-3,4-dichlorophenylacetamido)morphinan, 17-phenethyl-4,5α-epoxy-14β-acetoxy-6α-(N-methylcinnamamido)morphinan, 17-phenethyl-4,5α-epoxy-14β-acetoxy-6α-(N-methylbenzyloxycarbamido)morphinan, 17-phenethyl-4,5α-epoxy-14β-acetoxy-6α-(N-methylphenylmethanesulfonamido)morphinan, 17-cyclopropylmethyl-4,5α-epoxy-3-methoxy-14β-hydroxy-6α-(N-methyl-3,4-dichlorophenylacetamido)morphinan, 17-cyclopropylmethyl-4,5α-epoxy-3-methoxy-14β-hydroxy-6α-(N-methylcinnamamido)morphinan, 17-cyclopropylmethyl-4,5α-epoxy-3-methoxy-14β-hydroxy-6α-(N-methylbenzyloxycarbamido)morphinan, 17-cyclopropylmethyl-4,5α-epoxy-3-methoxy-14β-hydroxy-6α-(N-methylphenylmethanesulfonamido)morphinan, 17-allyl-4,5α-epoxy-3-methoxy-14β-hydroxy-6α-(N-methyl-3,4-dichlorophenylacetamido)morphinan, 17-allyl-4,5α-epoxy-3-methoxy-14β-hydroxy-6α-(N-methylcinamamido)morphinan, 17-allyl-4,5α-epoxy-3-methoxy-14β-hydroxy-6α-(N-methylbenzyloxycarbamido)morphinan, 17-allyl-4,5α-epoxy-3-methoxy-14β-hydroxy-6α-(N-methylphenylmethanesulfonamido)morphinan, 17-methyl-4,5α-epoxy-3-methoxy-14β-hydroxy-6α-(N-methyl-3,4-dichlorophenylacetamido)morphinan, 17-methyl-4,5α-epoxy-3-methoxy-14β-hydroxy-6α-(N-methylcinnamamido)morphinan, 17-methyl-4,5α-epoxy-3-methoxy-14β-hydroxy-6α-(N-methylbenzyloxycarbamido)morphinan, 17-methyl-4,5α-epoxy-3-methoxy-14β-hydroxy-6α-(N-methylphenylmethanesulfonamido)morphinan, 17-phenethyl-4,5α-epoxy-3-methoxy-14β-hydroxy-6α-(N-methyl-3,4-dichlorophenylacetamido)morphinan, 17-phenethyl-4,5α-epoxy-3-methoxy-14β-hydroxy-6α-(N-methylcinnamamido)morphinan, 17-phenethyl-4,5α-epoxy-3-methoxy-14β-hydroxy-6α-(N-methylbenzyloxycarbamido)morphinan, 17-phenethyl-4,5α-epoxy-3-methoxy-14β-hydroxy-6α-(N-methylphenylmethanesulfonamido)morphinan, 17-cyclopropylmetyl-4,5α-epoxy-3-methoxy-14β-acetoxy-6α-(N-methyl-3,4-dichlorophenylacetamido)morphinan, 17-cyclopropylmethyl-4,5α-epoxy-3-methoxy-14β-acetoxy-6α-(N-methylcinnamamido)morphinan, 17-cyclopropylmethyl-4,5α-epoxy-3-methoxy-14β-acetoxy-6α-(N-methylbenzyloxycarbamido)morphinan, 17-cyclopropylmethyl-4,5α-epoxy-3-methoxy-14β-acetoxy-6α-(N-methylphenylmethanesulfonamido)morphinan, 17-allyl-4,5α-epoxy-3-methoxy-14β-acetoxy-6α-(N-methyl-3,4-dichlorophenylacetamido)morphinan, 17-allyl-4,5α-epoxy-3-methoxy-14β-acetoxy-6α-(N-methylcinnamamido)morphinan, 17-allyl-4,5α-epoxy-3-methoxy-14β-acetoxy-6α-(N-methylbenzyloxycarbamido)morphinan, 17-allyl-4,5α-epoxy-3-methoxy-14β-acetoxy-6α-(N-methylphenylmethanesulfonamido)morphinan, 17-methyl-4,5α-epoxy-3-methoxy-14β-acetoxy-6α-(N-methyl-3,4-dichlorophenylacetamido)morphinan, 17-methyl-4,5α-epoxy-3-methoxy-14β-acetoxy-6α-(N-methylcinnamamido)morphinan, 17-methyl-4,5α-epoxy-3-methoxy-14β-acetoxy-6α-(N-methylbenzyloxycarbamido)morphinan, 17-methyl-4,5α-epoxy-3-methoxy-14β-acetoxy-6α-(N-methylphenylmethanesulfonamido)morphinan, 17-phenethyl-4,5α-epoxy-3-methoxy-14β-acetoxy-6α-(N-methyl-3,4-dichlorophenylacetamido)morphinan, 17-phenethyl-4,5α-epoxy-3-methoxy-14β-acetoxy-6α-(N-methylcinnamamido)morphinan, 17-phenethyl-4,5α-epoxy-3-methoxy-14β-acetoxy-6α-(N-methylbenzyloxycarbamido)morphinan, 17-phenethyl-4,5α-epoxy-3-methoxy-14β-acetoxy-6α-(N-methylphenylmethanesulfonamido)morphinan, 17-cyclopropylmethyl-4,5α-epoxy-3-acetoxy-14β-hydroxy-6α-(N-methyl-3,4-dichlorophenylacetamido)morphinan, 17-cyclopropylmethyl-4,5α-epoxy-3-acetoxy-14β-hydroxy-6α-(N-methylcinnamamido)morphinan, 17-cyclopropylmethyl-4,5α-epoxy-3-acetoxy-14β-hydroxy-6α-(N-methylbenzyloxycarbamido)morphinan, 17-cyclopropylmethyl-4,5α-epoxy-3-acetoxy-14β-hydroxy-6α-(N-methylphenylmethanesulfonamido)morphinan, 17-allyl-4,5α-epoxy-3-acetoxy-14β-hydroxy-6α-(N-methyl-3,4-dichlorophenylacetamido)morphinan, 17-allyl-4,5α-epoxy-3-acetoxy-14β-hydroxy-6α-(N-methylcinnamamido)morphinan, 17-allyl-4,5α-epoxy-3-acetoxy-14β-hydroxy-6α-(N-methylbenzyloxycarbamido)morphinan, 17-allyl-4,5α-epoxy-3-acetoxy-14β-hydroxy-6α-(N-methylphenylmethanesulfonamido)morphinan, 17-methyl-4,5α-epoxy-3-acetoxy-14β-hydroxy-6α-(N-methyl-3,4-dichlorophenylacetamido)morphinan, 17-methyl-4,5α-epoxy-3-acetoxy-14β-hydroxy-6α-(N-methylcinnamamido)morphinan, 17-methyl-4,5α-epoxy-3-acetoxy-14β-hydroxy-6α-(N-methylbenzyloxycarbamido)morphinan, 17-methyl-4,5α-epoxy-3-acetoxy-14β-hydroxy-6α-(N-methylphenylmethanesulfonamido)morphinan, 17-phenethyl-4,5α-epoxy-3-acetoxy-14β-hydroxy-6α-(N-methyl-3,4-dichlorophenylacetamido)morphinan, 17-phenethyl-4,5α-epoxy-3-acetoxy-14β-hydroxy-6α-(N-methylcinnamamido)morphinan, 17-phenethyl-4,5α-epoxy-3-acetoxy-14β-hydroxy-6α-(N-methylbenzyloxycarbamido)morphinan, 17-phenethyl-4,5α-epoxy-3-acetoxy-14β-hydroxy-6α-(N-methylphenylmethanesulfonamido)morphinan, 17-cyclopropylmethyl-4,5α-epoxy-3,14β-diacetoxy-6α-(N-methyl-3,4-dichlorophenylacetamido)morphinan, 17-cyclopropylmethyl-4,5α-epoxy-3,14β-diacetoxy-6α-(N-methylcinnamamido)morphinan, 17-cyclopropylmethyl-4,5α-epoxy-3,14β-diacetoxy-6α-(N-methylbenzyloxycarbamido)morphinan, 17-cyclopropylmethyl-4,5α-epoxy-3,14β-diacetoxy-6α-(N-methylphenylmethanesulfonamido)morphinan, 17-allyl-4,5α-epoxy-3,14β-diacetoxy-6α-(N-methyl-3,4-dichlorophenylacetamido)morphinan, 17-allyl-4,5α-epoxy-3,14β-diacetoxy-6α-(N-methylcinnamamido)morphinan, 17-allyl-4,5α-epoxy-3,14β-diacetoxy-6α-(N-methylbenzyloxycarbamido)morphinan, 17-allyl-4,5α-epoxy-3,14β-diacetoxy-6α-(N-methylphenylmethanesulfonamido)morphinan, 17-methyl-4,5α-epoxy-3,14β-diacetoxy-6α-(N-methyl-3,4-dichlorophenylacetamido)morphinan, 17-methyl-4,5α-epoxy-3,14β-diacetoxy-6α-(N-methylcinnamamido)morphinan, 17-methyl-4,5α-epoxy-3,14β-diacetoxy-6α-(N-methylbenzyloxycarbamido)morphinan, 17-methyl-4,5α-epoxy-3,14β-diacetoxy-6α-(N-methylphenylmethanesulfonamido)morphinan, 17-phenethyl-4,5α-epoxy-3,14β-diacetoxy-6α-(N- methyl-3,4-dichlorophenylacetamido)morphinan, 17-phenethyl-4,5α-epoxy-3,14β-diacetoxy-6α-(N-methylcinnamamido)morphinan, 17-phenethyl-4,5α-epoxy-3,14β-diacetoxy-6α-(N-methylbenzyloxycarbamido)morphinan, 17-phenethyl-4,5α-epoxy-3,14β-diacetoxy-6α-(N-methylphenylmethanesulfonamido)morphinan, 17-cyclopropylmethyl-4,5α-epoxy-3,14β-dihydroxy-6α-(N-isobutyl-3,4-dichlorophenylacetamido)morphinan, 17-cyclopropylmetyl-4,5α-epoxy-3,14β-dihydroxy-6α-(N-isobutylcinnamamido)morphinan, 17-cyclopropylmethyl-4,5α-epoxy-3,14β-dihydroxy-6α-(N-isobutylbenzyloxycarbamido)morphinan, 17-cyclopropylmethyl-4,5α-epoxy-3,14β-dihydroxy-6α-(N-isobutylphenylmethanesulfonamamido)morphinan, 17-allyl-4,5α-epoxy-3,14β-dihydroxy-6α-(N-isobutyl-3,4-dichlorophenylacetamido)morphinan, 17-allyl-4,5α-epoxy-3,14β-dihydroxy-6α-(N-isobutylcinnamamido)morphinan, 17-allyl-4,5α-epoxy-3,14β-dihydroxy-6α-(N-isobutylbenzyloxycarbamido)morphinan.

17-allyl-4,5α-epoxy-3,14β-dihydroxy-6α-(N-isobutylphenylmethanesulfonamido)morphinan, 17-methyl-4,5α-epoxy-3,14β-dihydroxy-6α-(N-isobutyl-3,4-dichlorophenylacetamido)morphinan, 17-methyl-4,5α-epoxy-3,14β-dihydroxy-6α-(N-isobutylcinnamamido)morphinan, 17-methyl-4,5α-epoxy-3,14β-dihydroxy-6α-(N-isobutylbenzyloxycarbamido)morphinan, 17-methyl-4,5α-epoxy-3,14β-dihydroxy-6α-(N-isobutylphenylmethanesulfonamido)morphinan, 17-phenethyl-4,5α-epoxy-3,14β-dihydroxy-6α-(N-isobutyl-3,4-dichlorophenylacetamido)morphinan, 17-phenethyl-4,5α-epoxy-3,14β-dihydroxy-6α-(N-isobutylcinnamamido)morphinan, 17-phenethyl-4,5α-epoxy-3,14β-dihydroxy-6α-(N-isobutylbenzyloxycarbamido)morphinan.

17-phenethyl-4,5α-epoxy-3,14β-dihydroxy-6α-(N-isobutylphenylmethanesulfonamido)morphinan, 17-cyclopropylmethyl-4,5α-epoxy-3-hydroxy-14β-acetoxy-6α-(N-isobutyl-3,4-dichlorophenylacetamido)morphinan, 17-cyclopropylmetyl-4,5α-epoxy-3-hydroxy-14β-acetoxy-6α-(N-isobutylcinnamamido)morphinan, 17-cyclopropylmethyl-4,5α-epoxy-3-hydroxy-14β-acetoxy-6α-(N-isobutylbenzyloxycarbamido)morphinan, 17-cyclopropylmethyl-4,5α-epoxy-3-hydroxy-14β-acetoxy-6α-(N-isobutylphenylmethanesulfonamido)morphinan, 17-allyl-4,5α-epoxy-3-hydroxy-14β-acetoxy-6α-(N-isobutyl-3,4-dichlorophenylacetamido)morphinan, 17-allyl-4,5α-epoxy-3-hydroxy-14β-acetoxy-6α-(N-isobutylcinnamamido)morphinan, 17-allyl-4,5α-epoxy-3-hydroxy-14β-acetoxy-6α-(N-isobutylbenzyloxycarbamido)morphinan.

17-allyl-4,5α-epoxy-3-hydroxy-14β-acetoxy-6α-(N-isobutylphenylmethanesulfonamido)morphinan, 17-methyl-4,5α-epoxy-3-hydroxy-14β-acetoxy-6α-(N-isobutyl-3,4-dichlorophenylacetamido)morphinan, 17-methyl-4,5α-epoxy-3-hydroxy-14β-acetoxy-6α-(N-isobutylcinnamamido)morphinan, 17-methyl-4,5α-epoxy-3-hydroxy-14β-acetoxy-6α-(N-isobutylbenzyloxycarbamido)morphinan, 17-methyl-4,5α-epoxy-3-hydroxy-14β-acetoxy-6α-(N-isobutylphenylmethanesulfonamido)morphinan, 17-phenethyl-4,5α-epoxy-3-hydroxy-14β-acetoxy-6α-(N-isobutyl-3,4-dichlorophenylacetamido)morphinan, 17-phenethyl-4,5α-epoxy-3-hydroxy-14β-acetoxy-6α-(N-isobutylcinnamamido)morphinan, 17-phenethyl-4,5α-epoxy-3-hydroxy-14β-acetoxy-6α-(N-isobutylbenzyloxycarbamido)morphinan, 17-phenethyl-4,5α-epoxy-3-hydroxy-14β-acetoxy-6α-(N-isobutylphenylmethanesulfonamido)morphinan, 17-cyclopropylmethyl-4,5α-epoxy-14β-hydroxy-6α-(N-isobutyl-3,4-dichlorophenylacetamido)morphinan, 17-cyclopropylmethyl-4,5α-epoxy-14β-hydroxy-6α-(N-isobutylcinnamamido)morphinan, 17-cyclopropylmethyl-4,5α-epoxy-14β-hydroxy-6α-(N-isobutylbenzyloxycarbamido)morphinan, 17-cyclopropylmethyl-4,5α-epoxy-14β-hydroxy-6α-(N-isobutylphenylmethanesulfonamido)morphinan, 17-allyl-4,5α-epoxy-14β-hydroxy-6α-(N-isobutyl-3,4-dichlorophenylacetamido)morphinan, 17-allyl-4,5α-epoxy-14β-hydroxy-6α-(N-isobutylcinnamamido)morphinan, 17-allyl-4,5α-epoxy-14β-hydroxy-6α-(N-isobutylbenzyloxycarbamido)morphinan, 17-allyl-4,5α-epoxy-14β-hydroxy-6α-(N-isobutylphenylmethanesulfonamido)morphinan, 17-methyl-4,5α-epoxy-14β-hydroxy-6α-(N-isobutyl-3,4-dichlorophenylacetamido)morphinan, 17-methyl-4,5α-epoxy-14β-hydroxy-6α-(N-isobutylcinnamamido)morphinan, 17-methyl-4,5α-epoxy-14β-hydroxy-6α-(N-isobutylbenzyloxycarbamido)morphinan, 17-methyl-4,5α-epoxy-14β-hydroxy-6α-(N-isobutylphenylmethanesulfonamido)morphinan, 17-phenethyl-4,5α-epoxy-14β-hydroxy-6α-(N-isobutyl-3,4-dichlorophenylacetamido)morphinan, 17-phenethyl-4,5α-epoxy-14β-hydroxy-6α-(N-isobutylcinnamamido)morphinan, 17-phenethyl-4,5α-epoxy-14β-hydroxy-6α-(N-isobutylbenzyloxycarbamido)morphinan, 17-phenethyl-4,5α-epoxy-14β-hydroxy-6α-(N-isobutylphenylmethanesulfonamido)morphinan, 17-cyclopropylmethyl-4,5α-epoxy-14β-acetoxy-6α-(N-isobutyl-3,4-dichlorophenylacetamido)morphinan, 17-cyclopropylmethyl-4,5α-epoxy-14β-acetoxy-6α-(N-isobutylcinnamamido)morphinan, 17-cyclopropylmethyl-4,5α-epoxy-14β-acetoxy-6α-(N-isobutylbenzyloxycarbamido)morphinan, 17-cyclopropylmethyl-4,5α-epoxy-14β-acetoxy-6α-(N-isobutylphenylmethanesulfonamido)morphinan, 17-allyl-4,5α-epoxy-14β-acetoxy-6α-(N-isobutyl-3,4-dichlorophenylacetamido)morphinan, 17-allyl-4,5α-epoxy-14β-acetoxy-6α-(N-isobutylcinnamamido)morphinan, 17-allyl-4,5α-epoxy-14β-acetoxy-6α-(N-isobutylbenzyloxycarbamido)morphinan, 17-allyl-4,5α-epoxy-14β-acetoxy-6α-(N-isobutylphenylmethanesulfonamido)morphinan, 17-methyl-4,5α-epoxy-14β-acetoxy-6α-(N-isobutyl-3,4-dichlorophenylacetamido)morphinan.

17-methyl-4,5α-epoxy-14β-acetoxy-6α-(N-isobutylcinnamamido)morphinan, 17-methyl-4,5α-epoxy-14β-acetoxy-6α-(N-isobutylbenzyloxycarbamido)morphinan, 17-methyl-4,5α-epoxy-14β-acetoxy-6α-(N-isobutylphenylmethanesulfonamido)morphinan, 17-phenethyl-4,5α-epoxy-14β-acetoxy-6α-(N-isobutyl-3,4-dichlorophenylacetamido)morphinan, 17-phenethyl-4,5α-epoxy-14β-acetoxy-6α-(N-isobutylcinnamamido)morphinan, 17-phenethyl-4,5α-epoxy-14β-acetoxy-6α-(N-isobutylbenzyloxycarbamido)morphinan, 17-phenethyl-4,5α-epoxy-14β-acetoxy-6α-(N-isobutylphenylmethanesulfonamido)morphinan, 17-cyclopropylmethyl-4,5α-epoxy-3-methoxy-14β-hydroxy-6α-(N-isobutyl-3,4-dichlorophenylacetamido)morphinan,
17-cyclopropylmethyl-4,5α-epoxy-3-methoxy-14β-hydroxy-6α-(N-isobutylcinnamamido)morphinan,
17-cyclopropylmethyl-4,5α-epoxy-3-methoxy-14β-hydroxy-6α-(N-isobutylbenzyloxycarbamido)morphinan, 17-cyclopropylmethyl-4,5α-epoxy-3-methoxy-14β-hydroxy-6α-(N-isobutylphenylmethanesulfonamido)morphinan,
17-allyl-4,5α-epoxy-3-methoxy-14β-hydroxy-6α-(N-isobutyl-3,4-dichlorophenylacetamido)morphinan,
17-allyl-4,5α-epoxy-3-methoxy-14β-hydroxy-6α-(N-isobutylcinnamamido)morphinan, 17-allyl-4,5α-epoxy-3-methoxy-14β-hydroxy-6α-(N-isobutylbenzyloxycarbamido)morphinan, 17-allyl-4,5α-epoxy-3-methoxy-14β-hydroxy-6α-(N-isobutylphenylmethanesulfonamido)morphinan,
17-methyl-4,5α-epoxy-3-methoxy-14β-hydroxy-6α-(N-isobutyl-3,4-dichlorophenylacetamido)morphinan,
17-methyl-4,5α-epoxy-3-methoxy-14β-hydroxy-6α-(N-isobutylcinnamamido)morphinan, 17-methyl-4,5α-epoxy-3-methoxy-14β-hydroxy-6α-(N-isobutylbenzyloxycarbamido)morphinan, 17-methyl-4,5α-epoxy-3-methoxy-14β-hydroxy-6α-(N-isobutylphenylmethanesulfonamido)morphinan,
17-phenethyl-4,5α-epoxy-3-methoxy-14β-hydroxy-6α-(N-isobutyl-3,4-dichlorophenylacetamido)morphinan, 17-phenethyl-4,5α-epoxy-3-methoxy-14β-hydroxy-6α-(N-isobutylcinnamamido)morphinan,
17-phenethyl-4,5α-epoxy-3-methoxy-14β-hydroxy-6α-(N-isobutylbenzyloxycarbamido)morphinan,
17-phenethyl-4,5α-epoxy-3-methoxy-14β-hydroxy-6α-(N-isobutylphenylmethanesulfonamido)morphinan,
17-cyclopropylmethyl-4,5α-epoxy-3-methoxy-14β-acetoxy-6α-(N-isobutyl-3,4-dichlorophenylacetamido)morphinan, 17-cyclopropylmethyl-4,5α-epoxy-3-methoxy-14β-acetoxy-6α-(N-isobutylcinnamamido)morphinan, 17-cyclopropylmethyl-4,5α-epoxy-3-methoxy-14β-acetoxy-6α-(N-isobutylbenzyloxycarbamido)morphinan, 17-cyclopropylmethyl-4,5α-epoxy-3-methoxy-14β-acetoxy-6α-(N-isobutylphenylmethanesulfonamido)morphinan, 17-allyl-4,5α-epoxy-3-methoxy-14β-acetoxy-6α-(N-isobutyl-3,4-dichlorophenylacetamido)morphinan, 17-allyl-4,5α-epoxy-3-methoxy-14β-acetoxy-6α-(N-isobutylcinnamamido)morphinan, 17-allyl-4,5α-epoxy-3-methoxy-14β-acetoxy-6α-(N-isobutylbenzyloxycarbamido)morphinan, 17-allyl-4,5α-epoxy-3-methoxy-14β-acetoxy-6α-(N-isobutylphenylmethanesulfonamido)morphinan,
17-methyl-4,5α-epoxy-3-methoxy-14β-acetoxy-6α-(N-isobutyl-3,4-dichlorophenylacetamido)morphinan, 17-methyl-4,5α-epoxy-3-methoxy-14β-acetoxy-6α-(N-isobutylcinnamamido)morphinan, 17-methyl-4,5α-epoxy-3-methoxy-14β-acetoxy-6α-(N-isobutylbenzyloxycarbamido)morphinan, 17-methyl-4,5α-epoxy-3-methoxy-14β-acetoxy-6α-(N-isobutylphenylmethanesulfonamido)morphinan, 17-phenethyl-4,5α-epoxy-3-methoxy-14β-acetoxy-6α-(N-isobutyl-3,4-dichlorophenylacetamido)morphinan, 17-phenethyl-4,5α-epoxy-3-methoxy-14β-acetoxy-6α-(N-isobutylcinnamamido)morphinan, 17-phenethyl-4,5α-epoxy-3-methoxy-14β-acetoxy-6α-(N-isobutylbenzyloxycarbamido)morphinan, 17-phenethyl-4,5α-epoxy-3-methoxy-14β-acetoxy-6α-(N-isobutylphenylmethanesulfonamido)morphinan,
17-cyclopropylmethyl-4,5α-epoxy-3-acetoxy-14β-hydroxy-6α-(N-isobutyl-3,4-dichlorophenylacetamido)morphinan, 17-cyclopropylmethyl-4,5α-epoxy-3-acetoxy-14β-hydroxy-6α-(N-isobutylcinnamamido)morphinan, 17-cyclopropylmethyl-4,5α-epoxy-3-acetoxy-14β-hydroxy-6α-(N-isobutylbenzyloxycarbamido)morphinan, 17-cyclopropylmethyl-4,5α-epoxy-3-acetoxy-14β-hydroxy-6α-(N-isobutylphenylmethanesulfonamido)morphinan,
17-allyl-4,5α-epoxy-3-acetoxy-14β-hydroxy-6α-(N-isobutyl-3,4-dichlorophenylacetamido)morphinan, 17-allyl-4,5α-epoxy-3-acetoxy-14β-hydroxy-6α-(N-isobutylcinnamamido)morphinan, 17-allyl-4,5α-epoxy-3-acetoxy-14β-hydroxy-6α-(N-isobutylbenzyloxycarbamido)morphinan, 17-allyl-4,5α-epoxy-3-acetoxy-14β-hydroxy-6α-(N-isobutylphenylmethanesulfonamido)morphinan,
17-methyl-4,5α-epoxy-3-acetoxy-14β-hydroxy-6α-(N-isobutyl-3,4-dichlorophenylacetamido)morphinan, 17-methyl-4,5α-epoxy-3-acetoxy-14β-hydroxy-6α-(N-isobutylcinnamamido)morphinan, 17-methyl-4,5α-epoxy-3-acetoxy-14β-hydroxy-6α-(N-isobutylbenzyloxycarbamido)morphinan, 17-methyl-4,5α-epoxy-3-acetoxy-14β-hydroxy-6α-(N-isobutylphenylmethanesulfonamido)morphinan,
17-phenethyl-4,5α-epoxy-3-acetoxy-14β-hydroxy-6α-(N-isobutyl-3,4-dichlorophenylacetamido)morphinan, 17-phenethyl-4,5α-epoxy-3-acetoxy-14β-hydroxy-6α-(N-isobutylcinnamamido)morphinan, 17-phenethyl-4,5α-epoxy-3-acetoxy-14β-hydroxy-6α-(N-isobutylbenzyloxycarbamido)morphinan, 17-phenethyl-4,5α-epoxy-3-acetoxy-14β-hydroxy-6α-(N-isobutylphenylmethanesulfonamido)morphinan,
17-cyclopropylmethyl-4,5α-epoxy-3,14β-diacetoxy-6α-(N-isobutyl-3,4-dichlorophenylacetamido)morphinan, 17-cyclopropylmethyl-4,5α-epoxy-3,14β-diacetoxy-6α-(N-isobutylcinnamamido)morphinan, 17-cyclopropylmethyl-4,5α-epoxy-3,14β-diacetoxy-6α-(N-isobutylbenzyloxycarbamido)morphinan, 17-cyclopropylmethyl-4,5α-epoxy-3,14β-diacetoxy-6α-(N-isobutylphenylmethanesulfonamido)morphinan, 17-allyl-4,5α-epoxy-3,14β-diacetoxy-6α-(N-isobutyl-3,4-dichlorophenylacetamido)morphinan, 17-allyl-4,5α-epoxy-3,14β-diacetoxy-6α-(N-isobutylcinnamamido)morphinan, 17-allyl-4,5α-epoxy-3,14β-diacetoxy-6α-(N-isobutylbenzyloxycarbamido)morphinan, 17-allyl-4,5α-epoxy-3,14β-diacetoxy-6α-(N-isobutylphenylmethanesulfonamido)morphinan,
17-methyl-4,5α-epoxy-3,14β-diacetoxy-6α-(N-isobutyl-3,4-dichlorophenylacetamido)morphinan, 17-methyl-4,5α-epoxy-3,14β-diacetoxy-6α-(N-isobutylcinnamamido)morphinan, 17-methyl-4,5α-epoxy-3,14β-diacetoxy-6α-(N-isobutylbenzyloxycarbamido)morphinan, 17-methyl-4,5α-epoxy-3,14β-diacetoxy-6α-(N-isobutylphenylmethanesulfonamido)morphinan, 17-phenethyl-4,5α-epoxy-3,14β-diacetoxy-6α-(N-isobutyl-3,4-dichlorophenylacetamido)morphinan, 17-phenethyl-4,5α-epoxy-3,14β-diacetoxy-6α-(N-isobutylcinnamamido)morphinan, 17-phenethyl-4,5α-epoxy-3,14β-diacetoxy-6α-(N-isobutylbenzyloxycarbamido)morphinan, 17-phenethyl-4,5α-epoxy-3,14β-diacetoxy-6α-(N-isobutylphenylmethanesulfonamido)morphinan,
17-cyclopropylmethyl-4,5α-epoxy-3,14β-dihydroxy-6β-(N-methyl-3,4-dichlorophenylacetamido)morphinan, 17-cyclopropylmethyl-4,5α-epoxy-3,14β-dihydroxy-6β-(N-methylcinnamamido)morphinan,
17-cyclopropylmethyl-4,5α-epoxy-3,14β-dihydroxy-6β-(N-methylbenzyloxycarbamido)morphinan,
17-cyclopropylmethyl-4,5α-epoxy-3,14β-dihydroxy-6β-(N-methylphenylmethanesulfonamido)morphinan,
17-allyl-4,5α-epoxy-3,14β-dihydroxy-6β-(N-methyl-3,4-dichlorophenylacetamido)morphinan, 17-allyl-4,5α-epoxy-3,14β-dihydroxy-6α-(N-methylcinnamamido)morphinan, 17-allyl-4,5α-epoxy-3,14β-dihydroxy-6β-(N-methylbenzyloxycarbamido)morphinan,
17-allyl-4,5α-epoxy-3,14β-dihydroxy-6β-(N-methylphenylmethanesulfonamido)morphinan,
17-methyl-4,5α-epoxy-3,14β-dihydroxy-6β-(N-methyl-3,4-dichlorophenylacetamido)morphinan,
17-methyl-4,5α-epoxy-3,14β-dihydroxy-6β-(N-methylcinnamamido)morphinan, 17-methyl-4,5α-epoxy-3,14β-dihydroxy-6α-(N-methylbenzyloxycarbamido)morphinan, 17-methyl-4,5α-epoxy-3,14β-dihydroxy-6α-(N-methylphenylmethanesulfonamido)morphinan,
17-phenethyl-4,5α-epoxy-3,14β-dihydroxy-6β-(N-methyl-3,4-dichlorophenylacetamido)morphinan,
17-phenethyl-4,5α-epoxy-3,14β-dihydroxy-6β-(N-methylcinnamamido)morphinan, 17-phenethyl-4,5α-epoxy-3,14β-dihydroxy-6β-(N-methylbenzyloxycarbamido)morphinan, 17-phenethyl-4,5α-epoxy-3,14β-dihydroxy-6β-(N-methylphenylmethanesulfonamido)morphinan, 17-cyclopropylmethyl-4,5α-epoxy-3-hydroxy-14β-acetoxy-6β-(N-methyl-3,4-dichlorophenylacetamido)morphinan, 17-cyclopropylmethyl-4,5α-epoxy-3-hydroxy-14β-acetoxy-6β-(N-methylcinnamamido)morphinan, 17-cyclopropylmethyl-4,5α-epoxy-3-hydroxy-14β-acetoxy-6β-(N-methylbenzyloxycarbamido)morphinan,
17-cyclopropylmethyl-4,5α-epoxy-3-hydroxy-14β-acetoxy-6β-(N-methylphenylmethanesulfonamido)morphinan, 17-allyl-4,5α-epoxy-3-hydroxy-14β-acetoxy-6β-(N-methyl-3,4-dichlorophenylacetamido)morphinan, 17-allyl-4,5α-epoxy-3-hydroxy-14β-acetoxy-6β-(N-methylcinnamamido)morphinan, 17-allyl-4,5α-epoxy-3-hydroxy-14β-acetoxy-6β-(N-methylbenzyloxycarbamido)morphinan,
17-allyl-4,5α-epoxy-3-hydroxy-14β-acetoxy-6β-(N-methylphenylmethanesulfonamido)morphinan,
17-methyl-4,5α-epoxy-3-hydroxy-14β-acetoxy-6β-(N-methyl-3,4-dichlorophenylacetamido)morphinan,
17-methyl-4,5α-epoxy-3-hydroxy-14β-acetoxy-6β-(N-methylcinnamamido)morphinan, 17-methyl-4,5α-epoxy-3-hydroxy-14β-acetoxy-6β-(N-methylbenzyloxycarbamido)morphinan, 17-methyl-4,5α-epoxy-3-hydroxy-14β-acetoxy-6β-(N-methylphenylmethanesulfonamido)morphinan,
17-phenethyl-4,5α-epoxy-3-hydroxy-14β-acetoxy-6β-(N-methyl-3,4-dichlorophenylacetamido)morphinan,
17-phenethyl-4,5α-epoxy-3-hydroxy-14β-acetoxy-6β-(N-methylcinnamamido)morphinan,
17-phenethyl-4,5α-epoxy-3-hydroxy-14β-acetoxy-6β-(N-methylbenzyloxycarbamido)morphinan,
17-phenethyl-4,5α-epoxy-3-hydroxy-14β-acetoxy-6β-(N-methylphenylmethanesulfonamido)morphinan, 17-cyclopropylmethyl-4,5α-epoxy-14β-hydroxy-6β-(N-methyl-3,4-dichlorophenylacetamido)morphinan,
17-cyclopropylmethyl-4,5α-epoxy-14β-hydroxy-6β-(N-methylcinnamamido)morphinan,
17-cyclopropylmethyl-4,5α-epoxy-14β-hydroxy-6β-(N-methylbenzyloxycarbamido)morphinan,
17-cyclopropylmethyl-4,5α-epoxy-14β-hydroxy-6β-(N-methylphenylmethanesulfonamido)morphinan,
17-allyl-4,5α-epoxy-14β-hydroxy-6β-(N-methyl-3,4-dichlorophenylacetamido)morphinan, 17-allyl-4,5α-epoxy-14β-hydroxy-6β-(N-methylcinnamamido)morphinan, 17-allyl-4,5α-epoxy-14β-hydroxy-6β-(N-methylbenzyloxycarbamido)morphinan,
17-allyl-4,5α-epoxy-14β-hydroxy-6α-(N-methylphenylmethanesulfonamido)morphinan,
17-methyl-4,5α-epoxy-14β-hydroxy-6β-(N-methyl-3,4-dichlorophenylacetamido)morphinan, 17-methyl-4,5α-epoxy-14β-hydroxy-6β-(N-methylcinnamamido)morphinan, 17-methyl-4,5α-epoxy-14β-hydroxy-6β-(N-methylbenzyloxycarbamido)morphinan,
17-methyl-4,5α-epoxy-14β-hydroxy-6β-(N-methylphenylmethanesulfonamido)morphinan,
17-phenethyl-4,5α-epoxy-14β-hydroxy-6β-(N-methyl-3,4-dichlorophenylacetamido)morphinan,
17-phenethyl-4,5α-epoxy-14β-hydroxy-6β-(N-methylcinnamamido)morphinan, 17-phenethyl-4,5α-epoxy-14β-hydroxy-6β-(N-methylbenzyloxycarbamido)morphinan, 17-phenethyl-4,5α-epoxy-14β-hydroxy-6β-(N-methylphenylmethanesulfonamido)morphinan, 17-cyclopropylmethyl-4,5α-epoxy-14β-acetoxy-6β-(N-methyl-3,4-dichlorophenylacetamido)morphinan,
17-cyclopropylmethyl-4,5α-epoxy-14β-acetoxy-6β-(N-methylcinnamamido)morphinan,
17-cyclopropylmethyl-4,5α-epoxy-14β-acetoxy-6β-(N-methylbenzyloxycarbamido)morphinan,
17-cyclopropylmethyl-4,5α-epoxy-14β-acetoxy-6β-(N-methylphenylmethanesulfonamido)morphinan,
17-allyl-4,5α-epoxy-14β-acetoxy-6β-(N-methyl-3,4-dichlorophenylacetamido)morphinan, 17-allyl-4,5α-epoxy-14β-acetoxy-6β-(N-methylcinnamamido)morphinan, 17-allyl-4,5α-epoxy-14β-acetoxy-6β-(N-methylbenzyloxycarbamido)morphinan, 17-allyl-4,5α-epoxy-14β-acetoxy-6β-(N-methylphenylmethanesulfonamido)morphinan,
17-methyl-4,5α-epoxy-14β-acetoxy-6β-(N-methyl-3,4-dichlorophenylacetamido)morphinan,
17-methyl-4,5α-epoxy-14β-acetoxy-6β-(N-methylcinnamamido)morphinan, 17-methyl-4,5α-epoxy-14β-acetoxy-6β-(N-methylbenzyloxycarbamido)morphinan, 17-methyl-4,5α-epoxy-14β-acetoxy-6β-(N-methylphenylmethanesulfonamido)morphinan,
17-phenethyl-4,5α-epoxy-14β-acetoxy-6β-(N-methyl-3,4-dichlorophenylacetamido)morphinan,
17-phenethyl-4,5α-epoxy-14β-acetoxy-6β-(N-methylcinnamamido)morphinan, 17-phenethyl-4,5α-epoxy-14β-acetoxy-6β-(N-methylbenzyloxycarbamido)morphinan, 17-phenethyl-4,5α-epoxy-14β-acetoxy-6β-(N-methylphenylmethanesulfonamido)morphinan, 17-cyclopropylmethyl-4,5α-epoxy-3-methoxy-14β-hydroxy-6β-(N-methyl-3,4-dichlorophenylacetamido)morphinan, 17-cyclopropylmethyl-4,5α-epoxy-3-methoxy-14β-hydroxy-6β-(N-methylcinnamamido)morphinan, 17-cyclopropylmethyl-4,5α-epoxy-3-methoxy-14β-hydroxy-6β-(N-methylbenzyloxycarbamido)morphinan,
17-cyclopropylmethyl-4,5α-epoxy-3-methoxy-14β-hydroxy-6β-(N-methylphenylmethanesulfonamido)morphinan, 17-allyl-4,5α-epoxy-3-methoxy-14β- hydroxy-6β-(N-methyl-3,4-dichlorophenylacetamido) morphinan, 17-allyl-4,5α-epoxy-3-methoxy-14β-hydroxy-6β-(N-methylcinnamamido)morphinan, 17-allyl-4,5α-epoxy-3-methoxy-14β-hydroxy-6β-(N-methylbenzyloxycarbamido)morphinan, 17-allyl-4,5α-epoxy-3-methoxy-14β-hydroxy-6β-(N-methylphenylmethanesulfonamido)morphinan, 17-methyl-4,5α-epoxy-3-methoxy-14β-hydroxy-6β-(N-methyl-3,4-dichlorophenylacetamido)morphinan, 17-methyl-4,5α-epoxy-3-methoxy-14β-hydroxy-6β-(N-methylcinnamamido)morphinan, 17-methyl-4,5α-epoxy-3-methoxy-14β-hydroxy-6β-(N-methylbenzyloxycarbamido)morphinan, 17-methyl-4,5α-epoxy-3-methoxy-14β-hydroxy-6α-(N-methylphenylmethanesulfonamido)morphinan, 17-phenethyl-4,5α-epoxy-3-methoxy-14β-hydroxy-6α-(N-methyl-3,4-dichlorophenylacetamido) morphinan, 17-phenethyl-4,5α-epoxy-3-methoxy-14β-hydroxy-6β-(N-methylcinnamamido)morphinan, 17-phenethyl-4,5α-epoxy-3-methoxy-14β-hydroxy-6α-(N-methylbenzyloxycarbamido)morphinan, 17-phenethyl-4,5α-epoxy-3-methoxy-14β-hydroxy-6β-(N-methylphenylmethanesulfonamido)morphinan, 17-cyclopropylmethyl-4,5α-epoxy-3-methoxy-14β-acetoxy-6β-(N-methyl-3,4-dichlorophenylacetamido) morphinan, 17-cyclopropylmethyl-4,5α-epoxy-3-methoxy-14β-acetoxy-6β-(N-methylcinnamamido)morphinan, 17-cyclopropylmethyl-4,5α-epoxy-3-methoxy-14β-acetoxy-6β-(N-methylbenzyloxycarbamido)morphinan, 17-cyclopropylmethyl-4,5α-epoxy-3-methoxy-14β-acetoxy-6β-(N-methylphenylmethanesulfonamido) morphinan, 17-allyl-4,5α-epoxy-3-methoxy-14β-acetoxy-6β-(N-methyl-3,4-dichlorophenylacetamido) morphinan, 17-allyl-4,5α-epoxy-3-methoxy-14β-acetoxy-6β-(N-methylcinnamamido)morphinan, 17-allyl-4,5α-epoxy-3-methoxy-14β-acetoxy-6β-(N-methylbenzyloxycarbamido)morphinan, 17-allyl-4,5α-epoxy-3-methoxy-14β-acetoxy-6β-(N-methylphenylmethanesulfonamido)morphinan, 17-methyl-4,5α-epoxy-3-methoxy-14β-acetoxy-6β-(N-methyl-3,4-dichlorophenylacetamido)morphinan, 17-methyl-4,5α-epoxy-3-methoxy-14β-acetoxy-6β-(N-methylcinnamamido)morphinan, 17-methyl-4,5α-epoxy-3-methoxy-14β-acetoxy-6β-(N-methylbenzyloxycarbamido)morphinan, 17-methyl-4,5α-epoxy-3-methoxy-14β-acetoxy-6β-(N-methylphenylmethanesulfonamido)morphinan, 17-phenethyl-4,5α-epoxy-3-methoxy-14β-acetoxy-6β-(N-methyl-3,4-dichlorophenylacetamido)morphinan, 17-phenethyl-4,5α-epoxy-3-methoxy-14β-acetoxy-6β-(N-methylcinnamamido)morphinan, 17-phenethyl-4,5α-epoxy-3-methoxy-14β-acetoxy-6β-(N-methylbenzyloxycarbamido)morphinan, 17-phenethyl-4,5α-epoxy-3-methoxy-14β-acetoxy-6β-(N-methylphenylmethanesulfonamido)morphinan, 17-cyclopropylmethyl-4,5α-epoxy-3-acetoxy-14β-hydroxy-6β-(N-methyl-3,4-dichlorophenylacetamido) morphinan, 17-cyclopropylmethyl-4,5α-epoxy-3-acetoxy-14β-hydroxy-6β-(N-methylcinnamamido) morphinan, 17-cyclopropylmethyl-4,5α-epoxy-3-acetoxy-14β-hydroxy-6β-(N-methylbenzyloxycarbamido)morphinan, 17-cyclopropylmethyl-4,5α-epoxy-3-acetoxy-14β-hydroxy-6β-(N-methylphenylmethanesulfonamido) morphinan, 17-allyl-4,5α-epoxy-3-acetoxy-14β-hydroxy-6β-(N-methyl-3,4-dichlorophenylacetamido) morphinan, 17-allyl-4,5α-epoxy-3-acetoxy-14β-hydroxy-6β-(N-methylcinnamamido)morphinan, 17-allyl-4,5α-epoxy-3-acetoxy-14β-hydroxy-6β-(N-methylbenzyloxycarbamido)morphinan, 17-allyl-4,5α-epoxy-3-acetoxy-14β-hydroxy-6β-(N-methylphenylmethanesulfonamido)morphinan, 17-methyl-4,5α-epoxy-3-acetoxy-14β-hydroxy-6α-(N-methyl-3,4-dichlorophenylacetamido)morphinan, 17-methyl-4,5α-epoxy-3-acetoxy-14β-hydroxy-6α-(N-methylcinnamamido)morphinan, 17-methyl-4,5α-epoxy-3-acetoxy-14β-hydroxy-6β-(N-methylbenzyloxycarbamido)morphinan, 17-methyl-4,5α-epoxy-3-acetoxy-14β-hydroxy-6β-(N-methylphenylmethanesulfonamido)morphinan, 17-phenethyl-4,5α-epoxy-3-acetoxy-14β-hydroxy-6β-(N-methyl-3,4-dichlorophenylacetamido)morphinan, 17-phenethyl-4,5α-epoxy-3-acetoxy-14β-hydroxy-6β-(N-methylcinnamamido)morphinan, 17-phenethyl-4,5α-epoxy-3-acetoxy-14β-hydroxy-6β-(N-methylbenzyloxycarbamido)morphinan, 17-phenethyl-4,5α-epoxy-3-acetoxy-14β-hydroxy-6β-(N-methylphenylmethanesulfonamido)morphinan, 17-cyclopropylmethyl-4,5α-epoxy-3,14β-diacetoxy-6β-(N-methyl-3,4-dichlorophenylacetamido)morphinan, 17-cyclopropylmethyl-4,5α-epoxy-3,14β-diacetoxy-6β-(N-methylcinnamamido)morphinan, 17-cyclopropylmethyl-4,5α-epoxy-3,14β-diacetoxy-6β-(N-methylbenzyloxycarbamido)morphinan, 17-cyclopropylmethyl-4,5α-epoxy-3,14β-diacetoxy-6β-(N-methylphenylmethanesulfonamido)morphinan, 17-allyl-4,5α-epoxy-3,14β-diacetoxy-6β-(N-methyl-3,4-dichlorophenylacetamido)morphinan, 17-allyl-4,5α-epoxy-3,14β-diacetoxy-6β-(N-methylcinnamamido) morphinan, 17-allyl-4,5α-epoxy-3,14β-diacetoxy-6β-(N-methylbenzyloxycarbamido)morphinan, 17-allyl-4,5α-epoxy-3,14β-diacetoxy-6β-(N-methylphenylmethanesulfonamido)morphinan, 17-methyl-4,5α-epoxy-3,14β-diacetoxy-6β-(N-methyl-3,4-dichlorophenylacetamido)morphinan, 17-methyl-4,5α-epoxy-3,14β-diacetoxy-6β-(N-methylcinnamamido)morphinan, 17-methyl-4,5α-epoxy-3,14β-diacetoxy-6β-(N-methylbenzyloxycarbamido)morphinan, 17-methyl-4,5α-epoxy-3,14β-diacetoxy-6β-(N-methylphenylmethanesulfonamido)morphinan, 17-phenethyl-4,5α-epoxy-3,14β-diacetoxy-6β-(N-methyl-3,4-dichlorophenylacetamido)morphinan, 17-phenethyl-4,5α-epoxy-3,14β-diacetoxy-6β-(N-methylcinnamamido)morphinan, 17-phenethyl-4,5α-epoxy-3,14β-diacetoxy-6β-(N-methylbenzyloxycarbamido)morphinan, 17-phenethyl-4,5α-epoxy-3,14β-diacetoxy-6β-(N-methylphenylmethanesulfonamido)morphinan, 17-cyclopropylmethyl-4,5α-epoxy-3,14β-dihydroxy-6β-(N-isobutyl-3,4-dichlorophenylacetamido)morphinan, 17-cyclopropylmethyl-4,5α-epoxy-3,14β-dihydroxy-6β-(N-isobutylcinnamamido)morphinan, 17-cyclopropylmethyl-4,5α-epoxy-3,14β-dihydroxy-6β-(N-isobutylbenzyloxycarbamido)morphinan, 17-cyclopropylmethyl-4,5α-epoxy-3,14β-dihydroxy-6β-(N-isobutylphenylmethanesulfonamido) morphinan, 17-allyl-4,5α-epoxy-3,14β-dihydroxy-6β-(N-isobutyl-3,4-dichlorophenylacetamido)morphinan, 17-allyl-4,5α-epoxy-3,14β-dihydroxy-6β-(N-isobutylcinnamamido)morphinan, 17-allyl-4,5α-epoxy-3,14β-dihydroxy-6β-(N-isobutylbenzyloxycarbamido)morphinan, 17-allyl-4, 5α-epoxy-3,14β-dihydroxy-6β-(N-isobutylphenylmethanesulfonamido)morphinan, 17-methyl-4,5α-epoxy-3,14β-dihydroxy-6β-(N-isobutyl-3,4-dichlorophenylacetamido)morphinan, 17-methyl-4,5α-epoxy-3,14β-dihydroxy-6β-(N-isobutylcinnamamido)morphinan, 17-methyl-4,5α-epoxy-3,14β-dihydroxy-6α-(N-isobutylbenzyloxycarbamido)morphinan, 17-methyl-4,5α-epoxy-3,14β-dihydroxy-6β-(N-isobutylphenylmethanesulfonamido)morphinan, 17-phenethyl-4,5α-epoxy-3,14β-dihydroxy-6β-(N-isobutyl-3,4-dichlorophenylacetamido)morphinan, 17-phenethyl-4,5α-epoxy-3,14β-dihydroxy-6β-(N-isobutylcinnamamido)morphinan, 17-phenethyl-4,5α-epoxy-3,14β-dihydroxy-6β-(N-isobutylbenzyloxycarbamido)morphinan, 17-phenethyl-4,5α-epoxy-3,14β-dihydroxy-6β-(N-isobutylphenylmethanesulfonamido)morphinan, 17-cyclopropylmethyl-4,5α-epoxy-3-hydroxy-14β-acetoxy-6β-(N-isobutyl-3,4-dichlorophenylacetamido)morphinan, 17-cyclopropylmethyl-4,5α-epoxy-3-hydroxy-14β-acetoxy-6β-(N-isobutylcinnamamido)morphinan, 17-cyclopropylmethyl-4,5α-epoxy-3-hydroxy-14β-acetoxy-6β-(N-isobutylbenzyloxycarbamido)morphinan, 17-cyclopropylmethyl-4,5α-epoxy-3-hydroxy-14β-acetoxy-6β-(N-isobutylphenylmethanesulfonamido)morphinan, 17-allyl-4,5α-epoxy-3-hydroxy-14β-acetoxy-6β-(N-isobutyl-3,4-dichlorophenylacetamido)morphinan, 17-allyl-4,5α-epoxy-3-hydroxy-14β-acetoxy-6β-(N-isobutylcinnamamido)morphinan, 17-allyl-4,5α-epoxy-3-hydroxy-14β-acetoxy-6β-(N-isobutylbenzyloxycarbamido)morphinan, 17-allyl-4,5α-epoxy-3-hydroxy-14β-acetoxy-6β-(N-isobutylphenylmethanesulfonamido)morphinan, 17-methyl-4,5α-epoxy-3-hydroxy-14β-acetoxy-6β-(N-isobutyl-3,4-dichlorophenylacetamido)morphinan, 17-methyl-4,5α-epoxy-3-hydroxy-14β-acetoxy-6β-(N-isobutylcinnamamido)morphinan, 17-methyl-4,5α-epoxy-3-hydroxy-14β-acetoxy-6β-(N-isobutylbenzyloxycarbamido)morphinan, 17-methyl-4,5α-epoxy-3-hydroxy-14β-acetoxy-6β-(N-isobutylphenylmethanesulfonamido)morphinan, 17-phenethyl-4,5α-epoxy-3-hydroxy-14β-acetoxy-6β-(N-isobutyl-3,4-dichlorophenylacetamido)morphinan, 17-phenethyl-4,5α-epoxy-3-hydroxy-14β-acetoxy-6β-(N-isobutylcinnamamido)morphinan, 17-phenethyl-4,5α-epoxy-3-hydroxy-14β-acetoxy-6β-(N-isobutylbenzyloxycarbamido)morphinan, 17-phenethyl-4,5α-epoxy-3-hydroxy-14β-acetoxy-6β-(N-isobutylphenylmethanesulfonamido)morphinan, 17-cyclopropylmethyl-4,5α-epoxy-14β-hydroxy-6β-(N-isobutyl-3,4-dichlorophenylacetamido)morphinan, 17-cyclopropylmethyl-4,5α-epoxy-14β-hydroxy-6β-(N-isobutylcinnamamido)morphinan, 17-cyclopropylmethyl-4,5α-epoxy-14β-hydroxy-6β-(N-isobutylbenzyloxycarbamido)morphinan, 17-cyclopropylmethyl-4,5α-epoxy-14β-hydroxy-6β-(N-isobutylphenylmethanesulfonamido)morphinan, 17-allyl-4,5α-epoxy-14β-hydroxy-6β-(N-isobutyl-3,4-dichlorophenylacetamido)morphinan, 17-allyl-4,5α-epoxy-14β-hydroxy-6β-(N-isobutylcinnamamido)morphinan, 17-allyl-4,5α-epoxy-14β-hydroxy-6β-(N-isobutylbenzyloxycarbamido)morphinan, 17-allyl-4,5α-epoxy-14β-hydroxy-6β-(N-isobutylphenylmethanesulfonamido)morphinan, 17-methyl-4,5α-epoxy-14β-hydroxy-6β-(N-isobutyl-3,4-dichlorophenylacetamido)morphinan, 17-methyl-4,5α-epoxy-14β-hydroxy-6β-(N-isobutylcinnamamido)morphinan, 17-methyl-4,5α-epoxy-14β-hydroxy-6β-(N-isobutylbenzyloxycarbamido)morphinan, 17-methyl-4,5α-epoxy-14β-hydroxy-6β-(N-isobutylphenylmethanesulfonamido)morphinan, 17-phenethyl-4,5α-epoxy-14β-hydroxy-6β-(N-isobutyl-3,4-dichlorophenylacetamido)morphinan, 17-phenethyl-4,5α-epoxy-14β-hydroxy-6β-(N-isobutylcinnamamido)morphinan, 17-phenethyl-4,5α-epoxy-14β-hydroxy-6β-(N-isobutylbenzyloxycarbamido)morphinan, 17-phenethyl-4,5α-epoxy-14β-hydroxy-6β-(N-isobutylphenylmethanesulfonamido)morphinan, 17-cyclopropylmethyl-4,5α-epoxy-14β-acetoxy-6β-(N-isobutyl-3,4-dichlorophenylacetamido)morphinan, 17-cyclopropylmethyl-4,5α-epoxy-14β-acetoxy-6β-(N-isobutylcinnamamido)morphinan, 17-cyclopropylmethyl-4,5α-epoxy-14β-acetoxy-6β-(N-isobutylbenzyloxycarbamido)morphinan, 17-cyclopropylmethyl-4,5α-epoxy-14β-acetoxy-6β-(N-isobutylphenylmethanesulfonamido)morphinan, 17-allyl-4,5α-epoxy-14β-acetoxy-6β-(N-isobutyl-3,4-dichlorophenylacetamido)morphinan, 17-allyl-4,5α-epoxy-14β-acetoxy-6β-(N-isobutylcinnamamido)morphinan, 17-allyl-4,5α-epoxy-14β-acetoxy-6β-(N-isobutylbenzyloxycarbamido)morphinan, 17-allyl-4,5α-epoxy-14β-acetoxy-6β-(N-isobutylphenylmethanesulfonamido)morphinan, 17-methyl-4,5α-epoxy-14β-acetoxy-6β-(N-isobutyl-3,4-dichlorophenylacetamido)morphinan, 17-methyl-4,5α-epoxy-14β-acetoxy-6β-(N-isobutylcinnamamido)morphinan, 17-methyl-4,5α-epoxy-14β-acetoxy-6β-(N-isobutylbenzyloxycarbamido)morphinan, 17-methyl-4,5α-epoxy-14β-acetoxy-6β-(N-isobutylphenylmethanesulfonamido)morphinan, 17-phenethyl-4,5α-epoxy-14β-acetoxy-6β-(N-isobutyl-3,4-dichlorophenylacetamido)morphinan, 17-phenethyl-4,5α-epoxy-14β-acetoxy-6β-(N-isobutylcinnamamido)morphinan, 17-phenethyl-4,5α-epoxy-14β-acetoxy-6β-(N-isobutylbenzyloxycarbamido)morphinan, 17-phenethyl-4,5α-epoxy-14β-acetoxy-6β-(N-isobutylphenylmethanesulfonamido)morphinan, 17-cyclopropylmethyl-4,5α-epoxy-3-methoxy-14β-hydroxy-6β-(N-isobutyl-3,4-dichlorophenylacetamido)morphinan, 17-cyclopropylmethyl-4,5α-epoxy-3-methoxy-14β-hydroxy-6β-(N-isobutylcinnamamido)morphinan, 17-cyclopropylmethyl-4,5α-epoxy-3-methoxy-14β-hydroxy-6β-(N-isobutylbenzyloxycarbamido)morphinan, 17-cyclopropylmethyl-4,5α-epoxy-3-methoxy-14β-hydroxy-6β-(N-isobutylphenylmethanesulfonamido)morphinan, 17-allyl-4,5α-epoxy-3-methoxy-14β-hydroxy-6β-(N-isobutyl-3,4-dichlorophenylacetamido)morphinan, 17-allyl-4,5α-epoxy-3-methoxy-14β-hydroxy-6β-(N-isobutylcinnamamido)morphinan, 17-allyl-4,5α-epoxy-3-methoxy-14β-hydroxy-6β-(N-isobutylbenzyloxycarbamido)morphinan, 17-allyl-4,5α-epoxy-3-methoxy-14β-hydroxy-6β-(N-isobutylphenylmethanesulfonamido)morphinan, 17-methyl-4,5α-epoxy-3-methoxy-14β-hydroxy-6β-(N-isobutyl-3,4-dichlorophenylacetamido)morphinan, 17-methyl-4,5α-epoxy-3-methoxy-14β-hydroxy-6β-(N-isobutylcinnamamido)morphinan, 17-methyl-4,5α- epoxy-3-methoxy-14β-hydroxy-6β-(N-isobutylbenzyloxycarbamido)morphinan, 17-methyl-4,5α-epoxy-3-methoxy-14β-hydroxy-6β-(N-isobutylphenylmethanesulfonamido)morphinan, 17-phenethyl-4,5α-epoxy-3-methoxy-14β-hydroxy-6β-(N-isobutyl-3,4-dichlorophenylacetamido)morphinan, 17-phenethyl-4,5α-epoxy-3-methoxy-14β-hydroxy-6β-(N-isobutylcinnamamido)morphinan, 17-phenethyl-4,5α-epoxy-3-methoxy-14β-hydroxy-6β-(N-isobutylbenzyloxycarbamido)morphinan, 17-phenethyl-4,5α-epoxy-3-methoxy-14β-hydroxy-6β-(N-isobutylphenylmethanesulfonamido)morphinan.

17-cyclopropylmethyl-4,5α-epoxy-3-methoxy-14β-acetoxy-6β-(N-isobutyl-3,4-dichlorophenylacetamido)morphinan, 17-cyclopropylmethyl-4,5α-epoxy-3-methoxy-14β-acetoxy-6β-(N-isobutylcinnamamido)morphinan, 17-cyclopropylmethyl-4,5α-epoxy-3-methoxy-14β-acetoxy-6β-(N-isobutylbenzyloxycarbamido)morphinan, 17-cyclopropylmethyl-4,5α-epoxy-3-methoxy-14β-acetoxy-6β-(N-isobutylphenylmethanesulfonamido)morphinan, 17-allyl-4,5α-epoxy-3-methoxy-14β-acetoxy-6β-(N-isobutyl-3,4-dichlorophenylacetamido)morphinan, 17-allyl-4,5α-epoxy-3-methoxy-14β-acetoxy-6β-(N-isobutylcinnamamido)morphinan, 17-allyl-4,5α-epoxy-3-methoxy-14β-acetoxy-6β-(N-isobutylbenzyloxycarbamido)morphinan, 17-allyl-4,5α-epoxy-3-methoxy-14β-acetoxy-6β-(N-isobutylphenylmethanesulfonamido)morphinan.

17-methyl-4,5α-epoxy-3-methoxy-14β-acetoxy-6β-(N-isobutyl-3,4-dichlorophenylacetamido)morphinan, 17-methyl-4,5α-epoxy-3-methoxy-14β-acetoxy-6β-(N-isobutylcinnamamido)morphinan, 17-methyl-4,5α-epoxy-3-methoxy-14β-acetoxy-6β-(N-isobutylbenzyloxycarbamido)morphinan, 17-methyl-4,5α-epoxy-3-methoxy-14β-acetoxy-6β-(N-isobutylphenylmethanesulfonamido)morphinan, 17-phenethyl-4,5α-epoxy-3-methoxy-14β-acetoxy-6β-(N-isobutyl-3,4-dichlorophenylacetamido)morphinan, 17-phenethyl-4,5α-epoxy-3-methoxy-14β-acetoxy-6β-(N-isobutylcinnamamido)morphinan, 17-phenethyl-4,5α-epoxy-3-methoxy-14β-acetoxy-6β-(N-isobutylbenzyloxycarbamido)morphinan, 17-phenethyl-4,5α-epoxy-3-methoxy-14β-acetoxy-6β-(N-isobutylphenylmethanesulfonamido)morphinan.

17-cyclopropylmethyl-4,5α-epoxy-3-acetoxy-14β-hydroxy-6β-(N-isobutyl-3,4-dichlorophenylacetamido)morphinan, 17-cyclopropylmethyl-4,5α-epoxy-3-acetoxy-14β-hydroxy-6β-(N-isobutylcinnamamido)morphinan, 17-cyclopropylmethyl-4,5α-epoxy-3-acetoxy-14β-hydroxy-6β-(N-isobutylbenzyloxycarbamido)morphinan, 17-cyclopropylmethyl-4,5α-epoxy-3-acetoxy-14β-hydroxy-6β-(N-isobutylphenylmethanesulfonamido)morphinan, 17-allyl-4,5α-epoxy-3-acetoxy-14β-hydroxy-6β-(N-isobutyl-3,4-dichlorophenylacetamido)morphinan, 17-allyl-4,5α-epoxy-3-acetoxy-14β-hydroxy-6β-(N-isobutylcinnamamido)morphinan, 17-allyl-4,5α-epoxy-3-acetoxy-14β-hydroxy-6β-(N-isobutylbenzyloxycarbamido)morphinan, 17-allyl-4,5α-epoxy-3-acetoxy-14β-hydroxy-6β-(N-isobutylphenylmethanesulfonamido)morphinan.

17-methyl-4,5α-epoxy-3-acetoxy-14β-hydroxy-6β-(N-isobutyl-3,4-dichlorophenylacetamido)morphinan, 17-methyl-4,5α-epoxy-3-acetoxy-14β-hydroxy-6β-(N-isobutylcinnamamido)morphinan, 17-methyl-4,5α-epoxy-3-acetoxy-14β-hydroxy-6β-(N-isobutylbenzyloxycarbamido)morphinan, 17-methyl-4,5α-epoxy-3-acetoxy-14β-hydroxy-6β-(N-isobutylphenylmethanesulfonamido)morphinan, 17-phenethyl-4,5α-epoxy-3-acetoxy-14β-hydroxy-6β-(N-isobutyl-3,4-dichlorophenylacetamido)morphinan, 17-phenethyl-4,5α-epoxy-3-acetoxy-14β-hydroxy-6β-(N-isobutylcinnamamido)morphinan, 17-phenethyl-4,5α-epoxy-3-acetoxy-14β-hydroxy-6β-(N-isobutylbenzyloxycarbamido)morphinan, 17-phenethyl-4,5α-epoxy-3-acetoxy-14β-hydroxy-6β-(N-isobutylphenylmethanesulfonamido)morphinan.

17-cyclopropylmethyl-4,5α-epoxy-3,14β-diacetoxy-6β-(N-isobutyl-3,4-dichlorophenylacetamido)morphinan, 17-cyclopropylmethyl-4,5α-epoxy-3,14β-diacetoxy-6β-(N-isobutylcinnamamido)morphinan, 17-cyclopropylmethyl-4,5α-epoxy-3,14β-diacetoxy-6β-(N-isobutylbenzyloxycarbamido)morphinan, 17-cyclopropylmethyl-4,5α-epoxy-3,14β-diacetoxy-6β-(N-isobutylphenylmethanesulfonamido)morphinan, 17-allyl-4,5α-epoxy-3,14β-diacetoxy-6β-(N-isobutyl-3,4-dichlorophenylacetamido)morphinan, 17-allyl-4,5α-epoxy-3,14β-diacetoxy-6β-(N-isobutylcinnamamido)morphinan, 17-allyl-4,5α-epoxy-3,14β-diacetoxy-6β-(N-isobutylbenzyloxycarbamido)morphinan, 17-allyl-4,5α-epoxy-3,14β-diacetoxy-6β-(N-isobutylphenylmethanesulfonamido)morphinan.

17-methyl-4,5α-epoxy-3,14β-diacetoxy-6β-(N-isobutyl-3,4-dichlorophenylacetamido)morphinan, 17-methyl-4,5α-epoxy-3,14β-diacetoxy-6β-(N-isobutylcinnamamido)morphinan, 17-methyl-4,5α-epoxy-3,14β-diacetoxy-6β-(N-isobutylbenzyloxycarbamido)morphinan, 17-methyl-4,5α-epoxy-3,14β-diacetoxy-6β-(N-isobutylphenylmethanesulfonamido)morphinan, 17-phenethyl-4,5α-epoxy-3,14β-diacetoxy-6β-(N-isobutyl-3,4-dichlorophenylacetamido)morphinan, 17-phenethyl-4,5α-epoxy-3,14β-diacetoxy-6β-(N-isobutylcinnamamido)morphinan, 17-phenethyl-4,5α-epoxy-3,14β-diacetoxy-6β-(N-isobutylbenzyloxycarbamido)morphinan, 17-phenethyl-4,5α-epoxy-3,14β-diacetoxy-6β-(N-isobutylphenylmethanesulfonamido)morphinan.

17-cyclopropylmethyl-4,5α-epoxy-3,14β-dihydroxy-6α-(N-methyl-3,4-dichlorobenzamido)morphinan, 17-allyl-4,5α-epoxy-3,14β-dihydroxy-6α-(N-methyl-3,4-dichlorobenzamido)morphinan, 17-cyclopropylmethyl-4,5α-epoxy-3,14β-dihydroxy-6β-(N-methyl-3,4-dichlorobenzamido)morphinan, 17-allyl-4,5α-epoxy-3,14β-dihydroxy-6β-(N-methyl-3,4-dichlorobenzamido)morphinan, 17-cyclopropylmethyl-4,5α-epoxy-3,14β-dihydroxy-6α-(N-ethyl-3,4-dichlorophenylacetamido)morphinan, 17-allyl-4,5α-epoxy-3,14β-dihydroxy-6α-(N-ethyl-3,4-dichlorophenylacetamido)morphinan, 17-cyclopropylmethyl-4,5α-epoxy-3,14β-dihydroxy-6β-(N-ethyl-3,4-dichlorophenylacetamido)morphinan, 17-allyl-4,5α-epoxy-3,14β-dihydroxy-6β-(N-ethyl-3,4-dichlorophenylacetamido)morphinan.

17-cyclopropylmethyl-4,5α-epoxy-3,14β-dihydroxy-6α-(N-methyl-3-phenylpropionamido)morphinan, 17-allyl-4,5α-epoxy-3,14β-dihydroxy-6α-(N-methyl-3-phenylpropionamido)morphinan, 17-cyclopropylmethyl-4,5α-epoxy-3,14β-dihydroxy-6β-(N-methyl-3-phenylpropionamido)morphinan, 17-allyl-4,5α-epoxy-3,14β-dihydroxy-6β-(N-methyl-3-phenylpropionamido)morphinan, 17-cyclopropylmethyl-4,5α-epoxy-3,14β-dihydroxy-6α-[N-methyl-3-(5-chlorobenzo[b]thienyl)acetamido]morphinan, 17-allyl-4,5α-epoxy-3,14β-dihydroxy-6α-[N-methyl-3-(5-chlorobenzo[b]thienyl)acetamido]morphinan, 17-cyclopropylmethyl-4,5α-epoxy-3,14β-dihydroxy-6β-[N-methyl-3-(5-chlorobenzo[b]thienyl)acetamido]morphinan, 17-allyl-4,5α-epoxy-3,14β-dihydroxy-6β-[N-methyl-3-(5-chlorobenzo[b]thienyl)acetamido]morphinan, 17-cyclopropylmethyl-4,5α-epoxy-3,14β-dihydroxy-6α-(N-methylphenylacetamido)morphinan, 17-allyl-4,5α-epoxy-3,14β-dihydroxy-6α-(N-methylphenylacetamido)morphinan, 17-cyclopropylmethyl-4,5α-epoxy-3,14β-dihydroxy-6β-(N-methylphenylacetamido)morphinan, 17-allyl-4,5α-epoxy-3,14β-dihydroxy-6β-(N-methylphenylacetamido)morphinan, 17-cyclopropylmethyl-4,5α-epoxy-3,14β-dihydroxy-6α-(N-methylcyclohexylacetamido)morphinan, 17-allyl-4,5α-epoxy-3,14β-dihydroxy-6α-(N-methylcyclohexylacetamido)morphinan, 17-cyclopropylmethyl-4,5α-epoxy-3,14β-dihydroxy-6β-(N-methylcyclohexylacetamido)morphinan, 17-allyl-4,5α-epoxy-3,14β-dihydroxy-6β-(N-methylcyclohexylacetamido)morphinan, 17-cyclopropylmethyl-4,5α-epoxy-3,14β-dihydroxy-6α-(N-methyl-3-bromophenylacetamido)morphinan, 17-allyl-4,5α-epoxy-3,14-dihydroxy-6α-(N-methyl-3-bromophenylacetamido)morphinan, 17-cyclopropylmethyl-4,5α-epoxy-3,14β-dihydroxy-6β-(N-methyl-3-bromophenylacetamido)morphinan, 17-allyl-4,5α-epoxy-3,14β-dihydroxy-6β-(N-methyl-3-bromophenylacetamido)morphinan, 17-cyclopropylmethyl-4,5α-epoxy-3,14β-dihydroxy-6α-(N-methyl-4-benzo[b]thienylacetamido)morphinan, 17-allyl-4,5α-epoxy-3,14β-dihydroxy-6α-(N-methyl-4-benzo[b]thienylacetamido)morphinan, 17-cyclopropylmethyl-4,5α-epoxy-3,14β-dihydroxy-6β-(N-methyl-4-benzo[b]thienylacetamido)morphinan, 17-allyl-4,5α-epoxy-3,14β-dihydroxy-6β-(N-methyl-4-benzo[b]thienylacetamido)morphinan, 17-cyclopropylmethyl-4,5α-epoxy-3,14β-dihydroxy-6α-(N-methyl-3,4-dichlorocinnamamido)morphinan, 17-allyl-4,5α-epoxy-3,14β-dihydroxy-6α-(N-methyl-3,4-dichlorocinnamamido)morphinan, 17-cyclopropylmethyl-4,5α-epoxy-3,14β-dihydroxy-6β-(N-methyl-3,4-dichlorocinnamamido)morphinan, 17-allyl-4,5α-epoxy-3,14β-dihydroxy-6β-(N-methyl-3,4-dichlorocinnamamido)morphinan, 17-cyclopropylmethyl-4,5α-epoxy-3,14β-dihydroxy-6α-(N-methyl-4-bromophenylacetamido)morphinan, 17-allyl-4,5α-epoxy-3,14β-dihydroxy-6α-(N-methyl-4-bromophenylacetamido)morphinan, 17-cyclopropylmethyl-4,5α-epoxy-3,14β-dihydroxy-6β-(N-methyl-4-bromophenylacetamido)morphinan, 17-allyl-4,5α-epoxy-3,14β-dihydroxy-6β-(N-methyl-4-bromophenylacetamido)morphinan, 17-cyclopropylmethyl-4,5α-epoxy-3,14β-dihydroxy-6α-[(R)-N-methyl-2-phenylpropionamido]morphinan, 17-allyl-4,5α-epoxy-3,14β-dihydroxy-6α-[(R)-N-methyl-2-phenylpropionamido]morphinan, 17-cyclopropylmethyl-4,5α-epoxy-3,14β-dihydroxy-6β-[(R)-N-methyl-2-phenylpropionamido]morphinan, 17-allyl-4,5α-epoxy-3,14β-dihydroxy-6β-[(R)-N-methyl-2-phenylpropionamido]morphinan, 17-cyclopropylmethyl-4,5α-epoxy-3,14β-dihydroxy-6α-[(R)-N-methylmethoxyphenylacetamido]morphinan, 17-allyl-4,5α-epoxy-3,14β-dihydroxy-6α-[(R)-N-methylmethoxyphenylacetamido]morphinan, 17-cyclopropylmethyl-4,5α-epoxy-3,14β-dihydroxy-6β-[(R)-N-methylmethoxyphenylacetamido]morphinan, 17-allyl-4,5α-epoxy-3,14β-dihydroxy-6α-[(R)-N-methylmethoxyphenylacetamido]morphinan, 17-cyclopropylmethyl-4,5α-epoxy-3,14β-dihydroxy-6α-[(S)-N-methylmethoxyphenylacetamido]morphinan, 17-allyl-4,5α-epoxy-3,14β-dihydroxy-6α-[(S)-N-methylmethoxyphenylacetamido]morphinan, 17-cyclopropylmethyl-4,5α-epoxy-3,14β-dihydroxy-6β-[(S)-N-methylmethoxyphenylacetamido]morphinan, 17-allyl-4,5α-epoxy-3,14β-dihydroxy-6β-[(S)-N-methylmethoxyphenylacetamido]morphinan, 17-cyclopropylmethyl-4,5α-epoxy-3,14β-dihydroxy-6α-(3,4-dichlorophenylacetamido)morphinan, 17-allyl-4,5α-epoxy-3,14β-dihydroxy-6α-(3,4-dichlorophenylacetamido)morphinan, 17-cyclopropylmethyl-4,5α-epoxy-3,14β-dihydroxy-6β-(3,4-dichlorophenylacetamido)morphinan, 17-allyl-4,5α-epoxy-3,14β-dihydroxy-6β-(3,4-dichlorophenylacetamido)morphinan, 17-cyclopropylmethyl-4,5α-epoxy-3,14β-dihydroxy-6α-(N-methyl-3,4-difluorophenylacetamido)morphinan, 17-allyl-4,5α-epoxy-3,14β-dihydroxy-6α-(N-methyl-3,4-difluorophenylacetamido)morphinan, 17-cyclopropylmethyl-4,5α-epoxy-3,14β-dihydroxy-6β-(N-methyl-3,4-difluorophenylacetamido)morphinan, 17-allyl-4,5α-epoxy-3,14β-dihydroxy-6β-(N-methyl-3,4-difluorophenylacetamido)morphinan, 17-cyclopropylmethyl-4,5α-epoxy-3,14β-dihydroxy-6α-(N-methyl-3-trifluoromethylphenylacetamido)morphinan, 17-allyl-4,5α-epoxy-3,14β-dihydroxy-6α-(N-methyl-3-trifluoromethylphenylacetamido)morphinan, 17-cyclopropylmethyl-4,5α-epoxy-3,14β-dihydroxy-6β-(N-methyl-3-trifluoromethylphenylacetamido)morphinan, 17-allyl-4,5α-epoxy-3,14β-dihydroxy-6β-(N-methyl-3-trifluoromethylphenylacetamido)morphinan, 17-cyclopropylmethyl-4,5α-epoxy-3,14β-dihydroxy-6α-[(S)-N-methyl-2-phenylpropionamido]morphinan, 17-allyl-4,5α-epoxy-3,14β-dihydroxy-6α-[(S)-N-methyl-2-phenylpropionamido]morphinan, 17-cyclopropylmethyl-4,5α-epoxy-3,14β-dihydroxy-6β-[(S)-N-methyl-2-phenylpropionamido]morphinan, 17-allyl-4,5α-epoxy-3,14β-dihydroxy-6β-[(S)-N-methyl-2-phenylpropionamido]morphinan, 17-cyclopropylmethyl-4,5α-epoxy-3,14β-dihydroxy-6α-[N-methyl-N-2-(3,4-dichlorophenyl)ethylamino]morphinan, 17-allyl-4,5α-epoxy-3,14β-dihydroxy-6α-[N-methyl-N-2-(3,4-dichlorophenyl)ethylamino]morphinan, 17-cyclopropylmethyl-4,5α-epoxy-3,14β-dihydroxy-6β-[N-methyl-N-2-(3,4-dichlorophenyl)ethylamino]morphinan, 17-allyl-4,5α-epoxy-3,14β-dihydroxy-6β-[N-methyl-N-2-(3,4-dichlorophenyl)ethylamino]morphinan, 17-cyclopropylmethyl-4,5α-epoxy-3,14β-dihydroxy-6α-(N-methyl-4-nitrophenylacetamido)morphinan, 17-allyl-4,5α-epoxy-3,14β-dihydroxy-6α-(N-methyl-4-nitrophenylacetamido)morphinan, 17-cyclopropylmethyl-4,5α-epoxy-3,14β-dihydroxy-6β-(N-methyl-4-nitrophenylacetamido)morphinan, 17-allyl-4,5α-epoxy-3,14β-dihydroxy-6β-(N-methyl- 4-nitrophenylacetamido)morphinan,
17-cyclopropylmethyl-4,5α-epoxy-3,14β-dihydroxy-6α-(N-methyl-4-aminophenylacetamido)morphinan,
17-allyl-4,5α-epoxy-3,14β-dihydroxy-6α-(N-methyl-4-aminophenylacetamido)morphinan,
17-cyclopropylmethyl-4,5α-epoxy-3,14β-dihydroxy-6β-(N-methyl-4-aminophenylacetamido)morphinan,
17-allyl-4,5α-epoxy-3,14β-dihydroxy-6β-(N-methyl-4-aminophenylacetamido)morphinan, 17-cyclopropylmethyl-4,5α-epoxy-3,14β-dihydroxy-6α-(N-methylcyclohexylcarboxyamido)morphinan,
17-allyl-4,5α-epoxy-3,14β-dihydroxy-6α-(N-methylcyclohexylcarboxyamido)morphinan,
17-cyclopropylmethyl-4,5α-epoxy-3,14β-dihydroxy-6β-(N-methylcyclohexylcarboxyamido)morphinan,
17-allyl-4,5α-epoxy-3,14β-dihydroxy-6β-(N-methylcyclohexylcarboxyamido)morphinan,
17-cyclopropylmethyl-4,5α-epoxy-3,14β-dihydroxy-6α-(N-methylbenzamido)morphinan, 17-allyl-4,5α-epoxy-3,14β-dihydroxy-6α-(N-methylbenzamido)morphinan, 17-cyclopropylmethyl-4,5α-epoxy-3,14β-dihydroxy-6β-(N-methylbenzamido)morphinan,
17-allyl-4,5α-epoxy-3,14β-dihydroxy-6β-(N-methylbenzamido)morphinan, 17-cyclopropylmethyl-4,5α-epoxy-3,14β-dihydroxy-6α-(N-methyl-4-phenylbutyroamido)morphinan, 17-allyl-4,5α-epoxy-3,14β-dihydroxy-6α-(N-methyl-4-phenylbutyroamido)morphinan,
17-cyclopropylmethyl-4,5α-epoxy-3,14β-dihydroxy-6β-(N-methyl-4-phenylbutyroamido)morphinan,
17-allyl-4,5α-epoxy-3,14β-dihydroxy-6β-(N-methyl-4-phenylbutyroamido)morphinan, 17-cyclopropylmethyl-4,5α-epoxy-3,14β-dihydroxy-6α-(N-methyl-2-bromophenylacetamido)morphinan,
17-allyl-4,5α-epoxy-3,14β-dihydroxy-6α-(N-methyl-2-bromophenylacetamido)morphinan,
17-cyclopropylmethyl-4,5α-epoxy-3,14β-dihydroxy-6β-(N-methyl-2-bromophenylacetamido)morphinan,
17-allyl-4,5α-epoxy-3,14β-dihydroxy-6β-(N-methyl-2-bromophenylacetamido)morphinan, 17-cyclopropylmethyl-4,5α-epoxy-3,14β-dihydroxy-6α-(N-methyl-6-phenylhexanamido)morphinan, 17-allyl-4,5α-epoxy-3,14β-dihydroxy-6α-(N-methyl-6-phenylhexanamido)morphinan, 17-cyclopropylmethyl-4,5α-epoxy-3,14β-dihydroxy-6β-(N-methyl-6-phenylhexanamido)morphinan, 17-allyl-4,5α-epoxy-3,14β-dihydroxy-6β-(N-methyl-6-phenylhexanamido)morphinan, 17-cyclopropylmethyl-4,5α-epoxy-3,14β-dihydroxy-6α-(N-methyl-3-fluorophenylacetamido)morphinan,
17-allyl-4,5α-epoxy-3,14β-dihydroxy-6α-(N-methyl-3-fluorophenylacetamido)morphinan,
17-cyclopropylmethyl-4,5α-epoxy-3,14β-dihydroxy-6β-(N-methyl-3-fluorophenylacetamido)morphinan,
17-allyl-4,5α-epoxy-3,14β-dihydroxy-6β-(N-methyl-3-fluorophenylacetamido)morphinan, 17-cyclopropylmethyl-4,5α-epoxy-3,14β-dihydroxy-6α-[N-methyl-N'-(3,4-dichlorophenyl)ureido]morphinan,
17-allyl-4,5α-epoxy-3,14β-dihydroxy-6α-[N-methyl-N'-(3,4-dichlorophenyl)ureido]morphinan,
17-cyclopropylmethyl-4,5α-epoxy-3,14β-dihydroxy-6β-[N-methyl-N'-(3,4-dichlorophenyl)ureido]morphinan, 17-allyl-4,5α-epoxy-3,14β-dihydroxy-6β-[N-methyl-N'-(3,4-dichlorophenyl)ureido]morphinan, 17-cyclopropylmethyl-4,5α-epoxy-3,14β-dihydroxy-6α-(N-methyl-N'-benzylureido)morphinan, 17-allyl-4,5α-epoxy-3,14β-dihydroxy-6α-(N-methyl-N'-benzylureido)morphinan, 17-cyclopropylmethyl-4,5α-epoxy-3,14β-dihydroxy-6β-(N-methyl-N'-benzylureido)morphinan, 17-allyl-4,5α-epoxy-3,14β-dihydroxy-6β-(N-methyl-N'-benzylureido)morphinan, 17-cyclopropylmethyl-4,5α-epoxy-3,14β-dihydroxy-6α-(N-methyl-3-nitrophenylacetamido)morphinan,
17-allyl-4,5α-epoxy-3,14β-dihydroxy-6α-(N-methyl-3-nitrophenylacetamido)morphinan,
17-cyclopropylmethyl-4,5α-epoxy-3,14β-dihydroxy-6β-(N-methyl-3-nitrophenylacetamido)morphinan,
17-allyl-4,5α-epoxy-3,14β-dihydroxy-6β-(N-methyl-3-nitrophenylacetamido)morphinan,
17-cyclopropylmethyl-4,5α-epoxy-3,14β-dihydroxy-6α-(N-methyl-4-pyridylacetamido)morphinan,
17-allyl-4,5α-epoxy-3,14β-dihydroxy-6α-(N-methyl-4-pyridylacetamido)morphinan,
17-cyclopropylmethyl-4,5α-epoxy-3,14β-dihydroxy-6β-(N-methyl-4-pyridylacetamido)morphinan,
17-allyl-4,5α-epoxy-3,14β-dihydroxy-6β-(N-methyl-4-pyridylacetamido)morphinan, 17-cyclopropylmethyl-4,5α-epoxy-3,14β-dihydroxy-6α-[N-methyl-trans-3-(3-thienyl)acrylamido]morphinan,
17-allyl-4,5α-epoxy-3,14β-dihydroxy-6α-[N-methyl-trans-3-(3-thienyl)acrylamido]morphinan,
17-cyclopropylmethyl-4,5α-epoxy-3,14β-dihydroxy-6β-[N-methyl-trans-3-(3-thienyl)acrylamido]morphinan, 17-allyl-4,5α-epoxy-3,14β-dihydroxy-6β-[N-methyl-trans-3-(3-thienyl)acrylamido]morphinan, 17-cyclopropylmethyl-4,5α-epoxy-3,14β-dihydroxy-6α-(N-methylthiophenoxyacetamido)morphinan, 17-allyl-4,5α-epoxy-3,14β-dihydroxy-6α-(N-methylthiophenoxyacetamido)morphinan,
17-cyclopropylmethyl-4,5α-epoxy-3,14β-dihydroxy-6β-(N-methylthiophenoxyacetamido)morphinan,
17-allyl-4,5α-epoxy-3,14β-dihydroxy-6β-(N-methylthiophenoxyacetamido)morphinan, 17-cyclopropylmethyl-4,5α-epoxy-3,14β-dihydroxy-6α-(N-methylphenoxyacetamido)morphinan, 17-allyl-4,5α-epoxy-3,14β-dihydroxy-6α-(N-methylphenoxyacetamido)morphinan,
17-cyclopropylmethyl-4,5α-epoxy-3,14β-dihydroxy-6β-(N-methylphenoxyacetamido)morphinan, 17-allyl-4,5α-epoxy-3,14β-dihydroxy-6β-(N-methylphenoxyacetamido)morphinan, 17-cyclopropylmethyl-4,5α-epoxy-3,14β-dihydroxy-6α-(N-methyl-4-nitrobenzyloxycarbamido)morphinan,
17-allyl-4,5α-epoxy-3,14β-dihydroxy-6α-(N-methyl-4-nitrobenzyloxycarbamido)morphinan,
17-cyclopropylmethyl-4,5α-epoxy-3,14β-dihydroxy-6β-(N-methyl-4-nitrobenzyloxycarbamido)morphinan,
17-allyl-4,5α-epoxy-3,14β-dihydroxy-6β-(N-methyl-4-nitrobenzyloxycarbamido)morphinan, 17-cyclopropylmethyl-4,5α-epoxy-3,14β-dihydroxy-6α-(N-methyl-3-pyridylmethoxycarbamido)morphinan,
17-allyl-4,5α-epoxy-3,14β-dihydroxy-6α-(N-methyl-3-pyridylmethoxycarbamido)morphinan,
17-cyclopropylmethyl-4,5α-epoxy-3,14β-dihydroxy-6β-(N-methyl-3-pyridylmethoxycarbamido)morphinan, 17-allyl-4,5α-epoxy-3,14β-dihydroxy-6β-(N-methyl-3-pyridylmethoxycarbamido)morphinan,
17-cyclopropylmethyl-4,5α-epoxy-3,14β-dihydroxy-6α-(N-methyl-3,4-dichlorophenylmethanesulfonamido)morphinan, 17-allyl-4,5α-epoxy-3,14β-dihydroxy-6α-(N-methyl-3,4-dichlorophenylmethanesulfonamido)morphinan, 17-cyclopropylmethyl-4,5α- epoxy-3,14β-dihydroxy-6β-(N-methyl-3,4-dichlorophenylmethanesulfonamido)morphinan,
17-allyl-4,5α-epoxy-3,14β-dihydroxy-6β-(N-methyl-3,4-dichlorophenylmethanesulfonamido)morphinan,
17-cyclopropylmethyl-4,5α-epoxy-3,14β-dihydroxy-6α-(N-methyl-N'-benzylthioureido)morphinan,
17-allyl-4,5α-epoxy-3,14β-dihydroxy-6α-(N-methyl-N'-benzylthioureido)morphinan,
17-cyclopropylmethyl-4,5α-epoxy-3,14β-dihydroxy-6β-(N-methyl-N'-benzylthioureido)morphinan,
17-allyl-4,5α-epoxy-3,14β-dihydroxy-6β-N-methyl-N'-benzylthioureido)morphinan,
17-cyclopropylmethyl-4,5α-epoxy-3,14β-dihydroxy-6α-(N-methylhexanamido)morphinan, 17-allyl-4,5α-epoxy-3,14β-dihydroxy-6α-(N-methylhexanamido)morphinan, 17-cyclopropylmethyl-4,5α-epoxy-3,14β-dihydroxy-6β-(N-methylhexanamido)morphinan,
17-allyl-4,5α-epoxy-3,4β-dihydroxy-6β-(N-methylhexanamido)morphinan, 17-cyclopropylmethyl-4,5α-epoxy-3,14β-dihydroxy-6α-(N-methylheptanamido)morphinan, 17-allyl-4,5α-epoxy-3,14β-dihydroxy-6α-(N-methylheptanamido)morphinan, 17-cyclopropylmethyl-4,5α-epoxy-3,14β-dihydroxy-6β-(N-methylheptanamido)morphinan,
17-allyl-4,5α-epoxy-3,14β-dihydroxy-6β-(N-methylheptanamido)morphinan, 17-cyclopropylmethyl-4,5α-epoxy-3,14β-dihydroxy-6α-(N-methyl-3-aminophenylacetamido)morphinan,
17-allyl-4,5α-epoxy-3,14β-dihydroxy-6α-(N-methyl-3-aminophenylacetamido)morphinan,
17-cyclopropylmethyl-4,5α-epoxy-3,14β-dihydroxy-6β-(N-methyl-3-aminophenylacetamido)morphinan,
17-allyl-4,5α-epoxy-3,14β-dihydroxy-6β-(N-methyl-3-aminophenylacetamido)morphinan,
17-cyclopropylmethyl-4,5α-epoxy-3,4β-dihydroxy-6α-(N-methyl-2-pyridylacetamido)morphinan,
17-allyl-4,5α-epoxy-3,14β-dihydroxy-6α-(N-methyl-2-pyridylacetamido)morphinan,
17-cyclopropylmethyl-4,5α-epoxy-3,14β-dihydroxy-6β-(N-methyl-2-pyridylacetamido)morphinan,
17-allyl-4,5α-epoxy-3,14β-dihydroxy-6β-(N-methyl-2-pyridylacetamido)morphinan, 17-cyclopropylmethyl-4,5α-epoxy-3,14β-dihydroxy-6α-[N-methyl-3-(3-pyridyl)propionamido]morphinan,
17-allyl-4,5α-epoxy-3,14β-dihydroxy-6α-[N-methyl-3-(3-pyridyl)propionamido]morphinan,
17-cyclopropylmethyl-4,5α-epoxy-3,14β-dihydroxy-6β-[N-methyl-3-(3-pyridyl)propionamido]morphinan,
17-allyl-4,5α-epoxy-3,14β-dihydroxy-6β-[N-methyl-3-(3-pyridyl)propionamido]morphinan.

17-cyclopropylmethyl-4,5α-epoxy-3,14β-dihydroxy-6α-(3-phenylpropioyloxy)morphinan, 17-allyl-4,5α-epoxy-3,14β-dihydroxy-6α-(3-phenylpropioyloxy)morphinan, 17-cyclopropylmethyl-4,5α-epoxy-3,14β-dihydroxy-6β-(3-phenylpropioyloxy)morphinan,
17-allyl-4,5α-epoxy-3,14β-dihydroxy-6β-(3-phenylpropioyloxy)morphinan, 17-cyclopropylmethyl-4,5α-epoxy-3,14β-dihydroxy-6α-[2-(3-furyl)ethenylsulfonyloxy]morphinan, 17-allyl-4,5α-epoxy-3,14β-dihydroxy-6α-[2-(3-furyl)ethenylsulfonyloxy]morphinan,
17-cyclopropylmethyl-4,5α-epoxy-3,14β-dihydroxy-6β-[2-(3-furyl)ethenylsulfonyloxy]morphinan,
17-allyl-4,5α-epoxy-3,14β-dihydroxy-6β-[2-(3-furyl)ethenylsulfonyloxy]morphinan, 17-cyclopropylmethyl-4,5α-epoxy-3,14β-dihydroxy-6α-(N-methyl-3-trifluoromethylcinnamamido)morphinan, 17-cyclopropylmethyl-4,5α-epoxy-3,14β-dihydroxy-6α-[N-methyl-trans-3-(3-furyl)acrylamido]morphinan,
17-cyclopropylmethyl-4,5α-epoxy-3,14β-dihydroxy-6α-(N-methyl-4-trifluoromethylcinnamamido)morphinan, 17-cyclopropylmethyl-4,5α-epoxy-3,14β-dihydroxy-6α-(N-methyl-3-phenylpropiolamido)morphinan, 17-allyl-4,5α-epoxy-3,14β-dihydroxy-6α-(N-methyl-3-trifluoromethylcinnamamido)morphinan,
17-allyl-4,5α-epoxy-3,14β-dihydroxy-6α-[N-methyl-trans-3-(3-furyl)acrylamido]morphinan, 17-allyl-4,5α-epoxy-3,14β-dihydroxy-6α-(N-methyl-4-trifluoromethylcinnamamido)morphinan, 17-allyl-4,5α-epoxy-3,14β-dihydroxy-6α-(N-methyl-3-phenylpropiolamido)morphinan, 17-methyl-4,5α-epoxy-3,14β-dihydroxy-6α-(N-methyl-3-trifluoromethylcinnamamido)morphinan, 17-methyl-4,5α-epoxy-3,14β-dihydroxy-6α-[N-methyl-trans-3-(3-furyl)acrylamido]morphinan, 17-methyl-4,5α-epoxy-3,14β-dihydroxy-6α-(N-methyl-4-trifluoromethylcinnamamido)morphinan, 17-methyl-4,5α-epoxy-3,14β-dihydroxy-6α-(N-methyl-3-phenylpropiolamido)morphinan, 17-phenethyl-4,5α-epoxy-3,14β-dihydroxy-6α-(N-methyl-3-trifluoromethylcinnamamido)morphinan, 17-phenethyl-4,5α-epoxy-3,14β-dihydroxy-6α-[N-methyl-trans-3-(3-furyl)acrylamido]morphinan, 17-phenethyl-4,5α-epoxy-3,14β-dihydroxy-6α-(N-methyl-4-trifluoromethylcinnamamido)morphinan, 17-phenethyl-4,5α-epoxy-3,14β-dihydroxy-6α-(N-methyl-3-phenylpropiolamido)morphinan, 17-cyclopropylmethyl-4,5α-epoxy-3-hydroxy-14β-acetoxy-6α-(N-methyl-3-trifluoromethylcinnamamido)morphinan, 17-cyclopropylmethyl-4,5α-epoxy-3-hydroxy-14β-acetoxy-6α-[N-methyl-trans-3-(3-furyl)acrylamido]morphinan, 17-cyclopropylmethyl-4,5α-epoxy-3-hydroxy-14β-acetoxy-6α-(N-methyl-4-trifluoromethylcinnamamido)morphinan, 17-cyclopropylmethyl-4,5α-epoxy-3-hydroxy-14β-acetoxy-6α-(N-methyl-3-phenylpropiolamido)morphinan, 17-allyl-4,5α-epoxy-3-hydroxy-14β-acetoxy-6α-(N-methyl-3-trifluoromethylcinnamamido)morphinan, 17-allyl-4,5α-epoxy-3-hydroxy-14β-acetoxy-6α-[N-methyl-trans-3-(3-furyl)acrylamido]morphinan, 17-allyl-4,5α-epoxy-3-hydroxy-14β-acetoxy-6α-(N-methyl-4-trifluoromethylcinnamamido)morphinan, 17-allyl-4,5α-epoxy-3-hydroxy-14β-acetoxy-6α-(N-methyl-3-phenylpropiolamido)morphinan, 17-methyl-4,5α-epoxy-3-hydroxy-14β-acetoxy-6α-(N-methyl-3-trifluoromethylcinnamamido)morphinan, 17-methyl-4,5α-epoxy-3-hydroxy-14β-acetoxy-6α-[N-methyl-trans-3-(3-furyl)acrylamido]morphinan, 17-methyl-4,5α-epoxy-3-hydroxy-14β-acetoxy-6α-(N-methyl-4-trifluoromethylcinnamamido)morphinan, 17-methyl-4,5α-epoxy-3-hydroxy-14β-acetoxy-6α-(N-methyl-3-phenylpropiolamido)morphinan, 17-phenethyl-4,5α-epoxy-3-hydroxy-14β-acetoxy-6α-(N-methyl-3-trifluoromethylcinnamamido)morphinan, 17-phenethyl-4,5α-epoxy-3-hydroxy-14β-acetoxy-6α-[N-methyl-trans-3-(3-furyl)acrylamido]morphinan, 17-phenethyl-4,5α-epoxy-3-hydroxy-14β-acetoxy-6α-(N-methyl-4-trifluoromethylcinnamamido)morphinan, 17-phenethyl-4,5α-epoxy-3-hydroxy-14β-acetoxy-6α-(N-methyl-3-phenylpropiolamido)morphinan, 17-cyclopropylmethyl-4,5α-epoxy-14β-hydroxy-6α-(N-methyl-3-trifluoromethylcinnamamido)morphinan, 17-cyclopropylmethyl-4,5α-epoxy-14β-hydroxy-6α-[N-methyl-trans-3-(3-furyl)acrylamido]morphinan, 17-cyclopropylmethyl-4,5α-epoxy-14β-hydroxy-6α-(N-methyl-4-trifluoromethylcinnamamido)morphinan, 17-cyclopropylmethyl-4,5α-epoxy-14β-hydroxy-6α-(N-methyl-3-phenylpropiolamido)morphinan, 17-allyl-4,5α-epoxy-14β-hydroxy-6α-(N-methyl-3-trifluoromethylcinnamamido)morphinan, 17-allyl-4,5α-epoxy-14 β-hydroxy-6α-[N-methyl-trans-3-(3-furyl)acrylamido]morphinan, 17-allyl-4,5α-epoxy-14β-hydroxy-6α-(N-methyl-4-trifluoromethylcinnamamido)morphinan, 17-allyl-4,5α-epoxy-14β-hydroxy-6α-(N-methyl-3-phenylpropiolamido)morphinan, 17-methyl-4,5α-epoxy-14β-hydroxy-6α-(N-methyl-3-trifluoromethylcinnamamido)morphinan, 17-methyl-4,5α-epoxy-14β-hydroxy-6α-[N-methyl-trans-3-(3-furyl)acrylamido]morphinan, 17-methyl-4,5α-epoxy-14β-hydroxy-6α-(N-methyl-4-trifluoromethylcinnamamido)morphinan, 17-methyl-4,5α-epoxy-14β-hydroxy-6α-(N-methyl-3-phenylpropiolamido)morphinan, 17-phenethyl-4,5α-epoxy-14β-hydroxy-6α-(N-methyl-3-trifluoromethylcinnamamido)morphinan, 17-phenethyl-4,5α-epoxy-14β-hydroxy-6α-[N-methyl-trans-3-(3-furyl)acrylamido]morphinan, 17-phenethyl-4,5α-epoxy-14β-hydroxy-6α-(N-methyl-4-trifluoromethylcinnamamido)morphinan, 17-phenethyl-4,5α-epoxy-14β-hydroxy-6α-(N-methyl-3-phenylpropiolamido)morphinan, 17-cyclopropylmethyl-4,5α-epoxy-14β-acetoxy-6α-(N-methyl-3-trifluoromethylcinnamamido)morphinan, 17-cyclopropylmethyl-4,5α-epoxy-14β-acetoxy-6α-[N-methyl-trans-3-(3-furyl)acrylamido]morphinan, 17-cyclopropylmethyl-4,5α-epoxy-14β-acetoxy-6α-(N-methyl-4-trifluoromethylcinnamamido)morphinan, 17-cyclopropylmethyl-4,5α-epoxy-14β-acetoxy-6α-(N-methyl-3-phenylpropiolamido)morphinan, 17-allyl-4,5α-epoxy-14β-acetoxy-6α-(N-methyl-3-trifluoromethylcinnamamido)morphinan, 17-allyl-4,5α-epoxy-14β-acetoxy-6α-[N-methyl-trans-3-(3-furyl)acrylamido ]morphinan, 17-allyl-4,5α-epoxy-14β-acetoxy-6α-(N-methyl-4-trifluoromethylcinnamamido)morphinan, 17-allyl-4,5α-epoxy-14β-acetoxy-6α-(N-methyl-3-phenylpropiolamido)morphinan, 17-methyl-4,5α-epoxy-14β-acetoxy-6α-(N-methyl-3-trifluoromethylcinnamamido)morphinan, 17-methyl-4,5α-epoxy-14β-acetoxy-6α-[N-methyl-trans-3-(3-furyl)acrylamido]morphinan, 17-methyl-4,5α-epoxy-14β-acetoxy-6α-(N-methyl-4-trifluoromethylcinnamamido)morphinan, 17-methyl-4,5α-epoxy-14β-acetoxy-6α-(N-methyl-3-phenylpropiolamido)morphinan, 17-phenethyl-14,5β-epoxy-14β-acetoxy-6α-(N-methyl-3-trifluoromethylcinnamamido)morphinan, 17-phenethyl-4,5α-epoxy-14β-acetoxy-6α-[N-methyl-trans-3-(3-furyl)acrylamido]morphinan, 17-phenethyl-4,5α-epoxy-14β-acetoxy-6α-(N-methyl-4-trifluoromethylcinnamamido)morphinan, 17-phenethyl-4,5α-epoxy-14β-acetoxy-6α-(N-methyl-3-phenylpropiolamido)morphinan, 17-cyclopropylmethyl-4,5α-epoxy-3-methoxy-14β-hydroxy-6α-(N-methyl-3-trifluoromethylcinnamamido)morphinan, 17-cyclopropylmethyl-4,5α-epoxy-3-methoxy-14β-hydroxy-6α-[N-methyl-trans-3-(3-furyl)acrylamido]morphinan, 17-cyclopropylmethyl-4,5α-epoxy-3-methoxy-14β-hydroxy-6α-(N-methyl-4-trifluoromethylcinnamamido)morphinan, 17-cyclopropylmethyl-4,5α-epoxy-3-methoxy-14β-hydroxy-6α-(N-methyl-3-phenylpropiolamido)morphinan, 17-allyl-4,5α-epoxy-3-methoxy-14β-hydroxy-6α-(N-methyl-3-trifluoromethylcinnamamido)morphinan, 17-allyl-4,5α-epoxy-3-methoxy-14β-hydroxy-6α-[N-methyl-trans-3-(3-furyl)acrylamido]morphinan, 17-allyl-4,5α-epoxy-3-methoxy-14β-hydroxy-6α-(N-methyl-4-trifluoromethylcinnamamido)morphinan, 17-allyl-4,5α-epoxy-3-methoxy-14β-hydroxy-6α-(N-methyl-3-phenylpropiolamido)morphinan, 17-methyl-4,5α-epoxy-3-methoxy-14β-hydroxy-6α-(N-methyl-3-trifluoromethylcinnamamido)morphinan, 17-methyl-4,5α-epoxy-3-methoxy-14β-hydroxy-6α-[N-methyl-trans-3-(3-furyl)acrylamido]morphinan, 17-methyl-4,5α-epoxy-3-methoxy-14β-hydroxy-6α-(N-methyl-4-trifluoromethylcinnamamido)morphinan, 17-methyl-4,5α-epoxy-3-methoxy-14β-hydroxy-6α-(N-methyl-3-phenylpropiolamido)morphinan, 17-phenethyl-4,5α-epoxy-3-methoxy-14β-hydroxy-6α-(N-methyl-3-trifluoromethylcinnamamido)morphinan, 17-phenethyl-4,5α-epoxy-3-methoxy-14β-hydroxy-6α-[N-methyl-trans-3-(3-furyl)acrylamido]morphinan, 17-phenethyl-4,5α-epoxy-3-methoxy-14β-hydroxy-6α-(N-methyl-4-trifluoromethylcinnamamido)morphinan, 17-phenethyl-4,5α-epoxy-3-methoxy-14β-hydroxy-6α-(N-methyl-3-phenylpropiolamido)morphinan, 17-cyclopropylmethyl-4,5α-epoxy-3-methoxy-14β-acetoxy-6α-(N-methyl-3-trifluoromethylcinnamamido)morphinan, 17-cyclopropylmethyl-4,5α-epoxy-3-methoxy-14β-acetoxy-6α-[N-methyl-trans-3-(3-furyl)acrylamido] morphinan, 17-cyclopropylmethyl-4,5α-epoxy-3-methoxy-14β-acetoxy-6α-(N-methyl-4-trifluoromethylcinnamamido)morphinan, 17-cyclopropylmethyl-4,5α-epoxy-3-methoxy-14β-acetoxy-6α-(N-methyl-3-phenylpropionamido)morphinan, 17-allyl-4,5α-epoxy-3-methoxy-14β-acetoxy-6α-(N-methyl-3-trifluoromethylcinnamamido)morphinan, 17-allyl-4,5α-epoxy-3-methoxy-14β-acetoxy-6α-[N-methyl-trans-3-(3-furyl)acrylamido]morphinan, 17-allyl-4,5α-epoxy-3-methoxy-14β-acetoxy-6α-(N-methyl-4-trifluoromethylcinnamamido)morphinan, 17-allyl-4,5α-epoxy-3-methoxy-14β-acetoxy-6α-(N-methyl-3-phenylpropiolamido)morphinan, 17-methyl-4,5α-epoxy-3-methoxy-14β-acetoxy-6α-(N-methyl-3-trifluoromethylcinnamamido)morphinan, 17-methyl-4,5α-epoxy-3-methoxy-14β-acetoxy-6α-[N-methyl-trans-3-(3-furyl)acrylamido]morphinan, 17-methyl-4,5α-epoxy-3-methoxy-14β-acetoxy-6α-(N-methyl-4-trifluoromethylcinnamamido)morphinan, 17-methyl-4,5α-epoxy-3-methoxy-4α-acetoxy-6α-(N-methyl-3-phenylpropiolamido)morphinan, 17-phenethyl-4,5α-epoxy-3-methoxy-14β-acetoxy-6α-(N-methyl-3-trifluoromethylcinnamamido)morphinan, 17-phenethyl-4,5α-epoxy-3-methoxy-14β-acetoxy-6α-[N-methyl-trans-3-(3-furyl)acrylamido]morphinan, 17-phenethyl-4,5α-epoxy-3-methoxy-14β-acetoxy-6α-(N-methyl-4-trifluoromethylcinnamamido) morphinan, 17-phenethyl-4,5α-epoxy-3-methoxy-14β-acetoxy-6α-(N-methyl-3-phenylpropiolamido) morphinan, 17-cyclopropylmethyl-4,5α-epoxy-3-acetoxy-14β-hydroxy-6α-(N-methyl-3- trifluoromethylcinnamamido)morphinan,
17-cyclopropylmethyl-4,5α-epoxy-3-acetoxy-14β-hydroxy-6α-[N-methyl-trans-3-(3-furyl)acrylamido]morphinan, 17-cyclopropylmethyl-4,5α-epoxy-3-acetoxy-14β-hydroxy-6α-(N-methyl-4-trifluoromethylcinnamamido)morphinan, 17-cyclopropylmethyl-4,5α-epoxy-3-acetoxy-14β-hydroxy-6α-(N-methyl-3-phenylpropiolamido)morphinan, 17-allyl-4,5α-epoxy-3-acetoxy-14β-hydroxy-6α-(N-methyl-3-trifluoromethylcinnamamido)morphinan, 17-allyl-4,5α-epoxy-3-acetoxy-14β-hydroxy-6α-[N-methyl-trans-3-(3-furyl)acrylamido]morphinan, 17-allyl-4,5α-epoxy-3-acetoxy-14β-hydroxy-6α-(N-methyl-4-trifluoromethylcinnamamido)morphinan, 17-allyl-4,5α-epoxy-3-acetoxy-14β-hydroxy-6α-(N-methyl-3-phenylpropiolamido)morphinan, 17-methyl-4,5α-epoxy-3-acetoxy-14β-hydroxy-6α-(N-methyl-3-trifluoromethylcinnamamido)morphinan, 17-methyl-4,5α-epoxy-3-acetoxy-14β-hydroxy-6α-[N-methyl-trans-3-(3-furyl)acrylamido]morphinan, 17-methyl-4,5α-epoxy-3-acetoxy-14β-hydroxy-6α-(N-methyl-4-trifluoromethylcinnamamido)morphinan, 17-methyl-4,5α-epoxy-3-acetoxy-14β-hydroxy-6α-(N-methyl-3-phenylpropiolamido)morphinan, 17-phenethyl-4,5α-epoxy-3-acetoxy-14β-hydroxy-6α-(N-methyl-3-trifluoromethylcinnamamido)morphinan, 17-phenethyl-4,5α-epoxy-3-acetoxy-14β-hydroxy-6α-[N-methyl-trans-3-(3-furyl)acrylamido]morphinan, 17-phenethyl-4,5α-epoxy-3-acetoxy-14β-hydroxy-6α-(N-methyl-4-trifluoromethylcinnamamido)morphinan, 17-phenethyl-4,5α-epoxy-3-acetoxy-14β-hydroxy-6α-(N-methyl-3-phenylpropiolamido)morphinan, 17-cyclopropylmethyl-4,5α-epoxy-3,14β-diacetoxy-6α-(N-methyl-3-trifluoromethylcinnamamido)morphinan, 17-cyclopropylmethyl-4,5α-epoxy-3,14β-diacetoxy-6α-[N-methyl-trans-3-(3-furyl)acrylamido]morphinan, 17-cyclopropylmethyl-4,5α-epoxy-3,14β-diacetoxy-6α-(N-methyl-4-trifluoromethylcinnamamido)morphinan, 17-cyclopropylmethyl-4,5α-epoxy-3,14β-diacetoxy-6α-(N-methyl-3-phenylpropiolamido)morphinan, 17-allyl-4,5α-epoxy-3,14β-diacetoxy-6α-(N-methyl-3-trifluoromethylcinnamamido)morphinan, 17-allyl-4,5α-epoxy-3,14β-diacetoxy-6α-[N-methyl-trans-3-(3-furyl)acrylamido]morphinan, 17-allyl-4,5α-epoxy-3,14β-diacetoxy-6α-(N-methyl-4-trifluoromethylcinnamamido)morphinan, 17-allyl-4,5α-epoxy-3,14β-diacetoxy-6α-(N-methyl-3-phenylpropiolamido)morphinan, 17-methyl-4,5α-epoxy-3,14β-diacetoxy-6α-(N-methyl-3-trifluoromethylcinnamamido)morphinan, 17-methyl-4,5α-epoxy-3,14β-diacetoxy-6α-[N-methyl-trans-3-(3-furyl)acrylamido]morphinan, 17-methyl-4,5α-epoxy-3,14β-diacetoxy-6α-(N-methyl-4-trifluoromethylcinnamamido)morphinan, 17-methyl-4,5α-epoxy-3,14β-diacetoxy-6α-(N-methyl-3-phenylpropiolamido)morphinan, 17-phenethyl-4,5α-epoxy-3,14β-diacetoxy-6α-(N-methyl-3-trifluoromethylcinnamamido)morphinan, 17-phenethyl-4,5α-epoxy-3,14β-diacetoxy-6α-[N-methyl-trans-3-(3-furyl)acrylamido]morphinan, 17-phenethyl-4,5α-epoxy-3,14β-diacetoxy-6α-(N-methyl-4-trifluoromethylcinnamamido)morphinan, 17-phenethyl-4,5α-epoxy-3,14β-diacetoxy-6α-(N-methyl-3-phenylpropiolamido)morphinan, 17-cyclopropylmethyl-4,5α-epoxy-3,14β-dihydroxy-6α-(N-isobutyl-3-trifluoromethylcinnamamido)morphinan, 17-cyclopropylmethyl-4,5α-epoxy-3,14β-dihydroxy-6α-[N-isobutyl-trans-3-(3-furyl)acrylamido]morphinan, 17-cyclopropylmethyl-4,5α-epoxy-3,14β-dihydroxy-6α-(N-isobutyl-4-trifluoromethylcinnamamido)morphinan, 17-cyclopropylmethyl-4,5α-epoxy-3,14β-dihydroxy-6α-(N-isobutyl-3-phenylpropiolamido)morphinan, 17-allyl-4,5α-epoxy-3,14β-dihydroxy-6α-(N-isobutyl-3-trifluoromethylcinnamamido)morphinan, 17-allyl-4,5α-epoxy-3,14β-dihydroxy-6α-[N-isobutyl-trans-3-(3-furyl)acrylamido]morphinan, 17-allyl-4,5α-epoxy-3,14β-dihydroxy-6α-(N-isobutyl-4-trifluoromethylcinnamamido)morphinan, 17-allyl-4,5α-epoxy-3,14β-dihydroxy-6α-(N-isobutyl-3-phenylpropiolamido)morphinan, 17-methyl-4,5α-epoxy-3,14β-dihydroxy-6α-(N-isobutyl-3-trifluoromethylcinnamamido)morphinan, 17-methyl-4,5α-epoxy-3,14β-dihydroxy-6α-[N-isobutyl-trans-3-(3-furyl)acrylamido]morphinan, 17-methyl-4,5α-epoxy-3,14β-dihydroxy-6α-(N-isobutyl-4-trifluoromethylcinnamamido)morphinan, 17-methyl-4,5α-epoxy-3,14β-dihydroxy-6α-(N-isobutyl-3-phenylpropiolamido)morphinan, 17-phenethyl-4,5α-epoxy-3,14β-dihydroxy-6α-(N-isobutyl-3-trifluoromethylcinnamamido)morphinan, 17-phenethyl-4,5α-epoxy-3,14β-dihydroxy-6α-[N-isobutyl-trans-3-(3-furyl)acrylamido]morphinan, 17-phenethyl-4,5α-epoxy-3,14β-dihydroxy-6α-(N-isobutyl-4-trifluoromethylcinnamamido)morphinan, 17-phenethyl-4,5α-epoxy-3,14β-dihydroxy-6α-(N-isobutyl-3-phenylpropiolamido)morphinan, 17-cyclopropylmethyl-4,5α-epoxy-3-hydroxy-14β-acetoxy-6α-(N-isobutyl-3-trifluoromethylcinnamamido)morphinan, 17-cyclopropylmethyl-4,5α-epoxy-3-hydroxy-14β-acetoxy-6α-[N-isobutyl-trans-3-(3-furyl)acrylamido]morphinan, 17-cyclopropylmethyl-4,5α-epoxy-3-hydroxy-14β-acetoxy-6α-(N-isobutyl-4-trifluoromethylcinnamamido)morphinan, 17-cyclopropylmethyl-4,5α-epoxy-3-hydroxy-14β-acetoxy-6α-(N-isobutyl-3-phenylpropiolamido)morphinan, 17-allyl-4,5α-epoxy-3-hydroxy-14β-acetoxy-6α-(N-isobutyl-3-trifluoromethylcinnamamido)morphinan, 17-allyl-4,5α-epoxy-3-hydroxy-14β-acetoxy-6α-[N-isobutyl-trans-3-(3-furyl)acrylamido]morphinan, 17-allyl-4,5α-epoxy-3-hydroxy-14β-acetoxy-6α-(N-isobutyl-4-trifluoromethylcinnamamido)morphinan, 17-allyl-4,5α-epoxy-3-hydroxy-14β-acetoxy-6α-(N-isobutyl-3-phenylpropiolamido)morphinan, 17-methyl-4,5α-epoxy-3-hydroxy-14β-acetoxy-6α-(N-isobutyl-3-trifluoromethylcinnamamido)morphinan, 17-methyl-4,5α-epoxy-3-hydroxy-14β-acetoxy-6α-[N-isobutyl-trans-3-(3-furyl)acrylamido]morphinan, 17-methyl-4,5α-epoxy-3-hydroxy-14β-acetoxy-6α-(N-isobutyl-4-trifluoromethylcinnamamido)morphinan, 17-methyl-4,5α-epoxy-3-hydroxy-14β-acetoxy-6α-(N-isobutyl-3-phenylpropiolamido)morphinan, 17-phenethyl-4,5α-epoxy-3-hydroxy-14β-acetoxy-6α-(N-isobutyl-3-trifluoromethylcinnamamido)morphinan, 17-phenethyl-4,5α-epoxy-3-hydroxy-14β-acetoxy-6α-[N-isobutyl-trans-3-(3-furyl)acrylamido]morphinan, 17-phenethyl-4,5α-epoxy-3-hydroxy-14β-acetoxy-6α-(N-isobutyl-4-trifluoromethylcinnamamido)morphinan, 17-phenethyl-4,5α-epoxy-3-hydroxy-14β-acetoxy-6α-(N-isobutyl-3-phenylpropiolamido)

morphinan, 17-cyclopropylmethyl-4,5α-epoxy-14β-hydroxy-6α-(N-isobutyl-3-trifluoromethylcinnamamido)morphinan, 17-cyclopropylmethyl-4,5α-epoxy-14β-hydroxy-6α-[N-isobutyl-trans-3-(3-furyl)acrylamido]morphinan, 17-cyclopropylmethyl-4,5α-epoxy-14β-hydroxy-6α-(N-isobutyl-4-trifluoromethylcinnamamido)morphinan, 17-cyclopropylmethyl-4,5α-epoxy-14β-hydroxy-6α-(N-isobutyl-3-phenylpropiolamido)morphinan, 17-allyl-4,5α-epoxy-14β-hydroxy-6α-(N-isobutyl-3-trifluoromethylcinnamamido)morphinan, 17-allyl-4,5α-epoxy-14β-hydroxy-6α-[N-isobutyl-trans-3-(3-furyl)acrylamido]morphinan, 17-allyl-4,5α-epoxy-14β-hydroxy-6α-(N-isobutyl-4-trifluoromethylcinnamamido)morphinan, 17-allyl-4,5α-epoxy-14β-hydroxy-6α-(N-isobutyl-3-phenylpropiolamido)morphinan, 17-methyl-4,5α-epoxy-14β-hydroxy-6α-(N-isobutyl-3-trifluoromethylcinnamamido)morphinan, 17-methyl-4,5α-epoxy-14β-hydroxy-6α-[N-isobutyl-trans-3-(3-furyl)acrylamido]morphinan, 17-methyl-4,5α-epoxy-14β-hydroxy-6α-(N-isobutyl-4-trifluoromethylcinnamamido)morphinan, 17-methyl-4,5α-epoxy-14β-hydroxy-6α-(N-isobutyl-3-phenylpropiolamido)morphinan, 17-phenethyl-4,5α-epoxy-14β-hydroxy-6α-(N-isobutyl-3-trifluoromethylcinnamamido)morphinan, 17-phenethyl-4,5α-epoxy-14β-hydroxy-6α-[N-isobutyl-trans-3-(3-furyl)acrylamido]morphinan, 17-phenethyl-4,5α-epoxy-14β-hydroxy-6α-(N-isobutyl-4-trifluoromethylcinnamamido)morphinan, 17-phenethyl-4,5α-epoxy-14β-hydroxy-6α-(N-isobutyl-3-phenylpropiolamido)morphinan, 17-cyclopropylmethyl-4,5α-epoxy-14β-acetoxy-6α-(N-isobutyl-3-trifluoromethylcinnamamido)morphinan, 17-cyclopropylmethyl-4,5α-epoxy-14β-acetoxy-6α-[N-isobutyl-trans-3-(3-furyl)acrylamido]morphinan, 17-cyclopropylmethyl-4,5α-epoxy-14β-acetoxy-6α-(N-isobutyl-4-trifluoromethylcinnamamido)morphinan, 17-cyclopropylmethyl-4,5α-epoxy-14β-acetoxy-6α-(N-isobutyl-3-phenylpropiolamido)morphinan, 17-allyl-4,5α-epoxy-14β-acetoxy-6α-(N-isobutyl-3-trifluoromethylcinnamamido)morphinan, 17-allyl-4,5α-epoxy-14β-acetoxy-6α-[N-isobutyl-trans-3-(3-furyl)acrylamido]morphinan, 17-allyl-4,5α-epoxy-14β-acetoxy-6α-(N-isobutyl-4-trifluoromethylcinnamamido)morphinan, 17-allyl-4,5α-epoxy-14β-acetoxy-6α-(N-isobutyl-3-phenylpropiolamido)morphinan, 17-methyl-4,5α-epoxy-14β-acetoxy-6α-(N-isobutyl-3-trifluoromethylcinnamamido)morphinan, 17-methyl-4,5α-epoxy-14β-acetoxy-6α-[N-isobutyl-trans-3-(3-furyl)acrylamido]morphinan, 17-methyl-4,5α-epoxy-14β-acetoxy-6α-(N-isobutyl-4-trifluoromethylcinnamamido)morphinan, 17-methyl-4,5α-epoxy-14β-acetoxy-6α-(N-isobutyl-3-phenylpropiolamido)morphinan, 17-phenethyl-4,5α-epoxy-14β-acetoxy-6α-(N-isobutyl-3-trifluoromethylcinnamamido)morphinan, 17-phenethyl-4,5α-epoxy-14β-acetoxy-6α-[N-isobutyl-trans-3-(3-furyl)acrylamido]morphinan, 17-phenethyl-4,5α-epoxy-14β-acetoxy-6α-(N-isobutyl-4-trifluoromethylcinnamamido)morphinan, 17-phenethyl-4,5α-epoxy-14β-acetoxy-6α-(N-isobutyl-3-phenylpropiolamido)morphinan, 17-cyclopropylmethyl-4,5α-epoxy-3-methoxy-14β-hydroxy-6α-(N-isobutyl-3-trifluoromethylcinnamamido)morphinan, 17-cyclopropylmethyl-4,5α-epoxy-3-methoxy-14β-hydroxy-6α-[N-isobutyl-trans-3-(3-furyl)acrylamido] morphian, 17-cyclopropylmethyl-4,5α-epoxy-3-methoxy-14β-hydroxy-6α-(N-isobutyl-4-trifluoromethylcinnamamido)morphinan, 17-cyclopropylmethyl-4,5α-epoxy-3-methoxy-14β-hydroxy-6α-(N-isobutyl-3-phenylpropiolamido)morphinan, 17-allyl-4,5α-epoxy-3-methoxy-14β-hydroxy-6α-(N-isobutyl-3-trifluoromethylcinnamamido)morphinan, 17-allyl-4,5α-epoxy-3-methoxy-14β-hydroxy-6α-[N-isobutyl-trans-3-(3-furyl)acrylamido]morphinan, 17-allyl-4,5α-epoxy-3-methoxy-14β-hydroxy-6α-(N-isobutyl-4-trifluoromethylcinnamamido)morphinan, 17-allyl-4,5α-epoxy-3-methoxy-14β-hydroxy-6α-(N-isobutyl-3-phenylpropiolamido)morphinan, 17-methyl-4,5α-epoxy-3-methoxy-14β-hydroxy-6α-(N-isobutyl-3-trifluoromethylcinnamamido)morphinan, 17-methyl-4,5α-epoxy-3-methoxy-14β-hydroxy-6α-[N-isobutyl-trans-3-(3-furyl)acrylamido]morphinan, 17-methyl-4,5α-epoxy-3-methoxy-14β-hydroxy-6α-(N-isobutyl-4-trifluoromethylcinnamamido)morphinan, 17-methyl-4,5α-epoxy-3-methoxy-14β-hydroxy-6α-(N-isobutyl-3-phenylpropiolamido)morphinan, 17-phenethyl-4,5α-epoxy-3-methoxy-14β-hydroxy-6α-(N-isobutyl-3-trifluoromethylcinnamamido)morphinan, 17-phenethyl-4,5α-epoxy-3-methoxy-14β-hydroxy-6α-[N-isobutyl-trans-3-(3-furyl)acrylamido]morphinan, 17-phenethyl-4,5α-epoxy-3-methoxy-14β-hydroxy-6α-(N-isobutyl-4-trifluoromethylcinnamamido)morphinan, 17-phenethyl-4,5α-epoxy-3-methoxy-14β-hydroxy-6α-(N-isobutyl-3-phenylpropiolamido)morphinan, 17-cyclopropylmethyl-4,5α-epoxy-3-methoxy-14β-acetoxy-6α-(N-isobutyl-3-trifluoromethylcinnamamido)morphinan, 17-cyclopropylmethyl-4,5α-epoxy-3-methoxy-14β-acetoxy-6α-[N-isobutyl-trans-3-(3-furyl)acrylamido]morphinan, 17-cyclopropylmethyl-4,5α-epoxy-3-methoxy-14β-acetoxy-6α-(N-isobutyl-4-trifluoromethylcinnamamido)morphinan, 17-cyclopropylmethyl-4,5α-epoxy-3-methoxy-14β-acetoxy-6α-(N-isobutyl-3-phenylpropiolamido)morphinan, 17-allyl-4,5α-epoxy-3-methoxy-14β-acetoxy-6α-(N-isobutyl-3-trifluoromethylcinnamamido)morphinan, 17-allyl-4,5α-epoxy-3-methoxy-14β-acetoxy-6α-[N-isobutyl-trans-3-(3-furyl)acrylamido]morphinan, 17-allyl-4,5α-epoxy-3-methoxy-14β-acetoxy-6α-(N-isobutyl-4-trifluoromethylcinnamamido)morphinan, 17-allyl-4,5α-epoxy-3-methoxy-14β-acetoxy-6α-(N-isobutyl-3-phenylpropiolamido)morphinan, 17-methyl-4,5α-epoxy-3-methoxy-14β-acetoxy-6α-(N-isobutyl-3-trifluoromethylcinnamamido)morphinan, 17-methyl-4,5α-epoxy-3-methoxy-14β-acetoxy-6α-[N-isobutyl-trans-3-(3-furyl)acrylamido]morphinan, 17-methyl-4,5α-epoxy-3-methoxy-14β-acetoxy-6α-(N-isobutyl-4-trifluoromethylcinnamamido)morphinan, 17-methyl-4,5α-epoxy-3-methoxy-14β-acetoxy-6α-(N-isobutyl-3-phenylpropiolamido)morphinan, 17-phenethyl-4,5α-epoxy-3-methoxy-14β-acetoxy-6α-(N-isobutyl-3-trifluoromethylcinnamamido)morphinan, 17-phenethyl-4,5α-epoxy-3-methoxy-14β-acetoxy- 6α-[N-isobutyl-trans-3-(3-furyl)acrylamido]morphinan, 17-phenethyl-4,5α-epoxy-3-methoxy-14β-acetoxy-6α-(N-isobutyl-4-trifluoromethylcinnamamido)morphinan, 17-phenethyl-4,5α-epoxy-3-methoxy-14β-acetoxy-6α-(N-isobutyl-3-phenylpropiolamido)morphinan, 17-cyclopropylmethyl-4,5α-epoxy-3-acetoxy-14β-hydroxy-6α-(N-isobutyl-3-trifluoromethylcinnamamido)morphinan, 17-cyclopropylmethyl-4,5α-epoxy-3-acetoxy-14β-hydroxy-6α-[N-isobutyl-trans-3-(3-furyl)acrylamido]morphinan, 17-cyclopropylmethyl-4,5α-epoxy-3-acetoxy-14β-hydroxy-6α-(N-isobutyl-4-trifluoromethylcinnamamido)morphinan, 17-cyclopropylmethyl-4,5α-epoxy-3-acetoxy-14β-hydroxy-6α-(N-isobutyl-3-phenylpropiolamido)morphinan, 17-allyl-4,5α-epoxy-3-acetoxy-14β-hydroxy-6α-(N-isobutyl-3-trifluoromethylcinnamamido)morphinan, 17-allyl-4,5α-epoxy-3-acetoxy-14β-hydroxy-6α-[N-isobutyl-trans-3-(3-furyl)acrylamido]morphinan, 17-allyl-4,5α-epoxy-3-acetoxy-14β-hydroxy-6α-(N-isobutyl-4-trifluoromethylcinnamamido)morphinan, 17-allyl-4,5α-epoxy-3-acetoxy-14β-hydroxy-6α-(N-isobutyl-3-phenylpropiolamido)morphinan, 17-methyl-4,5α-epoxy-3-acetoxy-14β-hydroxy-6α-(N-isobutyl-3-trifluoromethylcinnamamido)morphinan, 17-methyl-4,5α-epoxy-3-acetoxy-14β-hydroxy-6α-[N-isobutyl-trans-3-(3-furyl)acrylamido]morphinan, 17-methyl-4,5α-epoxy-3-acetoxy-14β-hydroxy-6α-(N-isobutyl-4-trifluoromethylcinnamamido)morphinan, 17-methyl-4,5α-epoxy-3-acetoxy-14β-hydroxy-6α-(N-isobutyl-3-phenylpropiolamido)morphinan, 17-phenethyl-4,5α-epoxy-3-acetoxy-14β-hydroxy-6α-(N-isobutyl-3-trifluoromethylcinnamamido)morphinan, 17-phenethyl-4,5α-epoxy-3-acetoxy-14β-hydroxy-6α-[N-isobutyl-trans-3-(3-furyl)acrylamido]morphinan, 17-phenethyl-4,5α-epoxy-3-acetoxy-14β-hydroxy-6α-(N-isobutyl-4-trifluoromethylcinnamamido)morphinan, 17-phenethyl-4,5α-epoxy-3-acetoxy-14β-hydroxy-6α-(N-isobutyl-3-phenylpropiolamido)morphinan, 17-cyclopropylmethyl-4,5α-epoxy-3,14β-diacetoxy-6α-(N-isobutyl-3-trifluoromethylcinnamamido)morphinan, 17-cyclopropylmethyl-4,5α-epoxy-3,14β-diacetoxy-6α-[N-isobutyl-trans-3-(3-furyl)acrylamido]morphinan, 17-cyclopropylmethyl-4,5α-epoxy-3,14β-diacetoxy-6α-(N-isobutyl-4-trifluoromethylcinnamamido)morphinan, 17-cyclopropylmethyl-4,5α-epoxy-3,14β-diacetoxy-6α-(N-isobutyl-3-phenylpropiolamido)morphinan, 17-allyl-4,5α-epoxy-3,14β-diacetoxy-6α-(N-isobutyl-3-trifluoromethylcinnamamido)morphinan, 17-allyl-4,5α-epoxy-3,14β-diacetoxy-6α-[N-isobutyl-trans-3-(3-furyl)acrylamido]morphinan, 17-allyl-4,5α-epoxy-3,14β-diacetoxy-6α-(N-isobutyl-4-trifluoromethylcinnamamido)morphinan, 17-allyl-4,5α-epoxy-3,14β-diacetoxy-6α-(N-isobutyl-3-phenylpropiolamido)morphinan, 17-methyl-4,5α-epoxy-3,14β-diacetoxy-6α-(N-isobutyl-3-trifluoromethylcinnamamido)morphinan, 17-methyl-4,5α-epoxy-3,14β-diacetoxy-6α-[N-isobutyl-trans-3-(3-furyl)acrylamido]morphinan, 17-methyl-4,5α-epoxy-3,14β-diacetoxy-6α-(N-isobutyl-4-trifluoromethylcinnamamido)morphinan, 17-methyl-4,5α-epoxy-3,14β-diacetoxy-6α-(N-isobutyl-3-phenylpropiolamido)morphinan, 17-phenethyl-4,5α-epoxy-3,14β-diacetoxy-6α-(N-isobutyl-3-trifluoromethylcinnamamido)morphinan, 17-phenethyl-4,5α-epoxy-3,14β-diacetoxy-6α-[N-isobutyl-trans-3-(3-furyl)acrylamido]morphinan, 17-phenethyl-4,5α-epoxy-3,14β-diacetoxy-6α-(N-isobutyl-4-trifluoromethylcinnamamido)morphinan, 17-phenethyl-4,5α-epoxy-3,14β-diacetoxy-6α-(N-isobutyl-3-phenylpropiolamido)morphinan, 17-cyclopropylmethyl-4,5α-epoxy-3,14β-dihydroxy-6β-(N-methyl-3-trifluoromethylcinnamamido)morphinan, 17-cyclopropylmethyl-4,5α-epoxy-3,14β-dihydroxy-6α-[N-methyl-trans-3-(3-furyl)acrylamido]morphinan, 17-cyclopropylmethyl-4,5α-epoxy-3,14β-dihydroxy-6β-(N-methyl-4-trifluoromethylcinnamamido)morphinan, 17-cyclopropylmethyl-4,5α-epoxy-3,14β-dihydroxy-6β-(N-methyl-3-phenylpropiolamido)morphinan, 17-allyl-4,5α-epoxy-3,14β-dihydroxy-6β-(N-methyl-3-trifluoromethylcinnamamido)morphinan, 17-allyl-4,5α-epoxy-3,14β-dihydroxy-6β-[N-methyl-trans-3-(3-furyl)acrylamido]morphinan, 17-allyl-4,5α-epoxy-3,14β-dihydroxy-6β-(N-methyl-4-trifluoromethylcinnamamido)morphinan, 17-allyl-4,5α-epoxy-3,14β-dihydroxy-6β-(N-methyl-3-phenylpropiolamido)morphinan, 17-methyl-4,5α-epoxy-3,14β-dihydroxy-6β-(N-methyl-3-trifluoromethylcinnamamido)morphinan, 17-methyl-4,5α-epoxy-3,14β-dihydroxy-6β-[N-methyl-trans-3-(3-furyl)acrylamido]morphinan, 17-methyl-4,5α-epoxy-3,14β-dihydroxy-6β-(N-methyl-4-trifluoromethylcinnamamido)morphinan, 17-methyl-4,5α-epoxy-3,14β-dihydroxy-6β-(N-methyl-3-phenylpropiolamido)morphinan, 17-phenethyl-4,5α-epoxy-3,14β-dihydroxy-6β-(N-methyl-3-trifluoromethylcinnamamido)morphinan, 17-phenethyl-4,5α-epoxy-3,14β-dihydroxy-6β-[N-methyl-trans-3-(3-furyl)acrylamido]morphinan, 17-phenethyl-4,5α-epoxy-3,14β-dihydroxy-6β-(N-methyl-4-trifluoromethylcinnamamido)morphinan, 17-phenethyl-4,5α-epoxy-3,14β-dihydroxy-6β-(N-methyl-3-phenylpropiolamido)morphinan, 17-cyclopropylmethyl-4,5α-epoxy-3-hydroxy-14β-acetoxy-6β-(N-methyl-3-trifluoromethylcinnamamido)morphinan, 17-cyclopropylmethyl-4,5α-epoxy-3-hydroxy-14β-acetoxy-6β-[N-methyl-trans-3-(3-furyl)acrylamido]morphinan, 17-cyclopropylmethyl-4,5α-epoxy-3-hydroxy-14β-acetoxy-6β-(N-methyl-4-trifluoromethylcinnamamido)morphinan, 17-cyclopropylmethyl-4,5α-epoxy-3-hydroxy-14β-acetoxy-6β-(N-methyl-3-phenylpropiolamido)morphinan, 17-allyl-4,5α-epoxy-3-hydroxy-14β-acetoxy-6β-(N-methyl-3-trifluoromethylcinnamamido)morphinan, 17-allyl-4,5α-epoxy-3-hydroxy-14β-acetoxy-6β-[N-methyl-trans-3-(3-furyl)acrylamido]morphinan, 17-allyl-4,5α-epoxy-3-hydroxy-14β-acetoxy-6β-(N-methyl-4-trifluoromethylcinnamamido)morphinan, 17-allyl-4,5α-epoxy-3-hydroxy-14β-acetoxy-6β-(N-methyl-3-phenylpropiolamido)morphinan, 17-methyl-4,5α-epoxy-3-hydroxy-14β-acetoxy-6β-(N-methyl-3-trifluoromethylcinnamamido)morphinan, 17-methyl-4,5α-epoxy-3-hydroxy-14β-acetoxy-6β-[N-methyl-trans-3-(3-furyl)acrylamido]morphinan, 17-methyl-4,5α-epoxy-3-hydroxy-14β-acetoxy-6β-(N-methyl-4-trifluoromethylcinnamamido)morphinan, 17-methyl-4,5α-epoxy-3-hydroxy-14β-acetoxy-6β-(N-methyl-3- phenylpropiolamido)morphinan, 17-phenethyl-4,5α-epoxy-3-hydroxy-14β-acetoxy-6β-(N-methyl-3-trifluoromethylcinnamamido)morphinan, 17-phenethyl-4,5α-epoxy-3-hydroxy-14β-acetoxy-6β-[N-methyl-trans-3-(3-furyl)acrylamido]morphinan, 17-phenethyl-4,5α-epoxy-3-hydroxy-14β-acetoxy-6β-(N-methyl-4-trifluoromethylcinnamamido)morphinan, 17-phenethyl-4,5α-epoxy-3-hydroxy-14β-acetoxy-6β-(N-methyl-3-phenylpropiolamido)morphinan, 17-cyclopropylmethyl-4,5α-epoxy-14β-hydroxy-6β-(N-methyl-3-trifluoromethylcinnamamido)morphinan, 17-cyclopropylmethyl-4,5α-epoxy-14β-hydroxy-6β-[N-methyl-trans-3-(3-furyl)acrylamido]morphinan, 17-cyclopropylmethyl-4,5α-epoxy-14β-hydroxy-6β-(N-methyl-4-trifluoromethylcinnamamido)morphinan, 17-cyclopropylmethyl-4,5α-epoxy-14β-hydroxy-6β-(N-methyl-3-phenylpropiolamido)morphinan, 17-allyl-4,5α-epoxy-14β-hydroxy-6β-(N-methyl-3-trifluoromethylcinnamamido)morphinan, 17-allyl-4,5α-epoxy-14β-hydroxy-6β-[N-methyl-trans-3-(3-furyl)acrylamido]morphinan, 17-allyl-4,5α-epoxy-14β-hydroxy-6β-(N-methyl-4-trifluoromethylcinnamamido)morphinan, 17-allyl-4,5α-epoxy-14β-hydroxy-6β-(N-methyl-3-phenylpropiolamido)morphinan, 17-methyl-4,5α-epoxy-14β-hydroxy-6β-(N-methyl-3-trifluoromethylcinnamamido)morphinan, 17-methyl-4,5α-epoxy-14β-hydroxy-6β-[N-methyl-trans-3-(3-furyl)acrylamido]morphinan, 17-methyl-4,5α-epoxy-14β-hydroxy-6β-(N-methyl-4-trifluoromethylcinnamamido)morphinan, 17-methyl-4,5α-epoxy-14β-hydroxy-6β-(N-methyl-3-phenylpropiolamido)morphinan, 17-phenethyl-4,5α-epoxy-14β-hydroxy-6β-(N-methyl-3-trifluoromethylcinnamamido)morphinan, 17-phenethyl-4,5α-epoxy-14β-hydroxy-6β-[N-methyl-trans-3-(3-furyl)acrylamido]morphinan, 17-phenethyl-4,5α-epoxy-14β-hydroxy-6β-(N-methyl-4-trifluoromethylcinnamamido)morphinan, 17-phenethyl-4,5α-epoxy-14β-hydroxy-6β-(N-methyl-3-phenylpropiolamido)morphinan, 17-cyclopropylmethyl-4,5α-epoxy-14β-acetoxy-6β-(N-methyl-3-trifluoromethylcinnamamido)morphinan, 17-cyclopropylmethyl-4,5α-epoxy-14β-acetoxy-6β-[N-methyl-trans-3-(3-furyl)acrylamido]morphinan, 17-cyclopropylmethyl-4,5α-epoxy-14β-acetoxy-6β-(N-methyl-4-trifluoromethylcinnamamido)morphinan, 17-cyclopropylmethyl-4,5α-epoxy-14β-acetoxy-6β-(N-methyl-3-phenylpropiolamido)morphinan, 17-allyl-4,5α-epoxy-14β-acetoxy-6β-(N-methyl-3-trifluoromethylcinnamamido)morphinan, 17-allyl-4,5α-epoxy-14β-acetoxy-6β-[N-methyl-trans-3-(3-furyl)acrylamido]morphinan, 17-allyl-4,5α-epoxy-14β-acetoxy-6β-(N-methyl-4-trifluoromethylcinnamamido)morphinan, 17-allyl-4,5α-epoxy-14β-acetoxy-6β-(N-methyl-3-phenylpropiolamido)morphinan, 17-methyl-4,5α-epoxy-14β-acetoxy-6β-(N-methyl-3-trifluoromethylcinnamamido)morphinan, 17-methyl-4,5α-epoxy-14β-acetoxy-6β-[N-methyl-trans-3-(3-furyl)acrylamido]morphinan, 17-methyl-4,5α-epoxy-14β-acetoxy-6β-(N-methyl-4-trifluoromethylcinnamamido)morphinan, 17-methyl-4,5α-epoxy-14β-acetoxy-6β-(N-methyl-3-phenylpropiolamido)morphinan, 17-phenethyl-4,5α-epoxy-14β-acetoxy-6β-(N-methyl-3-trifluoromethylcinnamamido)morphinan, 17-phenethyl-4,5α-epoxy-14β-acetoxy-6β-[N-methyl-trans-3-(3-furyl)acrylamido]morphinan, 17-phenethyl-4,5α-epoxy-14β-acetoxy-6β-(N-methyl-4-trifluoromethylcinnamamido)morphinan, 17-phenethyl-4,5α-epoxy-14β-acetoxy-6β-(N-methyl-3-phenylpropiolamido)morphinan, 17-cyclopropylmethyl-4,5α-epoxy-3-methoxy-14β-hydroxy-6β-(N-methyl-3-trifluoromethylcinnamamido)morphinan, 17-cyclopropylmethyl-4,5α-epoxy-3-methoxy-14β-hydroxy-6β-[N-methyl-trans-3-(3-furyl)acrylamido]morphinan, 17-cyclopropylmethyl-4,5α-epoxy-3-methoxy-14β-hydroxy-6β-(N-methyl-4-trifluoromethylcinnamamido)morphinan, 17-cyclopropylmethyl-4,5α-epoxy-3-methoxy-14β-hydroxy-6β-(N-methyl-3-phenylpropiolamido)morphinan, 17-allyl-4,5α-epoxy-3-methoxy-14β-hydroxy-6β-(N-methyl-3-trifluoromethylcinnamamido)morphinan, 17-allyl-4,5α-epoxy-3-methoxy-14β-hydroxy-6β-[N-methyl-trans-3-furyl)acrylamido]morphinan, 17-allyl-4,5α-epoxy-3-methoxy-14β-hydroxy-6β-(N-methyl-4-trifluoromethylcinnamamido)morphinan, 17-allyl-4,5α-epoxy-3-methoxy-14β-hydroxy-6β-(N-methyl-3-phenylpropiolamido)morphinan, 17-methyl-4,5α-epoxy-3-methoxy-14β-hydroxy-6β-(N-methyl-3-trifluoromethylcinnamamido)morphinan, 17-methyl-4,5α-epoxy-3-methoxy-14β-hydroxy-6β-[N-methyl-trans-3-(3-furyl)acrylamido]morphinan, 17-methyl-4,5α-epoxy-3-methoxy-14β-hydroxy-6β-(N-methyl-4-trifluoromethylcinnamamido)morphinan, 17-methyl-4,5α-epoxy-3-methoxy-14β-hydroxy-6β-(N-methyl-3-phenylpropiolamido)morphinan, 17-phenethyl-4,5α-epoxy-3-methoxy-14β-hydroxy-6β-(N-methyl-3-trifluoromethylcinnamamido)morphinan, 17-phenethyl-4,5α-epoxy-3-methoxy-14β-hydroxy-6β-[N-methyl-trans-3-(3-furyl)acrylamido]morphinan, 17-phenethyl-4,5α-epoxy-3-methoxy-14β-hydroxy-6β-(N-methyl-4-trifluoromethylcinnamamido)morphinan, 17-phenethyl-4,5α-epoxy-3-methoxy-14β-hydroxy-6β-(N-methyl-3-phenylpropiolamido)morphinan, 17-cyclopropylmethyl-4,5α-epoxy-3-methoxy-14β-acetoxy-6β-(N-methyl-3-trifluoromethylcinnamamido)morphinan, 17-cyclopropylmethyl-4,5α-epoxy-3-methoxy-14β-acetoxy-6β-[N-methyl-trans-3-(3-furyl)acrylamido]morphinan, 17-cyclopropylmethyl-4,5α-epoxy-3-methoxy-14β-acetoxy-6β-(N-methyl-4-trifluoromethylcinnamamido)morphinan, 17-cyclopropylmethyl-4,5α-epoxy-3-methoxy-14β-acetoxy-6β-(N-methyl-3-phenylpropiolamido)morphinan, 17-allyl-4,5α-epoxy-3-methoxy-14β-acetoxy-6β-(N-methyl-3-trifluoromethylcinnamamido)morphinan, 17-allyl-4,5α-epoxy-3-methoxy-14β-acetoxy-6β-[N-methyl-trans-3-(3-furyl)acrylamido]morphinan, 17-allyl-4,5α-epoxy-3-methoxy-14β-acetoxy-6β-(N-methyl-4-trifluoromethylcinnamamido)morphinan, 17-allyl-4,5α-epoxy-3-methoxy-14β-acetoxy-6β-(N-methyl-3-phenylpropiolamido)morphinan, 17-methyl-4,5α-epoxy-3-methoxy-14β-acetoxy-6β-(N-methyl-3-trifluoromethylcinnamamido)morphinan, 17-methyl-4,5α-epoxy-3-methoxy-14β-acetoxy-6β-[N-methyl-trans-3-(3-furyl)acrylamido]morphinan, 17-methyl-4,5α-epoxy-3-methoxy-14β-acetoxy-6β-(N-methyl-4-trifluoromethylcinnamamido)morphinan, 17-methyl-4,5α-epoxy-3-methoxy-14β-acetoxy-6β-(N-methyl-3- phenylpropiolamido)morphinan, 17-phenethyl-4,5α-epoxy-3-methoxy-14β-acetoxy-6β-(N-methyl-3-trifluoromethylcinnamamido)morphinan, 17-phenethyl-4,5α-epoxy-3-methoxy-14β-acetoxy-6β-[N-methyl-trans-3-(3-furyl)acrylamido]morphinan, 17-phenethyl-4,5α-epoxy-3-methoxy-14β-acetoxy-6β-(N-methyl-4-trifluoromethylcinnamamido)morphinan, 17-phenethyl-4,5α-epoxy-3-methoxy-14β-acetoxy-6β-(N-methyl-3-phenylpropiolamido)morphinan, 17-cyclopropylmethyl-4,5α-epoxy-3-acetoxy-14β-hydroxy-6β-(N-methyl-3-trifluoromethylcinnamamido)morphinan, 17-cyclopropylmethyl-4,5α-epoxy-3-acetoxy-14β-hydroxy-6β-[N-methyl-trans-3-(3-furyl)acrylamido]morphinan, 17-cyclopropylmethyl-4,5α-epoxy-3-acetoxy-14β-hydroxy-6β-(N-methyl-4-trifluoromethylcinnamamido)morphinan, 17-cyclopropylmethyl-4,5α-epoxy-3-acetoxy-14β-hydroxy-6β-(N-methyl-3-phenylpropiolamido)morphinan, 17-allyl-4,5α-epoxy-3-acetoxy-14β-hydroxy-6β-(N-methyl-3-trifluoromethylcinnamamido)morphinan, 17-allyl-4,5α-epoxy-3-acetoxy-14β-hydroxy-6β-[N-methyl-trans-3-(3-furyl)acrylamido]morphinan, 17-allyl-4,5α-epoxy-3-acetoxy-14β-hydroxy-6β-(N-methyl-4-trifluoromethylcinnamamido)morphinan, 17-allyl-4,5α-epoxy-3-acetoxy-14β-hydroxy-6β-(N-methyl-3-phenylpropiolamido)morphinan, 17-methyl-4,5α-epoxy-3-acetoxy-14β-hydroxy-6β-(N-methyl-3-trifluoromethylcinnamamido)morphinan, 17-methyl-4,5α-epoxy-3-acetoxy-14β-hydroxy-6β-[N-methyl-trans-3-(3-furyl)acrylamido]morphinan, 17-methyl-4,5α-epoxy-3-acetoxy-14β-hydroxy-6β-(N-methyl-4-trifluoromethylcinnamamido)morphinan, 17-methyl-4,5α-epoxy-3-acetoxy-14β-hydroxy-6β-(N-methyl-3-phenylpropiolamido)morphinan, 17-phenethyl-4,5α-epoxy-3-acetoxy-14β-hydroxy-6β-(N-methyl-3-trifluoromethylcinnamamido)morphinan, 17-phenethyl-4,5α-epoxy-3-acetoxy-14β-hydroxy-6β-[N-methyl-trans-3-(3-furyl)acrylamido]morphinan, 17-phenethyl-4,5α-epoxy-3-acetoxy-14β-hydroxy-6β-(N-methyl-4-trifluoromethylcinnamamido)morphinan, 17-phenethyl-4,5α-epoxy-3-acetoxy-14β-hydroxy-6β-(N-methyl-3-phenylpropiolamido)morphinan, 17-cyclopropylmethyl-4,5α-epoxy-3,14β-diacetoxy-6β-(N-methyl-3-trifluoromethylcinnamamido)morphinan, 17-cyclopropylmethyl-4,5α-epoxy-3,14β-diacetoxy-6β-[N-methyl-trans-3-(3-furyl)acrylamido]morphinan, 17-cyclopropylmethyl-4,5α-epoxy-3,14β-diacetoxy-6β-(N-methyl-4-trifluoromethylcinnamamido)morphinan, 17-cyclopropylmethyl-4,5α-epoxy-3,14β-diacetoxy-6β-(N-methyl-3-phenylpropiolamido)morphinan, 17-allyl-4,5α-epoxy-3,14β-diacetoxy-6β-(N-methyl-3-trifluoromethylcinnamamido)morphinan, 17-allyl-4,5α-epoxy-3,14β-diacetoxy-6β-[N-methyl-trans-3-(3-furyl)acrylamido]morphinan, 17-allyl-4,5α-epoxy-3,14β-diacetoxy-6β-(N-methyl-4-trifluoromethylcinnamamido)morphinan, 17-allyl-4,5α-epoxy-3,14β-diacetoxy-6β-(N-methyl-3-phenylpropiolamido)morphinan, 17-methyl-4,5α-epoxy-3,14β-diacetoxy-6β-(N-methyl-3-trifluoromethylcinnamamido)morphinan, 17-methyl-4,5α-epoxy-3,14β-diacetoxy-6β-[N-methyl-trans-3-(3-furyl)acrylamido]morphinan, 17-methyl-4,5α-epoxy-3,14β-diacetoxy-6β-(N-methyl-4-trifluoromethylcinnamamido)morphinan, 17-methyl-4,5α-epoxy-3,14β-diacetoxy-6β-(N-methyl-3-phenylpropiolamido)morphinan, 17-phenethyl-4,5α-epoxy-3,14β-diacetoxy-6β-(N-methyl-3-trifluoromethylcinnamamido)morphinan, 17-phenethyl-4,5α-epoxy-3,14β-diacetoxy-6β-[N-methyl-trans-3-(3-furyl)acrylamido]morphinan, 17-phenethyl-4,5α-epoxy-3,14β-diacetoxy-6β-(N-methyl-4-trifluoromethylcinnamamido)morphinan, 17-phenethyl-4,5α-epoxy-3,14β-diacetoxy-6β-(N-methyl-3-phenylpropiolamido)morphinan, 17-cyclopropylmethyl-4,5α-epoxy-3,14β-dihydroxy-6β-(N-isobutyl-3-trifluoromethylcinnamamido)morphinan, 17-cyclopropylmethyl-4,5α-epoxy-3,14β-dihydroxy-62-[N-isobutyl-trans-3-(3-furyl)acrylamido]morphinan, 17-cyclopropylmethyl-4,5α-epoxy-3,14β-dihydroxy-6β-(N-isobutyl-4-trifluoromethylcinnamamido)morphinan, 17-cyclopropylmethyl-4,5α-epoxy-3,14β-dihydroxy-6β-(N-isobutyl-3-phenylpropiolamido)morphinan, 17-allyl-4,5α-epoxy-3,14β-dihydroxy-6β-(N-isobutyl-3-trifluoromethylcinnamamido)morphinan, 17-allyl-4,5α-epoxy-3,14β-dihydroxy-6β-[N-isobutyl-trans-3-(3-furyl)acrylamido]morphinan, 17-allyl-4,5α-epoxy-3,14β-dihydroxy-6β-(N-isobutyl-4-trifluoromethylcinnamamido)morphinan, 17-allyl-4,5α-epoxy-3,14β-dihydroxy-6β-(N-isobutyl-3-phenylpropiolamido)morphinan, 17-methyl-4,5α-epoxy-3,14β-dihydroxy-6β-(N-isobutyl-3-trifluoromethylcinnamamido)morphinan, 17-methyl-4,5α-epoxy-3,14β-dihydroxy-6β-[N-isobutyl-trans-3-(3-furyl)acrylamido]morphinan, 17-methyl-4,5α-epoxy-3,14β-dihydroxy-6β-(N-isobutyl-4-trifluoromethylcinnamamido)morphinan, 17-methyl-4,5α-epoxy-3,14β-dihydroxy-6β-(N-isobutyl-3-phenylpropiolamido)morphinan, 17-phenethyl-4,5α-epoxy-3,14β-dihydroxy-6α-(N-isobutyl-3-trifluoromethylcinnamamido)morphinan, 17-phenethyl-4,5α-epoxy-3,14β-dihydroxy-6β-[N-isobutyl-trans-3-(3-furyl)acrylamido]morphinan, 17-phenethyl-4,5α-epoxy-3,14β-dihydroxy-6β-(N-isobutyl-4-trifluoromethylcinnamamido)morphinan, 17-phenethyl-4,5α-epoxy-3,14β-dihydroxy-6β-(N-isobutyl-3-phenylpropiolamido)morphinan, 17-cyclopropylmethyl-4,5α-epoxy-3-hydroxy-14β-acetoxy-6β-(N-isobutyl-3-trifluoromethylcinnamamido)morphinan, 17-cyclopropylmethyl-4,5α-epoxy-3-hydroxy-14β-acetoxy-6β-[N-isobutyl-trans-3-(3-furyl)acrylamido]morphinan, 17-cyclopropylmethyl-4,5α-epoxy-3-hydroxy-14β-acetoxy-6β-(N-isobutyl-4-trifluoromethylcinnamamido)morphinan, 17-cyclopropylmethyl-4,5α-epoxy-3-hydroxy-14β-acetoxy-6β-(N-isobutyl-3-phenylpropiolamido)morphinan, 17-allyl-4,5α-epoxy-3-hydroxy-14β-acetoxy-6β-(N-isobutyl-3-trifluoromethylcinnamamido)morphinan, 17-allyl-4,5α-epoxy-3-hydroxy-14β-acetoxy-6β-[N-isobutyl-trans-3-(3-furyl)acrylamido]morphinan, 17-allyl-4,5α-epoxy-3-hydroxy-14β-acetoxy-6β-(N-isobutyl-4-trifluoromethylcinnamamido)morphinan, 17-allyl-4,5α-epoxy-3-hydroxy-14β-acetoxy-6β-(N-isobutyl-3-phenylpropiolamido)morphinan, 17-methyl-4,5α-epoxy-3-hydroxy-14β-acetoxy-6β-(N-isobutyl-3-trifluoromethylcinnamamido)morphinan, 17-methyl-4,5α-epoxy-3-hydroxy-14β-acetoxy-6β-[N-isobutyl-trans-3-(3-furyl)acrylamido]morphinan, 17-methyl-4,5α-epoxy-3-hydroxy-14β- acetoxy-6β-(N-isobutyl-4-trifluoromethylcinnamamido)morphinan, 17-methyl-4,5α-epoxy-3-hydroxy-14β-acetoxy-6β-(N-isobutyl-3-phenylpropiolamido)morphinan, 17-phenethyl-4,5α-epoxy-3-hydroxy-14β-acetoxy-6β-(N-isobutyl-3-trifluoromethylcinnamamido)morphinan, 17-phenethyl-4,5α-epoxy-3-hydroxy-14β-acetoxy-6β-[N-isobutyl-trans-3-(3-furyl)acrylamido]morphinan, 17-phenethyl-4,5α-epoxy-3-hydroxy-14β-acetoxy-6β-(N-isobutyl-4-trifluoromethylcinnamamido)morphinan, 17-phenethyl-4,5α-epoxy-3-hydroxy-14β-acetoxy-6β-(N-isobutyl-3-phenylpropiolamido)morphinan, 17-cyclopropylmethyl-4,5α-epoxy-14β-hydroxy-6β-(N-isobutyl-3-trifluoromethylcinnamamido)morphinan, 17-cyclopropylmethyl-4,5α-epoxy-14β-hydroxy-6β-[N-isobutyl-trans-3-(3-furyl)acrylamido]morphinan, 17-cyclopropylmethyl-4,5α-epoxy-14β-hydroxy-6β-(N-isobutyl-4-trifluoromethylcinnamamido)morphinan, 17-cyclopropylmethyl-4,5α-epoxy-14β-hydroxy-6β-(N-isobutyl-3-phenylpropiolamido)morphinan, 17-allyl-4,5α-epoxy-14β-hydroxy-6β-(N-isobutyl-3-trifluoromethylcinnamamido)morphinan, 17-allyl-4,5α-epoxy-14β-hydroxy-6β-[N-isobutyl-trans-3-(3-furyl)acrylamido]morphinan, 17-allyl-4,5α-epoxy-14β-hydroxy-6β-(N-isobutyl-4-trifluoromethylcinnamamido)morphinan, 17-allyl-4,5α-epoxy-14β-hydroxy-6β-(N-isobutyl-3-phenylpropiolamido)morphinan, 17-methyl-4,5α-epoxy-14β-hydroxy-6β-(N-isobutyl-3-trifluoromethylcinnamamido)morphinan, 17-methyl-4,5α-epoxy-14β-hydroxy-6β-[N-isobutyl-trans-3-(3-furyl)acrylamido]morphinan, 17-methyl-4,5α-epoxy-14β-hydroxy-6β-(N-isobutyl-4-trifluoromethylcinnamamido)morphinan, 17-methyl-4,5α-epoxy-14β-hydroxy-6β-(N-isobutyl-3-phenylpropiolamido)morphinan, 17-phenethyl-4,5α-epoxy-14β-hydroxy-6β-(N-isobutyl-3-trifluoromethylcinnamamido)morphinan, 17-phenethyl-4,5α-epoxy-14β-hydroxy-6β-[N-isobutyl-trans-3-(3-furyl)acrylamido]morphinan, 17-phenethyl-4,5α-epoxy-14β-hydroxy-6β-(N-isobutyl-4-trifluoromethylcinnamamido)morphinan, 17-phenethyl-4,5α-epoxy-14β-hydroxy-6β-(N-isobutyl-3-phenylpropiolamido)morphinan, 17-cyclopropylmethyl-4,5α-epoxy-14β-acetoxy-6β-(N-isobutyl-3-trifluoromethylcinnamamido)morphinan, 17-cyclopropylmethyl-4,5α-epoxy-14β-acetoxy-6β-[N-isobutyl-trans-3-(3-furyl)acrylamido]morphinan, 17-cyclopropylmethyl-4,5α-epoxy-14β-acetoxy-6β-(N-isobutyl-4-trifluoromethylcinnamamido)morphinan, 17-cyclopropylmethyl-4,5α-epoxy-14β-acetoxy-6β-(N-isobutyl-3-phenylpropiolamido)morphinan, 17-allyl-4,5α-epoxy-14β-acetoxy-6β-(N-isobutyl-3-trifluoromethylcinnamamido)morphinan, 17-allyl-4,5α-epoxy-14β-acetoxy-6β-[N-isobutyl-trans-3-(3-furyl)acrylamido]morphinan, 17-allyl-4,5α-epoxy-14β-acetoxy-6β-(N-isobutyl-4-trifluoromethylcinnamamido)morphinan, 17-allyl-4,5α-epoxy-14β-acetoxy-6β-(N-isobutyl-3-phenylpropiolamido)morphinan, 17-methyl-4,5α-epoxy-14β-acetoxy-6β-(N-isobutyl-3-trifluoromethylcinnamamido)morphinan, 17-methyl-4,5α-epoxy-14β-acetoxy-6β-[N-isobutyl-trans-3-(3-furyl)acrylamido]morphinan, 17-methyl-4,5α-epoxy-14β-acetoxy-6β-(N-isobutyl-4-trifluoromethylcinnamamido)morphinan, 17-methyl-4,5α-epoxy-14β-acetoxy-6β-(N-isobutyl-3-phenylpropiolamido)morphinan, 17-phenethyl-4,5α-epoxy-14β-acetoxy-6β-(N-isobutyl-3-trifluoromethylcinnamamido)morphinan, 17-phenethyl-4,5α-epoxy-14β-acetoxy-6β-[N-isobutyl-trans-3-(3-furyl)acrylamido]morphinan, 17-phenethyl-4,5α-epoxy-14β-acetoxy-6β-(N-isobutyl-4-trifluoromethylcinnamamido)morphinan, 17-phenethyl-4,5α-epoxy-14β-acetoxy-6β-(N-isobutyl-3-phenylpropiolamido)morphinan, 17-cyclopropylmethyl-4,5α-epoxy-3-methoxy-14β-hydroxy-6β-(N-isobutyl-3-trifluoromethylcinnamamido)morphinan, 17-cyclopropylmethyl-4,5α-epoxy-3-methoxy-14β-hydroxy-6β-[N-isobutyl-trans-3-(3-furyl)acrylamido]morphinan, 17-cyclopropylmethyl-4,5α-epoxy-3-methoxy-14β-hydroxy-6β-(N-isobutyl-4-trifluoromethylcinnamamido)morphinan, 17-cyclopropylmethyl-4,5α-epoxy-3-methoxy-14β-hydroxy-6β-(N-isobutyl-3-phenylpropiolamido)morphinan, 17-allyl-4,5α-epoxy-3-methoxy-14β-hydroxy-6β-(N-isobutyl-3-trifluoromethylcinnamamido)morphinan, 17-allyl-4,5α-epoxy-3-methoxy-14β-hydroxy-6β-[N-isobutyl-trans-3-(3-furyl)acrylamido]morphinan, 17-allyl-4,5α-epoxy-3-methoxy-14β-hydroxy-6β-(N-isobutyl-4-trifluoromethylcinnamamido)morphinan, 17-allyl-4,5α-epoxy-3-methoxy-14β-hydroxy-6β-(N-isobutyl-3-phenylpropiolamido)morphinan, 17-methyl-4,5α-epoxy-3-methoxy-14β-hydroxy-6β-(N-isobutyl-3-trifluoromethylcinnamamido)morphinan, 17-methyl-4,5α-epoxy-3-methoxy-14β-hydroxy-6β-[N-isobutyl-trans-3-(3-furyl)acrylamido]morphinan, 17-methyl-4,5α-epoxy-3-methoxy-14β-hydroxy-6β-(N-isobutyl-4-trifluoromethylcinnamamido)morphinan, 17-methyl-4,5α-epoxy-3-methoxy-14β-hydroxy-6β-(N-isobutyl-3-phenylpropiolamido)morphinan, 17-phenethyl-4,5α-epoxy-3-methoxy-14β-hydroxy-6β-(N-isobutyl-3-trifluoromethylcinnamamido)morphinan, 17-phenethyl-4,5α-epoxy-3-methoxy-14β-hydroxy-6β-[N-isobutyl-trans-3-(3-furyl)acrylamido]morphinan, 17-phenethyl-4,5α-epoxy-3-methoxy-14β-hydroxy-6β-(N-isobutyl-4-trifluoromethylcinnamamido)morphinan, 17-phenethyl-4,5α-epoxy-3-methoxy-14β-hydroxy-6β-(N-isobutyl-3-phenylpropiolamido)morphinan, 17-cyclopropylmethyl-4,5α-epoxy-3-methoxy-14β-acetoxy-6β-(N-isobutyl-3-trifluoromethylcinnamamido)morphinan, 17-cyclopropylmethyl-4,5α-epoxy-3-methoxy-14β-acetoxy-6β-[N-isobutyl-trans-3-(3-furyl)acrylamido]morphinan, 17-cyclopropylmethyl-4,5α-epoxy-3-methoxy-14β-acetoxy-6β-(N-isobutyl-4-trifluoromethylcinnamamido)morphinan, 17-cyclopropylmethyl-4,5α-epoxy-3-methoxy-14β-acetoxy-6β-(N-isobutyl-3-phenylpropiolamido)morphinan, 17-allyl-4,5α-epoxy-3-methoxy-14β-acetoxy-6β-(N-isobutyl-3-trifluoromethylcinnamamido)morphinan, 17-allyl-4,5α-epoxy-3-methoxy-14β-acetoxy-6β-[N-isobutyl-trans-3-(3-furyl)acrylamido]morphinan, 17-allyl-4,5α-epoxy-3-methoxy-14β-acetoxy-6β-(N-isobutyl-4-trifluoromethylcinnamamido)morphinan, 17-allyl-4,5α-epoxy-3-methoxy-14β-acetoxy-6β-(N-isobutyl-3-phenylpropiolamido)morphinan, 17-methyl-4,5α-epoxy-3-methoxy-14β-acetoxy-6β-(N-isobutyl-3-trifluoromethylcinnamamido)morphinan, 17-methyl-4,5α-epoxy-3-methoxy-14β-acetoxy-6β-[N-isobutyl-trans-3-(3-furyl)acrylamido]morphinan,
17-methyl-4,5α-epoxy-3-methoxy-14β-acetoxy-6β-(N-isobutyl-4-trifluoromethylcinnamamido)morphinan, 17-methyl-4,5α-epoxy-3-methoxy-14β-acetoxy-6β-(N-isobutyl-3-phenylpropiolamido)morphinan, 17-phenethyl-4,5α-epoxy-3-methoxy-14β-acetoxy-6β-(N-isobutyl-3-trifluoromethylcinnamamido)morphinan, 17-phenethyl-4,5α-epoxy-3-methoxy-14β-acetoxy-6β-[N-isobutyl-trans-3-(3-furyl)acrylamido]morphinan, 17-phenethyl-4,5α-epoxy-3-methoxy-14β-acetoxy-6β-(N-isobutyl-4-trifluoromethylcinnamamido)morphinan, 17-phenethyl-4,5α-epoxy-3-methoxy-14β-acetoxy-6β-(N-isobutyl-3-phenylpropiolamido)morphinan, 17-cyclopropylmethyl-4,5α-epoxy-3-acetoxy-14β-hydroxy-6β-(N-isobutyl-3-trifluoromethylcinnamamido)morphinan, 17-cyclopropylmethyl-4,5α-epoxy-3-acetoxy-14β-hydroxy-6β-[N-isobutyl-trans-3-(3-furyl)acrylamido] morphinan, 17-cyclopropylmethyl-4,5α-epoxy-3-acetoxy-14β-hydroxy-6β-(N-isobutyl-4-trifluoromethylcinnamamido)morphinan, 17-cyclopropylmethyl-4,5α-epoxy-3-acetoxy-14β-hydroxy-6β-(N-isobutyl-3-phenylpropiolamido) morphinan, 17-allyl-4,5α-epoxy-3-acetoxy-14β-hydroxy-6β-(N-isobutyl-3-trifluoromethylcinnamamido)morphinan, 17-allyl-4,5α-epoxy-3-acetoxy-14β-hydroxy-6β-[N-isobutyl-trans-3-(3-furyl)acrylamido]morphinan, 17-allyl-4,5α-epoxy-3-acetoxy-14β-hydroxy-6β-(N-isobutyl-4-trifluoromethylcinnamamido)morphinan, 17-allyl-4,5α-epoxy-3-acetoxy-14β-hydroxy-6β-(N-isobutyl-3-phenylpropiolamido)morphinan, 17-methyl-4,5α-epoxy-3-acetoxy-14β-hydroxy-6β-(N-isobutyl-3-trifluoromethylcinnamamido)morphinan, 17-methyl-4,5α-epoxy-3-acetoxy-14β-hydroxy-6β-[N-isobutyl-trans-3-(3-furyl)acrylamido]morphinan, 17-methyl-4,5α-epoxy-3-acetoxy-14β-hydroxy-6β-(N-isobutyl-4-trifluoromethylcinnamamido) morphinan, 17-methyl-4,5α-epoxy-3-acetoxy-14β-hydroxy-6β-(N-isobutyl-3-phenylpropiolamido) morphinan, 17-phenethyl-4,5α-epoxy-3-acetoxy-14β-hydroxy-6β-(N-isobutyl-3-trifluoromethylcinnamamido)morphinan, 17-phenethyl-4,5α-epoxy-3-acetoxy-14β-hydroxy-6β-[N-isobutyl-trans-3-(3-furyl)acrylamido]morphinan, 17-phenethyl-4,5α-epoxy-3-acetoxy-14β-hydroxy-6β-(N-isobutyl-4-trifluoromethylcinnamamido)morphinan, 17-phenethyl-4,5α-epoxy-3-acetoxy-14β-hydroxy-6β-(N-isobutyl-3-phenylpropiolamido)morphinan, 17-cyclopropylmethyl-4,5α-epoxy-3,14β-diacetoxy-6β-(N-isobutyl-3-trifluoromethylcinnamamido)morphinan, 17-cyclopropylmethyl-4,5α-epoxy-3,14β-diacetoxy-6β-[N-isobutyl-trans-3-(3-furyl)acrylamido]morphinan, 17-cyclopropylmethyl-4,5α-epoxy-3,14β-diacetoxy-6β-(N-isobutyl-4-trifluoromethylcinnamamido)morphinan, 17-cyclopropylmethyl-4,5α-epoxy-3,14β-diacetoxy-6β-(N-isobutyl-3-phenylpropiolamido)morphinan, 17-allyl-4,5α-epoxy-3,14β-diacetoxy-6β-(N-isobutyl-3-trifluoromethylcinnamamido)morphinan, 17-allyl-4,5α-epoxy-3,14β-diacetoxy-6β-[N-isobutyl-trans-3-(3-furyl)acrylamido]morphinan, 17-allyl-4,5α-epoxy-3,14β-diacetoxy-6β-(N-isobutyl-4-trifluoromethylcinnamamido)morphinan, 17-allyl-4,5α-epoxy-3,14β-diacetoxy-6β-(N-isobutyl-3-phenylpropiolamido)morphinan, 17-methyl-4,5α-epoxy-3,14β-diacetoxy-6β-(N-isobutyl-3-trifluoromethylcinnamamido)morphinan, 17-methyl-4,5α-epoxy-3,14β-diacetoxy-6β-[N-isobutyl-trans-3-(3-furyl)acrylamido]morphinan, 17-methyl-4,5α-epoxy-3,14β-diacetoxy-6β-(N-isobutyl-4-trifluoromethylcinnamamido)morphinan, 17-methyl-4,5α-epoxy-3,14β-diacetoxy-6β-(N-isobutyl-3-phenylpropiolamido)morphinan, 17-phenethyl-4,5α-epoxy-3,14β-diacetoxy-6β-(N-isobutyl-3-trifluoromethylcinnamamido)morphinan, 17-phenethyl-4,5α-epoxy-3,14β-diacetoxy-6β-[N-isobutyl-trans-3-(3-furyl)acrylamido]morphinan, 17-phenethyl-4,5α-epoxy-3,14β-diacetoxy-6β-(N-isobutyl-4-trifluoromethylcinnamamido)morphinan, 17-phenethyl-4,5α-epoxy-3,14β-diacetoxy-6β-(N-isobutyl-3-phenylpropiolamido)morphinan, 17-cyclopropylmethyl-4,5α-epoxy-3,14β-dihydroxy-6α-(N-methyl-3-cyclohexylpropionamido)morphinan, 17-allyl-4,5α-epoxy-3,14β-dihydroxy-6α-(N-methyl-3-cyclohexylpropionamido)morphinan, 17-cyclopropylmethyl-4,5α-epoxy-3,14β-dihydroxy-6β-(N-methyl-3-cyclohexylpropionamido)morphinan, 17-allyl-4,5α-epoxy-3,14β-dihydroxy-6β-(N-methyl-3-cyclohexylpropionamido)morphinan, 17-cyclopropylmethyl-4,5α-epoxy-3,14β-dihydroxy-6α-(N-methylbutyloxycarbamido)morphinan, 17-allyl-4,5α-epoxy-3,14β-dihydroxy-6α-(N-methylbutyloxycarbamido)morphinan, 17-cyclopropylmethyl-4,5α-epoxy-3,14β-dihydroxy-6β-(N-methylbutyloxycarbamido)morphinan, 17-allyl-4,5α-epoxy-3,14β-dihydroxy-6β-(N-methylbutyloxycarbamido)morphinan, 17-cyclopropylmethyl-4,5α-epoxy-3,14β-dihydroxy-6α-(N-methyl-3-isothiocyanatophenylacetamido)morphinan, 17-allyl-4,5α-epoxy-3,14β-dihydroxy-6α-(N-methyl-3-isothiocyanatophenylacetamido)morphinan, 17-cyclopropylmethyl-4,5α-epoxy-3,14β-dihydroxy-6β-(N-methyl-3-isothiocyanatophenylacetamido)morphinan, 17-allyl-4,5α-epoxy-3,14β-dihydroxy-6β-(N-methyl-3-isothiocyanatophenylacetamido)morphinan, 17-cyclopropylmethyl-4,5α-epoxy-3,14β-dihydroxy-6α-(N-methyl-2-hexenamido)morphinan, 17-allyl-4,5α-epoxy-3,14β-dihydroxy-6α-(N-methyl-2-hexenamido)morphinan, 17-cyclopropylmethyl-4,5α-epoxy-3,14β-dihydroxy-6β-(N-methyl-2-hexenamido)morphinan, 17-allyl-4,5α-epoxy-3,14β-dihydroxy-6β-(N-methyl-2-hexenamido)morphinan, 17-cyclopropylmethyl-4,5α-epoxy-3,14β-dihydroxy-6α-(N-methyl-3-fluorocinnamamido)morphinan, 17-allyl-4,5α-epoxy-3,14β-dihydroxy-6α-(N-methyl-3-fluorocinnamamido)morphinan, 17-cyclopropylmethyl-4,5α-epoxy-3,14β-dihydroxy-6β-(N-methyl-3-fluorocinnamamido)morphinan, 17-allyl-4,5α-epoxy-3,14β-dihydroxy-6β-(N-methyl-3-fluorocinnamamido)morphinan, 17-cyclopropylmethyl-4,5α-epoxy-3,14β-dihydroxy-6α-(N-methyl-3-methoxycinnamamido)morphinan, 17-allyl-4,5α-epoxy-3,14β-dihydroxy-6α-(N-methyl-3-methoxycinnamamido)morphinan, 17-cyclopropylmethyl-4,5α-epoxy-3,14β-dihydroxy-6β-(N-methyl-3-methoxycinnamamido)morphinan, 17-allyl-4,5α-epoxy-3,14β-dihydroxy-6β-(N-methyl-3-methoxycinnamamido)morphinan, 17-cyclopropylmethyl-4,5α-epoxy-3,14β-dihydroxy-6α-(N-methyl-2-cyclopentylpropionamido)morphinan,
17-allyl-4,5α-epoxy-3,14β-dihydroxy-6α-(N-methyl-2-cyclopentylpropionamido)morphinan,
17-cyclopropylmethyl-4,5α-epoxy-3,14β-dihydroxy-6β-(N-methyl-2-cyclopentylpropionamido)morphinan,
17-allyl-4,5α-epoxy-3,14β-dihydroxy-6β-(N-methyl-2-cyclopentylpropionamido)morphinan, 17-cyclopropylmethyl-4,5α-epoxy-3,14β-dihydroxy-6α-(N-methyl-2-naphthamido)morphinan, 17-allyl-4,5α-epoxy-3,14β-dihydroxy-6α-(N-methyl-2-naphthamido)morphinan, 17-cyclopropylmethyl-4,5α-epoxy-3,14β-dihydroxy-6β-(N-methyl-2-naphthamido)morphinan, 17-allyl-4,5α-epoxy-3,14β-dihydroxy-6β-(N-methyl-2-naphthamido)morphinan, 17-cyclopropylmethyl-4,5α-epoxy-3,14β-dihydroxy-6α-(N-methyl-3-nitrocinnamamido)morphinan, 17-allyl-4,5α-epoxy-3,14β-dihydroxy-6α-(N-methyl-3-nitrocinnamamido)morphinan, 17-cyclopropylmethyl-4,5α-epoxy-3,14β-dihydroxy-6β-(N-methyl-3-nitrocinnamamido)morphinan, 17-allyl-4,5α-epoxy-3,14β-dihydroxy-6β-(N-methyl-3-nitrocinnamamido)morphinan, 17-cyclopropylmethyl-4,5α-epoxy-3,14β-dihydroxy-6α-(N-methyl-2-methoxyethoxycarbamido)morphinan, 17-allyl-4,5α-epoxy-3,14β-dihydroxy-6α-(N-methyl-2-methoxyethoxycarbamido)morphinan, 17-cyclopropylmethyl-4,5α-epoxy-3,14β-dihydroxy-6β-(N-methyl-2-methoxyethoxycarbamido)morphinan, 17-allyl-4,5α-epoxy-3,14β-dihydroxy-6β-(N-methyl-2-methoxyethoxycarbamido)morphinan, 17-cyclopropylmethyl-4,5α-epoxy-3,14β-dihydroxy-6α-(N-methyl-trans-3-cyclohexylacrylamido)morphinan, 17-allyl-4,5α-epoxy-3,14β-dihydroxy-6α-(N-methyl-trans-3-cyclohexylacrylamido)morphinan, 17-cyclopropylmethyl-4,5α-epoxy-3,14β-dihydroxy-6β-(N-methyl-trans-3-cyclohexylacrylamido)morphinan, 17-allyl-4,5α-epoxy-3,14β-dihydroxy-6β-(N-methyl-trans-3-cyclohexylacrylamido)morphinan, 17-cyclopropylmethyl-4,5α-epoxy-3,14β-dihydroxy-6α-(N-methylbenzoylacetamido)morphinan, 17-allyl-4,5α-epoxy-3,14β-dihydroxy-6α-(N-methylbenzoylacetamido)morphinan, 17-cyclopropylmethyl-4,5α-epoxy-3,14β-dihydroxy-6β-(N-methylbenzoylacetamido)morphinan, 17-allyl-4,5α-epoxy-3,14β-dihydroxy-6β-(N-methylbenzoylacetamido)morphinan, 17-cyclopropylmethyl-4,5α-epoxy-3,14β-dihydroxy-6α-[N-methyl-trans-3-(2-furyl)acrylamido]morphinan, 17-allyl-4,5α-epoxy-3,14β-dihydroxy-6α-[N-methyl-trans-3-(2-furyl)acrylamido]morphinan, 17-cyclopropylmethyl-4,5α-epoxy-3,14β-dihydroxy-6β-[N-methyl-trans-3-(2-furyl)acrylamido]morphinan, 17-allyl-4,5α-epoxy-3,14β-dihydroxy-6β-[N-methyl-trans-3-(2-furyl)acrylamido]morphinan, 17-cyclopropylmethyl-4,5α-epoxy-3,14β-dihydroxy-6α-(N-methyl-2-trifluoromethylcinnamamido)morphinan, 17-allyl-4,5α-epoxy-3,14β-dihydroxy-6α-(N-methyl-2-trifluoromethylcinnamamido)morphinan, 17-cyclopropylmethyl-4,5α-epoxy-3,14β-dihydroxy-6β-(N-methyl-2-trifluoromethylcinnamamido)morphinan, 17-allyl-4,5α-epoxy-3,14β-dihydroxy-6β-(N-methyl-2-trifluoromethylcinnamamido)morphinan, 17-cyclopropylmethyl-4,5α-epoxy-3,14β-dihydroxy-6α-(N-methyl-3-isothiocyanatocinnamamido)morphinan, 17-allyl-4,5α-epoxy-3,14β-dihydroxy-6α-(N-methyl-3-isothiocyanatocinnamamido)morphinan, 17-cyclopropylmethyl-4,5α-epoxy-3,14β-dihydroxy-6β-(N-methyl-3-isothiocyanatocinnamamido)morphinan, 17-allyl-4,5α-epoxy-3,14β-dihydroxy-6β-(N-methyl-3-isothiocyanatocinnamamido)morphinan, 17-cyclopropylmethyl-4,5α-epoxy-3,14β-dihydroxy-6α-(N-methyl-3-methylcinnamamido)morphinan, 17-cyclopropylmethyl-4,5α-epoxy-3,14β-dihydroxy-6α-[N-methyl-3-(4-trifluoromethylphenyl)propiolamido]morphinan, 17-allyl-4,5α-epoxy-3,14β-dihydroxy-6α-(N-methyl-3-methylcinnamamido)morphinan, 17-allyl-4,5α-epoxy-3,14β-dihydroxy-6α-[N-methyl-3-(4-trifluoromethylphenyl)propiolamido]morphinan, 17-methyl-4,5α-epoxy-3,14β-dihydroxy-6α-(N-methyl-3-methylcinnamamido)morphinan, 17-methyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-6α-(N-methyl-3-methylcinnamamido)morphinan, 17-phenethyl-4,5α-epoxy-3,14β-dihydroxy-6α-[N-methyl-3-(4-trifluoromethylphenyl)propiolamido]morphinan, 17-cyclopropylmethyl-4,5α-epoxy-14β-acetoxy-3-hydroxy-6α-(N-methyl-3-methylcinnamamido)morphinan, 17-cyclopropylmethyl-4,5α-epoxy-14β-acetoxy-3-hydroxy-6α-[N-methyl-3-(4-trifluoromethylphenyl)propiolamido]morphinan, 17-allyl-4,5α-epoxy-14β-acetoxy-3-hydroxy-6α-(N-methyl-3-methylcinnamamido)morphinan, 17-allyl-4,5α-epoxy-14β-acetoxy-3-hydroxy-6α-[N-methyl-3-(4-trifluoromethylphenyl)propiolamido]morphinan, 17-methyl-4,5α-epoxy-14β-acetoxy-3-hydroxy-6α-(N-methyl-3-methylcinnamamido)morphinan, 17-methyl-4,5α-epoxy-14β-acetoxy-3-hydroxy-6α-[N-methyl-3-(4-trifluoromethylphenyl)propiolamido]morphinan, 17-phenethyl-4,5α-epoxy-14β-acetoxy-3-hydroxy-6α-(N-methyl-3-methylcinnamamido)morphinan, 17-phenethyl-4,5α-epoxy-14β-acetoxy-3-hydroxy-6α-[N-methyl-3-(4-trifluoromethylphenyl)propiolamido]morphinan, 17-cyclopropylmethyl-4,5α-epoxy-14β-hydroxy-6α-(N-methyl-3-methylcinnamamido)morphinan, 17-cyclopropylmethyl-4,5α-epoxy-14β-hydroxy-6α-[N-methyl-3-(4-trifluoromethylphenyl)propiolamido]morphinan, 17-allyl-4,5α-epoxy-14β-hydroxy-6α-(N-methyl-3-methylcinnamamido)morphinan, 17-allyl-4,5α-epoxy-14β-hydroxy-6α-[N-methyl-3-(4-trifluoromethylphenyl)propiolamido]morphinan, 17-methyl-4,5α-epoxy-14β-hydroxy-6α-(N-methyl-3-methylcinnamamido)morphinan, 17-methyl-4,5α-epoxy-14β-hydroxy-6α-[N-methyl-3-(4-trifluoromethylphenyl)propiolamido]morphinan, 17-phenethyl-4,5α-epoxy-14β-hydroxy-6α-(N-methyl-3-methylcinnamamido)morphinan, 17-phenethyl-4,5α-epoxy-14β-hydroxy-6α-[N-methyl-3-(4-trifluoromethylphenyl)propiolamido]morphinan, 17-cyclopropylmethyl-4,5α-epoxy-14β-acetoxy-6α-(N-methyl-3-methylcinnamamido)morphinan, 17-cyclopropylmethyl-4,5α-epoxy-14β-acetoxy-6α-[N-methyl-3-(4-trifluoromethylphenyl)propiolamido]morphinan, 17-allyl-4,5α-epoxy-14β-acetoxy-6α-(N-methyl-3-methylcinnamamido)morphinan, 17-allyl-4,5α-epoxy-14β-acetoxy-6α-[N-methyl-3-(4-trifluoromethylphenyl)propiolamido]morphinan, 17-methyl-4,5α-epoxy-14β-acetoxy-6α-(N-methyl-3-methylcinnamamido)morphinan, 17-methyl-4,5α- epoxy-14β-acetoxy-6α-[N-methyl-3-(4-trifluoromethylphenyl)propiolamido]morphinan, 17-phenethyl-4,5α-epoxy-14β-acetoxy-6α-(N-methyl-3-methylcinnamamido)morphinan, 17-phenethyl-4,5α-epoxy-14β-acetoxy-6α-[N-methyl-3-(4-trifluoromethylphenyl)propiolamido]morphinan, 17-cyclopropylmethyl-4,5α-epoxy-14β-hydroxy-3-methoxy-6α-(N-methyl-3-methylcinnamamido)morphinan, 17-cyclopropylmethyl-4,5α-epoxy-14β-hydroxy-3-methoxy-6α-[N-methyl-3-(4-trifluoromethylphenyl)propiolamido]morphinan, 17-allyl-4,5α-epoxy-14β-hydroxy-3-methoxy-6α-(N-methyl-3-methylcinnamamido)morphinan, 17-allyl-4,5α-epoxy-14β-hydroxy-3-methoxy-6α-[N-methyl-3-(4-trifluoromethylphenyl)propiolamido]morphinan, 17-methyl-4,5α-epoxy-14β-hydroxy-3-methoxy-6α-(N-methyl-3-methylcinnamamido)morphinan, 17-methyl-4,5α-epoxy-14β-hydroxy-3-methoxy-6α-[N-methyl-3-(4-trifluoromethylphenyl)propiolamido]morphinan, 17-phenethyl-4,5α-epoxy-14β-hydroxy-3-methoxy-6α-(N-methyl-3-methylcinnamamido)morphinan, 17-phenethyl-4,5α-epoxy-14β-hydroxy-3-methoxy-6α-[N-methyl-3-(4-trifluoromethylphenyl)propiolamido]morphinan, 17-cyclopropylmethyl-4,5α-epoxy-14β-acetoxy-3-methoxy-6α-(N-methyl-3-methylcinnamamido)morphinan, 17-cyclopropylmethyl-4,5α-epoxy-14β-acetoxy-3-methoxy-6α-[N-methyl-3-(4-trifluoromethylphenyl)propiolamido]morphinan, 17-allyl-4,5α-epoxy-14β-acetoxy-3-methoxy-6α-(N-methyl-3-methylcinnamamido)morphinan, 17-allyl-4,5α-epoxy-14β-acetoxy-3-methoxy-6α-[N-methyl-3-(4-trifluoromethylphenyl)propiolamido]morphinan, 17-methyl-4,5α-epoxy-14β-acetoxy-3-methoxy-6α-(N-methyl-3-methylcinnamamido)morphinan, 17-methyl-4,5α-epoxy-14β-acetoxy-3-methoxy-6α-[N-methyl-3-(4-trifluoromethylphenyl)propiolamido]morphinan, 17-phenethyl-4,5α-epoxy-14β-acetoxy-3-methoxy-6α-(N-methyl-3-methylcinnamamido)morphinan, 17-phenethyl-4,5α-epoxy-14β-acetoxy-3-methoxy-6α-[N-methyl-3-(4-trifluoromethylphenyl)propiolamido]morphinan, 17-cyclopropylmethyl-4,5α-epoxy-14β-hydroxy-3-acetoxy-6α-(N-methyl-3-methylcinnamamido)morphinan, 17-cyclopropylmethyl-4,5α-epoxy-14β-hydroxy-3-acetoxy-6α-[N-methyl-3-(4-trifluoromethylphenyl)propiolamido]morphinan, 17-allyl-4,5α-epoxy-14β-hydroxy-3-acetoxy-6α-(N-methyl-3-methylcinnamamido)morphinan, 17-allyl-4,5α-epoxy-14β-hydroxy-3-acetoxy-6α-[N-methyl-3-(4-trifluoromethylphenyl)propiolamido]morphinan, 17-methyl-4,5α-epoxy-14β-hydroxy-3-acetoxy-6α-(N-methyl-3-methylcinnamamido)morphinan, 17-methyl-4,5α-epoxy-14β-hydroxy-3-acetoxy-6α-[N-methyl-3-(4-trifluoromethyl-phenyl)propiolamido]morphinan, 17-phenethyl-4,5α-epoxy-14β-hydroxy-3-acetoxy-6α-(N-methyl-3-methylcinnamamido)morphinan, 17-phenethyl-4,5α-epoxy-14β-hydroxy-3-acetoxy-6α-[N-methyl-3-(4-trifluoromethylphenyl)propiolamido]morphinan, 17-cyclopropylmethyl-4,5α-epoxy-3,14β-diacetoxy-6α-(N-methyl-3-methylcinnamamido)morphinan, 17-cyclopropylmethyl-4,5α-epoxy-3,14β-diacetoxy-6α-[N-methyl-3-(4-trifluoromethylphenyl)propiolamido]morphinan, 17-allyl-4,5α-epoxy-3,14β-diacetoxy-6α-(N-methyl-3-methylcinnamamido)morphinan, 17-allyl-4,5α-epoxy-3,14β-diacetoxy-6α-[N-methyl-3-(4-trifluoromethylphenyl)propiolamido]morphinan, 17-methyl-4,5α-epoxy-3,14β-diacetoxy-6α-(N-methyl-3-methylcinnamamido)morphinan, 17-methyl-4,5α-epoxy-3,14β-diacetoxy-6α-[N-methyl-3-(4-trifluoromethylphenyl)propiolamido]morphinan, 17-phenethyl-4,5α-epoxy-3,14β-diacetoxy-6α-(N-methyl-3-methylcinnamamido)morphinan, 17-phenethyl-4,5α-epoxy-3,14β-diacetoxy-6α-[N-methyl-3-(4-trifluoromethylphenyl)propiolamido]morphinan, 17-cyclopropylmethyl-4,5α-epoxy-3,14β-dihydroxy-6α-(N-isobutyl-3-methylcinnamamido)morphinan, 17-cyclopropylmethyl-4,5α-epoxy-3,14α-dihydroxy-6α-[N-isobutyl-3-(4-trifluoromethylphenyl)propiolamido]morphinan, 17-allyl-4,5α-epoxy-3,14β-dihydroxy-6α-(N-isobutyl-3-methylcinnamamido)morphinan, 17-allyl-4,5α-epoxy-3,14β-dihydroxy-6α-[N-isobutyl-3-(4-trifluoromethylphenyl)propiolamido]morphinan, 17-methyl-4,5α-epoxy-3,14β-dihydroxy-6α-(N-isobutyl-3-methylcinnamamido)morphinan, 17-methyl-4,5α-epoxy-3,14β-dihydroxy-6α-[N-isobutyl-3-(4-trifluoromethylphenyl)propiolamido]morphinan, 17-phenethyl-4,5α-epoxy-3,14β-dihydroxy-6α-(N-isobutyl-3-methylcinnamamido)morphinan, 17-phenethyl-4,5α-epoxy-3,14β-dihydroxy-6α-[N-isobutyl-3-(4-trifluoromethylphenyl)propiolamido]morphinan, 17-cyclopropylmethyl-4,5α-epoxy-14β-acetoxy-3-hydroxy-6α-(N-isobutyl-3-methylcinnamamido)morphinan, 17-cyclopropylmethyl-4,5α-epoxy-14β-acetoxy-3-hydroxy-6α-[N-isobutyl-3-(4-trifluoromethylphenyl)propiolamido]morphinan, 17-allyl-4,5α-epoxy-14β-acetoxy-3-hydroxy-6α-(N-isobutyl-3-methylcinnamamido)morphinan, 17-allyl-4,5α-epoxy-14β-acetoxy-3-hydroxy-6α-[N-isobutyl-3-(4-trifluoromethylphenyl)propiolamido]morphinan, 17-methyl-4,5α-epoxy-14β-acetoxy-3-hydroxy-6α-(N-isobutyl-3-methylcinnamamido)morphinan, 17-methyl-4,5α-epoxy-14β-acetoxy-3-hydroxy-6α-[N-isobutyl-3-(4-trifluoromethylphenyl)propiolamido]morphinan, 17-phenethyl-4,5α-epoxy-14β-acetoxy-3-hydroxy-6α-(N-isobutyl-3-methylcinnamamido)morphinan, 17-phenethyl-4,5α-epoxy-14β-acetoxy-3-hydroxy-6α-[N-isobutyl-3-(4-trifluoromethylphenyl)propiolamido]morphinan, 17-cyclopropylmethyl-4,5α-epoxy-14β-hydroxy-6α-(N-isobutyl-3-methylcinnamamido)morphinan, 17-cyclopropylmethyl-4,5α-epoxy-14β-hydroxy-6α-[N-isobutyl-3-(4-trifluoromethylphenyl)propiolamido]morphinan, 17-allyl-4,5α-epoxy-14β-hydroxy-6α-(N-isobutyl-3-methylcinnamamido)morphinan, 17-allyl-4,5α-epoxy-14β-hydroxy-6α-[N-isobutyl-3-(4-trifluoromethylphenyl)propiolamido]morphinan, 17-methyl-4,5α-epoxy-14β-hydroxy-6α-(N-isobutyl-3-methylcinnamamido)morphinan, 17-methyl-4,5α-epoxy-14β-hydroxy-6α-[N-isobutyl-3-(4-trifluoromethylphenyl)propiolamido]morphinan, 17-phenethyl-4,5α-epoxy-14β-hydroxy-6α-(N-isobutyl-3-methylcinnamamido)morphinan, 17-phenethyl-4,5α-epoxy-14β-hydroxy-6α-[N-isobutyl-3-(4-trifluoromethylphenyl)propiolamido]morphinan, 17-cyclopropylmethyl-4,5α-epoxy-14β-acetoxy-6α-(N-isobutyl-3-methylcinnamamido)morphinan, 17-cyclopropylmethyl-4,5α-epoxy-14β-acetoxy-6α-[N-isobutyl-3-(4-trifluoromethylphenyl)propiolamido]

morphinan, 17-allyl-4,5α-epoxy-14β-acetoxy-6α-(N-isobutyl-3-methylcinnamamido)morphinan, 17-allyl-4,5α-epoxy-14β-acetoxy-6α-[N-isobutyl-3-(4-trifluoromethylphenyl)propiolamido]morphinan, 17-methyl-4,5α-epoxy-14β-acetoxy-6α-(N-isobutyl-3-methylcinnamamido)morphinan, 17-methyl-4,5α-epoxy-14β-acetoxy-6α-[N-isobutyl-3-(4-trifluoromethylphenyl)propiolamido]morphinan, 17-phenethyl-4,5α-epoxy-14β-acetoxy-6α-(N-isobutyl-3-methylcinnamamido)morphinan, 17-phenethyl-4,5α-epoxy-14β-acetoxy-6α-[N-isobutyl-3-(4-trifluoromethylphenyl)propiolamido]morphinan, 17-cyclopropylmethyl-4,5α-epoxy-14β-hydroxy-3-methoxy-6α-(N-isobutyl-3-methylcinnamamido)morphinan, 17-cyclopropylmethyl-4,5α-epoxy-14β-hydroxy-3-methoxy-6α-[N-isobutyl-3-(4-trifluoromethylphenyl)propiolamido]morphinan, 17-allyl-4,5α-epoxy-14β-hydroxy-3-methoxy-6α-(N-isobutyl-3-methylcinnamamido)morphinan, 17-allyl-4,5α-epoxy-14β-hydroxy-3-methoxy-6α-[N-isobutyl-3-(4-trifluoromethylphenyl)propiolamido]morphinan, 17-methyl-4,5α-epoxy-14β-hydroxy-3-methoxy-6α-(N-isobutyl-3-methylcinnamamido)morphinan, 17-methyl-4,5α-epoxy-14β-hydroxy-3-methoxy-6α-[N-isobutyl-3-(4-trifluoromethylphenyl)propiolamido]morphinan, 17-phenethyl-4,5α-epoxy-14β-hydroxy-3-methoxy-6α-(N-isobutyl-3-methylcinnamamido)morphinan, 17-phenethyl-4,5α-epoxy-14β-hydroxy-3-methoxy-6α-[N-isobutyl-3-(4-trifluoromethylphenyl)propiolamido]morphinan, 17-cyclopropylmethyl-4,5α-epoxy-14β-acetoxy-3-methoxy-6α-(N-isobutyl-3-methylcinnamamido)morphinan, 17-cyclopropylmethyl-4,5α-epoxy-14β-acetoxy-3-methoxy-6α-[N-isobutyl-3-(4-trifluoromethylphenyl)propiolamido]morphinan, 17-allyl-4,5α-epoxy-14β-acetoxy-3-methoxy-6α-(N-isobutyl-3-methylcinnamamido)morphinan, 17-allyl-4,5α-epoxy-14β-acetoxy-3-methoxy-6α-[N-isobutyl-3-(4-trifluoromethylphenyl)propiolamido]morphinan, 17-methyl-4,5α-epoxy-14β-acetoxy-3-methoxy-6α-(N-isobutyl-3-methylcinnamamido)morphinan, 17-methyl-4,5α-epoxy-14β-acetoxy-3-methoxy-6α-[N-isobutyl-3-(4-trifluoromethylphenyl)propiolamido]morphinan, 17-phenethyl-4,5α-epoxy-14β-acetoxy-3-methoxy-6α-(N-isobutyl-3-methylcinnamamido)morphinan, 17-phenethyl-4,5α-epoxy-14β-acetoxy-3-methoxy-6α-[N-isobutyl-3-(4-trifluoromethylphenyl)propiolamido]morphinan, 17-cyclopropylmethyl-4,5α-epoxy-14β-hydroxy-3-acetoxy-6α-(N-isobutyl-3-methylcinnamamido)morphinan, 17-cyclopropylmethyl-4,5α-epoxy-14β-hydroxy-3-acetoxy-6α-[N-isobutyl-3-(4-trifluoromethylphenyl)propiolamido]morphinan, 17-allyl-4,5α-epoxy-14β-hydroxy-3-acetoxy-6α-(N-isobutyl-3-methylcinnamamido)morphinan, 17-allyl-4,5α-epoxy-14β-hydroxy-3-acetoxy-6α-[N-isobutyl-3-(4-trifluoromethylphenyl)propiolamido]morphinan, 17-methyl-4,5α-epoxy-14β-hydroxy-3-acetoxy-6α-(N-isobutyl-3-methylcinnamamido)morphinan, 17-methyl-4,5α-epoxy-14β-hydroxy-3-acetoxy-6α-[N-isobutyl-3-(4-trifluoromethylphenyl)propiolamido]morphinan, 17-phenethyl-4,5α-epoxy-14β-hydroxy-3-acetoxy-6α-(N-isobutyl-3-methylcinnamamido)morphinan, 17-phenethyl-4,5α-epoxy-14β-hydroxy-3-acetoxy-6α-[N-isobutyl-3-(4-trifluoromethylphenyl)propiolamido]morphinan, 17-cyclopropylmethyl-4,5α-epoxy-3,14β-diacetoxy-6α-(N-isobutyl-3-methylcinnamamido)morphinan, 17-cyclopropylmethyl-4,5α-epoxy-3,14β-diacetoxy-6α-[N-isobutyl-3-(4-trifluoromethylphenyl)propiolamido]morphinan, 17-allyl-4,5α-epoxy-3,14β-diacetoxy-6α-(N-isobutyl-3-methylcinnamamido)morphinan, 17-allyl-4,5α-epoxy-3,4β-diacetoxy-6α-[N-isobutyl-3-trifluoromethylphenyl)propiolamido]morphinan, 17-methyl-4,5α-epoxy-3,14β-diacetoxy-6α-(N-isobutyl-3-methylcinnamamido)morphinan, 17-methyl-4,5α-epoxy-3,14β-diacetoxy-6α-[N-isobutyl-3-(4-trifluoromethylphenyl)propiolamido]morphinan, 17-phenethyl-4,5α-epoxy-3,14β-diacetoxy-6α-(N-isobutyl-3-methylcinnamamido)morphinan, 17-phenethyl-4,5α-epoxy-3,14β-diacetoxy-6α-[N-isobutyl-3-(4-trifluoromethylphenyl)propiolamido]morphinan, 17-cyclopropylmethyl-4,5α-epoxy-3,14β-dihydroxy-6β-(N-methyl-3-methylcinnamamido)morphinan, 17-cyclopropylmethyl-4,5α-epoxy-3,14β-dihydroxy-6β-[N-methyl-3-(4-trifluoromethylphenyl)propiolamido]morphinan, 17-allyl-4,5α-epoxy-3,14β-dihydroxy-6β-(N-methyl-3-methylcinnamamido)morphinan, 17-allyl-4,5α-epoxy-3,14β-dihydroxy-6β-[N-methyl-3-(4-trifluoromethylphenyl)propiolamido]morphinan, 17-methyl-4,5α-epoxy-3,14β-dihydroxy-6β-(N-methyl-3-methylcinnamamido)morphinan, 17-methyl-4,5α-epoxy-3,14β-dihydroxy-6β-[N-methyl-3-(4-trifluoromethylphenyl)propiolamido]morphinan, 17-phenethyl-4,5α-epoxy-3,14β-dihydroxy-6β-(N-methyl-3-methylcinnamamido)morphinan, 17-phenethyl-4,5α-epoxy-3,14β-dihydroxy-6β-[N-methyl-3-(4-trifluoromethylphenyl)propiolamido]morphinan, 17-cyclopropylmethyl-4,5α-epoxy-14β-acetoxy-3-hydroxy-6β-(N-methyl-3-methylcinnamamido)morphinan, 17-cyclopropylmethyl-4,5α-epoxy-14β-acetoxy-3-hydroxy-6β-[N-methyl-3-(4-trifluoromethylphenyl)propiolamido]morphinan, 17-allyl-4,5α-epoxy-14β-acetoxy-3-hydroxy-6β-(N-methyl-3-methylcinnamamido)morphinan, 17-allyl-4,5α-epoxy-14β-acetoxy-3-hydroxy-6β-[N-methyl-3-(4-trifluoromethylphenyl)propiolamido]morphinan, 17-methyl-4,5α-epoxy-14β-acetoxy-3-hydroxy-6β-(N-methyl-3-methylcinnamamido)morphinan, 17-methyl-4,5α-epoxy-14β-acetoxy-3-hydroxy-6β-[N-methyl-3-(4-trifluoromethylphenyl)propiolamido]morphinan, 17-phenethyl-4,5α-epoxy-14β-acetoxy-3-hydroxy-6β-(N-methyl-3-methylcinnamamido)morphinan, 17-phenethyl-4,5α-epoxy-14β-acetoxy-3-hydroxy-6β-[N-methyl-3-(4-trifluoromethylphenyl)propiolamido]morphinan, 17-cyclopropylmethyl-4,5α-epoxy-14β-hydroxy-6β-(N-methyl-3-methylcinnamamido)morphinan, 17-cyclopropylmethyl-4,5α-epoxy-14β-hydroxy-6β-[N-methyl-3-(4-trifluoromethylphenyl)propiolamido]morphinan, 17-allyl-4,5α-epoxy-14β-hydroxy-6β-(N-methyl-3-methylcinnamamido)morphinan, 17-allyl-4,5α-epoxy-14β-hydroxy-6β-[N-methyl-3-(4-trifluoromethylphenyl)propiolamido]morphinan, 17-methyl-4,5α-epoxy-14β-hydroxy-6β-(N-methyl-3-methylcinnamamido)morphinan, 17-methyl-4,5α-epoxy-14β-hydroxy-6β-[N-methyl-3-(4-trifluoromethylphenyl)propiolamido]morphinan, 17-phenethyl-4,5α-epoxy-14β-hydroxy-6β-(N-methyl-3-methylcinnamamido)morphinan, 17-phenethyl-4,5α-epoxy-14β-hydroxy-6β-[N- methyl-3-(4-trifluoromethylphenyl)propiolamido]morphinan, 17-cyclopropylmethyl-4,5α-epoxy-14β-acetoxy-6α-(N-methyl-3-methylcinnamamido)morphinan, 17-cyclopropylmethyl-4,5α-epoxy-14β-acetoxy-6β-[N-methyl-3-(4-trifluoromethylphenyl)propiolamido]morphinan, 17-allyl-4,5α-epoxy-14β-acetoxy-6β-(N-methyl-3-methylcinnamamido)morphinan, 17-allyl-4,5α-epoxy-14β-acetoxy-6β-[N-methyl-3-(4-trifluoromethylphenyl)propiolamido]morphinan, 17-methyl-4,5α-epoxy-14β-acetoxy-6β-(N-methyl-3-methylcinnamamido)morphinan, 17-methyl-4,5α-epoxy-14β-acetoxy-6β-[N-methyl-3-(4-trifluoromethylphenyl)propiolamido]morphinan, 17-phenethyl-4,5α-epoxy-14β-acetoxy-6β-(N-methyl-3-methylcinnamamido)morphinan, 17-phenethyl-4,5α-epoxy-14β-acetoxy-6β-[N-methyl-3-(4-trifluoromethylphenyl)propiolamido]morphinan, 17-cyclopropylmethyl-4,5α-epoxy-14β-hydroxy-3-methoxy-6β-(N-methyl-3-methylcinnamamido)morphinan, 17-cyclopropylmethyl-4,5α-epoxy-14β-hydroxy-3-methoxy-6β-[N-methyl-3-(4-trifluoromethylphenyl)propiolamido]morphinan, 17-allyl-4,5α-epoxy-14β-hydroxy-3-methoxy-6β-(N-methyl-3-methylcinnamamido)morphinan, 17-allyl-4,5α-epoxy-14β-hydroxy-3-methoxy-6β-[N-methyl-3-(4-trifluoromethylphenyl)propiolamido]morphinan, 17-methyl-4,5α-epoxy-14β-hydroxy-3-methoxy-6β-(N-methyl-3-methylcinnamamido)morphinan, 17-methyl-4,5α-epoxy-14β-hydroxy-3-methoxy-6β-[N-methyl-3-(4-trifluoromethylphenyl)propiolamido]morphinan, 17-phenethyl-4,5α-epoxy-14β-hydroxy-3-methoxy-6β-(N-methyl-3-methylcinnamamido)morphinan, 17-phenethyl-4,5α-epoxy-14β-hydroxy-3-methoxy-6β-[N-methyl-3-(4-trifluoromethylphenyl)propiolamido]morphinan, 17-cyclopropylmethyl-4,5α-epoxy-14β-acetoxy-3-methoxy-6β-(N-methyl-3-methylcinnamamido)morphinan, 17-cyclopropylmethyl-4,5α-epoxy-14β-acetoxy-3-methoxy-6β-[N-methyl-3-(4-trifluoromethylphenyl)propiolamido]morphinan, 17-allyl-4,5α-epoxy-14β-acetoxy-3-methoxy-6β-(N-methyl-3-methylcinnamamido)morphinan, 17-allyl-4,5α-epoxy-14β-acetoxy-3-methoxy-6β-[N-methyl-3-(4-trifluoromethylphenyl)propiolamido]morphinan, 17-methyl-4,5α-epoxy-14β-acetoxy-3-methoxy-6β-(N-methyl-3-methylcinnamamido)morphinan, 17-methyl-4,5α-epoxy-14β-acetoxy-3-methoxy-6β-[N-methyl-3-(4-trifluoromethylphenyl)propiolamido]morphinan, 17-phenethyl-4,5α-epoxy-14β-acetoxy-3-methoxy-6β-(N-methyl-3-methylcinnamamido)morphinan, 17-phenethyl-4,5α-epoxy-14β-acetoxy-3-methoxy-6β-[N-methyl-3-(4-trifluoromethylphenyl)propiolamido]morphinan, 17-cyclopropylmethyl-4,5α-epoxy-14β-hydroxy-3-acetoxy-6β-(N-methyl-3-methylcinnamamido)morphinan, 17-cyclopropylmethyl-4,5α-epoxy-14β-hydroxy-3-acetoxy-6β-[N-methyl-3-(4-trifluoromethylphenyl)propiolamido]morphinan, 17-allyl-4,5α-epoxy-14β-hydroxy-3-acetoxy-6β-(N-methyl-3-methylcinnamamido)morphinan, 17-allyl-4,5α-epoxy-14β-hydroxy-3-acetoxy-6β-[N-methyl-3-(4-trifluoromethylphenyl)propiolamido]morphinan, 17-methyl-4,5α-epoxy-14β-hydroxy-3-acetoxy-6β-(N-methyl-3-methylcinnamamido)morphinan, 17-methyl-4,5α-epoxy-14β-hydroxy-3-acetoxy-6β-[N-methyl-3-(4-trifluoromethylphenyl)propiolamido]morphinan, 17-phenethyl-4,5α-epoxy-14β-hydroxy-3-acetoxy-6β-(N-methyl-3-methylcinnamamido)morphinan, 17-phenethyl-4,5α-epoxy-14β-hydroxy-3-acetoxy-6β-[N-methyl-3-(4-trifluoromethylphenyl)propiolamido]morphinan, 17-cyclopropylmethyl-4,5α-epoxy-3,14β-diacetoxy-6β-(N-methyl-3-methylcinnamamido)morphinan, 17-cyclopropylmethyl-4,5α-epoxy-3,14β-diacetoxy-6β-[N-methyl-3-(4-trifluoromethylphenyl)propiolamido]morphinan, 17-allyl-4,5α-epoxy-3,14β-diacetoxy-6β-(N-methyl-3-methylcinnamamido)morphinan, 17-allyl-4,5α-epoxy-3,14β-diacetoxy-6β-[N-methyl-3-(4-trifluoromethylphenyl)propiolamido]morphinan, 17-methyl-4,5α-epoxy-3,14β-diacetoxy-6β-(N-methyl-3-methylcinnamamido)morphinan, 17-methyl-4,5α-epoxy-3,14β-diacetoxy-6β-[N-methyl-3-(4-trifluoromethylphenyl)propiolamido]morphinan, 17-phenethyl-4,5α-epoxy-3,14β-diacetoxy-6β-(N-methyl-3-methylcinnamamido)morphinan, 17-phenethyl-4,5α-epoxy-3,14β-diacetoxy-6β-[N-methyl-3-(4-trifluoromethylphenyl)propiolamido]morphinan, 17-cyclopropylmethyl-4,5α-epoxy-3,14β-dihydroxy-6β-(N-isobutyl-3-methylcinnamamido)morphinan, 17-cyclopropylmethyl-4,5α-epoxy-3,14β-dihydroxy-6β-[N-isobutyl-3-(4-trifluoromethylphenyl)propiolamido]morphinan, 17-allyl-4,5α-epoxy-3,14β-dihydroxy-6β-(N-isobutyl-3-methylcinnamamido)morphinan, 17-allyl-4,5α-epoxy-3,14β-dihydroxy-6β-[N-isobutyl-3-(4-trifluoromethylphenyl)propiolamido]morphinan, 17-methyl-4,5α-epoxy-3,14β-dihydroxy-6β-(N-isobutyl-3-methylcinnamamido)morphinan, 17-methyl-4,5α-epoxy-3,14β-dihydroxy-6β-[N-isobutyl-3-(4-trifluoromethylphenyl)propiolamido]morphinan, 17-phenethyl-4,5α-epoxy-3,14β-dihydroxy-6β-(N-isobutyl-3-methylcinnamamido)morphinan, 17-phenethyl-4,5α-epoxy-3,14β-dihydroxy-6β-[N-isobutyl-3-(4-trifluoromethylphenyl)propiolamido]morphinan, 17-cyclopropylmethyl-4,5α-epoxy-14β-acetoxy-3-hydroxy-6β-(N-isobutyl-3-methylcinnamamido)morphinan, 17-cyclopropylmethyl-4,5α-epoxy-14β-acetoxy-3-hydroxy-6β-[N-isobutyl-3-(4-trifluoromethylphenyl)propiolamido]morphinan, 17-allyl-4,5α-epoxy-14β-acetoxy-3-hydroxy-6β-(N-isobutyl-3-methylcinnamamido)morphinan, 17-allyl-4,5α-epoxy-14β-acetoxy-3-hydroxy-6β-[N-isobutyl-3-(4-trifluoromethylphenyl)propiolamido]morphinan, 17-methyl-4,5α-epoxy-14β-acetoxy-3-hydroxy-6α-(N-isobutyl-3-methylcinnamamido)morphinan, 17-methyl-4,5α-epoxy-14β-acetoxy-3-hydroxy-6β-[N-isobutyl-3-(4-trifluoromethylphenyl)propiolamido]morphinan, 17-phenethyl-4,5α-epoxy-14α-acetoxy-3-hydroxy-6β-(N-isobutyl-3-methylcinnamamido)morphinan, 17-phenethyl-4,5α-epoxy-14β-acetoxy-3-hydroxy-6β-[N-isobutyl-3-(4-trifluoromethylphenyl)propiolamido]morphinan, 17-cyclopropylmethyl-4,5α-epoxy-14β-hydroxy-6β-(N-isobutyl-3-methylcinnamamido)morphinan, 17-cyclopropylmethyl-4,5α-epoxy-14β-hydroxy-6β-[N-isobutyl-3-(4-trifluoromethylphenyl)propiolamido]morphinan, 17-allyl-4,5α-epoxy-14β-hydroxy-6β-(N-isobutyl-3-methylcinnamamido)morphinan, 17-allyl-4,5α-epoxy-14β-hydroxy-6β-[N-isobutyl-3-(4-trifluoromethylphenyl)propiolamido]morphinan, 17-methyl-4,5α-epoxy-14β-hydroxy-6β-(N-isobutyl-3-methylcinnamamido)morphinan, 17-methyl-4,5α- epoxy-14β-hydroxy-6β-[N-isobutyl-3-(4-trifluoromethylphenyl)propiolamido]morphinan, 17-phenethyl-4,5α-epoxy-14β-hydroxy-6β-(N-isobutyl-3-methylcinnamamido)morphinan, 17-phenethyl-4,5α-epoxy-14β-hydroxy-6β-[N-isobutyl-3-(4-trifluoromethylphenyl)propiolamido]morphinan, 17-cyclopropylmethyl-4,5α-epoxy-14β-acetoxy-6β-(N-isobutyl-3-methylcinnamamido)morphinan, 17-cyclopropylmethyl-4,5α-epoxy-14β-acetoxy-6β-[N-isobutyl-3-(4-trifluoromethylphenyl)propiolamido]morphinan, 17-allyl-4,5α-epoxy-14β-acetoxy-6β-(N-isobutyl-3-methylcinnamamido)morphinan, 17-allyl-4,5α-epoxy-14β-acetoxy-6β-[N-isobutyl-3-(4-trifluoromethylphenyl)propiolamido]morphinan, 17-methyl-4,5α-epoxy-14β-acetoxy-6β-(N-isobutyl-3-methylcinnamamido)morphinan, 17-methyl-4,5α-epoxy-14β-acetoxy-6β-[N-isobutyl-3-(4-trifluoromethylphenyl)propiolamido]morphinan, 17-phenethyl-4,5α-epoxy-14β-acetoxy-6β-(N-isobutyl-3-methylcinnamamido)morphinan, 17-phenethyl-4,5α-epoxy-14β-acetoxy-6β-[N-isobutyl-3-(4-trifluoromethylphenyl)propiolamido]morphinan, 17-cyclopropylmethyl-4,5α-epoxy-14β-hydroxy-3-methoxy-6β-(N-isobutyl-3-methylcinnamamido)morphinan, 17-cyclopropylmethyl-4,5α-epoxy-14β-hydroxy-3-methoxy-6β-[N-isobutyl-3-(4-trifluoromethylphenyl)propiolamido]morphinan, 17-allyl-4,5α-epoxy-14β-hydroxy-3-methoxy-6β-(N-isobutyl-3-methylcinnamamido)morphinan, 17-allyl-4,5α-epoxy-14β-hydroxy-3-methoxy-6β-[N-isobutyl-3-(4-trifluoromethylphenyl)propiolamido]morphinan, 17-methyl-4,5α-epoxy-14β-hydroxy-3-methoxy-6β-(N-isobutyl-3-methylcinnamamido)morphinan, 17-methyl-4,5α-epoxy-14β-hydroxy-3-methoxy-6β-[N-isobutyl-3-(4-trifluoromethylphenyl)propiolamido]morphinan, 17-phenethyl-4,5α-epoxy-14β-hydroxy-3-methoxy-6β-(N-isobutyl-3-methylcinnamamido)morphinan, 17-phenethyl-4,5α-epoxy-14β-hydroxy-3-methoxy-6β-[N-isobutyl-3-(4-trifluoromethylphenyl)propiolamido]morphinan, 17-cyclopropylmethyl-4,5α-epoxy-14β-acetoxy-3-methoxy-6β-(N-isobutyl-3-methylcinnamamido)morphinan, 17-cyclopropylmethyl-4,5α-epoxy-14β-acetoxy-3-methoxy-6β-[N-isobutyl-3-(4-trifluoromethylphenyl)propiolamido]morphinan, 17-allyl-4,5α-epoxy-14β-acetoxy-3-methoxy-6β-(N-isobutyl-3-methylcinnamamido)morphinan, 17-allyl-4,5α-epoxy-14β-acetoxy-3-methoxy-6β-[N-isobutyl-3-(4-trifluoromethylphenyl)propiolamido]morphinan, 17-methyl-4,5α-epoxy-14β-acetoxy-3-methoxy-6β-(N-isobutyl-3-methylcinnamamido)morphinan, 17-methyl-4,5α-epoxy-14β-acetoxy-3-methoxy-6β-[N-isobutyl-3-(4-trifluoromethylphenyl)propiolamido]morphinan, 17-phenethyl-4,5α-epoxy-14β-acetoxy-3-methoxy-6β-(N-isobutyl-3-methylcinnamamido)morphinan, 17-phenethyl-4,5α-epoxy-14β-acetoxy-3-methoxy-6β-[N-isobutyl-3-(4-trifluoromethylphenyl)propiolamido]morphinan, 17-cyclopropylmethyl-4,5α-epoxy-14β-hydroxy-3-acetoxy-6β-(N-isobutyl-3-methylcinnamamido)morphinan, 17-cyclopropylmethyl-4,5α-epoxy-14β-hydroxy-3-acetoxy-6β-[N-isobutyl-3-(4-trifluoromethylphenyl)propiolamido]morphinan, 17-allyl-4,5α-epoxy-14β-hydroxy-3-acetoxy-6β-(N-isobutyl-3-methylcinnamamido)morphinan, 17-allyl-4,5α-epoxy-14β-hydroxy-3-acetoxy-6β-[N-isobutyl-3-(4-trifluoromethylphenyl)propiolamido]morphinan, 17-methyl-4,5α-epoxy-14β-hydroxy-3-acetoxy-6β-(N-isobutyl-3-methylcinnamamido)morphinan, 17-methyl-4,5α-epoxy-14β-hydroxy-3-acetoxy-6β-[N-isobutyl-3-(4-trifluoromethylphenyl)propiolamido]morphinan, 17-phenethyl-4,5α-epoxy-14β-hydroxy-3-acetoxy-6β-(N-isobutyl-3-methylcinnamamido)morphinan, 17-phenethyl-4,5α-epoxy-14β-hydroxy-3-acetoxy-6β-[N-isobutyl-3-(4-trifluoromethylphenyl)propiolamido]morphinan, 17-cyclopropylmethyl-4,5α-epoxy-3,14β-diacetoxy-6β-(N-isobutyl-3-methylcinnamamido)morphinan, 17-cyclopropylmethyl-4,5α-epoxy-3,14β-diacetoxy-6β-[N-isobutyl-3-(4-trifluoromethylphenyl)propiolamido]morphinan, 17-allyl-4,5α-epoxy-3,14β-diacetoxy-6β-(N-isobutyl-3-methylcinnamamido)morphinan, 17-allyl-4,5α-epoxy-3,14β-diacetoxy-6β-[N-isobutyl-3-(4-trifluoromethylphenyl)propiolamido]morphinan, 17-methyl-4,5α-epoxy-3,14β-diacetoxy-6β-(N-isobutyl-3-methylcinnamamido)morphinan, 17-methyl-4,5α-epoxy-3,14β-diacetoxy-6β-[N-isobutyl-3-(4-trifluoromethylphenyl)propiolamido]morphinan, 17-phenethyl-4,5α-epoxy-3,14β-diacetoxy-6β-(N-isobutyl-3-methylcinnamamido)morphinan, 17-phenethyl-4,5α-epoxy-3,14β-diacetoxy-6β-[N-isobutyl-3-(4-trifluoromethylphenyl)propiolamido]morphinan, 17-cyclopropylmethyl-4,5α-epoxy-3,14β-dihydroxy-6α-[N-methyl-3-(3-trifluoromethylphenyl)propiolamido]morphinan, 17-allyl-4,5α-epoxy-3,14β-dihydroxy-6α-[N-methyl-3-(3-trifluoromethylphenyl)propiolamido]morphinan, 17-cyclopropylmethyl-4,5α-epoxy-3,14β-dihydroxy-6β-[N-methyl-3-(3-trifluoromethylphenyl)propiolamido]morphinan, 17-allyl-4,5α-epoxy-3,14β-dihydroxy-6β-[N-methyl-3-(3-trifluoromethylphenyl)propiolamido]morphinan, 17-cyclopropylmethyl-4,5α-epoxy-3,14β-dihydroxy-6α-[N-methyl-trans-3-(2-thienyl)acrylamido]morphinan, 17-allyl-4,5α-epoxy-3,14β-dihydroxy-6α-[N-methyl-trans-3-(2-thienyl)acrylamido]morphinan, 17-cyclopropylmethyl-4,5α-epoxy-3,14β-dihydroxy-6β-[N-methyl-trans-3-(2-thienyl)acrylamido]morphinan, 17-allyl-4,5α-epoxy-3,14β-dihydroxy-6β-[N-methyl-trans-3-(2-thienyl)acrylamido]morphinan, 17-cyclopropylmethyl-4,5α-epoxy-3-hydroxy-6α-(N-methyl-3-trifluoromethylcinnamamido)morphinan, 17-cyclopropylmethyl-4,5α-epoxy-3-hydroxy-6α-[N-methyl-trans-3-(3-furyl)acrylamido]morphinan, 17-cyclopropylmethyl-4,5α-epoxy-3-hydroxy-6α-(N-methyl-3-methylcinnamamido)morphinan, 17-cyclopropylmethyl-4,5α-epoxy-3-hydroxy-6α-[N-methyl-3-(4-trifluoromethylphenyl)propiolamido]morphinan, 17-allyl-4,5α-epoxy-3-hydroxy-6α-(N-methyl-3-trifluoromethylcinnamamido)morphinan, 17-allyl-4,5α-epoxy-3-hydroxy-6α-[N-methyl-trans-3-(3-furyl)acrylamido]morphinan, 17-allyl-4,5α-epoxy-3-hydroxy-6α-(N-methyl-3-methylcinnamamido)morphinan, 17-allyl-4,5α-epoxy-3-hydroxy-6α-[N-methyl-3-(4-trifluoromethylphenyl)propiolamido]morphinan, 17-methyl-4,5α-epoxy-3-hydroxy-6α-(N-methyl-3-trifluoromethylcinnamamido)morphinan, 17-methyl-4,5α-epoxy-3-hydroxy-6α-[N-methyl-trans-3-(3-furyl)acrylamido]morphinan, 17-methyl-4,5α-epoxy-3-hydroxy-6α-(N-methyl-3-methylcinnamamido)

morphinan, 17-methyl-4,5α-epoxy-3-hydroxy-6α-[N-methyl-3-(4-trifluoromethylphenyl)propiolamido]morphinan, 17-phenethyl-4,5α-epoxy-3-hydroxy-6α-(N-methyl-3-trifluoromethylcinnamamido)morphinan, 17-phenethyl-4,5α-epoxy-3-hydroxy-6α-[N-methyl-trans-3-(3-furyl)acrylamido]morphinan, 17-phenethyl-4,5α-epoxy-3-hydroxy-6α-(N-methyl-3-methylcinnamamido)morphinan, 17-phenethyl-4,5α-epoxy-3-hydroxy-6α-[N-methyl-3-(4-trifluoromethylphenyl)propiolamido]morphinan, 17-cyclopropylmethyl-4,5α-epoxy-3-hydroxy-14β-nitro-6α-(N-methyl-3-trifluoromethylcinnamamido)morphinan, 17-cyclopropylmethyl-4,5α-epoxy-3-hydroxy-14β-nitro-6α-[N-methyl-trans-3-(3-furyl)acrylamido]morphinan, 17-cyclopropylmethyl-4,5α-epoxy-3-hydroxy-14β-nitro-6α-(N-methyl-3-methylcinnamamido)morphinan, 17-cyclopropylmethyl-4,5α-epoxy-3-hydroxy-14β-nitro-6α-[N-methyl-3-(4-trifluoromethylphenyl)propiolamido]morphinan, 17-allyl-4,5α-epoxy-3-hydroxy-14β-nitro-6α-(N-methyl-3-trifluoromethylcinnamamido)morphinan, 17-allyl-4,5α-epoxy-3-hydroxy-14β-nitro-6α-[N-methyl-trans-3-(3-furyl)acrylamido]morphinan, 17-allyl-4,5α-epoxy-3-hydroxy-14β-nitro-6α-(N-methyl-3-methylcinnamamido)morphinan, 17-allyl-4,5α-epoxy-3-hydroxy-14β-nitro-6α-[N-methyl-3-(4-trifluoromethylphenyl)propiolamido]morphinan, 17-methyl-4,5α-epoxy-3-hydroxy-14β-nitro-6α-(N-methyl-3-trifluoromethylcinnamamido)morphinan, 17-methyl-4,5α-epoxy-3-hydroxy-14β-nitro-6α-[N-methyl-trans-3-(3-furyl)acrylamido]morphinan, 17-methyl-4,5α-epoxy-3-hydroxy-14β-nitro-6α-(N-methyl-3-methylcinnamamido)morphinan, 17-methyl-4,5α-epoxy-3-hydroxy-14β-nitro-6α-[N-methyl-3-(4-trifluoromethylphenyl)propiolamido]morphinan, 17-phenethyl-4,5α-epoxy-3-hydroxy-14β-nitro-6α-(N-methyl-3-trifluoromethylcinnamamido)morphinan, 17-phenethyl-4,5α-epoxy-3-hydroxy-14β-nitro-6α-[N-methyl-trans-3-(3-furyl)acrylamido]morphinan, 17-phenethyl-4,5α-epoxy-3-hydroxy-14β-nitro-6α-(N-methyl-3-methylcinnamamido)morphinan, 17-phenethyl-4,5α-epoxy-3-hydroxy-14β-nitro-6α-[N-methyl-3-(4-trifluoromethylphenyl)propiolamido]morphinan, 17-cyclopropylmethyl-4,5α-epoxy-3-hydroxy-14β-dimethylamino-6α-(N-methyl-3-trifluoromethylcinnamamido)morphinan, 17-cyclopropylmethyl-4,5α-epoxy-3-hydroxy-14β-dimethylamino-6α-[N-methyl-trans-3-(3-furyl)acrylamido]morphinan, 17-cyclopropylmethyl-4,5α-epoxy-3-hydroxy-14β-dimethylamino-6α-(N-methyl-3-methylcinnamamido)morphinan, 17-cyclopropylmethyl-4,5α-epoxy-3-hydroxy-14β-dimethylamino-6α-[N-methyl-3-(4-trifluoromethylphenyl)propiolamido]morphinan, 17-allyl-4,5α-epoxy-3-hydroxy-14β-dimethylamino-6α-(N-methyl-3-trifluoromethylcinnamamido)morphinan.

17-allyl-4,5α-epoxy-3-hydroxy-14β-dimethylamino-6α-[N-methyl-trans-3-(3-furyl)acrylamido]morphinan, 17-allyl-4,5α-epoxy-3-hydroxy-14β-dimethylamino-6α-(N-methyl-3-methylcinnamamido)morphinan, 17-allyl-4,5α-epoxy-3-hydroxy-14β-dimethylamino-6α-[N-methyl-3-(4-trifluoromethylphenyl)propiolamido]morphinan, 17-methyl-4,5α-epoxy-3-hydroxy-14β-dimethylamino-6α-(N-methyl-3-trifluoromethylcinnamamido)morphinan, 17-methyl-4,5α-epoxy-3-hydroxy-14β-dimethylamino-6α-[N-methyl-trans-3-(3-furyl)acrylamido]morphinan, 17-methyl-4,5α-epoxy-3-hydroxy-14β-dimethylamino-6α-(N-methyl-3-methylcinnamamido)morphinan, 17-methyl-4,5α-epoxy-3-hydroxy-14β-dimethylamino-6α-[N-methyl-3-(4-trifluoromethylphenyl)propiolamido]morphinan, 17-phenethyl-4,5α-epoxy-3-hydroxy-14β-dimethylamino-6α-(N-methyl-3-trifluoromethylcinnamamido)morphinan, 17-phenethyl-4,5α-epoxy-3-hydroxy-14β-dimethylamino-6α-[N-methyl-trans-3-(3-furyl)acrylamido]morphinan, 17-phenethyl-4,5α-epoxy-3-hydroxy-14β-dimethylamino-6α-(N-methyl-3-methylcinnamamido)morphinan, 17-phenethyl-4,5α-epoxy-3-hydroxy-14β-dimethylamino-6α-[N-methyl-3-(4-trifluoromethylphenyl)propiolamido]morphinan, 17-cyclopropylmethyl-4,5α-epoxy-3-hydroxy-14β-methyl-6α-(N-methyl-3-trifluoromethylcinnamamido)morphinan, 17-cyclopropylmethyl-4,5α-epoxy-3-hydroxy-14β-methyl-6α-[N-methyl-trans-3-(3-furyl)acrylamido]morphinan, 17-cyclopropylmethyl-4,5α-epoxy-3-hydroxy-14β-methyl-6α-(N-methyl-3-methylcinnamamido)morphinan, 17-cyclopropylmethyl-4,5α-epoxy-3-hydroxy-14β-methyl-6α-[N-methyl-3-(4-trifluoromethylphenyl)propiolamido]morphinan, 17-allyl-4,5α-epoxy-3-hydroxy-14β-methyl-6α-(N-methyl-3-trifluoromethylcinnamamido)morphinan, 17-allyl-4,5α-epoxy-3-hydroxy-14β-methyl-6α-[N-methyl-trans-3-(3-furyl)acrylamido]morphinan, 17-allyl-4,5α-epoxy-3-hydroxy-14β-methyl-6α-(N-methyl-3-methylcinnamamido)morphinan, 17-allyl-4,5α-epoxy-3-hydroxy-14β-methyl-6α-[N-methyl-3-(4-trifluoromethylphenyl)propiolamido]morphinan, 14β,17-dimethyl-4,5α-epoxy-3-hydroxy-6α-(N-methyl-3-trifluoromethylcinnamamido)morphinan, 14β,17-dimethyl-4,5α-epoxy-3-hydroxy-6α-[N-methyl-trans-3-(3-furyl)acrylamido]morphinan, 14β,17-dimethyl-4,5α-epoxy-3-hydroxy-6α-(N-methyl-3-methylcinnamamido)morphinan, 14β,17-dimethyl-4,5α-epoxy-3-hydroxy-6α-[N-methyl-3-(4-trifluoromethylphenyl)propiolamido]morphinan, 17-phenethyl-4,5α-epoxy-3-hydroxy-14β-methyl-6α-(N-methyl-3-trifluoromethylcinnamamido)morphinan, 17-phenethyl-4,5α-epoxy-3-hydroxy-14β-methyl-6α-[N-methyl-trans-3-(3-furyl)acrylamido]morphinan, 17-phenethyl-4,5α-epoxy-3-hydroxy-14β-methyl-6α-(N-methyl-3-methylcinnamamido)morphinan, 17-phenethyl-4,5α-epoxy-3-hydroxy-14β-methyl-6α-[N-methyl-3-(4-trifluoromethylphenyl)propiolamido]morphinan, 17-cyclopropylmethyl-3,14β-dihydroxy-6α-(N-methyl-3-trifluoromethylcinnamamido)morphinan, 17-cyclopropylmethyl-3,14β-dihydroxy-6α-[N-methyl-trans-3-(3-furyl)acrylamido]morphinan, 17-cyclopropylmethyl-3,14β-dihydroxy-6α-(N-methyl-3-methylcinnamamido)morphinan, 17-cyclopropylmethyl-3,14β-dihydroxy-6α-[N-methyl-3-(4-trifluoromethylphenyl)propiolamido]morphinan, 17-allyl-3,14β-dihydroxy-6α-(N-methyl-3-trifluoromethylcinnamamido)morphinan, 17-allyl-3,14β-dihydroxy-6α-[N-methyl-trans-3-(3-furyl)acrylamido]morphinan, 17-allyl-3,14β-dihydroxy-6α-(N-methyl-3-methylcinnamamido)morphinan, 17-allyl-3,14β- dihydroxy-6α-[N-methyl-3-(4-trifluoromethylphenyl)propiolamido]morphinan, 17-methyl-3,14β-dihydroxy-6α-(N-methyl-3-trifluoromethylcinnamamido)morphinan, 17-methyl-3,14β-dihydroxy-6α-[N-methyl-trans-3-(3-furyl)acrylamido]morphinan, 17-methyl-3,14β-dihydroxy-6α-(N-methyl-3-methylcinnamamido)morphinan, 17-methyl-3,14β-dihydroxy-6α-[N-methyl-3-(4-trifluoromethylphenyl)propiolamido]morphinan, 17-phenethyl-3,14β-dihydroxy-6α-(N-methyl-3-trifluoromethylcinnamamido)morphinan, 17-phenethyl-3,14β-dihydroxy-6α-[N-methyl-trans-3-(3-furyl)acrylamido]morphinan, 17-phenethyl-3,14β-dihydroxy-6α-(N-methyl-3-methylcinnamamido)morphinan, 17-phenethyl-3,14β-dihydroxy-6α-[N-methyl-3-(4-trifluoromethylphenyl)propiolamido]morphinan, 17-cyclopropylmethyl-3,14β-dihydroxy-4-methoxy-6α-(N-methyl-3-trifluoromethylcinnamamido)morphinan, 17-cyclopropylmethyl-3,14β-dihydroxy-4-methoxy-6α-[N-methyl-trans-3-(3-furyl)acrylamido]morphinan, 17-cyclopropylmethyl-3,14β-dihydroxy-4-methoxy-6α-(N-methyl-3-methylcinnamamido)morphinan, 17-cyclopropylmethyl-3,14β-dihydroxy-4-methoxy-6α-[N-methyl-3-(4-trifluoromethylphenyl)propiolamido]morphinan, 17-allyl-3,14β-dihydroxy-4-methoxy-6α-(N-methyl-3-trifluoromethylcinnamamido)morphinan, 17-allyl-3,14β-dihydroxy-4-methoxy-6α-[N-methyl-trans-3-(3-furyl)acrylamido]morphinan, 17-allyl-3,14β-dihydroxy-4-methoxy-6α-(N-methyl-3-methylcinnamamido)morphinan, 17-allyl-3,14β-dihydroxy-4-methoxy-6α-[N-methyl-3-(4-trifluoromethylphenyl)propiolamido]morphinan, 17-methyl-3,14β-dihydroxy-4-methoxy-6α-(N-methyl-3-trifluoromethylcinnamamido)morphinan, 17-methyl-3,14β-dihydroxy-4-methoxy-6α-[N-methyl-trans-3-(3-furyl)acrylamido]morphinan, 17-methyl-3,14β-dihydroxy-4-methoxy-6α-(N-methyl-3-methylcinnamamido)morphinan, 17-methyl-3,14β-dihydroxy-4-methoxy-6α-[N-methyl-3-(4-trifluoromethylphenyl)propiolamido]morphinan, 17-phenethyl-3,14β-dihydroxy-4-methoxy-6α-(N-methyl-3-trifluoromethylcinnamamido)morphinan, 17-phenethyl-3,14β-dihydroxy-4-methoxy-6α-[N-methyl-trans-3-(3-furyl)acrylamido]morphinan, 17-phenethyl-3,14β-dihydroxy-4-methoxy-6α-(N-methyl-3-methylcinnamamido)morphinan, 17-phenethyl-3,14β-dihydroxy-4-methoxy-6α-[N-methyl-3-(4-trifluoromethylphenyl)propiolamido]morphinan, 17-cyclopropylmethyl-4,5α-epoxy-3,14β-dihydroxy-5β-methyl-6α-(N-methyl-3-trifluoromethylcinnamamido)morphinan, 17-cyclopropylmethyl-4,5α-epoxy-3,14β-dihydroxy-5β-methyl-6α-[N-methyl-trans-3-(3-furyl)acrylamido]morphinan, 17-cyclopropylmethyl-4,5α-epoxy-3,14β-dihydroxy-5β-methyl-6α-(N-methyl-3-methylcinnamamido)morphinan, 17-cyclopropylmethyl-4,5α-epoxy-3,14β-dihydroxy-5β-methyl-6α-[N-methyl-3-(4-trifluoromethylphenyl)propiolamido]morphinan, 17-allyl-4,5α-epoxy-3,14β-dihydroxy-5β-methyl-6α-(N-methyl-3-trifluoromethylcinnamamido)morphinan, 17-allyl-4,5α-epoxy-3,14β-dihydroxy-5β-methyl-6α-[N-methyl-trans-3-(3-furyl)acrylamido]morphinan, 17-allyl-4,5α-epoxy-3,14β-dihydroxy-5β-methyl-6α-(N-methyl-3-methylcinnamamido)morphinan, 17-allyl-4,5α-epoxy-3,14β-dihydroxy-5β-methyl-6α-[N-methyl-3-(4-trifluoromethylphenyl)propiolamido]morphinan, 5β,17-dimethyl-4,5α-epoxy-3,14β-dihydroxy-6α-(N-methyl-3-trifluoromethylcinnamamido)morphinan, 5β,17-dimethyl-4,5α-epoxy-3,14β-dihydroxy-6α-[N-methyl-trans-3-(3-furyl)acrylamido]morphinan, 5β,17-dimethyl-4,5α-epoxy-3,14β-dihydroxy-6α-(N-methyl-3-methylcinnamamido)morphinan, 5β,17-dimethyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-5β-methyl-6α-(N-methyl-3-trifluoromethylcinnamamido)morphinan, 17-phenethyl-4,5α-epoxy-3,14β-dihydroxy-5β-methyl-6α-[N-methyl-trans-3-(3-furyl)acrylamido]morphinan, 17-phenethyl-4,5α-epoxy-3,14β-dihydroxy-5β-methyl-6α-(N-methyl-3-methylcinnamamido)morphinan, 17-phenethyl-4,5α-epoxy-3,14β-dihydroxy-5β-methyl-6α-[N-methyl-3-(4-trifluoromethylphenyl)propiolamido]morphinan, 17-cyclopropylmethyl-7,8-didehydro-4,5α-epoxy-3,14β-dihydroxy-6α-(N-methyl-3-trifluoromethylcinnamamido)morphinan, 17-cyclopropylmethyl-7,8-didehydro-4,5α-epoxy-3,14β-dihydroxy-6α-[N-methyl-trans-3-(3-furyl)acrylamido]morphinan, 17-cyclopropylmethyl-7,8-didehydro-4,5α-epoxy-3,14β-dihydroxy-6α-(N-methyl-3-methylcinnamamido)morphinan, 17-cyclopropylmethyl-7,8-didehydro-4,5α-epoxy-3,14β-dihydroxy-6α-[N-methyl-3-(4-trifluoromethylphenyl)propiolamido]morphinan, 17-allyl-7,8-didehydro-4,5α-epoxy-3,14β-dihydroxy-6α-(N-methyl-3-trifluoromethylcinnamamido)morphinan, 17-allyl-7,8-didehydro-4,5α-epoxy-3,14β-dihydroxy-6α-[N-methyl-trans-3-(3-furyl)acrylamido]morphinan, 17-allyl-7,8-didehydro-4,5α-epoxy-3,14β-dihydroxy-6α-(N-methyl-3-methylcinnamamido)morphinan, 17-allyl-7,8-didehydro-4,5α-epoxy-3,14β-dihydroxy-6α-[N-methyl-3-(4-trifluoromethylphenyl)propiolamido]morphinan, 17-methyl-7,8-didehydro-4,5α-epoxy-3,14β-dihydroxy-6α-(N-methyl-3-trifluoromethylcinnamamido)morphinan, 17-methyl-7,8-didehydro-4,5α-epoxy-3,14β-dihydroxy-6α-[N-methyl-trans-3-(3-furyl)acrylamido]morphinan, 17-methyl-7,8-didehydro-4,5α-epoxy-3,14β-dihydroxy-6α-(N-methyl-3-methylcinnamamido)morphinan, 17-methyl-7,8-didehydro-4,5α-epoxy-3,14β-dihydroxy-6α-[N-methyl-3-(4-trifluoromethylphenyl)propiolamido]morphinan, 17-phenethyl-7,8-didehydro-4,5α-epoxy-3,14β-dihydroxy-6α-(N-methyl-3-trifluoromethylcinnamamido)morphinan, 17-phenethyl-7,8-didehydro-4,5α-epoxy-3,14β-dihydroxy-6α-[N-methyl-trans-3-(3-furyl)acrylamido]morphinan, 17-phenethyl-7,8-didehydro-4,5α-epoxy-3,14β-dihydroxy-6α-(N-methyl-3-methylcinnamamido)morphinan, 17-phenethyl-7,8-didehydro-4,5α-epoxy-3,14β-dihydroxy-6α-[N-methyl-3-(4-trifluoromethylphenyl)propiolamido]morphinan.

17-cyclopropylmethyl-4,5α-epoxy-3-hydroxy-6β-(N-methyl-3-trifluoromethylcinnamamido)morphinan, 17-cyclopropylmethyl-4,5α-epoxy-3-hydroxy-6β-[N-methyl-trans-3-(3-furyl)acrylamido]morphinan, 17-cyclopropylmethyl-4,5α-epoxy-3-hydroxy-6β-(N-methyl-3-methylcinnamamido)morphinan, 17-cyclopropylmethyl-4,5α-epoxy-3-hydroxy-6β-[N- methyl-3-(4-trifluoromethylphenyl)propiolamido]morphinan, 17-allyl-4,5α-epoxy-3-hydroxy-6β-(N-methyl-3-trifluoromethylcinnamamido)morphinan, 17-allyl-4,5α-epoxy-3-hydroxy-6β-[N-methyl-trans-3-(3-furyl)acrylamido]morphinan, 17-allyl-4,5α-epoxy-3-hydroxy-6β-(N-methyl-3-methylcinnamamido)morphinan, 17-allyl-4,5α-epoxy-3-hydroxy-6β-[N-methyl-3-(4-trifluoromethylphenyl)propiolamido]morphinan, 17-methyl-4,5α-epoxy-3-hydroxy-6β-(N-methyl-3-trifluoromethylcinnamamido)morphinan, 17-methyl-4,5α-epoxy-3-hydroxy-6β-[N-methyl-trans-3-(3-furyl)acrylamido]morphinan, 17-methyl-4,5α-epoxy-3-hydroxy-6β-(N-methyl-3-methylcinnamamido)morphinan, 17-methyl-4,5α-epoxy-3-hydroxy-6β-[N-methyl-3-(4-trifluoromethylphenyl)propiolamido]morphinan, 17-phenethyl-4,5α-epoxy-3-hydroxy-6β-(N-methyl-3-trifluoromethylcinnamamido)morphinan, 17-phenethyl-4,5α-epoxy-3-hydroxy-6β-[N-methyl-trans-3-(3-furyl)acrylamido]morphinan, 17-phenethyl-4,5α-epoxy-3-hydroxy-6β-(N-methyl-3-methylcinnamamido)morphinan, 17-phenethyl-4,5α-epoxy-3-hydroxy-6β-[N-methyl-3-(4-trifluoromethylphenyl)propiolamido]morphinan, 17-cyclopropylmethyl-4,5α-epoxy-3-hydroxy-14β-nitro-6β-(N-methyl-3-trifluoromethylcinnamamido)morphinan, 17-cyclopropylmethyl-4,5α-epoxy-3-hydroxy-14β-nitro-6β-[N-methyl-trans-3-(3-furyl)acrylamido]morphinan, 17-cyclopropylmethyl-4,5α-epoxy-3-hydroxy-14β-nitro-6β-(N-methyl-3-methylcinnamamido)morphinan, 17-cyclopropylmethyl-4,5α-epoxy-3-hydroxy-14β-nitro-6β-[N-methyl-3-(4-trifluoromethylphenyl)propiolamido]morphinan, 17-allyl-4,5α-epoxy-3-hydroxy-14β-nitro-6β-(N-methyl-3-trifluoromethylcinnamamido)morphinan, 17-allyl-4,5α-epoxy-3-hydroxy-14β-nitro-6β-[N-methyl-trans-3-(3-furyl)acrylamido]morphinan, 17-allyl-4,5α-epoxy-3-hydroxy-14β-nitro-6β-(N-methyl-3-methylcinnamamido)morphinan, 17-allyl-4,5α-epoxy-3-hydroxy-14β-nitro-6β-[N-methyl-3-(4-trifluoromethylphenyl)propiolamido]morphinan, 17-methyl-4,5α-epoxy-3-hydroxy-14β-nitro-6β-(N-methyl-3-trifluoromethylcinnamamido)morphinan, 17-methyl-4,5α-epoxy-3-hydroxy-14β-nitro-6β-[N-methyl-trans-3-(3-furyl)acrylamido]morphinan, 17-methyl-4,5α-epoxy-3-hydroxy-14β-nitro-6β-(N-methyl-3-methylcinnamamido)morphinan, 17-methyl-4,5α-epoxy-3-hydroxy-14β-nitro-6β-[N-methyl-3-(4-trifluoromethylphenyl)propiolamido]morphinan, 17-phenethyl-4,5α-epoxy-3-hydroxy-14β-nitro-6β-(N-methyl-3-trifluoromethylcinnamamido)morphinan, 17-phenethyl-4,5α-epoxy-3-hydroxy-14β-nitro-6β-[N-methyl-trans-3-(3-furyl)acrylamido]morphinan, 17-phenethyl-4,5α-epoxy-3-hydroxy-14β-nitro-6β-(N-methyl-3-methylcinnamamido)morphinan, 17-phenethyl-4,5α-epoxy-3-hydroxy-14β-nitro-6β-[N-methyl-3-(4-trifluoromethylphenyl)propiolamido]morphinan, 17-cyclopropylmethyl-4,5α-epoxy-3-hydroxy-14β-dimethylamino-6β-(N-methyl-3-trifluoromethylcinnamamido)morphinan, 17-cyclopropylmethyl-4,5α-epoxy-3-hydroxy-14β-dimethylamino-6β-[N-methyl-trans-3-(3-furyl)acrylamido]morphinan, 17-cyclopropylmethyl-4,5α-epoxy-3-hydroxy-14β-dimethylamino-6β-(N-methyl-3-methylcinnamamido)morphinan, 17-cyclopropylmethyl-4,5α-epoxy-3-hydroxy-14β-dimethylamino-6β-[N-methyl-3-(4-trifluoromethylphenyl)propiolamido]morphinan, 17-allyl-4,5α-epoxy-3-hydroxy-14β-dimethylamino-6β-(N-methyl-3-trifluoromethylcinnamamido)morphinan, 17-allyl-4,5α-epoxy-3-hydroxy-14β-dimethylamino-6β-[N-methyl-trans-3-(3-furyl)acrylamido]morphinan, 17-allyl-4,5α-epoxy-3-hydroxy-14β-dimethylamino-6β-(N-methyl-3-methylcinnamamido)morphinan, 17-allyl-4,5α-epoxy-3-hydroxy-14β-dimethylamino-6β-[N-methyl-3-(4-trifluoromethylphenyl)propiolamido]morphinan, 17-methyl-4,5α-epoxy-3-hydroxy-14β-dimethylamino-6β-(N-methyl-3-trifluoromethylcinnamamido)morphinan, 17-methyl-4,5α-epoxy-3-hydroxy-14β-dimethylamino-6β-[N-methyl-trans-3-(3-furyl)acrylamido]morphinan, 17-methyl-4,5α-epoxy-3-hydroxy-14β-dimethylamino-6β-(N-methyl-3-methylcinnamamido)morphinan, 17-methyl-4,5α-epoxy-3-hydroxy-14β-dimethylamino-6β-[N-methyl-3-(4-trifluoromethylphenyl)propiolamido]morphinan, 17-phenethyl-4,5α-epoxy-3-hydroxy-14β-dimethylamino-6β-(N-methyl-3-trifluoromethylcinnamamido)morphinan, 17-phenethyl-4,5α-epoxy-3-hydroxy-14β-dimethylamino-6β-[N-methyl-trans-3-(3-furyl)acrylamido]morphinan, 17-phenethyl-4,5α-epoxy-3-hydroxy-14β-dimethylamino-6β-(N-methyl-3-methylcinnamamido)morphinan, 17-phenethyl-4,5α-epoxy-3-hydroxy-14β-dimethylamino-6β-[N-methyl-3-(4-trifluoromethylphenyl)propiolamido]morphinan, 17-cyclopropylmethyl-4,5α-epoxy-3-hydroxy-14β-methyl-6β-(N-methyl-3-trifluoromethylcinnamamido)morphinan, 17-cyclopropylmethyl-4,5α-epoxy-3-hydroxy-14β-methyl-6β-[N-methyl-trans-3-(3-furyl)acrylamido]morphinan, 17-cyclopropylmethyl-4,5α-epoxy-3-hydroxy-14β-methyl-6β-(N-methyl-3-methylcinnamamido)morphinan, 17-cyclopropylmethyl-4,5α-epoxy-3-hydroxy-14β-methyl-6β-[N-methyl-3-(4-trifluoromethylphenyl)propiolamido]morphinan, 17-allyl-4,5α-epoxy-3-hydroxy-14β-methyl-6β-(N-methyl-3-trifluoromethylcinnamamido)morphinan, 17-allyl-4,5α-epoxy-3-hydroxy-14β-methyl-6β-[N-methyl-trans-3-(3-furyl)acrylamido]morphinan, 17-allyl-4,5α-epoxy-3-hydroxy-14β-methyl-6β-(N-methyl-3-methylcinnamamido)morphinan, 17-allyl-4,5α-epoxy-3-hydroxy-14β-methyl-6β-[N-methyl-3-(4-trifluoromethylphenyl)propiolamido]morphinan, 14β,17-dimethyl-4,5α-epoxy-3-hydroxy-6β-(N-methyl-3-trifluoromethylcinnamamido)morphinan, 14β,17-dimethyl-4,5α-epoxy-3-hydroxy-6β-[N-methyl-trans-3-(3-furyl)acrylamido]morphinan, 14β,17-dimethyl-4,5α-epoxy-3-hydroxy-6β-(N-methyl-3-methylcinnamamido)morphinan, 14β,17-dimethyl-4,5α-epoxy-3-hydroxy-6β-[N-methyl-3-(4-trifluoromethylphenyl)propiolamido]morphinan, 17-phenethyl-4,5α-epoxy-3-hydroxy-14β-methyl-6β-(N-methyl-3-trifluoromethylcinnamamido)morphinan, 17-phenethyl-4,5α-epoxy-3-hydroxy-14β-methyl-6β-[N-methyl-trans-3-(3-furyl)acrylamido]morphinan, 17-phenethyl-4,5α-epoxy-3-hydroxy-14β-methyl-6β-(N-methyl-3-methylcinnamamido)morphinan, 17-phenethyl-4,5α-epoxy-3-hydroxy-14β-methyl-6β-[N-methyl-3-(4-trifluoromethylphenyl)propiolamido]

morphinan, 17-cyclopropylmethyl-3,14β-dihydroxy-6β-(N-methyl-3-trifluoromethylcinnamamido) morphinan, 17-cyclopropylmethyl-3,14β-dihydroxy-6β-[N-methyl-trans-3-(3-furyl)acrylamido]morphinan, 17-cyclopropylmethyl-3,14β-dihydroxy-6β-(N-methyl-3-methylcinnamamido)morphinan, 17-cyclopropylmethyl-3,14β-dihydroxy-6β-[N-methyl-3-(4-trifluoromethylphenyl)propiolamido]morphinan, 17-allyl-3,14β-dihydroxy-6β-(N-methyl-3-trifluoromethylcinnamamido)morphinan, 17-allyl-3,14β-dihydroxy-6β-[N-methyl-trans-3-(3-furyl)acrylamido]morphinan, 17-allyl-3,14β-dihydroxy-6β-(N-methyl-3-methylcinnamamido)morphinan, 17-allyl-3,14β-dihydroxy-6β-[N-methyl-3-(4-trifluoromethylphenyl)propiolamido]morphinan, 17-methyl-3,14β-dihydroxy-6β-(N-methyl-3-trifluoromethylcinnamamido)morphinan, 17-methyl-3,14β-dihydroxy-6β-[N-methyl-trans-3-(3-furyl)acrylamido]morphinan, 17-methyl-3,14β-dihydroxy-6β-(N-methyl-3-methylcinnamamido)morphinan, 17-methyl-3,14β-dihydroxy-6β-[N-methyl-3-(4-trifluoromethylphenyl)propiolamido]morphinan, 17-phenethyl-3,14β-dihydroxy-6β-(N-methyl-3-trifluoromethylcinnamamido)morphinan, 17-phenethyl-3,14β-dihydroxy-6β-[N-methyl-trans-3-(3-furyl)acrylamido]morphinan, 17-phenethyl-3,14β-dihydroxy-6β-(N-methyl-3-methylcinnamamido)morphinan, 17-phenethyl-3,14β-dihydroxy-6β-[N-methyl-3-(4-trifluoromethylphenyl)propiolamido]morphinan, 17-cyclopropylmethyl-3,14β-dihydroxy-4-methoxy-6β-(N-methyl-3-trifluoromethylcinnamamido)morphinan, 17-cyclopropylmethyl-3,14β-dihydroxy-4-methoxy-6β-[N-methyl-trans-3-(3-furyl)acrylamido]morphinan, 17-cyclopropylmethyl-3,14β-dihydroxy-4-methoxy-6β-(N-methyl-3-methylcinnamamido)morphinan, 17-cyclopropylmethyl-3,14β-dihydroxy-4-methoxy-6β-[N-methyl-3-(4-trifluoromethylphenyl)propiolamido]morphinan, 17-allyl-3,14β-dihydroxy-4-methoxy-6β-(N-methyl-3-trifluoromethylcinnamamido)morphinan, 17-allyl-3,14β-dihydroxy-4-methoxy-6β-[N-methyl-trans-3-(3-furyl)acrylamido]morphinan, 17-allyl-3,14β-dihydroxy-4-methoxy-6β-(N-methyl-3-methylcinnamamido)morphinan, 17-allyl-3,14β-dihydroxy-4-methoxy-6β-[N-methyl-3-(4-trifluoromethylphenyl)propiolamido]morphinan, 17-methyl-3,14β-dihydroxy-4-methoxy-6β-(N-methyl-3-trifluoromethylcinnamamido)morphinan, 17-methyl-3,14β-dihydroxy-4-methoxy-6β-[N-methyl-trans-3-(3-furyl)acrylamido]morphinan, 17-methyl-3,14β-dihydroxy-4-methoxy-6β-(N-methyl-3-methylcinnamamido)morphinan, 17-methyl-3,14β-dihydroxy-4-methoxy-6β-[N-methyl-3-(4-trifluoromethylphenyl)propiolamido]morphinan, 17-phenethyl-3,14β-dihydroxy-4-methoxy-6β-(N-methyl-3-trifluoromethylcinnamamido)morphinan, 17-phenethyl-3,14β-dihydroxy-4-methoxy-6β-[N-methyl-trans-3-(3-furyl)acrylamido]morphinan, 17-phenethyl-3,14β-dihydroxy-4-methoxy-6β-(N-methyl-3-methylcinnamamido)morphinan, 17-phenethyl-3,14β-dihydroxy-4-methoxy-6β-[N-methyl-3-(4-trifluoromethylphenyl)propiolamido]morphinan, 17-cyclopropylmethyl-4,5α-epoxy-3,14β-dihydroxy-5β-methyl-6β-(N-methyl-3-trifluoromethylcinnamamido)morphinan, 17-cyclopropylmethyl-4,5α-epoxy-3,14β-dihydroxy-5β-methyl-6β-[N-methyl-trans-3-(3-furyl)acrylamido]morphinan, 17-cyclopropylmethyl-4,5α-epoxy-3,14β-dihydroxy-5β-methyl-6β-(N-methyl-3-methylcinnamamido)morphinan, 17-cyclopropylmethyl-4,5α-epoxy-3,14β-dihydroxy-5β-methyl-6β-[N-methyl-3-(4-trifluoromethylphenyl)propiolamido]morphinan, 17-allyl-4,5α-epoxy-3,14β-dihydroxy-5β-methyl-6β-(N-methyl-3-trifluoromethylcinnamamido)morphinan, 17-allyl-4,5α-epoxy-3,14β-dihydroxy-5β-methyl-6β-[N-methyl-trans-3-(3-furyl)acrylamido]morphinan, 17-allyl-4,5α-epoxy-3,14β-dihydroxy-5β-methyl-6β-(N-methyl-3-methylcinnamamido)morphinan, 17-allyl-4,5α-epoxy-3,14β-dihydroxy-5β-methyl-6β-[N-methyl-3-(4-trifluoromethylphenyl)propiolamido]morphinan, 5β,17-dimethyl-4,5α-epoxy-3,14β-dihydroxy-6β-(N-methyl-3-trifluoromethylcinnamamido)morphinan, 5β,17-dimethyl-4,5α-epoxy-3,14β-dihydroxy-6β-[N-methyl-trans-3-(3-furyl)acrylamido]morphinan, 5β,17-dimethyl-4,5α-epoxy-3,14β-dihydroxy-6β-(N-methyl-3-methylcinnamamido)morphinan, 5β,17-dimethyl-4,5α-epoxy-3,14β-dihydroxy-6β-[N-methyl-3-(4-trifluoromethylphenyl)propiolamido]morphinan, 17-phenethyl-4,5α-epoxy-3,14β-dihydroxy-5β-methyl-6β-(N-methyl-3-trifluoromethylcinnamamido)morphinan, 17-phenethyl-4,5α-epoxy-3,14β-dihydroxy-5β-methyl-6β-[N-methyl-trans-3-(3-furyl)acrylamido]morphinan, 17-phenethyl-4,5α-epoxy-3,14β-dihydroxy-5β-methyl-6β-(N-methyl-3-methylcinnamamido)morphinan, 17-phenethyl-4,5α-epoxy-3,14β-dihydroxy-5β-methyl-6β-[N-methyl-3-(4-trifluoromethylphenyl)propiolamido]morphinan, 17-cyclopropylmethyl-7,8-didehydro-4,5α-epoxy-3,14β-dihydroxy-6β-(N-methyl-3-trifluoromethylcinnamamido)morphinan, 17-cyclopropylmethyl-7,8-didehydro-4,5α-epoxy-3,14β-dihydroxy-6β-[N-methyl-trans-3-(3-furyl)acrylamido]morphinan, 17-cyclopropylmethyl-7,8-didehydro-4,5α-epoxy-3,14β-dihydroxy-6β-(N-methyl-3-methylcinnamamido)morphinan, 17-cyclopropylmethyl-7,8-didehydro-4,5α-epoxy-3,14β-dihydroxy-6β-[N-methyl-3-(4-trifluoromethylphenyl)propiolamido]morphinan, 17-allyl-7,8-didehydro-4,5α-epoxy-3,14β-dihydroxy-6β-(N-methyl-3-trifluoromethylcinnamamido)morphinan, 17-allyl-7,8-didehydro-4,5α-epoxy-3,14β-dihydroxy-6β-[N-methyl-trans-3-(3-furyl)acrylamido]morphinan, 17-allyl-7,8-didehydro-4,5α-epoxy-3,14β-dihydroxy-6β-(N-methyl-3-methylcinnamamido)morphinan, 17-allyl-7,8-didehydro-4,5α-epoxy-3,14β-dihydroxy-6β-[N-methyl-3-(4-trifluoromethylphenyl)propiolamido]morphinan, 17-methyl-7,8-didehydro-4,5α-epoxy-3,14β-dihydroxy-6β-(N-methyl-3-trifluoromethylcinnamamido)morphinan, 17-methyl-7,8-didehydro-4,5α-epoxy-3,14β-dihydroxy-6β-[N-methyl-trans-3-(3-furyl)acrylamido]morphinan, 17-methyl-7,8-didehydro-4,5α-epoxy-3,14β-dihydroxy-6β-(N-methyl-3-methylcinnamamido)morphinan, 17-methyl-7,8-didehydro-4,5α-epoxy-3,14β-dihydroxy-6β-[N-methyl-3-(4-trifluoromethylphenyl)propiolamido]morphinan, 17-phenethyl-7,8-didehydro-4,5α-epoxy-3,14β-dihydroxy-6β-(N-methyl-3-trifluoromethylcinnamamido)morphinan, 17-phenethyl-7,8-didehydro-4,5α-epoxy-3,14β-dihydroxy-6β-[N-methyl-trans-3-(3-furyl)acrylamido]morphinan, 17-phenethyl-7,8-didehydro-4,5α-epoxy-3,14β-dihydroxy-6β-(N-methyl-3-methylcinnamamido)morphinan, 17-phenethyl-7,8-didehydro-4,5α-epoxy-3,14β-dihydroxy-6β-[N-methyl-3-(4-trifluoromethylphenyl)propiolamido]morphinan, 17-cyclopropylmethyl-4,5α-epoxy-3,14β-dihydroxy-6β-(N-methyl-3-trifluoromethoxycinnamamido)morphinan, 17-allyl-4,5α-epoxy-3,14β-dihydroxy-6α-(N-methyl-3-trifluoromethoxycinnamamido)morphinan, 17-cyclopropylmethyl-4,5α-epoxy-3,14β-dihydroxy-6β-(N-methyl-3-trifluoromethoxycinnamamido)morphinan, 17-allyl-4,5α-epoxy-3,14β-dihydroxy-6β-(N-methyl-3-trifluoromethoxycinnamamido)morphinan, etc., but this list is not intended to be restrictive.

Furthermore, the compounds of the present invention include the (+), (−) and (±) forms.

The compounds of general formula (I) of the present invention can be obtained, specifically, according to the methods described below.

Among the compounds represented by the general formula (I) of the present invention, those wherein A is —XC(=Y)—, —XC(=Y)Z— or —XSO$_2$— (wherein X represents NR$^4$ or O, Y represents O or S, Z represents O, NH or S, and R$^4$ is the same as previously defined) can be obtained, specifically, according to the methods described below.

In general, as shown in Chart 1, said compounds can be obtained by condensing a carboxylic acid derivative represented by the general formula (III) (wherein B and R$^5$ are the same as previously defined), a formic acid derivative represented by the general formula (IV) (wherein Z, B and R$^5$ are the same as previously defined), an isocyanic acid or isothiocyanic acid derivative represented by the general formula (V) (wherein B and R$^5$ are the same as previously defined) or a sulfonic acid derivative represented by the general formula (VI) (wherein B and R$^5$ are the same as previously defined), with a 6-amino or 6-hydroxy compound represented by the general formula (II) (wherein R$^1$, R$^2$, R$^3$, R$^6$, R$^7$ and R$^8$ are the same as previously defined, and E represents NHR$^4$ (wherein R$^4$ is the same as previously defined) or OH).

Chart 1

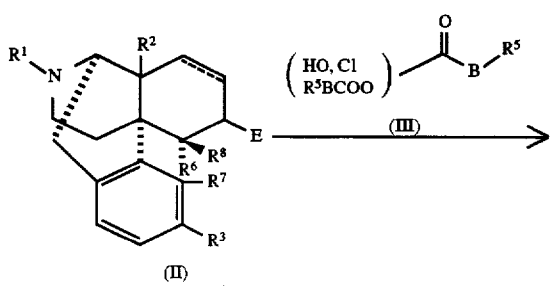

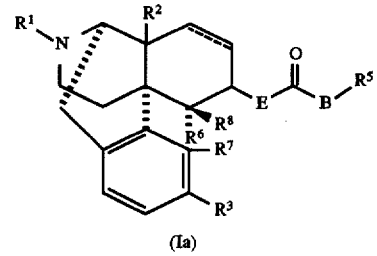

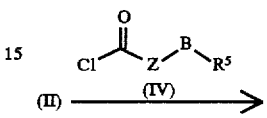

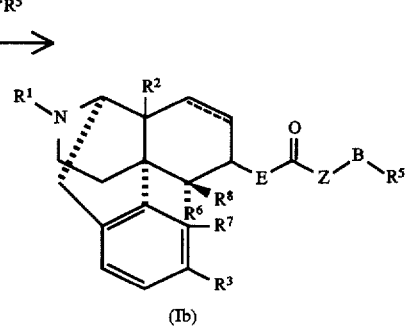

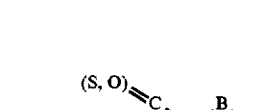

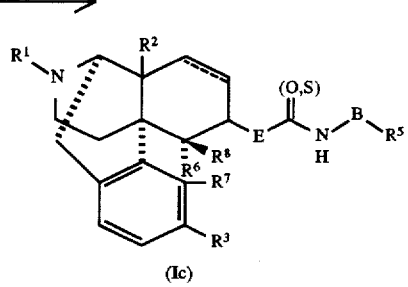

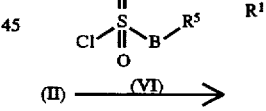

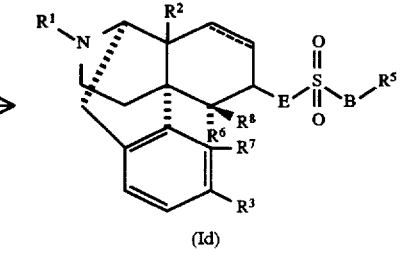

-continued
Chart 1

The 6-amino and 6-hydroxy compound used in this condensation can be obtained, specifically, by the processes described below.

As shown in Chart 2, a 6α-amino compound represented by the general formula (IIaα1) (wherein R$^1$, R$^2$, R$^3$, R$^6$, R$^7$ and R$^8$ are the same as previously described, and R$^4$ represents a straight-chain or branched alkyl group having 1–5 carbon atoms or an aryl group having 6–12 carbon atoms) is obtained by mixing a 6-keto compound represented the general formula (VIIa) (wherein R$^1$, R$^2$, R$^3$, R$^6$, R$^7$ and R$^8$ are the same as previously defined) and a primary amine represented by the general formula (VIII) (wherein R$^4$ is the same as previously defined) in a solvent and hydrogenating in the presence of suitable amounts of acid and metal catalyst, or reducing with a metal hydride reducing agent in the presence of acid. The hydrogenation reaction is more preferable in order to obtain the α-amino isomer with high selectivity. However, although the ratio varies according to the substrate, in the case of reduction using a metal hydride reducing agent, both the α form and β isomer are obtained simultaneously. Thus, this method is preferable in that it makes it possible to obtain a compound having the desired stereochemistry by using ordinary separation and purification techniques. In addition, the method in which the amine is obtained is also useful in the case of substrates having functional groups, such as olefins and so on, that react under hydrogenation conditions.

In the case of reduction using a hydrogenation reaction, 1–30 equivalents, and preferably 1–10 equivalents, of amine are used. Although any solvent including alcohols such as methanol and ethanol, ethers such as THF, ether, DME and dioxane, or aromatic hydrocarbons such as benzene and toluene, can be used as a reaction solvent as long as it is inert under hydrogenation conditions, alcohols are preferably used, with methanol used particularly preferably. Although any acid including inorganic acids such as hydrochloric acid, hydrobromic acid, sulfuric acid and phosphoric acid, or organic acids such as sulfonic acids including methanesulfonic acid and p-toluenesulfonic acid, benzoic acid, acetic acid or oxalic acid, can be used as long as it forms a salt with an amine, hydrochloric acid, sulfuric acid and methanesulfonic acid are preferably used. Normally, the use of hydrochloric acid in an amount of 1 equivalent less than the total amount of base yields satisfactory results. These acids can also be added to a reaction system after converting the substrate and reaction agents into salts in advance. Although all catalysts, including platinum catalysts such as platinum oxide and platinum hydroxide, palladium catalysts such as palladium hydroxide and palladium-carbon, and nickel catalysts such as Raney nickel, that are normally used in hydrogenation reactions can be used as a metal catalyst, platinum catalysts, and particularly platinum oxide, are used preferably. The reaction temperature is –30° C. to 80° C., and preferably –10° C. to 50° C., and the hydrogen pressure is 1–100 atmospheres and preferably 1–30 atmospheres. However, carrying out the reaction at room temperature and atmospheric pressure normally yields preferable results.

When reducing with a metal hydride, 1–30 equivalents, and preferably 1–15 equivalents, of amine are used. Although alcohols such as methanol and ethanol, ethers such as THF, ether, DME and dioxane, or aromatic hydrocarbons such as benzene and toluene, can be used for as a solvent, alcohols are used preferably, with methanol used particularly preferably. Although any acid, including inorganic acids such as hydrochloric acid, hydrobromic acid, sulfuric acid and phosphoric acid, and organic acids such as sulfonic acids including methanesulfonic acid, p-toluenesulfonic acid, benzoic acid, acetic acid and oxalic acid, may be used in the reaction provided that it normally forms a salt with amines, hydrochloric acid, sulfuric acid and methanesulfonic acid are preferably used. In addition, these acids may also be added to the reaction system after converting the substrate and reaction agents into salts in advance. The metal hydride reducing agent used is that which allows the reaction to be carried out relatively stably in the presence of acid, examples of which include sodium borohydride, sodium cyanoborohydride, zinc borohydride, sodium triacetoxyborohydride, tetramethylammonium triacetoxyborohydride and boranepyridine, with sodium cyanoborohydride used particularly preferably. Although the reaction can be carried out at a reaction temperature of –30° C. to 100° C. and preferably –10° C. to 50° C., satisfactory results can normally be obtained at room temperature.

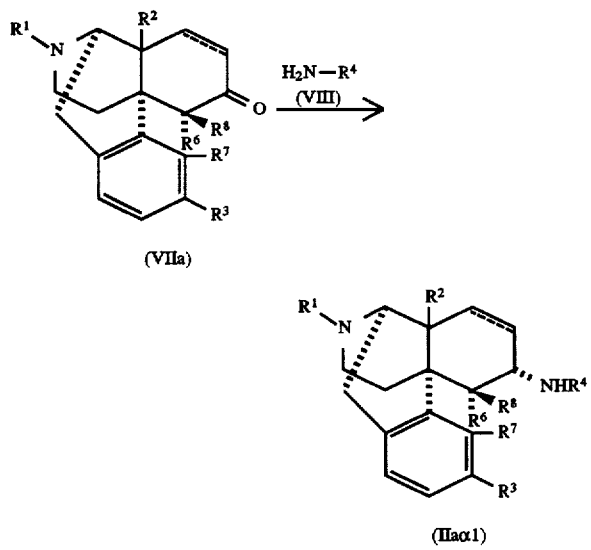

As shown in Chart 3, a 6β-amino compound represented by the general formula (IIaβ2) (wherein $R^1$, $R^2$, $R^3$, $R^6$, $R^7$ and $R^8$ are the same as previously defined, and $R^4$ represents a straight-chain or branched alkyl group having 1–5 carbon atoms or an aryl group having 6–12 carbon atoms) can be obtained from a 6-keto compound represented by the general formula (VIIb) (wherein $R^1$, $R^2$, $R^3$, $R^6$, $R^7$ and $R^8$ are the same as previously defined) with the 3 steps described below.

Step 1 involves the obtaining of an iminium intermediate represented by the general formula (X) (wherein $R^1$, $R^2$, $R^3$, $R^4$, $R^6$, $R^7$ and $R^8$ are the same as previously defined) by reaction of a keto compound with a secondary amine compound having at least one benzyl substituent group represented by the general formula (IX) (wherein $R^4$ is the same as defined above) in the presence of acid. It is desirable that the reaction be carried out while removing water produced either by azeotropic distillation or in the presence of a dehydrating agent. 1–30 equivalents, and preferably 1–10 equivalents, of secondary amine are used. Although any acid, including inorganic acids such as hydrochloric acid, hydrobromic acid, sulfuric acid and phosphoric acid, or organic acids such as sulfonic acids including methanesulfonic acid and p-toluenesulfonic acid, benzoic acid, acetic acid and oxalic acid, can be used in the reaction as long as it forms a salt with amine, hydrochloric acid, sulfuric acid, methanesulfonic acid and benzoic acid are used preferably, with hydrochloric acid and benzoic acid used particularly preferably. A method wherein these acids are added to the system after converting the substrate and reaction agents into salts in advance is also preferably carried out.

Moreover, in the case of carrying out the reaction in the presence of a weak acid, there are cases wherein preferable results are obtained if a strong acid such as inorganic acids such as hydrochloric acid, hydrobromic acid, sulfuric acid and phosphoric acid, or sulfonic acids such as methanesulfonic acid, p-toluenesulfonic acid and camphor-sulfonic acid, especially p-toluenesulfonic acid is added as an acid catalyst. Examples of reaction solvents that can be used include ethers such as THF, ether, DME and dioxane, halocarbons such as dichloromethane and chloroform, aromatic hydrocarbons such as benzene, toluene and xylene, esters such as ethyl acetate and methyl acetate, or mixtures thereof. When using a conventional Dean-Stark water separator for the purpose of removing water, solvents are used preferably that have excellent azeotropic efficiency and water separation efficiency, such as aromatic hydrocarbons such as benzene and toluene. In this case, the mixing of a solvent such as ethyl acetate, THF or the like, for the purpose of lowering the azeotropic temperature, in amounts that do not lower water separation efficiency may provide preferable results. Although a temperature of 40°–200° C., and preferably 50°–150° C., can be considered as a reaction temperature, satisfactory results can be obtained at a reaction temperature of 50°–130° C. In addition, it has also been found that a new method is effective wherein a dehydrating agent is packed into a Soxhlet type extractor followed by continuous removal of water. Although any of the solvents mentioned above can be used as a solvent in this case, ethers, esters and aromatic hydrocarbons, and particularly THF, DME, ethyl acetate, benzene and toluene, are preferably used. Although examples of dehydrating agents include molecular sieves and inorganic dehydrating agents such as anhydrous calcium sulfate, anhydrous copper sulfate, anhydrous sodium sulfate, anhydrous magnesium sulfate and calcium chloride, molecular sieves are used particularly preferably. The amount used is 1–100 times, and preferably 1–30 times as calculated from their water retentivity and the amount of moisture theoretically produced. Although a temperature of 40°–200° C., and preferably 50°–150° C., can be considered as a reaction temperature, satisfactory results are obtained at a reaction temperature of 50°–120° C. In addition, a method can also be carried out wherein the reaction is allowed to proceed by directly adding dehydrating agent to the reaction system. Examples of dehydrating agents include molecular sieves, inorganic dehydrating agents such as anhydrous calcium sulfate, anhydrous copper sulfate, anhydrous sodium sulfate, anhydrous magnesium sulfate and calcium chloride, or titanium compounds having dehydration ability such as tetraisopropoxytitanium and titanium tetrachloride. In this case also, an amount used is 1–100 times, and preferably 1–30 times as calculated from the water retentivity and the amount of moisture theoretically produced. Although a temperature of –80°–100° C. can be considered as a reaction temperature, satisfactory results are obtained at a reaction temperature of –30°–50° C.

Step 2 is a step involving conversion to a 6-N-alkyl-N-benzylamino compound represented by the general formula (XI) (wherein $R^1$, $R^2$, $R^3$, $R^4$, $R^6$, $R^7$ and $R^8$ are the same as previously defined) by reducing with metal hydride reducing agent without isolating iminium salt. Although the same solvent used in step 1 may be used as is for the reaction solvent of this step, preferable results are obtained by reacting after mixing an alcohols such as methanol or ethanol, and particularly methanol. Naturally, the reaction may also be carried out with only alcohols such as methanol or ethanol after distilling off the reaction solvent of step 1 under reduced pressure. The reaction can be carried out with metal hydride reducing agent that is relatively stable under conditions in the presence of acid, such as sodium borohydride, sodium cyanoborohydride, zinc borohydride, sodium triacetoxyborohydride, tetramethylammonium triacetoxyborohydride and boranepyridine, particularly preferably sodium cyanoborohydride. The reaction is carried out a reaction temperature of –20°–150° C., and preferably 0°–120° C. The resulting 6-N-alkyl-N-benzylamino compound represented by the general formula (XI) (wherein $R^1$, $R^2$, $R^3$, $R^4$, $R^6$, $R^7$ and $R^8$ are the same as previously defined) can also be obtained using a secondary amine by performing reductive amination using the metal hydride reducing agents of Chart 2. Moreover, if this step is performed using a corresponding secondary amine, the compound of general formula (I) can be obtained wherein A is —$NR^4$—.

Step 3 involves removing a benzyl group by hydrogenolysis to form a 6β-amino form (IIaβ2). In this step, reacting the substrate either after converting into a salt in advance using an inorganic acid such as hydrochloric acid, hydrobromic acid, sulfuric acid or phosphoric acid, or an organic acid such as sulfonic acids including methanesulfonic acid, p-toluenesulfonic acid or camphor-sulfonic acid, benzoic acid, acetic acid, oxalic acid or phthalic acid, and preferably hydrochloric acid or phthalic acid, or adding suitable amount of these acids prior to the reaction, yields favorable results. Since there are cases in which a resulting secondary amine salt can be purified as a crystal depending on the acid, selection of acid is important. For example, when phthalic acid is used with a compound wherein $R^1$ is a cyclopropylmethyl group, $R^2$ and $R^3$ are hydroxy groups, $R^4$ is a methyl group, $R^6$ and $R^7$ are together —O— and $R^8$ is a hydrogen atom, a crystalline salt is obtained that is easily purified. Although any solvent including alcohols such as methanol and ethanol, ethers such as THF, ether, DME and dioxane, and aromatic hydrocarbons such as benzene and toluene, can be used as a reaction solvent provided it is inert under hydrogenation conditions, alcohols are used preferably, with methanol used particularly preferably. Although any catalyst that is used in normal hydrogenation reactions, including, platinum catalysts such as platinum oxide and platinum hydroxide, palladium catalysts such as palladium hydroxide and palladium-carbon, and nickel catalysts such as Raney nickel, can be used as a metal catalyst, palladium catalysts, and particularly palladium-carbon, are preferably used. The reaction temperature is –30° to 80° C., and preferably –10° to 50° C. while hydrogen pressure is 1 to 100 atmospheres, and preferably 1 to 30 atmospheres. However, carrying out the reaction at room temperature and atmospheric pressure normally yields favorable results.

Chart 3

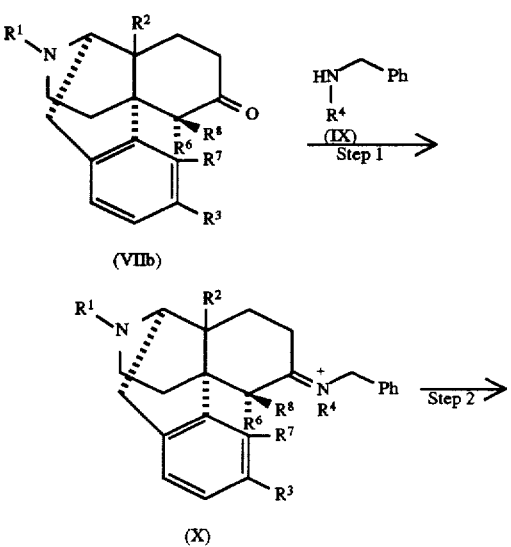

-continued
Chart 3

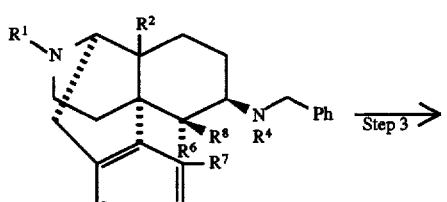

(XI)

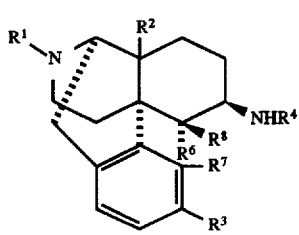

(IIaβ2)

In addition, when ammonium acetate is used in place of primary amine in the reductive amination reaction shown in Chart 2, when dibenzylamine is used in the method shown in Chart 3, or after converting ketone into oxime using the method described in the literature (J. Med. Chem., 27, 1727 (1984)), a primary amine can be obtained by reducing with borane or under hydrogenation conditions. This primary amine can be converted into a secondary amine by effecting the acylation and reduction of step 2. This is also useful as an alternative route for obtaining the secondary amine.

As shown in Chart 4, a 6-α-alcohol represented by the general formula (IIbα) (wherein $R^1$, $R^2$, $R^3$, $R^6$, $R^7$ and $R^8$ are the same as previously defined) is obtained from a 6-keto compound represented by the general formula (VIIa) (wherein $R^1$, $R^2$, $R^3$, $R^6$, $R^7$ and $R^8$ are the same as previously defined) either by reducing with metal hydride reducing agent or hydrogenation in the presence of acid and metal catalyst. Although metal hydride reducing agents including sodium borohydride, sodium cyanoborohydride, zinc borohydride, sodium triacetoxyborohydride, L-selectride and lithium aluminum hydride can be used, sufficiently satisfactory results are obtained with sodium borohydride. Although solvents including alcohols such as methanol and ethanol, and ethers such as THF, ether, DME and dioxane are used, alcohols, and particularly methanol, are preferably used. In the case of hydrogenation, examples of solvents that are used include alcohols such as methanol and ethanol, and ethers such as THF, ether and dioxane, with alcohols being used preferably, and methanol being used particularly preferably.

Although acids such as inorganic acids such as hydrochloric acid, hydrobromic acid, sulfuric acid or phosphoric acid, and organic acids such as sulfonic acids including methanesulfonic acid and p-toluenesulfonic acid, benzoic acid acetic acid or oxalic acid are used, hydrochloric acid is preferably used. Although all catalysts that are used in normal hydrogenation reactions including platinum catalysts such as platinum oxide or platinum hydroxide, palladium catalysts such as palladium hydroxide or palladium-carbon, and nickel catalysts such as Raney nickel can be used as a metal catalyst, platinum catalysts, and particularly platinum oxide are preferably used. Although the reaction can be carried out at a reaction temperature of −30°−80° C., and preferably −10°−50° C., and under a hydrogen pressure of 1–100 atmospheres, and preferably 1–30 atmospheres, favorable results are normally obtained at room temperature and under atmospheric pressure.

Chart 4

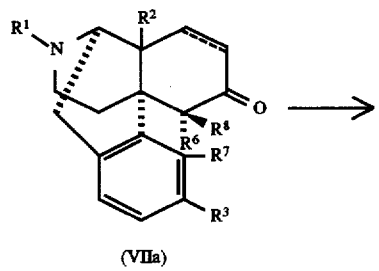

(VIIa)

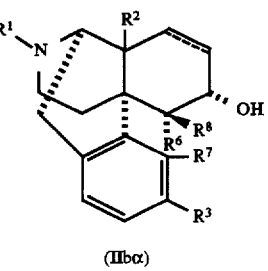

(IIbα)

As shown in Chart 5, a 6β-hydroxy form represented by the general formula (IIbβ) (wherein $R^1$, $R^2$, $R^3$, $R^6$, $R^7$ and $R^8$ are the same as previously defined) can be obtained by reacting a 6-keto form represented by the general formula (VIIa) (wherein $R^1$, $R^2$, $R^3$, $R^6$, $R^7$ and $R^8$ are the same as previously defined) with formamidinesulfinic acid in the presence of a base. Preferable examples of a base used include inorganic bases such as sodium hydroxide, potassium hydroxide, potassium carbonate and sodium bicarbonate, with sodium hydroxide being used particularly preferably. Although examples of reaction solvents used include water, alcohols such as methanol and ethanol, and aprotic dipolar solvents such as DMF and DMSO, the use of water normally yields satisfactory results. Although a temperature of 0°−150° C. is considered as a reaction temperature, a temperature of 60°−100° C. is preferable.

Chart 5

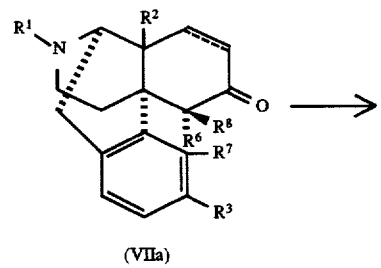

(VIIa)

-continued

Chart 5

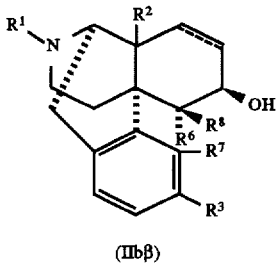

(IIbβ)

Among the 6-amino or 6-hydroxy compound synthesized in the above method, particularly a compound wherein $R^3$ is a hydrogen atom, is obtained by methods similar to those shown in Charts 2, 3, 4 and 5, using as a starting material a 3-dehydroxy-6-keto compound represented by the general formula (VIIe) (wherein $R^1$, $R^2$, $R^6$, $R^7$ and $R^8$ are the same as previously defined, provided that $R^7$ is not a hydroxy group), obtained by using as a substrate a 3-hydroxy-6-keto compound represented by the general formula (VIIc) (wherein $R^1$, $R^2$, $R^6$, $R^7$ and $R^8$ are the same as previously defined, provided that $R^7$ is not a hydroxy group) according to the scheme shown in Chart 6. In addition, an intermediate, wherein $R^3$ is a siloxy group, can be obtained by methods similar to those shown in Charts 2, 3, 4 and 5, by using for as a starting material a 3-siloxy-6-keto form represented by the general formula (VIIf) (wherein $R^1$, $R^2$, $R^6$, $R^7$ and $R^8$ are the same as previously defined, provided that $R^7$ is not a hydroxy group and G represents an alkylsilyl group), obtained from a 3-hydroxy-6-keto compound (VIIc) by the scheme shown in Chart 7.

Namely, as shown in Chart 6, the first step for obtaining a 3-dehydroxy-6-keto compound represented by the general formula (VIIe) (wherein $R^1$, $R^2$, $R^6$, $R^7$ and $R^8$ are the same as previously defined, provided that $R^7$ is not a hydroxy group) is a step wherein trifluoromethanesulfonic anhydride is caused to act on a phenolic hydroxyl group in the presence of a base to form a trifrate form represented by the general formula (VIId) (wherein $R^1$, $R^2$, $R^6$, $R^7$ and $R^8$ are the same as previously defined, provided that $R^7$ is not a hydroxy group). Although solvents including halocarbons such as dichloromethane and chloroform, ethers such as THF, ether, DME and dioxane, and amines having large steric hindrances that can be used as solvents such as 2,6-lutidine and diisopropylethylamine, can be considered for use as a reaction solvent, halocarbons, and particularly dichloromethane, are preferably used.

Although tertiary amines such as triethylamine, diisopropylethyl amine and proton sponge, as well as pyridine, 2,6-lutidine and imidazole are used as a coexisting base, 2,6-lutidine is preferably used. Although the reaction can be carried out at −30°–50° C., satisfactory results can be normally attained at a temperature of 0° C. to room temperature. Step 2 is a step wherein a trifrate form is reduced with formic acid in the presence of phosphorous ligand and a base using a palladium catalyst. Although amines usable as solvents such as triethylamine and diisopropylethylamine, ethers such as THF, ether, DME and dioxane, aromatic hydrocarbons such as benzene and toluene, and aprotic dipolar solvents such as DMF and DMSO are used for the reaction solvent, DMF is particularly preferably used. Although zero-valent complexes such as tetrakistriphenylphosphine palladium and bisbenzylideneacetone palladium, and bivalent complexes such as palladium acetate and palladium chloride are frequently used for the palladium catalyst, palladium acetate is used normally.

Although monodentate phosphines such as trimethylphosphine, triethylphosphine, triphenylphosphine and tris-o-toluphosphine, and bidentate phosphines such as bis-(diphenylphosphino)methane, 1,2-bis-(diphenylphosphino)ethane, 1,3-bis-(diphenylphosphino) propane and 1,1'-bis-diphenylphosphinoferrocene, are used as a phosphorous ligand, 1,1'-bis-diphenylphosphinoferrocene is particularly preferably used. Although amines such as triethylamine and diisopropylethylamine, and inorganic salts such as silver carbonate, sodium acetate and potassium acetate, are used as a base, triethylamine is preferably used. The reaction is carried out at a reaction temperature of 0°–150° C., and satisfactory results are normally obtained at a room temperature to 80° C.

Chart 6

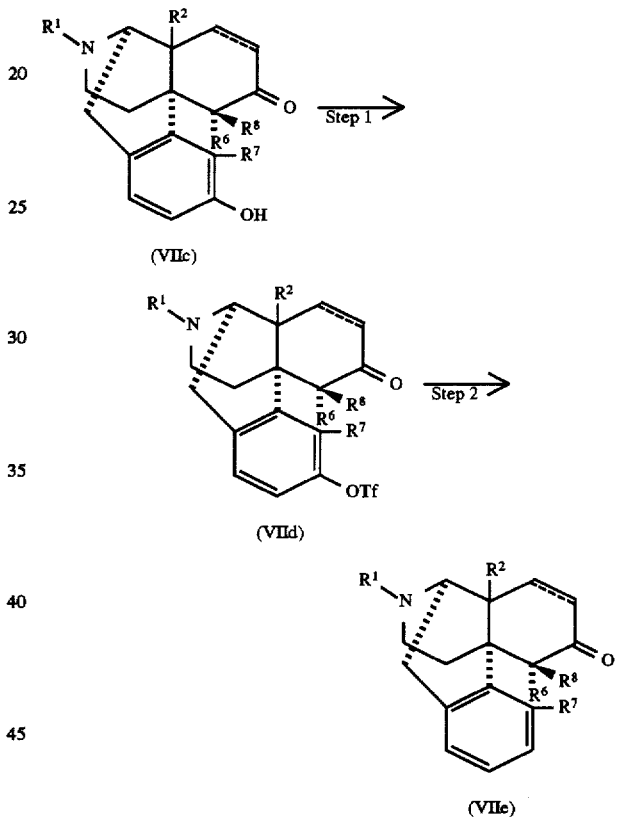

(VIIc)

(VIId)

(VIIe)

As shown in Chart 7, a 3-hydroxy-6-keto form represented by the general formula (VIIc) (wherein $R^1$, $R^2$, $R^6$, $R^7$ and $R^8$ are the same as previously defined) may be reacted with silylchloride in the presence of a base to obtain a 3-siloxy-6-keto form represented by the general formula (VIIf) (wherein $R^1$, $R^2$, $R^6$, $R^7$ and $R^8$ are the same as previously defined, provided that $R^7$ is not a hydroxy group and G represents an alkylsilyl group). Although silylchlorides such as trimethylsilylchloride, triphenylsilylchloride, t-butyldimethylsilylchloride and diphenylmethylsilylchloride are mentioned, t-butyldimethylsilylchloride is preferably used. Although tertiary amines such as triethylamine, diisopropylethylamine and proton sponge, as well as pyridine, dimethylaminopyridine and imidazole are used as a base, imidazole is preferably used. Although halocarbons such as dichloromethane, chloroform, carbon tetrachloride and 1,2-dichloroethane, ethers, such as ether, THF, DME and dioxane, and pyridine are used as a solvent, dichloromethane is preferably used. The reaction can be carried out within a range of −80°–100° C., and preferable results are obtained particularly in the vicinity of 0° C. to room temperature. Although the reaction can be carried out in 5–300 minutes, since there are cases in which 6th position ketone groups are also enolsilylated when reaction time is lengthened particularly with respect to compounds wherein ⁓⁓⁓ is a single bond and R6 and R7 together are —O—, a reaction time of 5–60 minutes is preferable.

Chart 7

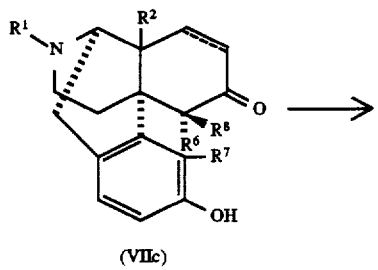

(VIIc)

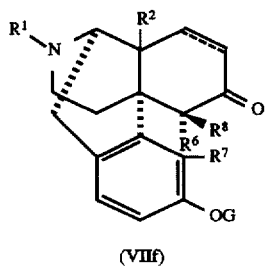

(VIIf)

As shown in Chart 8, compounds wherein X is NR$^4$ can be obtained by condensing a 6-amino form represented by the general formula (IIa) (wherein R$^1$, R$^2$, R$^3$, R$^6$, R$^7$ and R$^8$ are the same as previously defined, and R$^4$ represents a straight-chain or branched alkyl group having 1–5 carbon atoms or an aryl group having 6–12 carbon atoms), obtained by the methods shown in Charts 2 and 3, with a carboxylic acid and carboxylic acid derivative represented by the general formula (III) (wherein B and R$^5$ are the same as previously defined), or with a formic acid derivative represented by the general formula (IV) (wherein Z, B and R$^5$ are the same as previously defined), or with a isocyanic acid or isothiocyanic acid derivative represented by the general formula (V) (wherein B and R$^5$ are the same as previously defined), or with a sulfonic acid derivative represented by the general formula (VI) (wherein B and R$^5$ are the same as previously defined), etc.

Condensation with a carboxylic acid derivative can be performed by reacting a 6-amino form with an acid chloride or acid anhydride that reacts in the presence of a base, or by reacting with carboxylic acid itself using, for example, N,N'-dicyclohexylcarbodiimide (abbreviated as DCC), 1,1'-carbonyldiimidazole, or bis-(2-oxo-3-oxazolidinyl) phosphinate chloride (abbreviated as BOPCl), etc. Acid chloride or acid anhydride is used in an amount of 1–20 equivalents, and preferably 1–5 equivalents. Although halocarbons such as dichloromethane, chloroform, carbon tetrachloride and 1,2-dichloroethane, ethers such as ether, THF, DME and dioxane pyridine water or a mixture of these are used as reaction solvents, when using acid chloride, chloroform or a mixed solvent of THF and water is used preferably. In the case of using acid anhydride, pyridine is preferably used both as base and solvent. Although organic bases such as tertiary amines including triethylamine, diiso- propylethylamine and proton sponges, pyridine, dimethylaminopyridine and imidazole, and inorganic bases such as potassium carbonate, sodium carbonate, sodium bicarbonate, sodium hydroxide and potassium hydroxide are used as bases, when using chloroform as the solvent, triethylamine is normally used in an amount of 1–20 equivalents, and preferably 1–5 equvalents. In the case of using a mixed solvent of THF and water, the use of potassium carbonate, sodium carbonate or sodium bicarbonate in an amount of 1–20 equivalents, and preferably 1–5 equivalents, provides satisfactory results. The reaction can be carried out within a range of −80°–100° C., and preferable results are obtained particularly at a temperature of from 0° C. to room temperature. In the case of using DCC as a condensing agent an amount of 1–20 equivalents preferably 1–5 equivalents is used. Although halocarbons such as dichloromethane, chloroform, carbon tetrachloride and 1,2-dichloroethane, and ethers such as ether, THF, DME and dioxane are used as reaction solvents, dichloromethane and chloroform are particularly preferably used. Although organic bases such as tertiary amines including triethylamine, diisopropylethylamine and proton sponge, as well as pyridine, dimethylaminopyridine and imidazole are used as coexisting bases, dimethylaminopyridine in an amount of 0.01–2 equivalents is used particularly preferably. The reaction can be carried out within a range of −80°–100° C., and preferable results are obtained in the vicinity of 0° C. to room temperature in particular.

In the case of using 1,1'-carbonyldiimidazole as a condensing agent, an amount of 1–20 equivalents, and preferably 1–5 equivalents is used. Although ethers such as ether, THF, DME and dioxane, and halocarbons such as dichloromethane, chloroform, carbon tetrachloride and 1,2-dichloroethane are used as reaction solvents, THF is particularly preferably used. The reaction can be carried out within a range of −20°–120° C., and a temperature in the vicinity of room temperature to 100° C. is particularly preferable. In the case of using BOPCl as a condensing agent, it is used in an amount of 1–20 equivalents, and preferably 1–5 equivalents. Examples of solvents used for the reaction solvent include halocarbons such as dichloromethane, chloroform, carbon tetrachloride and 1,2-dichloroethane, and ethers such as ether, THF, DME and dioxane, though dichloromethane and chloroform are particularly preferably used. Although organic bases such as tertiary amines including triethylamine, diisopropylethylamine, proton sponge and N-ethylpiperidine, as well as pyridine, dimethylaminopyridine and imidazole are used as coexisting bases, N-ethylpiperidine in an amount of 1–20 equivalents, and preferably 1–5 equivalents, is particularly preferably used. The reaction can be carried out within a range of −80°–100° C., and preferable results are obtained at 0°–50° C. in particular.

Condensation with a formic acid derivative can be performed by reacting a 6-amino form with 1–20 equivalents and preferably 1–5 equivalents of an acid chloride that reacts in the presence of base. Although halocarbons such as dichloromethane, chloroform, carbon tetrachloride and 1,2-dichloroethane, ethers such as ether, THF, DME and dioxane, water or mixtures of these solvents are used as reaction solvents, chloroform and a mixed solvent of THF and water are particularly preferably used. Although organic bases such as tertiary amines including triethylamine, diisopropylethylamine and proton sponge, pyridine, dimethylaminopyridine and imidazole, and inorganic bases such as potassium carbonate, sodium carbonate and sodium bicarbonate are used as bases, triethylamine in an amount of 1–20 equivalents, and preferably 1-5 equivalents provides satisfactory results when chloroform is used as a solvent, while potassium carbonate, sodium carbonate and sodium bicarbonate used in an amount of 1-20 equivalents, and preferably 1-5 equivalents, normally provides favorable results when a mixed solvent of THF and water is used as a solvent. The reaction can be carried out within a range of −80°–100° C., and preferable results are obtained from 0° C. to the vicinity of room temperature.

Condensation with an isocyanic acid or isothiocyanic acid derivative can be performed by reacting 1-20 equivalents, and preferably 1-5 equivalents, of a corresponding isocyanate ester with a 6-amino form. Although halocarbons such as dichloromethane, chloroform, carbon tetrachloride and 1,2-dichloroethane, and ethers such as ether, THF, DME and dioxane are used as reaction solvents, chloroform is particularly preferably used. The reaction can be carried out within a range of −80°–100° C., and preferable results are obtained from 0° C. to the vicinity of room temperature.

Condensation with a sulfonic acid derivative can be performed by reacting 1-20 equivalents, and preferably 1-5 equivalents, of the corresponding sulfonic chloride with a 6-amino form in the presence of base. Examples of bases that are used include tertiary amines such as triethylamine, diisopropylethylamine and proton sponge, as well as pyridine, dimethylaminopyridine and imidazole. Although halocarbons such as dichloromethane, chloroform, carbon tetrachloride and 1,2-dichloroethane, ethers such as ether, THF, DME and dioxane, and pyridine are used as solvents, pyridine is particularly preferably used as both base and solvent. The reaction can be carried out within a range of −80°–100° C., and preferable results are obtained from 0° C. to the vicinity of room temperature in particular.

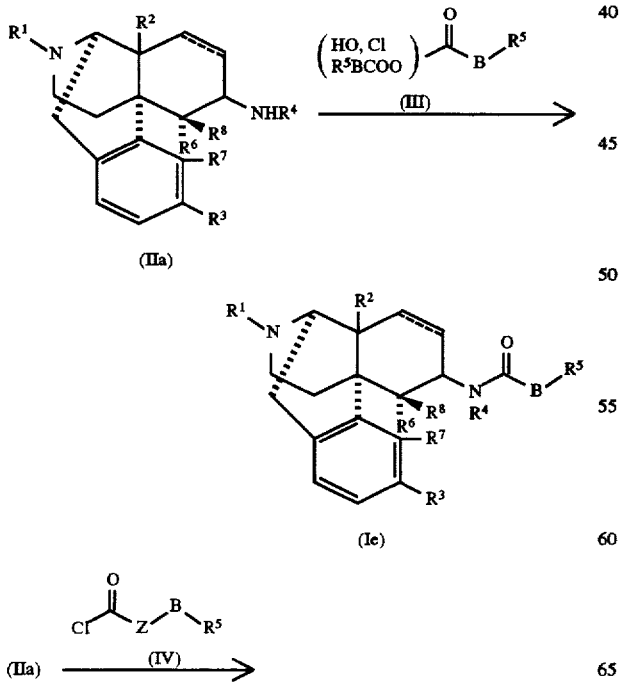

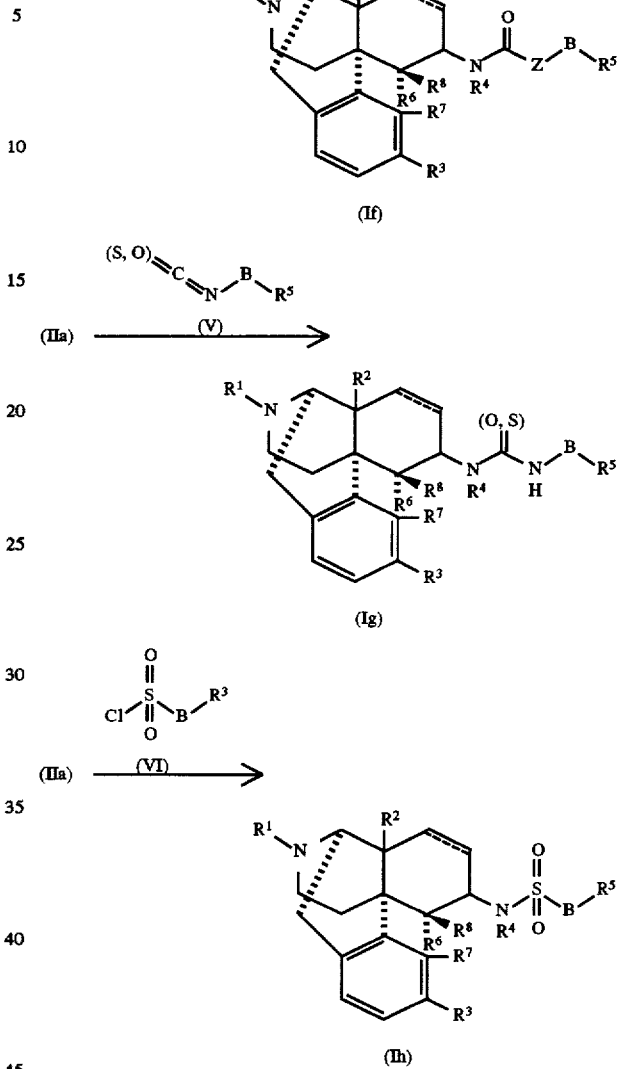

In the case of compounds wherein $R^3$ is a hydroxy group in particular, since there are cases in which phenolic hydroxyl groups may react simultaneously, as shown in Charts 9-11 with carboxylic acid derivative, formic acid derivative and isocyanic acid or isothiocyanic acid derivative, the target compound can be obtained after carrying out step 1 in the same manner as shown in Chart 8 by performing alkaline treatment for step 2. Examples of solvents used for a reaction solvent of step 2 include water, alcohols such as methanol and ethanol, ethers such as ether, THF, DME and dioxane, or mixed solvents of those solvents. When solubility is inadequate, halocarbons such as dichloromethane and chloroform can be suitably added. Examples of bases used include inorganic bases such as potassium carbonate, sodium carbonate, sodium bicarbonate, sodium hydroxide and potassium hydroxide. Normally, 1-20 equivalents, and preferably 1-10 equivalents, of potassium carbonate, sodium hydroxide and so forth are used preferably. The reaction can be carried out within a range of −80°–100° C., and favorable results are obtained from 0°–50° C. in particular.

Chart 9

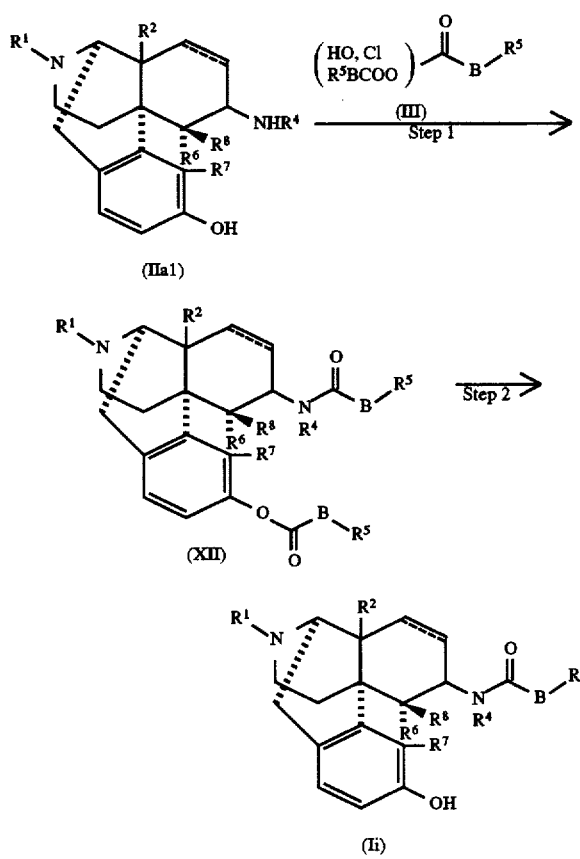

Chart 10

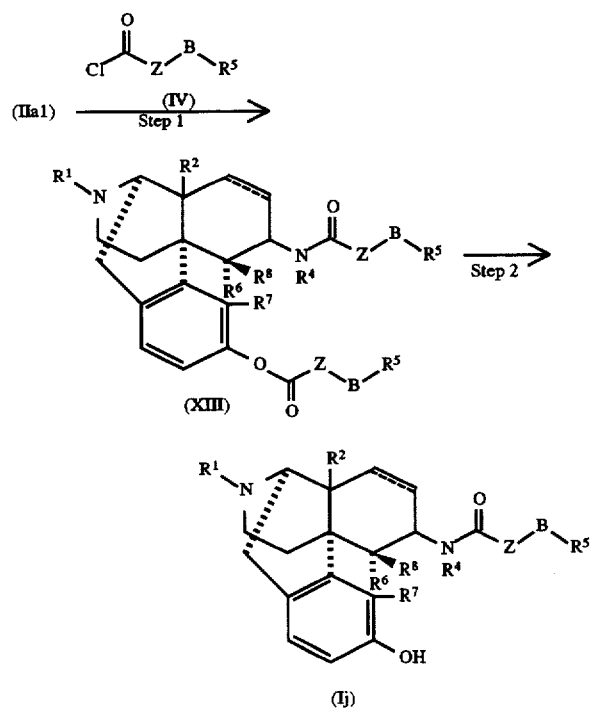

Chart 11
-continued

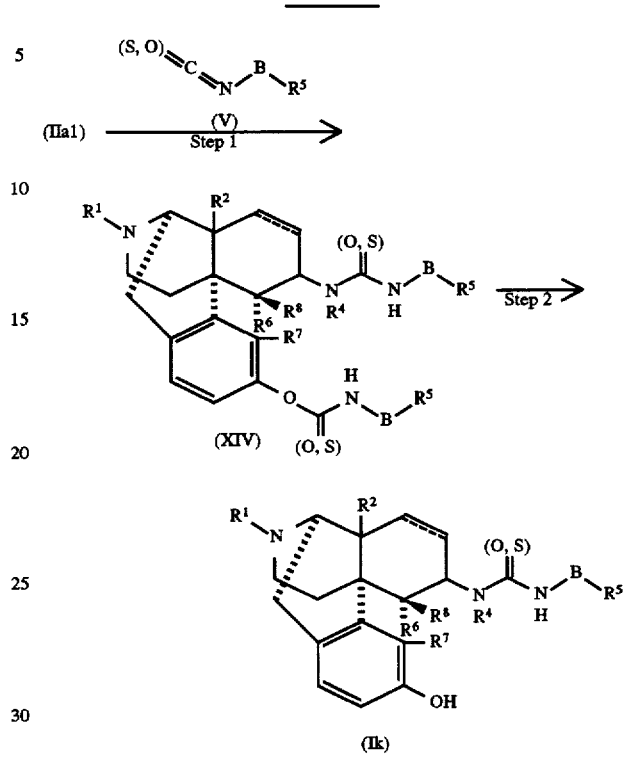

When condensing compounds wherein $R^3$ is a hydroxy group with sulfonic acid derivative, as shown in Chart 12, preferable results are obtained by using a 3-siloxy-6-amino form, wherein phenolic hydroxyl groups are protected in advance with silylether groups and so forth, represented by the general formula (IIc) (wherein R1, R2, R4, R6, R7, R8 and G are the same as previously defined). Naturally, the following method can also be applied to condensation with a carboxylic acid derivative, formic acid derivative and isocyanic acid or isothiocyanic acid derivative. Namely, this method involves removing silyl groups after carrying out step 1 in the same manner as shown in Chart 8. Although quaternary ammonium salts such as tetrabutylammonium fluoride, tetrabutylammonium chloride and pyridinium hydrofluoride, or acids such as acetic acid, hydrochloric acid, sulfuric acid and hydrofluoric acid, are used for removal of silyl groups in step 2, normally 1–20 equivalents, and preferably 1–5 equivalents, of tetrabutylammonium fluoride are used. Although ethers such as THF, ether, DME and dioxane, halocarbons such as dichloromethane and chloroform, and acetonitrile are used as solvents, THF is particularly preferably used. Although the reaction can be carried out at −20°–100° C., satisfactory results can normally be obtained at room temperature.

Chart 12

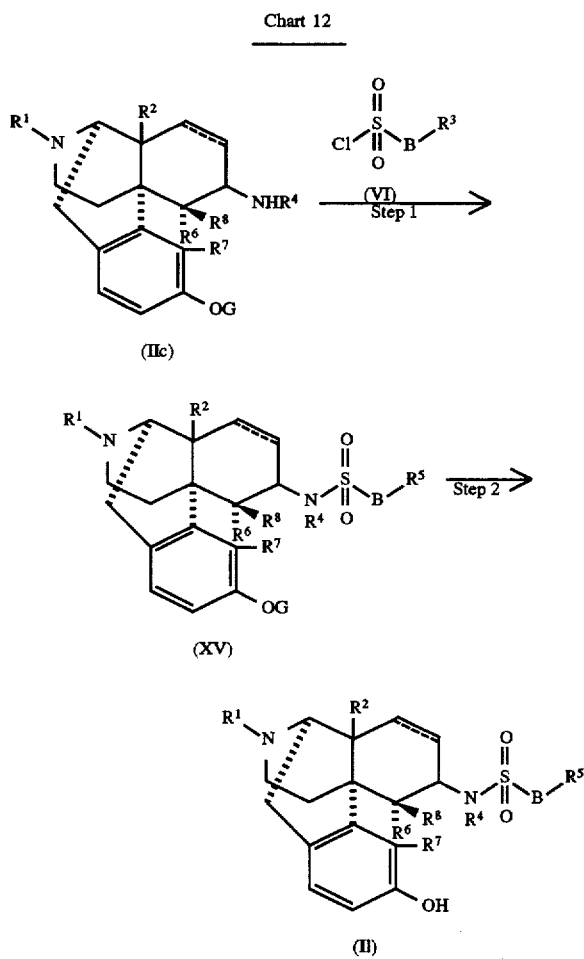

In addition, a 6-amino form represented by the general formula (Im) (wherein $R^1$, $R^2$, $R^3$, $R^4$, B, $R^5$, $R^6$, $R^7$ and $R^8$ are the same as previously defined), in which A is —$NR^4$—, is obtained by reducing an amide form represented by the general formula (Ie') (wherein $R^1$, $R^2$, $R^3$, $R^4$, $R^5$, $R^6$, $R^7$, $R^8$ and B are the same as previously defined) using a metal hydride reducing agent. Examples of reducing agents used include metal hydride compounds having a strong reducing activity such as lithium aluminum hydride, diisobutylaluminum hydride, aluminum hydride, lithium borohydride and diborane. 1–20 equivalents, and preferably 1–5 equivalents of diborane are particularly preferably used. Ethers such as THF, DME, ether and dioxane are used preferably as a solvent when using lithium aluminum hydride, lithium borohydride or diborane, with THF being used particularly preferably. Aromatic hydrocarbons such as benzene and toluene are used preferably as a solvent when diisobutylaluminum hydride or aluminum hydride are used. The reaction can be carried out within a range of –40° to 100° C., and a temperature from 0° C. to the vicinity of room temperature is preferable.

Chart 13

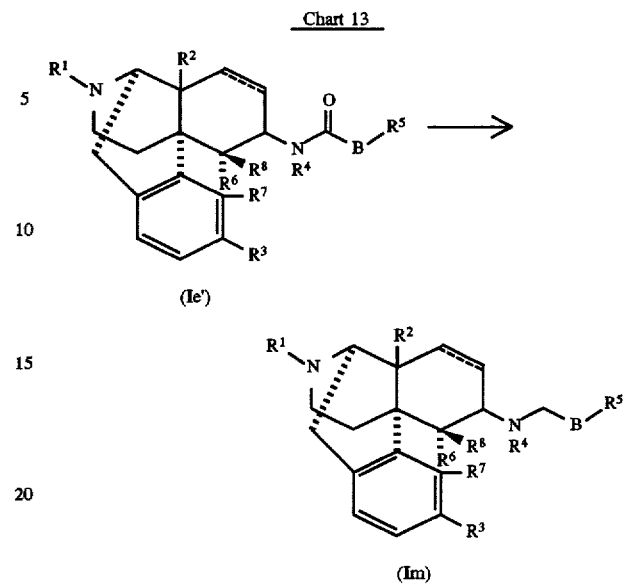

As shown in Chart 14, compounds wherein X is O can be obtained by condensing a 6-hydroxy form represented by the general formula (IIb) (wherein $R^1$, $R^2$, $R^3$, $R^6$, $R^7$ and $R^8$ are the same as previously defined) obtained in Charts 4 and 5, with a carboxylic acid derivative (III), a formic acid derivative (IV), an isocyanic acid, an isothiocyanic acid derivative (V), or sulfonic acid derivative (VI) and so forth.

Condensation with a carboxylic acid derivative can be performed by treatment of a 6-hydroxy compound with 1–20 equivalents, and preferably 1–5 equivalents of an acid chloride or acid anhydride in the presence of base. Although halocarbons such as dichloromethane, chloroform, carbon tetrachloride and 1,2-dichloroethane, ethers such as ether, THF, DME and dioxane, and pyridine are used as a reaction solvents, chloroform is used preferably when using acid chloride, while pyridine is used preferably in the case of using acid anhydride. Although tertiary amines such as triethylamine, diisopropylethylamine and proton sponge, as well as pyridine, dimethylaminopyridine and imidazole are used as bases, the use of both diisopropylethylamine and dimethylaminopyridine in an amount of 1–20 equivalents, and preferably 1–5 equivalents, normally provides satisfactory results. The reaction can be carried out at –80° to 100° C., and preferable results are obtained at a temperature of from the vicinity of room temperature to 80° C. in particular.

Condensation with a formic acid derivative can be performed by reacting a 6-hydroxy form with 1–20 equivalents, and preferably 1–5 equivalents, of an acid chloride that reacts in the presence of a base. Although halocarbons such as dichloromethane, chloroform, carbon tetrachloride and 1,2-dichloroethane, and ethers such as ether, THF, DME and dioxane are used as reaction solvents, chloroform and carbon tetrachloride are used particularly preferably. Although tertiary amines such as triethylamine, diisopropylethylamine and proton sponge, as well as pyridine, dimethylaminopyridine and imidazole are used as bases, the use of both diisopropylethylamine and dimethylaminopyridine in an amount of 1–20 equivalents, and preferably 1–5 equivalents, normally provides satisfactory results. The reaction can be carried out within a range of −80° to 100° C., and preferable results are obtained from the vicinity of room temperature to 80° C. in particular.

Condensation with an isocyanic acid or isothiocyanic acid derivative can be performed by reacting 1–20 equivalents, and preferably 1–5 equivalents, of the corresponding isocyanate ester with a 6-hydroxy form. Although halocarbons such as dichloromethane, chloroform, carbon tetrachloride and 1,2-dichloroethane, and ethers such as ether, THF, DME and dioxane are used as reaction solvent, chloroform is used particularly preferably. The reaction can be carried out within a range of −80° to 100° C., and preferable results are obtained at a temperature of from the vicinity of room temperature to 80° C. in particular.

Condensation with a sulfonic acid derivative can be carried out by treatment of 1–20 equivalents, and preferably 1–5 equivalents, of a corresponding sulfonic chloride with a 6-hydroxy form in the presence of a base. Examples of a base used include tertiary amines such as triethylamine, diisopropylethylamine and proton sponge, as well as pyridine, dimethylaminopyridine and imidazole. Although halocarbons such as dichloromethane, chloroform, carbon tetrachloride and 1,2-dichloroethane, ethers such as THF, DME and dioxane, and pyridine are used as reaction solvent, pyridine is used particularly preferably, both as base and solvent. The reaction can be carried out within a range of −80° to 100° C., and preferable results are obtained at a temperature of the vicinity of room temperature to 80° C. in particular.

Chart 14

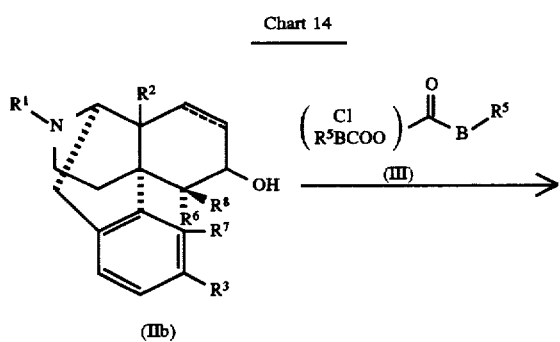

(IIb)

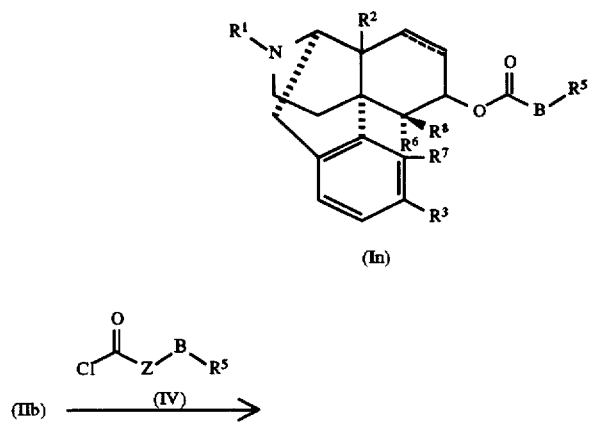

(In)

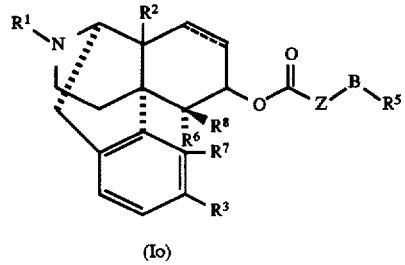

(IIb) —(IV)→

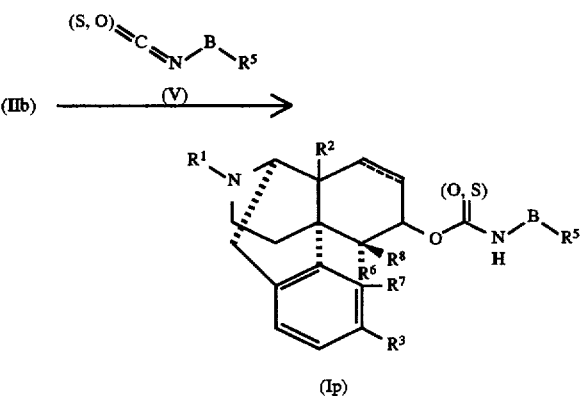

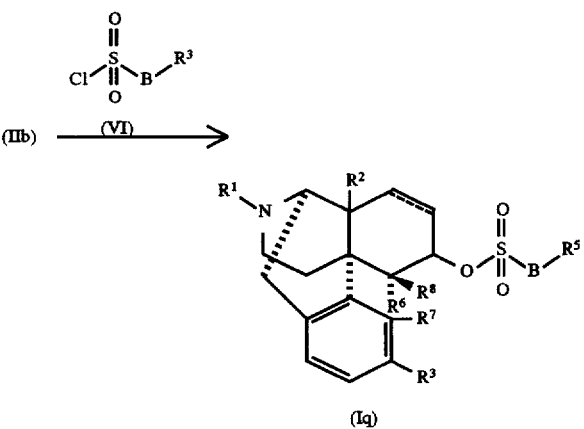

In the case of compounds wherein $R^3$ is a hydroxy group in particular, since phenolic hydroxyl group also reacts simultaneously, in the case of carboxylic acid derivative, formic acid derivative, and isocyanic acid or isothiocyanic acid derivative, after performing a condensation reaction in the same manner as shown in Chart 14 as step 1, the target compound can be obtained by performing alkaline treatment for step 2 as shown in Charts 15–17. Examples of solvents used as reaction solvent of step 2 include alcohols such as methanol and ethanol, and when solubility is not adequate, halocarbons such as dichloromethane, and chloroform can be suitably added. Examples of a base used include inorganic bases such as potassium carbonate, sodium carbonate, sodium bicarbonate, sodium hydroxide and potassium hydroxide, with potassium carbonate normally being used preferably. The reaction can be carried out within a range of −80° to 100° C., and preferable results are obtained at −20° to 50° C. in particular. However, since solvolysis of functional group at the 6 position may also proceed, in such cases, this problem is solved by either lowering the reaction temperature or shortening the reaction time.

Chart 15

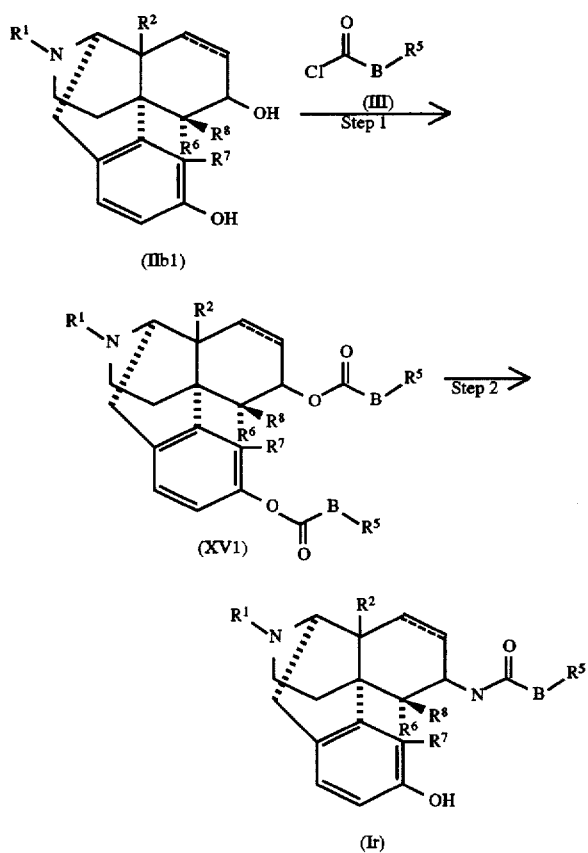

Chart 16

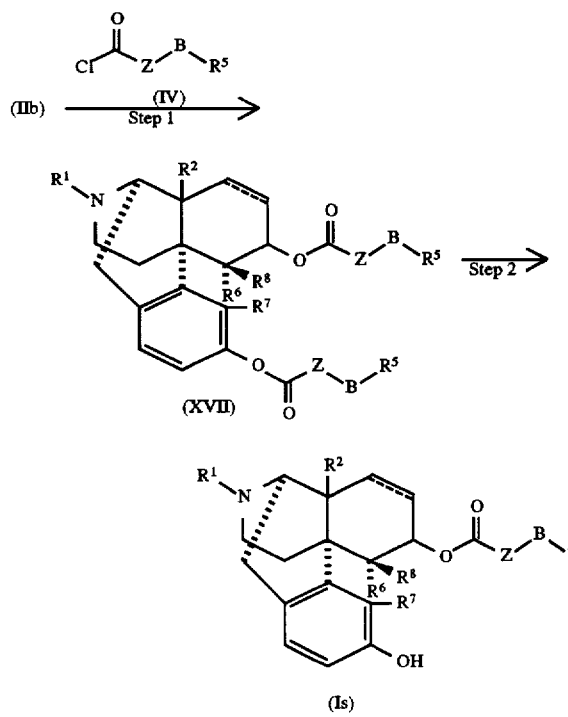

-continued
Chart 17

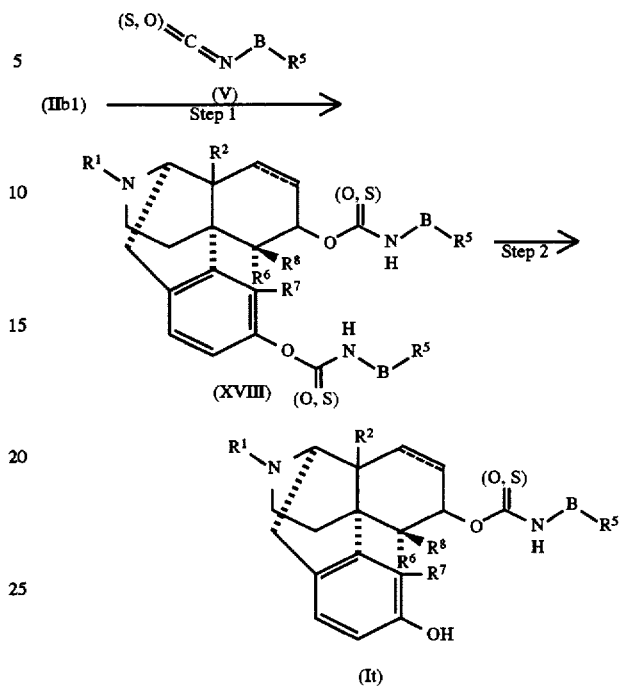

The use of a 3-siloxy-6-hydroxy form represented by the general formula (IId) (wherein $R^1$, $R^2$, $R^6$, $R^7$, $R^8$ and G are the same as previously defined), in which phenolic hydroxyl groups are protected in advance with silylether group and so forth, for condensation with a sulfonic acid derivative yields preferable results. Naturally, this method can be carried out for condensation with a carboxylic acid derivative, a formic acid derivative, an isocyanic acid or an isothiocyanic acid derivative. After performing condensation in the same manner as shown in Chart 14 as step 1, silyl group is removed in step 2. Although quaternary ammonium salts such as tetrabutylammonium fluoride, tetrabutylammonium chloride and pyridinium hydrofluoride, or acids such as acetic acid, hydrochloric acid, sulfuric acid and hydrofluoric acid, may be used for removal of silyl groups, normally 1–20 equivalents, and preferably 1–5 equivalents, of tetrabutylammonium fluoride are used. Examples of solvents used include ethers such as THF, DME and dioxane, acetonitrile and halocarbons such as dichloromethane and chloroform, though THF is used particularly preferably. Although the reaction can be carried out at −20°–100° C., satisfactory results are normally obtained at room temperature.

Chart 18

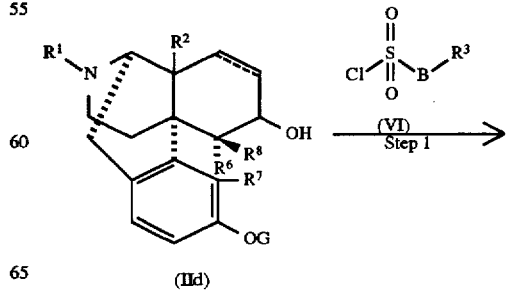

-continued
Chart 18

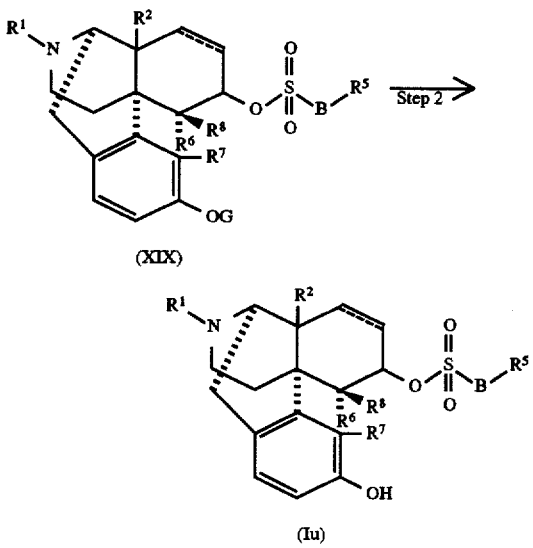

The free base obtained in the above steps can be converted into the salts with pharmacologically acceptable acids specifically by the methods shown below. Namely, a resulting free base is dissolved or suspended in a solvent followed by addition of acid and filtering of the precipitated solid or crystal, or in the case of not precipitating, a solvent of lower polarity is added, or the solvent is substituted with a solvent of lower polarity and filtering after precipitation. Alternatively, concentration and drying are performed after forming a salt. However, in the case organic solvent remains in these methods, drying under reduced pressure may be performed after freeze-drying in an aqueous solution. Examples of solvents used to dissolve or suspend the above free base include water, alcohols such as methanol, ethanol and isopropyl alcohol, halocarbons such as dichloromethane and chloroform, ethers such as ether, THF, DME and dioxane, esters such as ethyl acetate and methyl acetate, or their mixed solvents, while preferable examples include methanol, ethanol, isopropyl alcohol, ethyl acetate, chloroform, chloroform-methanol, water-methanol, and water-ethanol. Preferable examples of solvents used for precipitating solid include ether and ethyl acetate. Although it is desirable that an equivalent amount of acid be added, when it is possible to remove excess acid after washing the resulting salt, 1–10 equivalents may be used. In addition, acid may be added as is or suitably dissolved in the above-mentioned solvents and then added. For example, hydrochloric acid can be added in the form of concentrated hydrochloric acid, 1N aqueous solution, a saturated methanol solution or a saturated ethyl acetate solution, while tartaric acid can be added in the form of a solid, an aqueous solution or a methanol solution. At the time of salt formation, since the temperature of the system may rise due to the heat of neutralization, there are cases in which favorable results are obtained if a water bath or ice bath is used.

The compounds according to the present invention which are represented by general formula (I) have been found, as a result of pharmacological testing in vitro and in vivo, to have strong antitussive effects as opioid κ-agonists, and have therefore shown promise as useful antitussive agents.

For clinical use, the antitussive agents of the present invention may be used as free bases or as their salts themselves, or in appropriate combination with an additive such as a stabilizer, buffer, diluent, isotonizing agent or antiseptic. The form of administration may be, for example, as an injection; an oral preparation such as tablets, capsules, granules, powder or syrup; an enteral form of administration such as a suppository; or local administration in the form of an ointment, cream or patch. An antitussive agents of the present invention preferably contains the above-mentioned effective component in an amount of 1 to 90 wt %, and more preferably 30 to 70 wt %. The dosages are appropriately selected depending on factors such as symptoms, age, body weight and method of administration, but in the case of oral administration for adults, 0.001 mg to 10 g may be administered per day, either at once or spread over a few times.

EXAMPLES

The present invention is explained below by way of the following concrete examples which are not, however, intended to be restrictive.

Reference Example 1

6β-(N-benzyl)methylamino-17-cyclopropylmethyl-4,5α-epoxy-3,14β-dihydroxymorphinan (2)

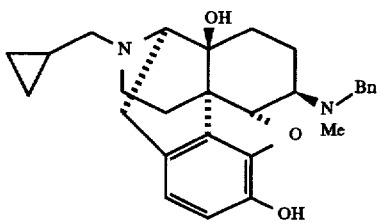

A 50.08 g (0.108 mole) portion of naltrexone benzoate was suspended in THF (350 ml), and 19.61 g (0.162 mole) of benzylmethylamine was added thereto. A Soxhlet extractor containing molecular sieve 4A (50 g) was attached for 23 hours' heating to reflux, and after methanol (200 ml) was then added to the reaction system, 10.2 g (0.162 mole) of sodium cyanoborohydride dissolved in methanol (50 ml) was added thereto and the mixture was stirred for 30 minutes. The solvent was then distilled off, ethyl acetate (400 ml) and a 1% aqueous solution of sodium bicarbonate (400 ml) were added to the residue for separation, and the aqueous layer was again extracted with ethyl acetate (80 ml). The resulting organic layer was washed with brine (250 ml), and then dried and concentrated. Methanol (240 ml) was added to the obtained residue for recrystallization to obtain 42.68 g (88% yield) of the object compound.

mp 71°–80° C. (decomposition)

NMR (400 MHz, CDCl$_3$) δ0.09–0.13 (2H, m), 0.49–0.55 (2H, m), 0.79–0.88 (1H, m), 1.25–1.35 (1H, m), 1.43–1.49 (1H, m), 1.59–1.66 (2H, m), 1.87–2.00 (1H, m), 2.11 (1H, dt, J=3.4, 11.7 Hz), 2.19–2.27 (1H, m), 2.34 (3H, s), 2.35 (2H, d, J=6.8 Hz), 2.50–2.59 (1H, m), 2.56 (1H, dd, J=5.4, 18.1 Hz), 2.62 (1H, dd, J=4.4, 11.7 Hz), 2.99 (1H, d, J=18.1 Hz), 3.04 (1H, d, J=5.4 Hz), 3.53 (1H, d, J=13.2 Hz), 3.82 (1H, d, J=13.7 Hz), 4.68 (1H, d, J=8.3 Hz), 6.51 (1H, d, J=8.3 Hz), 6.65 (1H, d, J=8.3 Hz), 7.20–7.35 (5H, m)

IR (KBr) ν3428, 3220, 1638, 1615, 1502, 1458, 1375, 1330, 1238, 1147, 1116, 1033, 990, 917, 857, 735 cm$^{-1}$

Mass (EI) m/z 446 (M$^+$), 355, 286, 160

Elemental analysis as C$_{28}$H$_{34}$N$_2$O$_3$·0.5 H$_2$O Calculated: C: 73.82, H: 7.74, N: 6.15 Found: C: 73.94, H: 7.79, N: 6.08

Reference Example 2

17-cyclopropylmethyl-4,5α-epoxy-3,14β-dihydroxy-6β-methylaminomorphinan (3)

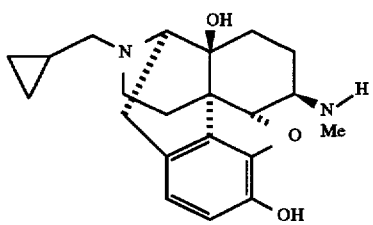

A 12.65 g portion of 6β-(N-benzyl)methylamino-17-cyclopropylmethyl-4,5α-epoxy-3,14β-dihydroxymorphinan (2).2HCl (converted to hydrochloride by established method) was dissolved in 250 ml of methanol, 2.53 g of 5% palladium carbon was added, and the mixture was stirred for 4 hours in a hydrogen atmosphere. The catalyst was removed with celite and the filtrate was then concentrated. To the obtained residue were added 100 ml of a solution of chloroform/ethanol at 4/1 and 100 ml of a saturated aqueous solution of sodium bicarbonate for separation, and the aqueous layer was extracted twice with 100 ml of a solution of chloroform/ethanol at 4/1. The organic layer was dried with anhydrous sodium sulfate and then concentrated to obtain 8.00 g of a crude product. This was recrystallized from methanol to obtain 5.84 g of the object compound (67% yield).

NMR (400 MHz, CDCl$_3$) δ0.10–0.14 (2H, m), 0.50–0.55 (2H, m), 0.79–0.86 (1H, m), 1.38 (1H, dt, J=2.9, 12.8 Hz), 1.41–1.48 (1H, m), 1.58–1.72 (2H, m), 1.78–1.91 (1H, m), 2.08–2.25 (2H, m), 2.36 (1H, d, J=6.6 Hz), 2.45 (3H, s), 2.49–2.65 (3H, m), 3.00 (1H, d, J=18.3 Hz), 3.05 (1H, d, J=5.9 Hz), 4.48 (1H, d, J=7.7 Hz), 6.54 (1H, d, J=8.1 Hz), 6.66 (1H, d, J=8.1 Hz)

IR (KBr) v3380, 2926, 1638, 1607, 1462, 1255, 1180, 795 cm$^{-1}$

Mass (EI) m/e 356 (M$^+$)

Elemental analysis as $C_{21}H_{28}O_3N_2$ Calculated: C: 70.76, H: 7.92, N: 7.86 Found: C: 70.51, H: 7.94, N: 7.84

Reference Example 3

17-cyclopropylmethyl-4,5α-epoxy-3,14β-dihydroxy-6β-methylaminomorphinan (3).phthalate

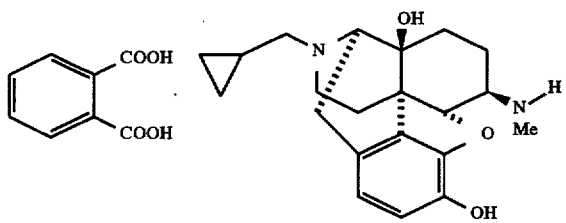

A 42.58 g (0.0953 mole) portion of 6β-(N-benzyl)methylamino-17-cyclopropylmethyl-4,5α-epoxy-3,14β-dihydroxymorphinan (2) and 17.42 g (0.105 mole) of phthalic acid were dissolved in 500 ml of methanol, 12.7 g of 10% palladium carbon was added thereto, and the mixture was stirred at 12 hours in a hydrogen atmosphere. After nitrogen substitution, 300 ml of methanol was added prior to heating to reflux, and after the precipitated crystals dissolved, celite was used for thermal time filtration of the catalyst. A 200 ml amount of the filtrate was distilled off under atomospheric pressure and then allowed to stand for recrystallization to obtain 26.82 g of the object compound (54% yield).

mp 151°–164° C. (decomposition)

NMR (400 MHz, D$_2$O) δ0.40–0.50 (2H, m), 0.73 (1H, m), 0.82 (1H, m), 1.08 (1H, m), 1.56 (1H, m), 1.67 (1H, m), 1.85 (1H, m), 1.89–2.02 (2H, m), 2.52 (1H, ddd, J=13.2, 13.2, 4.9 Hz), 2.75 (1H, ddd, J=12.9, 12.9, 4.2 Hz), 2.78 (3H, s), 2.93–3.04 (2H, m), 3.16–3.25 (2H, m), 3.32–3.43 (2H, m), 4.07 (1H, br d, J=5.9 Hz), 4.99 (1H, d, J=7.3 Hz), 6.85 (1H, d, J=8.0 Hz), 6.90 (1H, d, J=8.0 Hz), 7.34–7.39 (2H, m), 7.43–7.48 (2H, m)

IR (KBr) v3388, 3032, 1605, 1557, 1510, 1460, 1367, 1330, 1243, 1168, 1120, 1035, 992, 936, 859, 770 cm$^{-1}$

Mass (FAB) m/z 357 ((M+H)$^+$)

Elemental analysis as $C_{21}H_{28}N_2O_3 \cdot C_8H_6O_4 \cdot 0.8H_2O$ Calculated: C: 64.86, H: 6.68, N: 5.22 Found: C: 64.93, H: 6.61, N: 5.23

Reference Example 4

17-cyclopropylmethyl-4,5α-epoxy-3,14β-dihydroxy-6β-(N-methyl-3-trifluoromethylcinnamamido)morphinan.tartrate (4)

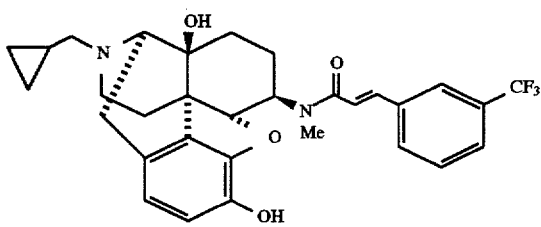

A 201 mg (0.56 mmol) portion of 17-cyclopropylmethyl-4,5α-epoxy-3,14β-dihydroxy-6β-methylaminomorphinan (3) was dissolved in chloroform (5 ml), 0.26 ml (1.86 mmol) of triethylamine and chloroform (1 ml) solution containing 397 mg (1.69 mmol) of 3-trifluromethylcinnamyl chloride, derived from the commercially available corresponding carboxylic acid using oxalyl chloride, were added thereto, for a 30 minute reaction at room temperature. Saturated sodium bicarbonate (10 ml) was added, extraction was performed with chloroform (10 ml×2), and drying was performed with anhydrous sodium sulfate prior to distilling off the solvent.

The above-mentioned reaction mixture was dissolved in methanol (4 ml) and chloroform (1 ml), and potassium carbonate (0.2 g) was added thereto for a 30 minute reaction at room temperature. Further addition of water (6 ml) and a saturated aqueous solution of sodium bicarbonate (6 ml) was followed by extraction with chloroform (10 ml×2), drying with anhydrous sodium sulfate and then distillation of the solvent. The product was purified by silica gel column chromatography (20 g; chloroform→2% methanol/chloroform) to obtain a free base.

This product was dissolved in methanol, and a methanol (1 ml) solution containing 40.2 mg (0.27 mmol) of tartaric acid was added thereto to produce a salt, which after distillation of the solvent was suspended in ether and filtered out to obtain 298 mg of the object compound (84% yield).

mp 156°–159° C.

NMR (400 MHz, DMSO-d$_6$) δ0.21 (2H, m), 0.52 (2H, m), 0.91 (1H, m), 1.2–1.5 (3H, m), 1.57 (1H, d, J=13.2 Hz), 2.12 (2H, m), 2.29 (1H, m), 2.49 (1H, m), 2.6–2.8 (3H, m), 2.90 (2H, s), 3.08 (1H, d, J=18.6 Hz), 3.17 (1H, s), 3.26 (1H, m), 3.67 (0.7H, m), 4.02 (1H, s), 4.21 (0.3H, m), 4.68 (0.7H, d, J=7.8 Hz), 4.79 (0.3H, d, J=8.3 Hz), 6.6–6.8 (2.6H, m), 7.37 (1H, dd, J=7.3, 16.1 Hz), 7.5–7.8 (3.8H, m), 8.02 (0.3H, d, J=7.8 Hz), 8.14 (0.3H, s)

IR (KBr) ν3350, 1649, 1601, 1336, 1168, 1127 cm$^{-1}$

Mass (FAB) m/z 555 ((M+H)$^+$)

Elemental analysis as $C_{31}H_{33}N_2O_4F_3 \cdot 0.5(C_4H_6O_6) \cdot 0.3H_2O$ Calculated: C: 62.41, H: 5.81, N: 4.41, F: 8.98 Found: C: 62.32, H: 5.99, N: 4.48 F: 8.88

Reference Example 5

17-cyclopropylmethyl-4,5α-epoxy-3,14β-dihydroxy-6β-[N-methyl-trans-3-(3-furyl)acrylamido] morphinan.HCl

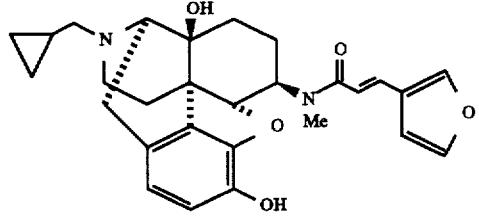

A 21.12 g (0.0404 mole) portion of 17-cyclopropylmethyl-4,5α-epoxy-3,14β-dihydroxy-6β-methylaminomorphinan (3) phthalate was dissolved in 110 ml of water, 110 ml of THF and 8.75 g (0.0808 mole) of sodium carbonate were added thereto, and then the reaction system was subjected to argon atmosphere. Then, 6.96 g (0.04444 mole) of trans-3-(3-furyl)acryloyl chloride was dissolved in 40 ml of THF and added thereto dropwise. After 30 minutes of stirring, 40 ml of methanol and 54 ml of a 3N aqueous solution of sodium hydroxide were added to the mixture which was then stirred for 1 hour. To the reaction system was further added 350 ml of ethyl acetate and 250 ml of a saturated aqueous solution of sodium bicarbonate for separation, and the aqueous layer was extracted again with 100 ml of ethyl acetate. The resulting organic layer was washed with 200 ml brine, and then dried with sodium sulfate and concentrated. The residue was heated to dissolution in 630 ml of ethyl acetate, and then 150 ml of the solvent was heat distilled and allowed to stand for recrystallization to contain 15.47 g of a free base of the object compound. A 9.03 g portion of this free base was collected and suspended in 90 ml of ethanol, 18.7 ml of 1N aqueous HCl was added thereto, and the mixture was concentrated to dryness to obtain 9.72 g of the object compound (80% yield).

mp 187° C. (decomposition)

NMR (400 MHz, DMSO-d$_6$) δ0.42 (1H, m), 0.51 (1H, m), 0.60 (1H, m), 0.68 (1H, m), 1.07 (1H, m), 1.26 (0.4H, m), 1.32–1.50 (3.6H, m), 1.73 (1H, br d, J=13.7 Hz), 2.13 (1H, m), 2.40–2.60 (3H, m), 2.88 (1H, m), 2.92 (1.8H, s), 3.06 (1H, br d, J=13.18 Hz), 3.16 (1.2H, s), 3.59 (0.6H, m), 3.86 (1H, m), 4.19 (0.4H, m), 4.86 (0.6H, d, J=7.8 Hz), 4.92 (0.4H, d, J=7.8 Hz), 6.35 (0.6H, d, J=15.6 Hz), 6.40 (0.4H, br s), 6.50 (0.6H, br s), 6.62 (0.6H, s), 6.64 (0.4H, d, J=8.3 Hz), 6.71 (1H, d, J=8.3 Hz), 6.85 (0.6H, d, J=8.3 Hz), 6.90 (0.4H, d, J=15.1 Hz), 6.99 (0.4H, s), 7.22 (0.6H, d, J=15.6 Hz), 7.36 (0.4H, d, J=15.1 Hz), 7.66 (0.6H, s), 7.72 (0.4H, s), 7.92 (0.6H, s) 8.03 (0.4H, s), 8.85 (1H, br s), 9.28 (0.4H, s), 9.68 (0.6H, s)

IR (KBr) ν3376, 1653, 1506, 1599, 1410, 1323, 1158, 1127, 1033, 872, 799 cm$^{-1}$

Mass (FAB) m/z 477 ((M+H)$^+$)

Elemental analysis as $C_{28}H_{32}N_2O_5 \cdot HCl \cdot 0.2H_2O$ Calculated: C: 65.10, H: 6.52 N: 5.42, Cl: 6.86 Found: C: 65.11, H: 6.63, N: 5.60 Cl: 6.80

Reference Example 6

17-cyclopropylmethyl-4,5α-epoxy-3,14β-dihydroxy-6β-(N-methyl-3-methylcinnamamido) morphinan.HCl (6)

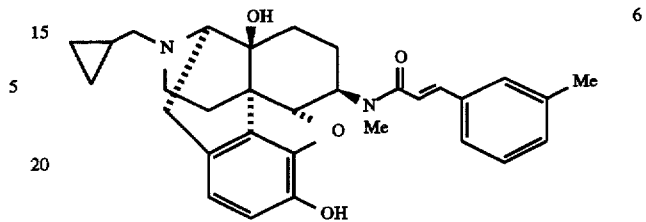

To a mixture of 0.20 g (0.56 mmol) of 17-cyclopropylmethyl-4,5α-epoxy-3,14β-dihydrozy-6β-methylaminomorphinan (3) phthalate, water (2.5 ml), THF (2.5 ml) and 0.23 g (1.68 mmol) of potassium carbonate was added a THF (0.5+0.5 ml) solution containing 0.2 g (1.12 mmol) of 3-methylcinnamyl chloride, derived from commercially available 3-methylcinnamic acid using oxalyl chloride, and the reaction was conducted at room temperature for 5 minutes. To the reaction mixture there were further added methanol (1.5 ml) and a 3M aqueous solution of sodium hydroxide (1.6 ml) and the reaction was continued for 1.5 hours at room temperature. Water (2.5 ml) was then added, extraction was performed with ethyl acetate (10+7 ml), drying was performed with anhydrous sodium sulfate, and then the solvent was distilled off. The obtained crude product was purified by silica gel column chromatography (30 g; chloroform→2% methanol/chloroform→5% methanol/chloroform) to isolate a free base. After dissolving this in methanol, hydrochloric acid/methanol was added thereto to produce a salt, which after distillation of the solvent was suspended in ether and filtered out to obtain 252 mg of the object compound (84% yield).

mp 245° C. (decomposition)

NMR (400 MHz, DMSO-d$_6$) δ0.42 (1H, m), 0.50 (1H, m), 0.59 (1H, m), 0.69 (1H, m), 1.07 (1H, m), 1.2–1.5 (3H, m) 1.72 (1H, d, J=13.7 Hz), 2.12 (1H, m), 2.34 (3H, s), 2.4–2.6 (2H, m), 2.88 (1H, m), 2.92 (2H, s), 3.0–3.1 (2H, m), 3.18 (1H, s), 3.3–3.4 (2H, m), 3.66 (0.7H, m), 3.83 (1H, m), 4.20 (0.3H, m), 4.83 (0.7H, d, J=7.8 Hz), 4.90 (0.3H, d, J=8.3 Hz), 6.6–6.8 (2H, m), 6.85 (0.7H, d, J=8.3 Hz), 7.1–7.3 (4.4H, m), 7.41 (0.3H, d, J=15.1 Hz), 7.48 (0.3H, d, J=7.3 Hz), 7.54 (0.3H, brs)

IR (KBr) ν3390, 1647, 1605, 1323, 1127, 1035 cm$^{-1}$

Mass (FAB) m/z 501 ((M+H)$^+$)

Elemental analysis as $C_{31}H_{36}N_2O_4 \cdot HCl \cdot 0.8H_2O$ Calculated: C: 67.51, H: 7.06 N: 5.08, Cl: 6.43 Found: C: 67.35, H: 7.05, N: 5.17 Cl: 6.53

Reference Example 7

17-cyclopropylmethyl-4,5α-epoxy-3,14β-dihydroxy-6β-[N-methyl-N-2-(3,4-dichlorophenyl)ethylamino]morphinan.1.9 HCl (7)

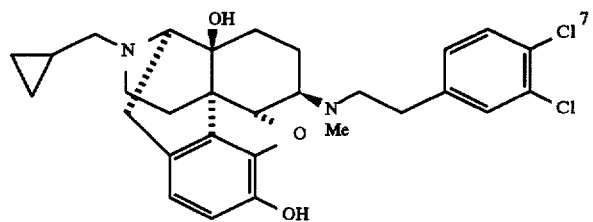

A 262.3 mg (0.403 mmol) portion of 17-cyclopropylmethyl-4,5α-epoxy-3,14β-dihydroxy-6β-(N-methyl-3,4-dichlorophenylacetamido)morphinan (obtained by the same method as in Reference Example 4 using 3,4-dichlorophenylacetyl chloride) was dissolved in 5.0 ml of anhydrous THF under an argon stream. 1.2 ml (2.4 mmol) of a 2.0M anhydrous THF solution containing a borane/dimethyl sulfide complex was added dropwise at 0° C. and the mixture was subjected to reflux for 2.1 hours. The reaction solution was then cooled to 0° C., 3.5 ml of 6N hydrochloric acid was added, and reflux was continued for one hour. The reaction solution was again cooled to 0° C., 35 ml of a saturated aqueous solution of sodium bicarbonate was added for basicity, extraction was performed with chloroform/methanol (4:1) (3×20 ml), and the organic layers were combined, dried and concentrated, upon which an oil was obtained. The oil was purified by column chromatography (20 g silica gel; ammonia saturated chloroform) to obtain 188.3 mg of a free base of the object compound (65% yield). This free base was dissolved in methanol and a methanol solution containing hydrogen chloride was added thereto, after which the mixture was concentrated and the obtained hydrochloride was purified by Sephadex gel column chromatography (methanol×2) to obtain 105.4 mg of the object compound.

mp>185° C. (decomposition)

NMR (400 MHz, CDCl$_3$; data of free base) δ0.12 (2H, m), 0.52 (2H, m), 0.83 (1H, m), 1.29 (1H, ddd, J=13.2, 13.2, 2.9 Hz), 1.44 (1H, m), 1.51 (1H, m), 1.61 (1H, ddd, J=13.2, 2.9, 2.9 Hz), 1.86 (1H, m), 2.0–3.8 (2H, br s, 2×OH), 2.11 (1H, ddd, 11.7, 11.7, 3.4 Hz), 2.21 (1H, ddd, J=12.2, 12.2, 4.9 Hz), 2.33–2.38 (2H, m), 2.41 (3H, s), 2.47–2.56 (2H, m), 2.57–2.75 (4H, m), 2.81 (1H, m), 2.97–3.06 (2H, m), 4.56 (1H, d, J=8.3 Hz), 6.56 (1H, d, J=8.1 Hz), 6.71 (1H, d, J=8.1 Hz), 7.01 (1H, dd, J=8.3, 2.0 Hz), 7.29 (1H, d, J=2.0 Hz), 7.30 (1H, d, J=8.3 Hz)

IR (KBr) v 3250, 1638, 1618, 1473, 1398, 1330, 1241, 1218, 1116, 1035, 982, 919, 855, 756 cm$^{-1}$

Mass (FAB) m/z 529 ((M+H)$^+$)

Elemental analysis as $C_{29}H_{34}Cl_{12}N_2O_3 \cdot 1.9HCl \cdot 0.5H_2O$
Calculated: C: 57.31, H: 6.12 N: 4.61, Cl: 22.75 Found: C: 57.40, H: 6.22, N: 4.55 Cl: 22.54

Reference Example 8

17-cyclopropylmethyl-4,5α-epoxy-3,14β-dihydroxy-6β-(N-methyl-benzyloxycarbamido)morphinan.HCl (8)

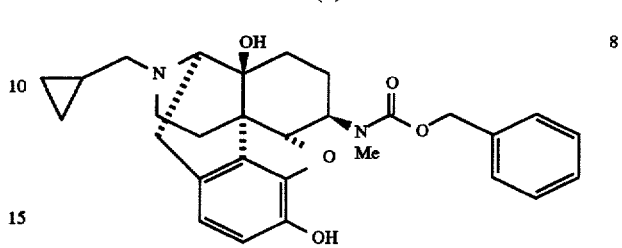

A 200 mg (0.56 mmol) portion of 17-cyclopropylmethyl-4,5α-epoxy-3,14β-dihydroxy-6β-methylaminomorphinan (3) was dissolved in chloroform (9 ml), 0.25 ml (1.86 mmol) of triethylamine and 637 mg (1.12 mmol) of commercially available benzyl formate chloride (30–35%; toluene solution) were added thereto, and the reaction was conducted at room temperature for 20 minutes. To the reaction mixture were then added a 1N aqueous solution of sodium hydroxide (3 ml) and methanol (12 ml) and the reaction was continued for 50 minutes at room temperature. After concentration, ethyl acetate (20 ml) was added, the mixture was washed with water (6 ml) and a saturated aqueous solution of sodium chloride (6 ml) and then dried with anhydrous sodium sulfate, after which the solvent was distilled off. The product was purified by silica gel column chromatography (25 g; ethyl acetate) to obtain a free base. This was dissolved in methanol, and an excess methanol hydrochloride solution was added thereto to produce a salt which after distillation of the solvent was suspended in ether and filtered out to obtain 128 mg of the object compound (43% yield).

mp 189.0°–192.0° C. (decomposition, diethyl ether)

NMR (400 MHz, DMSO-d$_6$) δ0.31–0.47 (1H, m), 0.47–0.56 (1H, m), 0.56–0.63 (1H, m), 0.63–0.76 (1H, m), 1.00–1.14 (1H, m), 1.20–1.52 (3H, m), 1.63–1.82 (1H, m), 2.03–2.22 (1H, m), 2.34–2.59 (1H, m), 2.80–2.90 (1H, m), 2.90 (1.7H, s), 2.93 (1.3H, s), 2.98–3.17 (2H, m), 3.22–3.40 (2H, m), 3.60–3.72 (0.6H, m), 3.72–3.80 (0.4H, m), 3.84 (1H, d, J=4.9 Hz), 4.83 (1H, brt), 4.98 (0.4H, d, J=13.2 Hz), 5.04 (1H, d, J=12.7 Hz), 5.09 (0.6H, d, J=13.2 Hz), 6.42 (1H, brs), 6.72 (0.6H, d, J=8.3 Hz), 6.77 (0.4H, d, J=7.8 Hz), 7.37 (5H, s), 7.16–7.45 (2H, m), 8.83 (1H, brs), 9.32 (0.4H, s), 9.45 (0.6H, s)

IR (KBr) v1678, 1560, 1543, 1460, 1315, 1152, 1033 cm$^{-1}$

Mass (FAB) m/z 491 ((M+H)$^+$)

Elemental analysis as $C_{29}H_{35}N_2O_5Cl$ Calculated: C: 66.09, H: 6.69 N: 5.31, Cl: 6.73 Found: C: 66.10, H: 6.64, N: 5.18 Cl: 6.56

Reference Example 9

17-cyclopropylmethyl-4,5α-epoxy-3,14β-dihydroxy-6α-(3-phenylpropionyloxy)morphinan.tartrate (9)

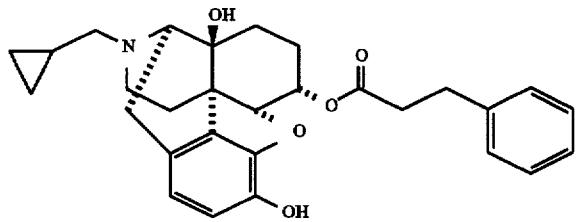

A 148 mg portion of 17-cyclopropylmethyl-4,5α-epoxy-3,6α,14β-trihydroxymorphinan (N. Chatterjie, C. E. Inturrisi, H. B. Dayton, and H. Blumberg, J. Med. Chem., 18, 490 (1975). H. C. Brown and S. Krishnamurthy, J. Am. Chem. Soc., 94, 7159 (1972)) was dissolved in 0.9 ml of carbon tetrachloride and 0.3 ml of methylene chloride, after which 0.225 ml of diisopropylethylamine and 26 mg of 4-dimethylaminopyridine were added thereto, and 0.13 ml of 3-phenylpropionyl chloride was added dropwise at 0° C. After the mixture was stirred at room temperature for 20 hours, 2 ml of a saturated aqueous solution of sodium bicarbonate was added to the reaction system for separation, and the aqueous layer was extracted twice with chloroform. The organic layer was dried with anhydrous sodium sulfate and concentrated. The obtained residue was then dissolved in a chloroform/methanol mixed solvent, and 30 mg of potassium carbonate was added to the mixture which was subsequently stirred for one hour. Water was then added to the reaction system for separation, and the aqueous layer was extracted twice with chloroform. The resulting organic layer was dried with anhydrous sodium sulfate and concentrated, and the residue was purified by silica gel column chromatography (15 g chloroform/methanol=20/1) to obtain 95.3 mg of a free base of the object compound. This was dissolved in methanol, and after addition of 15 mg of tartaric acid to total dissolution the solution was concentrated. The residue was reprecipitated from ether and filtered to obtain 103 mg of the object compound (43% yield).

mp>110° C. (decomposition)

NMR (500 MHz, DMSO-$d_6$) δ0.18–0.28 (2H, m), 0.47–0.60 (2H, m), 0.83–0.95 (1H, m), 1.19–1.28 (1H, m), 1.32–1.49 (3H, m), 1.74–1.82 (1H, m), 2.19–2.29 (2H, m), 2.40–2.47 (2H, m), 2.55–2.80 (6H, m), 3.08 (1H, brd, J=18.9 Hz), 3.28 (1H, brs), 3.36 (5H, m), 4.10 (2H, s), 4.64 (1H, d, J=4.9 Hz), 5.27–5.31 (1H, m), 6.51 (1H, d, J=8.2 Hz), 6.63 (1H, d, J=8.2 Hz), 7.13–7.19 (3H, m), 7.22–7.28 (2H, m), 9.10 (1H, brs)

IR (KBr) ν3400, 1719, 1460, 1307, 1267, 1122, 1069, 1036 cm$^{-1}$

Mass (FAB)

m/z 476 ((M+H)$^+$)

Elemental analysis as $C_{29}H_{33}NO_5 \cdot 0.95 C_4H_6O_6 \cdot 0.17 C_4H_{10}O \cdot 0.17 C_2H_6O \cdot 0.4 H_2O$
Calculated: C: 62.91, H: 6.59 N: 2.17 Found: C: 62.92, H: 6.56, N: 2.32

Reference Example 10

17-cyclopropylmethyl-4,5α-epoxy-3,14β-dihydroxy-6β-(N-methyl-3-trifluoromethoxycinnamamido)morphinan.tartrate (10)

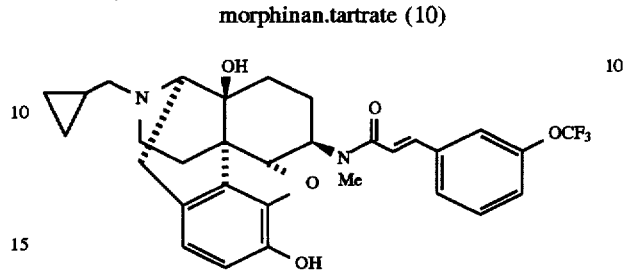

A 0.50 g (0.96 mmol) portion of 17-cyclopropylmethyl-4,5α-epoxy-3,14β-dihydroxy-6β-(N-methylamino)morphinan (3).phthalate was dissolved in 5 ml of water, and after 5 ml of THF and 0.20 g (1.91 mmol) of sodium carbonate were added, the reaction system was subjected to argon atmosphere. Then, 0.36 g (1.44 mmol) of 3-trifluoromethoxycinnamyl chloride dissolved in 1.5 ml of THF was added dropwise thereto. The mixture was stirred at room temperature for 15 minutes, after which 2 ml of methanol and 1.28 ml of a 3N aqueous solution of sodium hydroxide were added and the mixture was further stirred for one hour. To the reaction system were then added 30 ml of ethyl acetate and 20 ml of a saturated aqueous solution of sodium bicarbonate for separation, and the aqueous layer was again extracted with 10 ml of ethyl acetate. The resulting organic layer was washed with 20 ml of brine, and then dried with sodium sulfate and concentrated. The residue was purified by silica gel column chromatography (50 g of Merck 9385; chloroform/methanol=40/1) to obtain a free base of the object compound. This was dissolved in 10 ml of methanol, a tartaric acid (64.6 mg)/methanol solution (1.5 ml) was added, the solvent was distilled off under reduced pressure, and after azeotropic distillation with methanol (10 ml×2) the residue was suspended in ethyl acetate and filtered out to obtain the object compound (49% yield).

mp 152°–155° C.

NMR (400 MHz, DMSO-$d_6$) δ0.23 (2H, m), 0.52 (2H, m), 0.91 (1H, m), 1.25–1.45 (3H, m), 1.59 (1H, m), 2.05–2.20 (2H, m), 2.31 (1H, m), 2.53 (1H, m), 2.65–2.80 (3H, m), 2.90 (2H, s), 3.11 (1H, d, J=18.6 Hz), 3.16 (1H, s), 3.41 (1H, m), 3.63 (0.7H, m), 4.06 (1H, s), 4.20 (0.3H, m), 4.70 (0.7H, d, J=8.3 Hz), 4.80 (0.3H, d, J=8.3 Hz), 6.55–6.75 (2.7H, m), 7.30–7.55 (4.7H, m), 7.74 (0.3H, d, J=7.8 Hz), 7.81 (0.3H, s)

IR (KBr) ν3350, 1649, 1603, 1261, 1216, 1127 cm$^{-1}$

Mass (FAB) m/z 571 ((M+H)$^+$)

Elemental analysis as $C_{31}H_{33}N_2O_5F_3 \cdot 0.5 C_4H_6O_6 \cdot 1.3 H_2O$
Calculated: C: 59.24, H: 5.82 N: 4.19 F: 8.52 Found: C: 59.43, H: 5.66, N: 4.13 F: 8.45

Reference Example 11

17-cyclopropylmethyl-4,5α-epoxy-3,14β-dihydroxy-6β-[N-methyl-3-(3-methylphenyl)propiolamido]morphinan.HCl (11)

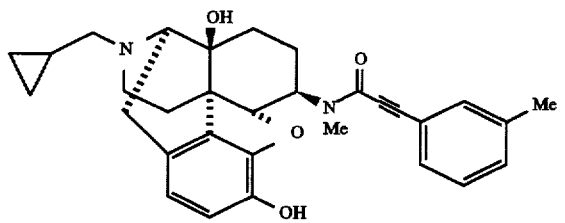

A 2.0085 g (5.7 mmol) portion of 17-cyclopropylmethyl-4,5α-epoxy-3,14β-dihydroxy-6β-methylaminomorphinan (3) and 1.8557 g (11.6 mmol) of 3-(3-methylphenyl)propiolic acid were dissolved in 60 ml of chloroform, after which 2.4 ml (17.4 mmol) of N-ethylpiperidine and 2.9249 g (11.6 mmol) of bis-(2-oxo-3-oxazolidinyl)phosphinic chloride were successively added and the mixture was stirred at room temperature for 3.5 hours. Then, 60 ml of a 1N aqueous solution of sodium hydroxide was added for separation, and the organic layer was washed with 60 ml each of water and brine, dried and then concentrated. The residue was dissolved in 200 ml of methanol, and 10 ml of a 1N aqueous solution of sodium hydroxide was added to the solution which was then stirred for 30 minutes. Then, 300 ml of ethyl acetate was added for separation, and the resulting organic layer was washed with 120 ml of brine, dried and then concentrated. The residue was purified by silica gel column chromatography (200 g of Merck 9385; ethyl acetate/cyclohexane/ammonia water=95/5/0.3) to obtain a free base of the object compound. This was dissolved in ethyl acetate, a hydrogen chloride/ethyl acetate solution was added in excess and stirred therewith, and the resulting precipitate was filtered out to obtain 1.6546 g of the object compound (53% yield).

mp182.0°–183.0° C.

NMR (400 MHz, DMSO-$d_6$) δ0.33–0.47 (1H, m), 0.47–0.56 (1H, m), 0.56–0.64 (1H, m), 0.64–0.76 (1H, m), 1.00–1.15 (1H, m), 1.21–1.36 (0.6H, m), 1.36–1.55 (2.4H, m), 1.70–1.87 (1H, m), 2.05–2.28 (1H, m), 2.29 (2.4H, s), 2.34 (0.6H, s), 2.48–2.63 (2H, m), 2.78–2.93 (1H, m), 2.98 (2.4H, s), 2.99–3.18 (2H, m), 3.30 (0.6H, s), 3.21–3.43 (2H, m), 3.80–3.93 (1H, m), 4.02–4.14 (0.2H, m), 4.14–4.26 (0.8H, m), 4.91 (0.8H, d, J=7.8 Hz), 4.96 (0.2H, d, J=8.3 Hz), 6.45 (0.2H, br s), 6.58 (0.8H, br s), 6.63 (0.8H, d, J=8.3 Hz), 6.65 (0.2H, d, J=8.3 Hz), 6.69 (0.8H, d, J=8.3 Hz), 6.72 (0.2H, d, J=8.3 Hz), 6.92 (0.8H, s), 7.05 (0.8H, d, J=6.8 Hz), 7.20–7.32 (1.6H, m), 7.32–7.40 (0.4H, m), 7.40–7.51 (0.4H, m), 8.85 (1H, br s), 9.33 (0.2H, s), 9.36 (0.8H, s)

IR (KBr) ν3410, 2218, 1613, 1508, 1460, 1410, 1377, 1321, 1125, 1033, 930, 789, 690 cm$^{-1}$

Mass (FAB) m/z 499 ((M+H)$^+$)

Elemental analysis as $C_{31}H_{35}N_2O_4Cl.0.4H_2O$ Calculated: C: 68.66, H: 6.65 N: 5.17 Cl: 6.54 Found: C: 68.86, H: 6.75, N: 5.22 Cl: 6.48

Reference Example 12

17-cyclopropylmethyl-4,5α-epoxy-3-methoxy-14β-hydroxy-6β-[N-methyl-trans-3-(3-furyl)acrylamido]morphinan.HCl (12)

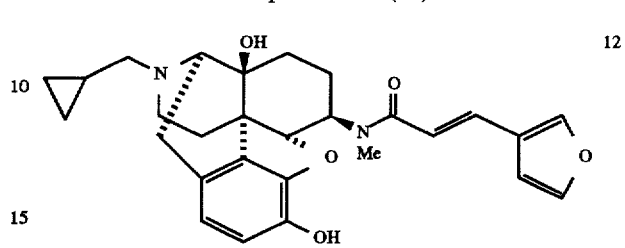

A 0.51 g (1.07 mmol) portion of the 17-cyclopropylmethyl-4,5α-epoxy-3,14β-dihydroxy-6β-[N-methyl-trans-3-(3-furyl)acrylamido]morphinan (5) obtained in Reference Example 5 was dissolved in chloroform (10 ml), a diazomethane/ether solution (1.0 ml) was added thereto and the reaction was conducted at room temperature for 2 hours, after which the diazomethane/ether solution was further added (1.0 ml) and the reaction continued for 4 hours. Acetic acid was added dropwise until the solution became colorless, and the solvent was then distilled off. Separation was performed with a saturated aqueous solution of sodium bicarbonate (15 ml) and chloroform (20 ml), and drying with anhydrous sodium sulfate was followed by concentration. The residue was purified by silica gel column chromatography (50 g of Merck 9385; chloroform/methanol=100/1, second time: 50 g of Merck 9385; chloroform/methanol=200/1) to obtain a free base. This was dissolved in methanol (10 ml), 1N hydrochloric acid (0.62 ml) was added, and after azeotropic distillation with methanol (10 ml×2) the residue was suspended in ethyl acetate and filtered out to obtain 278 mg of the object substance (49% yield).

mp 235°–245° C. (decomposition)

NMR (400 MHz, DMSO-$d_6$) δ0.42 (1H, m), 0.53 (1H, m), 0.60 (1H, m), 0.69 (1H, m), 1.08 (1H, m), 1.25 (0.5H, m), 1.36–1.53 (2.5H, m), 1.78 (1H, m), 2.15 (1H, m), 2.38–2.62 (3H, m), 2.88 (1H, m), 2.92 (1.5H, s), 3.02–3.15 (2H, m), 3.18 (1.5H, s), 3.35–3.45 (2H, m), 3.62 (1.5H, s), 3.66 (0.5H, m), 3.75 (1.5H, s), 3.90 (1H, m), 4.30 (0.5H, m), 4.88 (0.5H, d, J=7.8 Hz), 4.95 (0.5H, d, J=7.8 Hz), 6.38 (0.5H, d, J=15.6 Hz), 6.41 (0.5H, br s), 6.75–7.00 (3H, m), 7.28 (0.5H, d, J=15.6 Hz), 7.37 (0.5H, d, J=15.1 Hz), 7.69 (0.5H, s), 7.72 (0.5H, s), 7.92 (0.5H, s), 8.03 (0.5H, s)

IR (KBr) ν3350, 1651, 1505, 1405, 1323, 1156, 1122, 1029, 872, 800 cm$^{-1}$

Mass (FAB) m/z 491 ((M+H)$^+$)

Elemental analysis as $C_{29}H_{34}N_2O_5.HCl.0.3H_2O$ Calculated: C: 65.42, H: 6.74 N: 5.26 Cl: 6.66 Found: C: 65.25, H: 6.79, N: 5.53 Cl: 6.57

Reference Example 13

17-cyclopropylmethyl-4,5α-epoxy-3-methoxy-14β-hydroxy-6β-[N-methyl-3-(3-methylphenyl)propiolamido]morphinan.HCl (13)

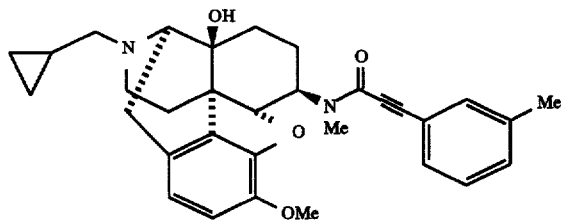

A 0.34 g (0.68 mmol) portion of the 17-cyclopropylmethyl-4,5α-epoxy-3,14β-dihydroxy-6β-[N-methyl-3-(3-methylphenyl)propiolamido]morphinan (11) obtained in Reference Example 11 was used instead of 17-cyclopropylmethyl-4,5α-epoxy-3,14β-dihydroxy-6β-[N-methyl-trans-3-(3-furyl)acrylamido]morphinan (5), in the same manner as in Reference Example 12 to obtain 107 mg of the object compound (29% yield).

mp225°–235° C.

NMR (400 MHz, DMSO-d$_6$) δ 0.38–0.47 (1H, m), 0.47–0.56 (1H, m), 0.56–0.64 (1H, m), 0.64–0.74 (1H, m), 1.05–1.13 (1H, m), 1.28–1.36 (0.3H, m), 1.36–1.52 (2.7H, m), 1.74–1.87 (1H, m), 2.08–2.25 (1H, m), 2.30 (2.1H, s), 2.34 (0.9H, s), 2.28–2.57 (2H, m), 2.83–2.92 (1H, m), 2.96 (2.1H, s), 3.00–3.24 (2H, m), 3.29 (0.9H, s), 3.34 (2.1H, s), 3.35–3.55 (2H, m), 3.77 (0.9H, s), 3.86–3.93 (1H, m), 4.15–4.25 (1H, m), 4.88 (0.7H, d, J=8.3 Hz), 4.94 (0.3H, d, J=8.3 Hz), 6.63 (0.7H, d, J=8.3 Hz), 6.77 (0.7H, s), 6.80 (0.3H, d, J=7.8 Hz), 6.83 (0.7H, d, J=8.3 Hz), 6.90 (0.3H, d, J=8.3 Hz), 6.97 (0.7H, d, J=7.8 Hz), 7.06 (0.3H, s), 7.25–7.46 (2.3H, m)

IR (KBr) v 3400, 2214, 1613, 1505, 1460, 1323, 1125, 932, 787 cm$^{-1}$

Mass (FAB) m/z 513 ((M+H)$^+$)

Elemental analysis as $C_{32}H_{37}N_2O_4Cl.0.6H_2O$ Calculated: C: 68.64, H: 6.88 N: 5.00 Cl: 6.33 Found: C: 68.58, H: 7.00, N: 5.01 Cl: 6.38

Reference Example 14

Opioid activity test using extracted mouse vas deferens sample

Male ddy mice were provided for experimentation. Vas deferens extracted from the mice were suspended in a Magnus tube filled with a 37° C.-heated Krebes-Henseleit solution (118 nM NaCl, 4.7 mM KCl, 2.5 mM CaCl$_2$, 1.1 mM KH$_2$PO$_4$, 25 mM NaHCO$_3$, 11 mM glucose) and aerated with 5% carbon dioxide and 95% oxygen. A 0.1 Hz, 5.0 mS electrical stimulus was applied via an annular platinum electrode. The tissue contraction was recorded on a polygraph using an isometric transducer.

First, a test compound was cumulatively added to a concentration at which 50% of the contraction of a sample due to the electrical stimulus was inhibited, and the IC$_{50}$ value was calculated. Then, the sample was adequately washed with a nutrient solution, and when the contraction reaction stabilized, the μ-antagonist naloxone, the δ-antagonist NTI or the κ-antagonist norBNI was added thereto, and after about 20 minutes the test compound was once again added cumulatively. The Ke value was calculated from the difference in potency between the two, according to the following equation. Ke=[concentration of added antagonist]/(IC$_{50}$ ratio −1) IC$_{50}$ ratio=IC$_{50}$ value in presence of antagonist/IC$_{50}$ value in absence of antagonist Table 1 lists the results of evaluation of compounds according to the present invention. In all cases, there was no large difference in the IC$_{50}$ values before and after use of naltrexone, suggesting that the agonist activity via μ-receptors is very weak, and that κ-receptors are generally the selective agonists.

TABLE 1

Opioid activity of compounds

| | | Ke (nM) | | |
|---|---|---|---|---|
| Compound | IC$_{50}$ (nM) | Naloxone | NTI | norBNI |
| 4 | 0.468 | — | 291 | 3.20 |
| 5 | 0.420 | 14000 | 41.6 | 0.164 |
| 6 | 0.320 | 1780 | 64.5 | 1.95 |
| 8 | 0.420 | — | 532 | 1.00 |
| 10 | 0.00007 | 10.8 | 17.6 | 0.17 |

Example 1

Evaluation of antitussive effect by guinea pig airway stimulation method

A group of five male Hartley guinea pigs (5 weeks old) with a body weight of 330–380 g were used. They were fixed in the supine position under light anesthesia by intraperitoneal administration of 15 mg/kg of pentobarbital sodium, and the necks were cut open to expose the airways. A small hole was opened in each exposed airway, from which stimulating hair was inserted about 3 cm into the airway at a 30° angle to stimulate the wall of the airway, and the occurrence or lack of coughing was noted. Only those guinea pigs which clearly exhibited coughing were used for the remainder of the test. The test compounds were subcutaneously administered, and the stimulation was performed twice at each point 15, 30, 60 and 120 minutes after administration, pronouncing effective those cases in which no coughing occurred either time. Table 2 lists the results of the evaluation, which show that all of the test compounds have strong antitussive effects.

TABLE 2

Antitussive activities of compounds

| Compound | Dosage (μg/kg) | Number of animals exhibiting coughing/ number of animals tested | ED$_{50}$ (μg/kg) |
|---|---|---|---|
| 4 | 1 | 1/5 | |
| | 3 | 3/5 | 2.6 |
| | 30 | 5/5 | |
| 5 | 1 | 2/5 | |
| | 3 | 3/5 | 3.7 |
| | 30 | 5/5 | |
| 6 | 1 | 1/5 | |
| | 3 | 1/5 | 12.5 |
| | 30 | 4/5 | |

Example 2

Evaluation of antitussive effect in rat capsaicin-induced cough models

Inducement of coughing

Coughing was induced by blowing in capsaicin (60 μM) with an artificial respirator, in the form of an aerosol produced by an ultrasonic nebulizer, which was then caused to be inhaled by being fed to the caps of the heads of the rats via a silicon tube. The blowing with the artificial respirator for inhalation of the capsaicin was performed at a volume of 10 ml each time, at a rate of 70 times per minute.

Testing schedule

The capsaicin was fed for inhalation for 5 minutes at a point 270 minutes prior to application of the compounds, during which time the inducement of coughing was confirmed. The capsaicin was then fed for inhalation for 5 minutes at a point 30 minutes after application of the compounds, during which time the number of coughs induced were counted. The antitussive effects were evaluated based on the number of coughs before and after application of the compounds, by calculating the rate of inhibition against the number of coughs prior to application of the compounds. Capsaicin was dissolved in physiological saline. The compounds were dissolved in 10% DMSO water, and all were applied intraperitoneally. The effects of the compounds were expressed as the ED50 values for the dosages exhibiting 50% inhibition of coughing.

TABLE 3

Antitussive activities of compounds

| Compound | $ED_{50}$ (μg/kg) |
|---|---|
| 4 | 107.2 |
| 5 | 4.30 |
| 7 | 437 |
| 8 | 1.79 |
| 9 | 3300 |
| 10 | 2.1 |
| 11 | 13.5 |
| 12 | 0.12 |
| 13 | 12.1 |

[INDUSTRIAL APPLICABILITY]

The compounds used according to the present invention have been found, as a result of activity testing in vitro and in vivo, to have strong antitussive effects as κ-agonists, and have therefore shown promise as useful antitussive agents.

We claim:

1. A method for the treatment of coughing in a subject in need thereof, the method comprising:

administering to said subject an antitussive effective amount of a morphinan derivative represented by formula (I) or a pharmacologically acceptable acid addition salt thereof,

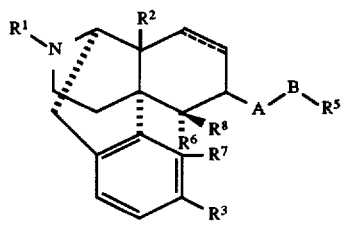

(I)

wherein:

------ represents a single or double bond;

$R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms, or a thiophen-2-ylalkyl group having 1–5 carbon atoms;

$R^2$ represents a hydrogen atom, a hydroxy group, a nitro group, an alkanoyloxy group having 1–5 carbon atoms, an alkoxy group having 1–5 carbon atoms, an alkyl group having 1–5 carbon atoms or —$NR^9R^{10}$, wherein $R^9$ represents a hydrogen atom or an alkyl group having 1–5 carbon atoms, $R^{10}$ represents a hydrogen atom, an alkyl group having 1–5 carbon atoms or —$C(=O)R^{11}$, and $R^{11}$ represents a hydrogen atom, a phenyl group or an alkyl group having 1–5 carbon atoms;

$R^3$ represents a hydrogen atom, a hydroxy group, an alkanoyloxy group having 1–5 carbon atoms or an alkoxy group having 1–5 carbon atoms;

A represents —$NR^4C(=O)$—, —$OC(=O)$—, —N—$R^4C(=O)O$— or —$N^4$— and $R^4$ represents a hydrogen atom, a straight-chain or branched-chain alkyl group having 1–5 carbon atoms or an aryl group having 6–12 carbon atoms, and wherein said $R^4$'s may be identical or different;

B represents:

(i) a valence bond, (ii) a straight-chain or branched-chain alkylene group having 1–14 carbon atoms, which alkylene group may be optionally substituted with one or more substituents selected from the group consisting of an alkoxy group having 1–5 carbon atoms, an alkanoyloxy group having 1–5 carbon atoms, a hydroxy group, a fluorine atom, a chlorine atom, a bromine atom, an iodine atom, an amino group, a nitro group, a cyano group, a trifluoromethyl group and a phenoxy group, and wherein from 1 to 3 methylene groups of said alkylene group may be replaced with carbonyl groups, (iii) a straight-chain or branched-chain acyclic unsaturated hydrocarbon containing 1 to 3 double bonds or triple bonds and having 2–14 carbon atoms, which acyclic hydrocarbon may be substituted with one or more substituents selected from the group consisting of an alkoxy group having 1–5 carbon atoms, an alkanoyloxy group having 1–5 carbon atoms, a hydroxy group, a fluorine atom, a chlorine atom, a bromine atom, an iodine atom, an amino group, a nitro group, a cyano group, a trifluoromethyl group, and a phenoxy group, and wherein 1 to 3 methylene groups of said acyclic hydrocarbon may be replaced with carbonyl groups, or (iv) a straight-chain or branched-chain saturated or unsaturated hydrocarbon containing from 1 to 5 thioether, ether or amino bonds and having 1–14 carbon atoms, wherein no hetero atoms are bonded directly to A, and 1 to 3 methylene groups of said hydrocarbon may be replaced with carbonyl groups;

$R^5$ represents a hydrogen atom or an organic group having a basic skeleton selected from the group consisting of:

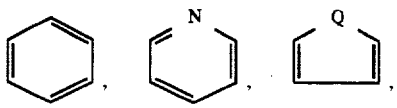

-continued

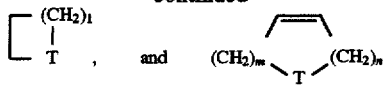 and 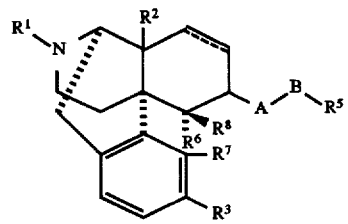

wherein, Q is N, O or S, T is CH, N, S or O, l is 0 to 3, m and n are each independently ≧1, and m+n≦3, provided that said organic group having a basic skeleton may be substituted with one or more substituents selected from the group consisting of an alkyl group having 1–5 carbon atoms, an alkoxy group having 1–5 carbon atoms, an alkanoyloxy group having 1–5 carbon atoms, a hydroxy group, a fluorine atom, a chlorine atom, a bromine atom, an iodine atom, an amino group, a nitro group, a cyano group, an isothiocyanate group, a trifluoromethyl group, and a methylenedioxy group;

$R^6$ represents a hydrogen atom, $R^7$ represents a hydrogen atom, a hydroxy group, an alkoxy group having 1–5 carbon atoms, an alkanoyloxy group having 1–5 carbon atoms, or $R^6$ and $R^7$ together represent —O—, —CH$_2$— or —S—;

$R^8$ represents a hydrogen atom, an alkyl group having 1–5 carbon atoms or an alkanoyl group having 1–5 carbon atoms, and formula (I) includes the (+) form, (−) form and (±) form of said morphinan derivative.

2. A method for the treatment of coughing according to claim 1, wherein said morphinan derivative of formula (I) is selected from the group consisting of:

(a) 17-cyclopropylmethyl-4,5α-epoxy-3,14β-dihydroxy-6β-(N-methyl-3-trifluoromethylcinnamamido)morphinan, (b) 17-cyclopropylmethyl-4,5α-epoxy-3,14β-dihydroxy-6β-[N-methyl-trans-3-(3-furyl)acrylamido]morphinan, (c) 17-cyclopropylmethyl-4,5α-epoxy-3,14β-dihydroxy-6β-[N-methyl-N-2-(3,4-dichlorophenyl)ethylamido]morphinan, (d) 17-cyclopropylmethyl-4,5α-epoxy-3,14β-dihydroxy-6β-(N-methyl-benzyloxycarbamido)morphinan, (e) 17-cyclopropylmethyl-4,5α-epoxy-3,14β-dihydroxy-6β-(N-methyl-3-trifluoromethoxycinnamamido)morphinan, (f) 17-cyclopropylmethyl-4,5α-epoxy-3,14β-dihydroxy-6β-[N-methyl-3-(3-methylphenyl)propiolamido]morphinan, (g) 17-cyclopropylmethyl-4,5α-epoxy-3-methoxy-14β-hydroxy-6β-[N-methyl-trans-3-(3-furyl)acrylamido]morphinan, (h) 17-cyclopropylmethyl-4,5α-epoxy-3-methoxy-14β-hydroxy-6β-[N-methyl-3-(3-methylphenyl)propiolamido]morphinan, and the pharmacologically acceptable acid addition salts thereof.

3. A method for the prophylaxis of coughing in a subject in need thereof, the method comprising:

administering to said subject an antitussive effective amount of a morphinan derivative represented by formula (I) or a pharmacologically acceptable acid addition salt thereof, wherein:

----- represents a single or double bond;

$R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms, or a thiophen-2-ylalkyl group having 1–5 carbon atoms;

$R^2$ represents a hydrogen atom, a hydroxy group, a nitro group, an alkanoyloxy group having 1–5 carbon atoms, an alkoxy group having 1–5 carbon atoms, an alkyl group having 1–5 carbon atoms or —NR$^9$R$^{10}$, wherein $R^9$ represents a hydrogen atom or an alkyl group having 1–5 carbon atoms, $R^{10}$ represents a hydrogen atom, an alkyl group having 1–5 carbon atoms or —C(=O)R$^{11}$, and $R^{11}$ represents a hydrogen atom, a phenyl group or an alkyl group having 1–5 carbon atoms;

$R^3$ represents a hydrogen atom, a hydroxy group, an alkanoyloxy group having 1–5 carbon atoms or an alkoxy group having 1–5 carbon atoms;

A represents —NR$^4$C(=O)—, —OC(=O)—, —N—R$^4$C(=O)— or —NR$^4$—; and R$^4$ represents a hydrogen atom, a straight-chain or branched-chain alkyl group having 1–5 carbon atoms or an aryl group having 6–12 carbon atoms, and wherein said R$^4$'s may be identical or different;

B represents:

(i) a valence bond, (ii) a straight-chain or branched-chain alkylene group having 1–14 carbon atoms, which alkylene group may be optionally substituted with one or more substituents selected from the group consisting of an alkoxy group having 1–5 carbon atoms, an alkanoyloxy group having 1–5 carbon atoms, a hydroxy group, a fluorine atom, a chlorine atom, a bromine atom, an iodine atom, an amino group, a nitro group, a cyano group, a trifluoromethyl group and a phenoxy group, and wherein from 1 to 3 methylene groups of said alkylene group may be replaced with carbonyl groups, (iii) a straight-chain or branched-chain acyclic unsaturated hydrocarbon containing 1 to 3 double bonds or triple bonds and having 2–14 carbon atoms, which acyclic hydrocarbon may be substituted with one or more substituents selected from the group consisting of an alkoxy group having 1–5 carbon atoms, an alkanoyloxy group having 1–5 carbon atoms, a hydroxy group, fluorine, a chlorine atom, a bromine atom, an iodine atom, an amino group, a nitro group, a cyano group, a trifluoromethyl group, and a phenoxy group, and wherein 1 to 3 methylene groups of said acyclic group may be replaced with carbonyl groups, or (iv) a straight-chain or branched-chain saturated or unsaturated hydrocarbon containing from 1 to 5 thioether, ether or amino bonds and having 1–14 carbon atoms, wherein no hetero atoms are bonded directly to A, and 1 to 3 methylene groups of said hydrocarbon may be replaced with carbonyl groups; R⁵ represents a hydrogen atom or an organic group having a basic skeleton selected from the group consisting of:

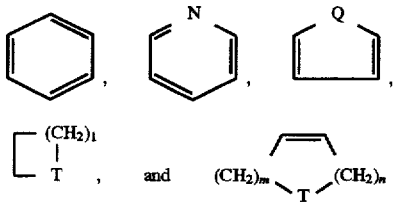

wherein, Q is N, O or S, T is CH, N, S or O, l is 0 to 3, m and n are each independently ≧1, and m+n≦3, provided that said organic group having a basic skeleton may be substituted with one or more substituents selected from the group consisting of an alkyl group having 1–5 carbon atoms, an alkoxy group having 1–5 carbon atoms, an alkanoyloxy group having 1–5 carbon atoms, a hydroxy group, a fluorine atom, a chlorine atom, a bromine atom, an iodine atom, an amino group, a nitro group, a cyano group, an isothiocyanate group, a trifluoromethyl group, and a methylenedioxy group;

R⁶ represents a hydrogen atom, R⁷ represents a hydrogen atom, a hydroxy group, an alkoxy group having 1–5 carbon atoms, an alkanoyloxy group having 1–5 carbon atoms, or R⁶ and R⁷ together represent —O—, —CH₂— or —S—;

R⁸ represents a hydrogen atom, an alkyl group having 1–5 carbon atoms or an alkanoyl group having 1–5 carbon atoms, and formula (I) includes the (+) form, (−) form and (±) form of said morphinan derivative.

4. The method for the prophylaxis of coughing according to claim 3, wherein said morphinan derivative of formula (I) is selected from the group considering of:

(a) 17-cyclopropylmethyl-4,5α-epoxy-3,14β-dihydroxy-6β-(N-methyl-3-trifluoromethylcinnamamido)morphinan, (b) 17-cyclopropylmethyl-4,5α-epoxy-3,14β-dihydroxy-6β-[N-methyl-trans-3-(3-furyl)acrylamido]morphinan, (c) 17-cyclopropylmethyl-4,5α-epoxy-3,14β-dihydroxy-6β-[N-methyl-N-2-(3,4-dichlorophenyl)ethylamido]morphinan, (d) 17-cyclopropylmethyl-4,5α-epoxy-3,14β-dihydroxy-6β-(N-methyl-benzyloxycarbamido)morphinan, (e) 17-cyclopropylmethyl-4,5α-epoxy-3,14β-dihydroxy-6β-(N-methyl-3-trifluoromethoxycinnamamido)morphinan, (f) 17-cyclopropylmethyl-4,5α-epoxy-3,14β-dihydroxy-6β-[N-methyl-3-(3-methylphenyl)propiolamido]morphinan, (g) 17-cyclopropylmethyl-4,5α-epoxy-3-methoxy-14β-hydroxy-6β-[N-methyl-trans-3-(3-furyl)acrylamido]morphinan, (h) 17-cyclopropylmethyl-4,5α-epoxy-3-methoxy-14β-hydroxy-6β-[N-methyl-3-(3-methylphenyl)propiolamido]morphinan, and the pharmacologically acceptable acid addition salts thereof.

5. An antitussive agent, which is a morphinan derivative selected from the group consisting of: p1 (a) 17-cyclopropylmethyl-4,5α-epoxy-3,14β-dihydroxy-6β-(N-methyl-3-trifluoromethylcinnamamido)morphinan, (b) 17-cyclopropylmethyl-4,5α-epoxy-3,14β-dihydroxy-6β-[N-methyl-trans-3-(3-furyl)acrylamido]morphinan, (c) 17-cyclopropylmethyl-4,5α-epoxy-3,14β-dihydroxy-6β-[N-methyl-N-2-(3,4-dichlorophenyl)ethylamido]morphinan, (d) 17-cyclopropylmethyl-4,5α-epoxy-3,14β-dihydroxy-6β-(N-methyl-benzyloxycarbamido)morphinan, (e) 17-cyclopropylmethyl-4,5α-epoxy-3,14β-dihydroxy-6β-(N-methyl-3-trifluoromethoxycinnamamido)morphinan, (f) 17-cyclopropylmethyl-4,5α-epoxy-3,14β-dihydroxy-6β-[N-methyl-3-(3-methylphenyl)propiolamido]morphinan, (g) 17-cyclopropylmethyl-4,5α-epoxy-3-methoxy-14β-hydroxy-6β-[N-methyl-trans-3-(3-furyl)acrylamido]morphinan, (h) 17-cyclopropylmethyl-4,5α-epoxy-3-methoxy-14β-hydroxy-6β-[N-methyl-3-(3-methylphenyl)propiolamido]morphinan, and the pharmacologically acceptable acid addition salts thereof.

* * * * *

UNITED STATES PATENT AND TRADEMARK OFFICE
CERTIFICATE OF CORRECTION

PATENT NO. : 5,739,145
DATED : April 14, 1998
INVENTOR(S) : Hiroshi NAGASE et al.

It is certified that error appears in the above-identified patent and that said Letters Patent is hereby corrected as shown below:

On the Title Page:

Item    [22] PCT Filed as follows:

Change "Jun. 28, 1995" to --Jun. 28, 1994--

Signed and Sealed this

Fifteenth Day of September, 1998

Attest:

Attesting Officer

BRUCE LEHMAN
Commissioner of Patents and Trademarks